US008951831B2

(12) United States Patent
Bae et al.

(10) Patent No.: US 8,951,831 B2
(45) Date of Patent: Feb. 10, 2015

(54) BINAPHTHALENE DERIVATIVES, PREPARATION METHOD THEREOF AND ORGANIC ELECTRONIC DEVICE USING THE SAME

(71) Applicant: LG Chem, Ltd., Seoul (KR)

(72) Inventors: Jae Soon Bae, Daejeon Metropolitan (KR); Dae Woong Lee, Daejeon Metropolitan (KR); Dong Hoon Lee, Seoul (KR); Jae Chol Lee, Daejeon Metropolitan (KR); Jun Gi Jang, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/174,431

(22) Filed: Feb. 6, 2014

(65) Prior Publication Data
US 2014/0183505 A1 Jul. 3, 2014

Related U.S. Application Data

(62) Division of application No. 11/583,794, filed on Oct. 20, 2006, now Pat. No. 8,674,138.

(30) Foreign Application Priority Data

Oct. 21, 2005 (KR) .......................... 10-2005-0099873

(51) Int. Cl.
| | |
|---|---|
| *H01L 51/00* | (2006.01) |
| *C07C 15/24* | (2006.01) |
| *C07C 15/28* | (2006.01) |
| *C07C 15/38* | (2006.01) |
| *C07C 15/40* | (2006.01) |
| *C07D 251/02* | (2006.01) |
| *C07D 401/04* | (2006.01) |
| *C07D 403/04* | (2006.01) |
| *H01L 51/05* | (2006.01) |
| *C07C 13/567* | (2006.01) |
| *C07C 13/72* | (2006.01) |
| *C07C 15/20* | (2006.01) |
| *C07C 15/58* | (2006.01) |
| *C07C 211/54* | (2006.01) |
| *C07C 211/58* | (2006.01) |
| *C07C 211/61* | (2006.01) |
| *C07D 235/18* | (2006.01) |
| *C07D 333/18* | (2006.01) |
| *C09K 11/06* | (2006.01) |
| *H05B 33/14* | (2006.01) |

(Continued)

(52) U.S. Cl.
CPC .......... *H01L 51/0512* (2013.01); *C07C 13/567* (2013.01); *C07C 13/72* (2013.01); *C07C 15/20* (2013.01); *C07C 15/28* (2013.01); *C07C 15/38* (2013.01); *C07C 15/58* (2013.01); *C07C 211/54* (2013.01); *C07C 211/58* (2013.01); *C07C 211/61* (2013.01); *C07D 235/18* (2013.01); *C07D 333/18* (2013.01); *C09K 11/06* (2013.01); *H01L 51/0058* (2013.01); *H01L 51/006* (2013.01); *H01L 51/0068* (2013.01); *H01L 51/0072* (2013.01); *H05B 33/14* (2013.01); *H01L 51/42* (2013.01); *H01L 51/50* (2013.01); *C07C 2103/18* (2013.01); *C07C 2103/24* (2013.01); *C07C 2103/50* (2013.01); *C07C 2103/52* (2013.01); *C07C 2103/94* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1092* (2013.01); *H01L 51/5012* (2013.01); *H01L 51/5048* (2013.01); *Y02E 10/549* (2013.01)
USPC .............. 438/99; 257/40; 564/427; 564/428; 544/180; 546/152; 546/268.1; 546/268.4; 548/302.7; 549/29

(58) Field of Classification Search
USPC ........................ 564/427, 428; 438/99; 257/40
See application file for complete search history.

(56) References Cited

U.S. PATENT DOCUMENTS

| | | | |
|---|---|---|---|
| 5,622,648 A | 4/1997 | Parri et al. | ................ 252/299.66 |
| 5,766,510 A | 6/1998 | Hanna et al. | ............. 252/299.62 |
| 5,935,721 A | 8/1999 | Shi et al. | |

(Continued)

FOREIGN PATENT DOCUMENTS

| | | |
|---|---|---|
| EP | 1 009 043 | 6/2000 |
| JP | 2000-182777 | 6/2000 |

(Continued)

OTHER PUBLICATIONS

MachineTranslation in English of JP 2003-081923, Mar. 19, 2003.

(Continued)

*Primary Examiner* — Venkataraman Balasubramanian
(74) *Attorney, Agent, or Firm* — McKenna Long & Aldridge LLP

(57) ABSTRACT

The present invention relates to a new binaphthalene derivative, a preparation method thereof, and an organic electronic device using the same. The binaphthalene derivative according to the present invention can perform functions of hole injection and transportation, electron injection and transportation, or light emission in an organic electronic device including an organic light-emitting device, and the device according to the present invention has excellent characteristics in terms of efficiency, drive voltage and stability, and in particular excellent effects such as a low voltage and a long life time.

8 Claims, 12 Drawing Sheets

(51) Int. Cl.
*H01L 51/42* (2006.01)
*H01L 51/50* (2006.01)

(56) References Cited

U.S. PATENT DOCUMENTS

| | | | |
|---|---|---|---|
| 6,596,415 B2 | 7/2003 | Shi et al. | 428/690 |
| 6,872,475 B2 | 3/2005 | Chen et al. | 428/690 |
| 6,884,477 B1 | 4/2005 | Takiguchi et al. | 428/1.1 |
| 7,851,071 B2 | 12/2010 | Yamamoto et al. | |
| 8,674,138 B2 * | 3/2014 | Bae et al. | 564/427 |
| 2001/0021478 A1 | 9/2001 | Shi et al. | |
| 2005/0095456 A1 | 5/2005 | Takeda | |
| 2007/0088185 A1 | 4/2007 | Kubota et al. | |
| 2007/0152565 A1 | 7/2007 | Kubota et al. | |
| 2008/0207864 A1 | 8/2008 | Nakagawa et al. | |

FOREIGN PATENT DOCUMENTS

| | | |
|---|---|---|
| JP | 2000-192028 | 7/2000 |
| JP | 2000-273055 | 10/2000 |
| JP | 2001-097897 | 4/2001 |
| JP | 2003-081923 | 3/2003 |
| JP | 2004-018510 | 1/2004 |
| JP | 2004-307472 | 11/2004 |
| JP | 2005-019219 | 1/2005 |
| JP | 2006-45503 | 2/2006 |
| KR | 10-2000-0048007 | 7/2000 |
| WO | WO 2004/080975 A1 | 9/2004 |
| WO | WO 2005/061656 | 7/2005 |
| WO | WO 2005/090365 A1 | 9/2005 |
| WO | WO 2005/112519 A1 | 11/2005 |
| WO | WO 2005/123634 A1 | 12/2005 |
| WO | WO 2006/003842 A1 | 1/2006 |
| WO | WO 2006/104044 | 10/2006 |

OTHER PUBLICATIONS

Journal of the American Chemical Society, 1977, vol. 99, No. 16, pp. 5393-5399.

* cited by examiner

BINAPHTHALENE DERIVATIVES, PREPARATION METHOD THEREOF AND ORGANIC ELECTRONIC DEVICE USING THE SAME

This application is a Divisional application of U.S. application Ser. No. 11/583,794, filed Oct. 20, 2006, which claims priority benefits from Korean Patent Application No. 10-2005-0099873, filed on Oct. 21, 2005, the entire contents of which are fully incorporated herein by reference.

TECHNICAL FIELD

This application claims priority benefits from Korean Patent Application No. 10-2005-0099873, filed on Oct. 21, 2005, the entire contents of which are fully incorporated herein by reference.

BACKGROUND ART

The term "organic electronic device" as used in the present specification refers to a device requiring charge exchange between an electrode and an organic material, using holes and/or electrons. The organic electronic device can be largely classified into two types according to its operational principle as follows: One type is an electronic device having a configuration in which an exciton is formed in an organic material layer by photons flown from an external light source into the device and the exciton is separated into an electron and a hole, the electron and the hole formed are transported to a different electrode, respectively and used as a current source (voltage source), and the other type is an electronic device having a configuration in which a hole and/or electron are/is injected into an organic material semiconductor forming an interface with an electrode by applying a voltage or current to two or more electrodes to allow the device to operate by means of the injected electron and hole.

Examples of the organic electronic device include an organic light-emitting device, an organic solar cell, an organic photoconductor (OPC) drum and an organic transistor, which all require a hole-injecting or hole-transporting material, an electron-injecting or electron-transporting material, or a light-emitting material for driving the device. Hereinafter, the organic light-emitting device will be mainly and specifically described, but in the above-mentioned organic electronic devices, the hole-injecting or hole-transporting material, the electron-injecting or electron-transporting material, or the light-emitting material functions according to a similar principle.

In general, the term "organic light-emitting phenomenon" refers to a phenomenon in which electric energy is converted to light energy by means of an organic material. The organic light-emitting device using the organic light-emitting phenomenon has a structure usually comprising an anode, a cathode and an organic material layer interposed therebetween. Herein, the organic material layer may be mostly formed in a multilayer structure comprising layers of different materials, for example, the hole-injecting layer, the hole-transporting layer, the light-emitting layer, the electron-transporting layer, the electron-injecting layer and the like, in order to improve efficiency and stability of the organic light-emitting device. In the organic light-emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light-emitting device is known to have characteristics such as self-luminescence, high brightness, high efficiency, low drive voltage, wide viewing angle, high contrast and high-speed response.

The materials used for the organic material layer of the organic light-emitting device can be classified into a light-emitting material and a charge-transporting material, for example, a hole-injecting material, a hole-transporting material, an electron-transporting material and an electron-injecting material, according to their functions. Further, the light-emitting material can be divided into a blue, green or red light-emitting material and a yellow or orange light-emitting material required for giving more natural color, according to a light-emitting color. On the other hand, an efficiency of a device is lowered owing to maximum luminescence wavelength moved to a longer wavelength due to the interaction between the molecules, the deterioration of color purity and the reduction in light emitting efficiency when only one material is used for the light-emitting material, and therefore a host/dopant system can be used as the light-emitting material for the purpose of enhancing the color purity and the light emitting efficiency through energy transfer.

In order to allow the organic light-emitting device to fully exhibit the above-mentioned excellent characteristics, a material constituting the organic material layer in the device, for example, a hole-injecting material, a hole-transporting material, a light-emitting material, an electron-transporting material and an electron-injecting material should be essentially composed of a stable and efficient material. However, the development of a stable and efficient organic material layer material for the organic light-emitting device has not yet been fully realized. Accordingly, the development of new materials is continuously desired. The development of such a material is equally required to the above-mentioned other organic electronic devices.

DISCLOSURE

Technical Problem

The present inventors have synthesized a binaphthalene derivative having a new structure, and then have found that the compound has effects of a low voltage and a long life time when it acts as a layer for electron transportation and electron injection in an organic light-emitting device, thus completing the present invention. In addition, the present inventors have found that the compound has effects of emitting blue, green or red light when it acts as a layer for light-emitting in an organic light-emitting device, thus completing the present invention.

Therefore, it is an object of the present invention to provide a new binaphthalene derivative and a preparation method thereof. Further, it is another object of the present invention to provide an organic electronic device using the binaphthalene derivative.

Technical Solution

The present invention provides a binaphthalene derivative represented by the following formula (1):

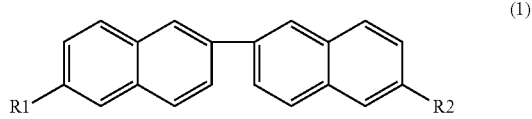

(1)

wherein R1 and R2 may be the same or different from each other, and are each respectively selected from the group consisting of a substituted or unsubstituted alkenyl group, a substituted or unsubstituted aryl group, a substituted or unsubstituted heteroaromatic group, and a substituted or unsubstituted arylamino group, provided that one of R1 and R2 may be hydrogen.

Preferable examples of the substituted or unsubstituted alkenyl group include an alkenyl group unsubstituted or substituted by a substituted or unsubstituted $C_6$~$C_{30}$ aryl group or a substituted or unsubstituted $C_5$~$C_{30}$ heteroaryl group.

Preferable examples of the substituted or unsubstituted aryl group include a $C_6$~$C_{30}$ aryl group unsubstituted or substituted by at least one group selected from the group consisting of a halogen atom, an amino group, a nitrile group, a nitro group, an alkylboronate, a $C_1$~$C_{30}$ alkyl group, a $C_2$~$C_{40}$ alkenyl group, a $C_1$~$C_{40}$ alkoxy group, a $C_3$~$C_{30}$ cycloalkyl group, a $C_3$~$C_{30}$ heterocycloalkyl group, a $C_6$~$C_{30}$ aryl group, a $C_5$~$C_{30}$ heteroaryl group and a $C_6$~$C_{30}$ arylamino group.

Preferable examples of the substituted or unsubstituted heteraromatic group include a $C_5$~$C_{30}$ heteroaromatic group unsubstituted or substituted by at least one group selected from the group consisting of a halogen atom, an amino group, a nitrile group, a nitro group, an alkylboronate, a $C_1$~$C_{30}$ alkyl group, a $C_2$~$C_{40}$ alkenyl group, a $C_1$~$C_{40}$ alkoxy group, a $C_3$~$C_{30}$ cycloalkyl group, a $C_3$~$C_{30}$ heterocycloalkyl group, a $C_6$~$C_{30}$ aryl group, a $C_5$~$C_{30}$ heteroaryl group and a $C_6$~$C_{30}$ arylamino group.

Preferable examples of the substituted or unsubstituted arylamino group include a $C_6$~$C_{30}$ arylamino group unsubstituted or substituted by at least one group selected from the group consisting of a halogen atom, an amino group, a nitrile group, a nitro group, an alkylboronate, a $C_1$~$C_{30}$ alkyl group, a $C_2$~$C_{40}$ alkenyl group, a $C_1$~$C_{40}$ alkoxy group, a $C_3$~$C_{30}$ cycloalkyl group, a $C_3$~$C_{30}$ heterocycloalkyl group, a $C_6$~$C_{30}$ aryl group, a $C_5$~$C_{30}$ heteroaryl group and a $C_6$~$C_{30}$ arylamino group.

Preferably, in the formula 1, R1 and R2 may be selected from the group consisting of the following structural formulas, but not limited thereto.

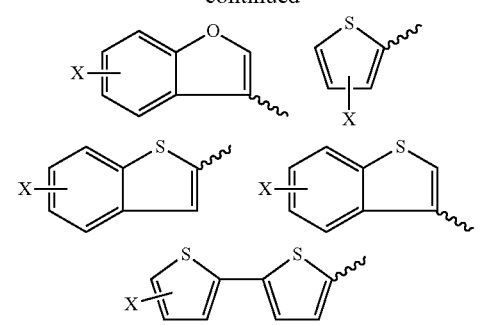
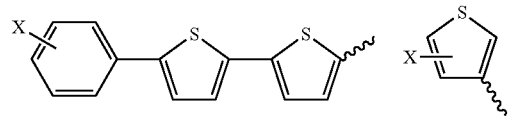
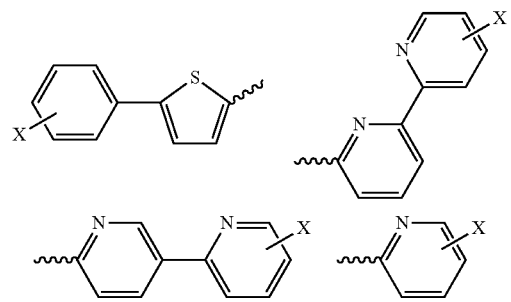
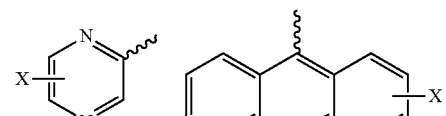
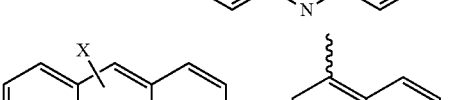
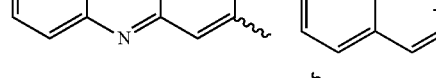
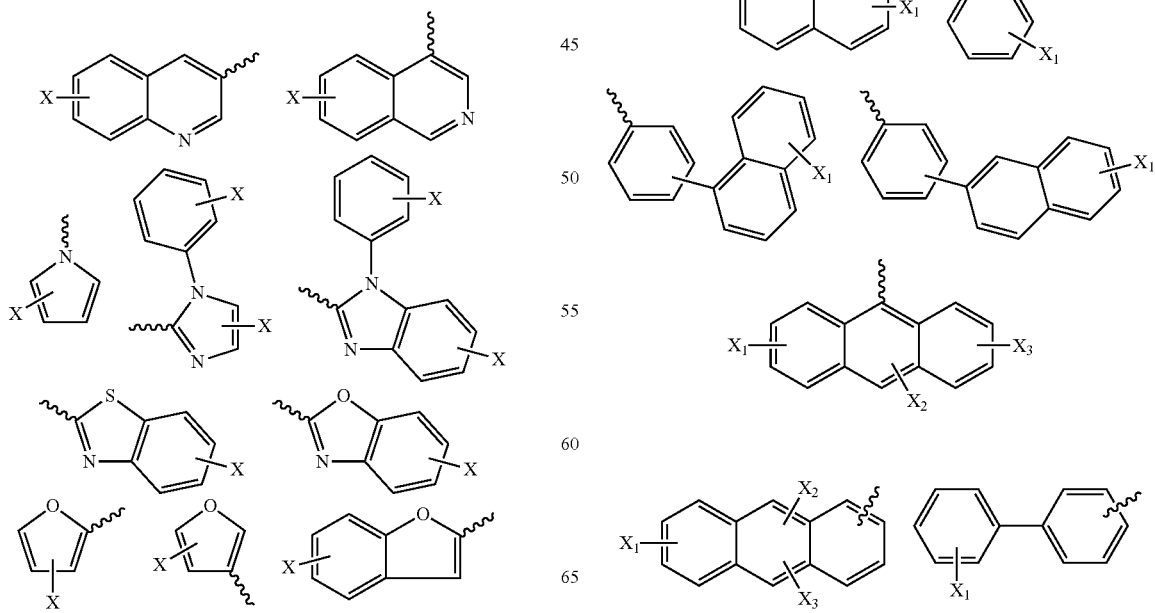

-continued
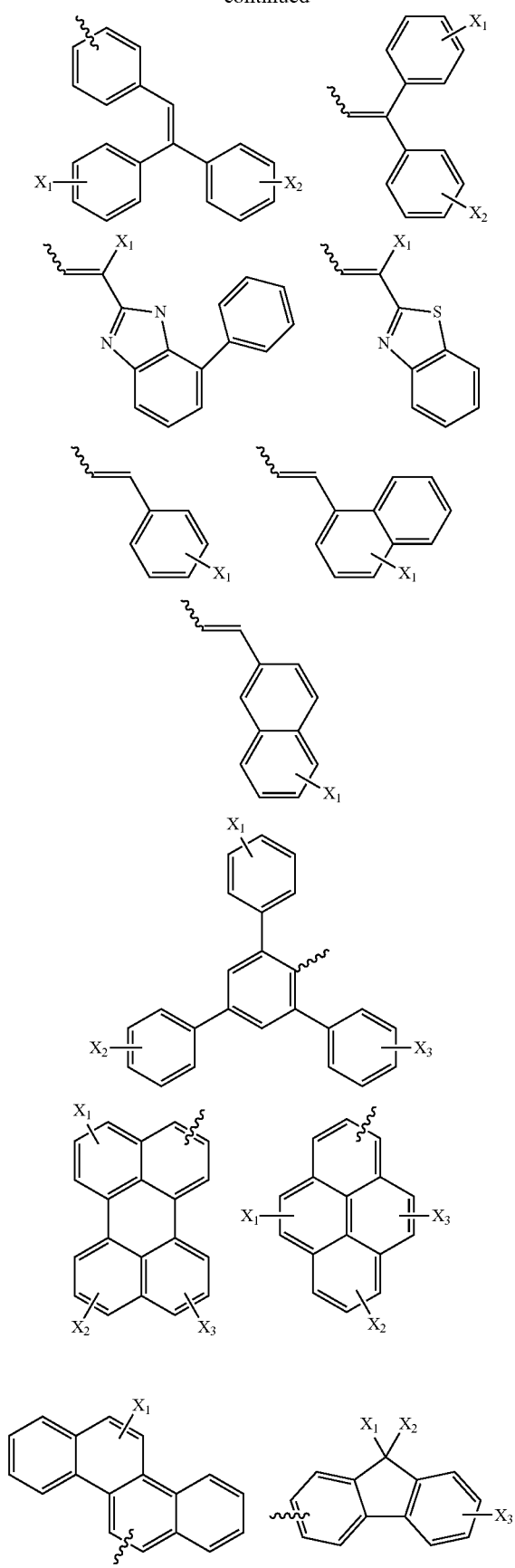
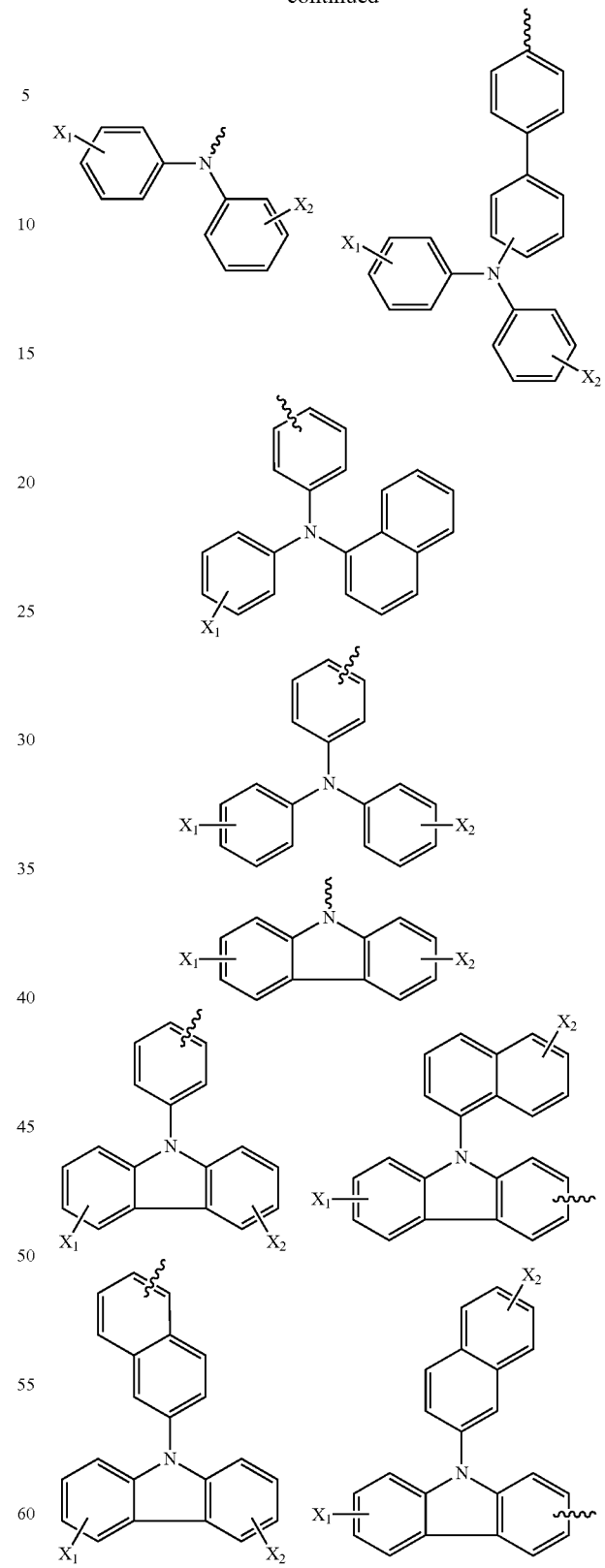
In the above structural formulas, X, $X_1$, $X_2$ and $X_3$ may be each respectively the same or different from each other, and are each selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted alicyclic group, a substituted or unsubstituted silicone group, a substituted or unsubstituted boron group, a substituted or unsubstituted amino group, a nitrile group, a nitro group, a halogen group, a substituted or unsubstituted amide group, and a substituted or unsubstituted ester group, and these may form an aliphatic, aromatic, or heterocyclic fused ring, together with the adjacent group.

The alkyl group preferably has 1 to 30 carbon atoms and does not give steric hindrance. Specific examples thereof include, but not limited thereto, a methyl group, an ethyl group, a propyl group, an isopropyl group, a butyl group, a t-butyl group, a pentyl group, a hexyl group and a heptyl group.

Examples of the alkoxy group include an alkoxy group having 1 to 30 carbon atoms.

Examples of the alkenyl group include an alkenyl group linked with an aryl group such as a stylbenzyl group and a styrenyl group.

Examples of the aryl group include those selected from the group consisting of a phenyl group, a naphthyl group, an anthracenyl group, a biphenyl group, a pyrenyl group and a perylenyl group.

Examples of the arylamine group include those selected from the group consisting of a diphenylamine group, a phenylnaphthylamine group, a ditolylamine group, a phenyltolylamine group, a carbazolyl group and a triphenylamine group.

Examples of the heterocyclic group include those selected from the group consisting of a pyridyl group, a bipyridyl group, an acridinyl group, a thiophene group, an imidazolyl group, an oxazolyl group, a thiazolyl group and a quinolyl group.

The alicyclic group preferably has 3 to 30 carbon atoms and does not give steric hindrance. More preferable specific examples thereof include, but not limited thereto, a cyclopentyl group or a cyclohexyl group.

Examples of the halogen group include fluorine, chlorine, bromine and iodine.

The term "unsubstituted," in the explanation regarding groups described in this specification, means that hydrogen is bonded to the groups.

Specific examples of the compound of the formula 1 are shown in the following Tables 1 and 2, but the scope of the present invention is not limited thereto. Table 1 shows specific examples of the compound in which R1 is hydrogen and R2 is a group selected from the groups defined above except for hydrogen. Table 2 shows specific examples of the compound in which R1 and R2 are groups selected from the groups defined above except for hydrogen.

As described in the following Preparation Examples and Examples of the present invention, a variety of derivatives, such as the compounds showed at Table 1 and 2, can be synthesized under the presence of a Pd catalyst. Also, simple intermediates can be synthesized as described in the following Preparation Examples. In other words, the compound containing the binaphthyl group of the above formula (1) can be synthesized by the method.

TABLE 1

Groups as R2 in the compounds of formula (1) having hydrogen as R1

No. R2

1-1 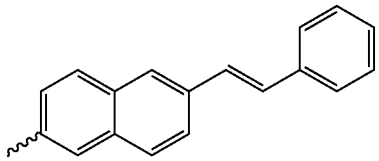

1-2 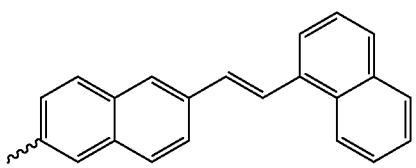

1-3 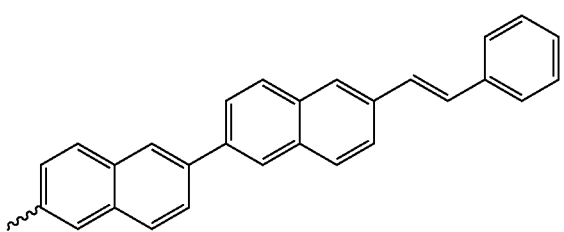

1-4 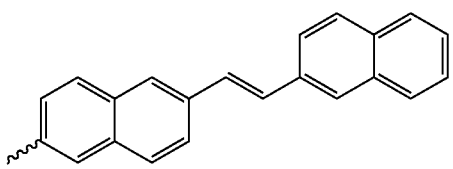

TABLE 1-continued
Groups as R2 in the compounds of formula (1) having hydrogen as R1
| No. | R2 |
|---|---|
| 1-5 | 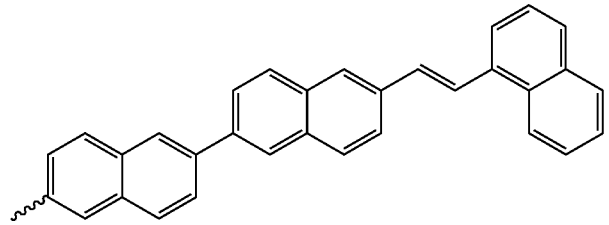 |
| 1-6 | 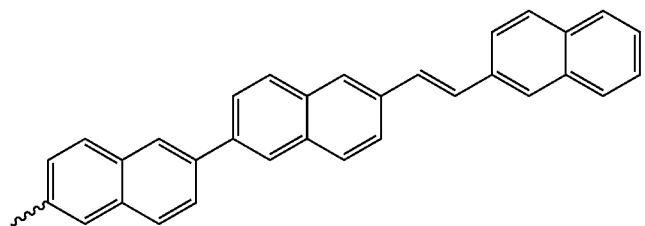 |
| 1-7 | 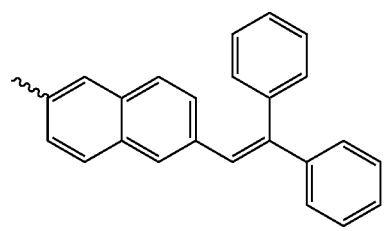 |
| 1-8 | 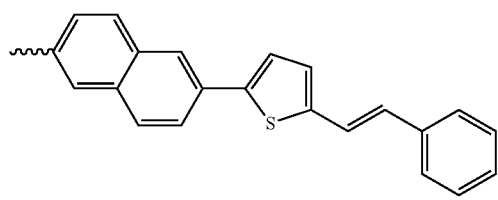 |
| 1-9 | 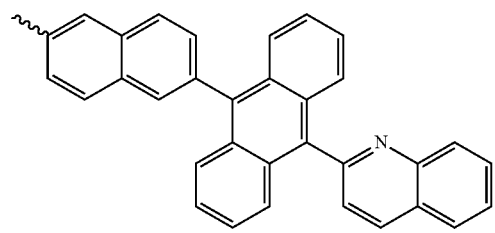 |
| 1-10 | 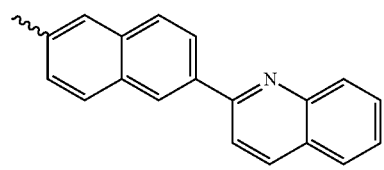 |
| 1-11 | 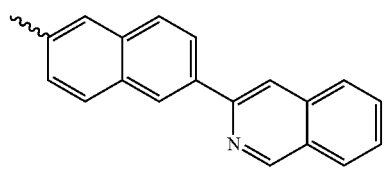 |

TABLE 1-continued
Groups as R2 in the compounds of formula (1) having hydrogen as R1
| No. | R2 |
|---|---|
| 1-12 | 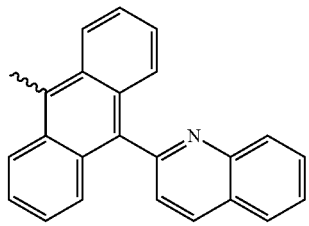 |
| 1-13 |  |
| 1-14 | 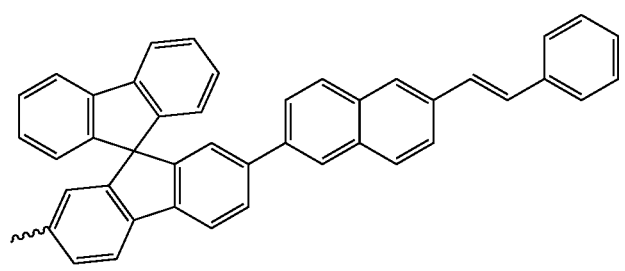 |
| 1-15 | 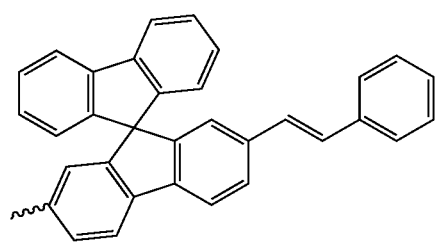 |
| 1-16 | 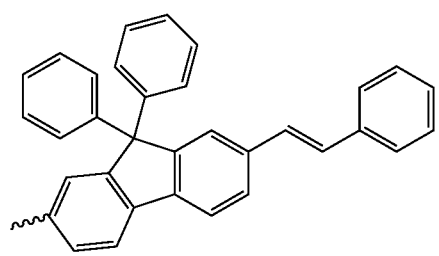 |
| 1-17 | 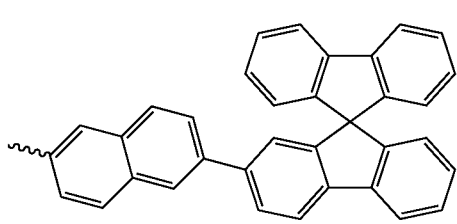 |

TABLE 1-continued
Groups as R2 in the compounds of formula (1) having hydrogen as R1
| No. | R2 |
|---|---|
| 1-18 | 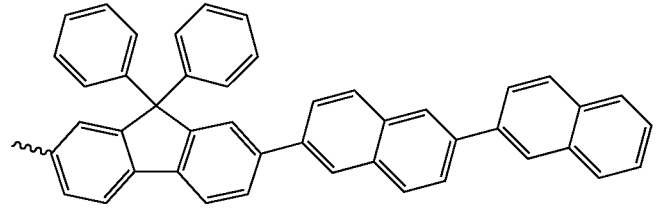 |
| 1-19 | 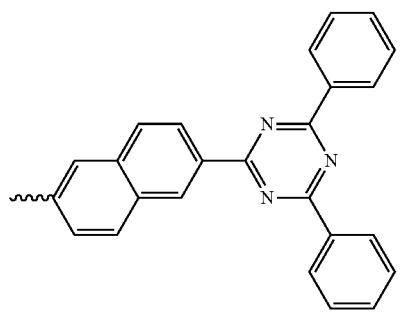 |
| 1-20 | 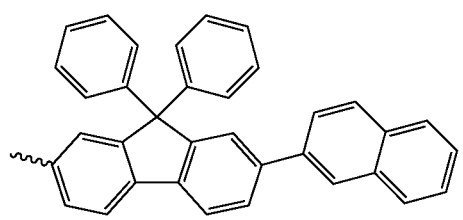 |
| 1-21 | 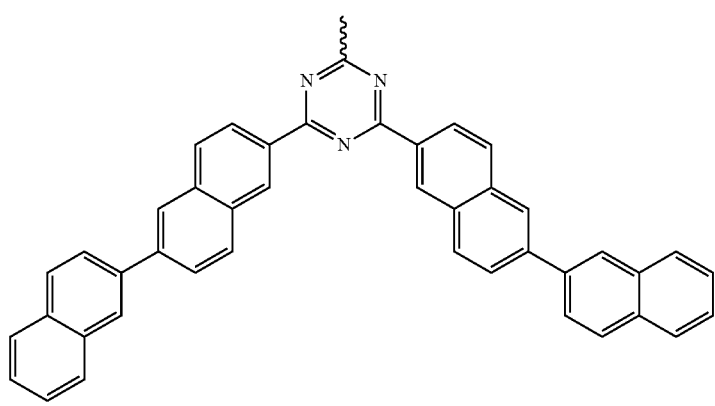 |
| 1-22 | 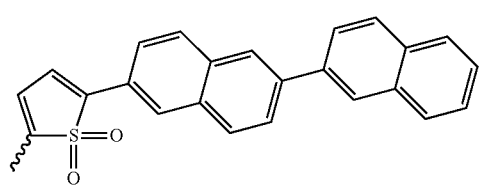 |
| 1-23 | 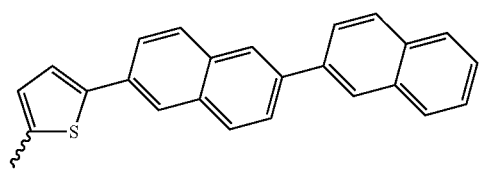 |

TABLE 1-continued
Groups as R2 in the compounds of formula (1) having hydrogen as R1
| No. | R2 |
|---|---|
| 1-24 | 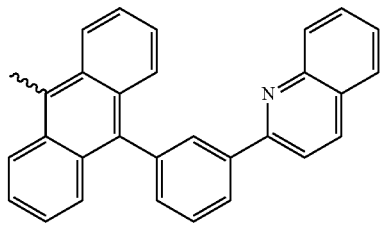 |
| 1-25 | 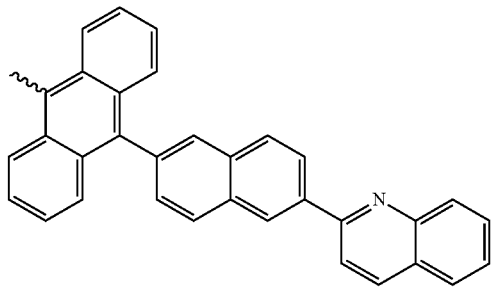 |
| 1-26 | 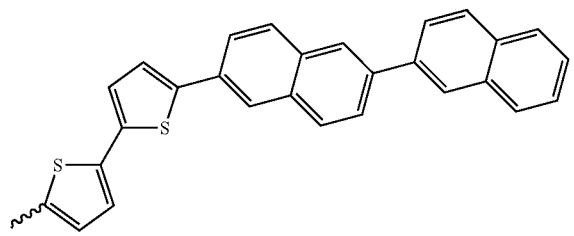 |
| 1-27 | 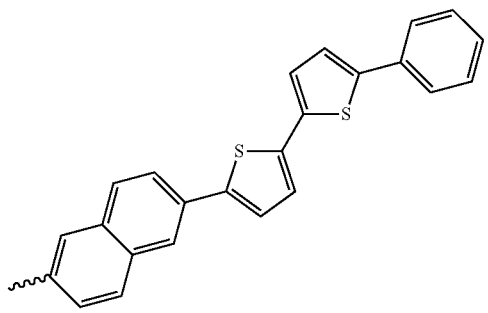 |
| 1-28 | 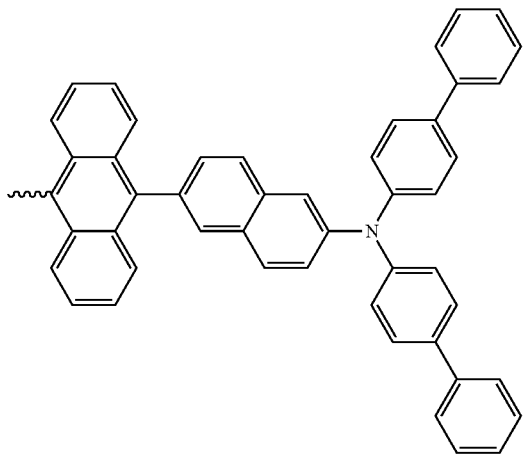 |

TABLE 1-continued
Groups as R2 in the compounds of formula (1) having hydrogen as R1
| No. | R2 |
|---|---|
| 1-29 | 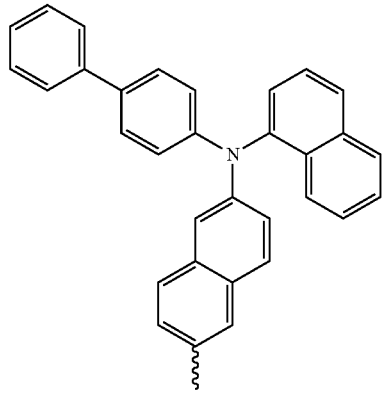 |
| 1-30 | 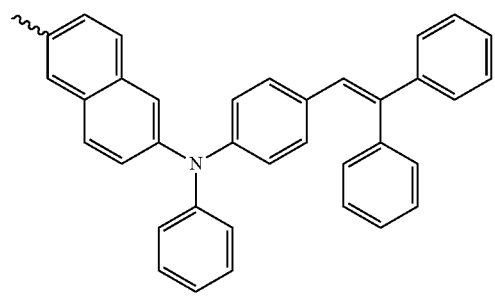 |
| 1-31 | 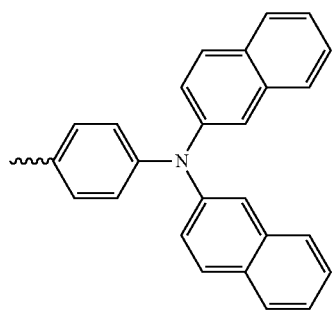 |
| 1-32 | 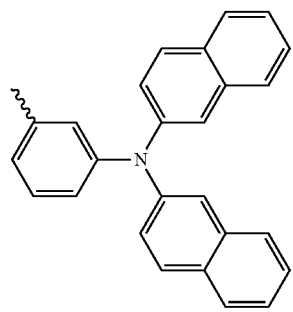 |
| 1-33 | 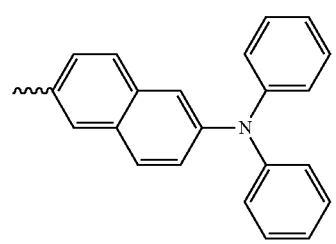 |

TABLE 1-continued
Groups as R2 in the compounds of formula (1) having hydrogen as R1
| No. | R2 |
|---|---|
| 1-34 | 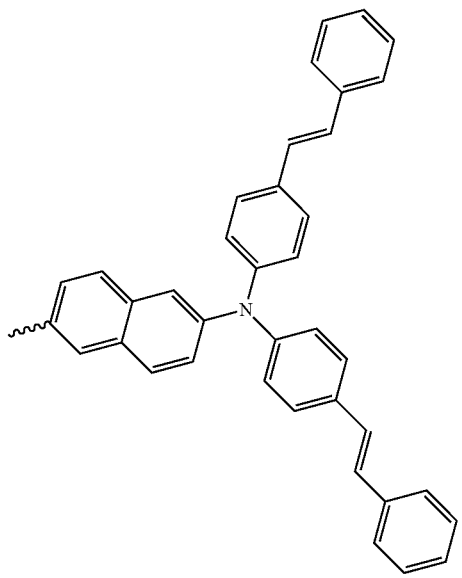 |
| 1-35 | 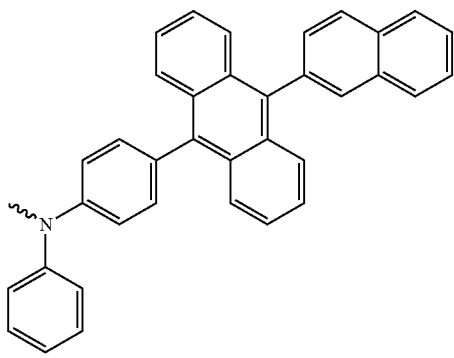 |
| 1-36 | 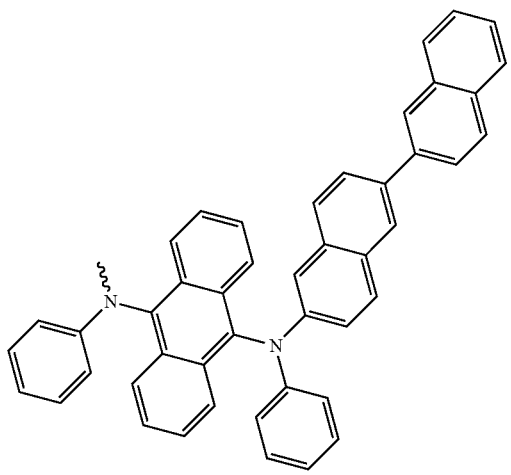 |

TABLE 1-continued
Groups as R2 in the compounds of formula (1) having hydrogen as R1
| No. | R2 |
|---|---|
| 1-37 | 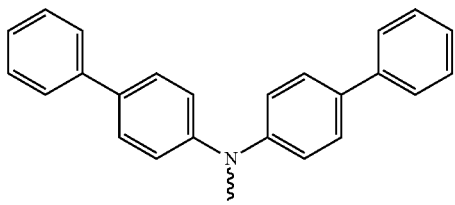 |
| 1-38 | 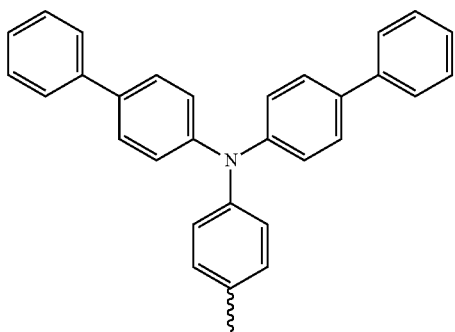 |
| 1-39 | 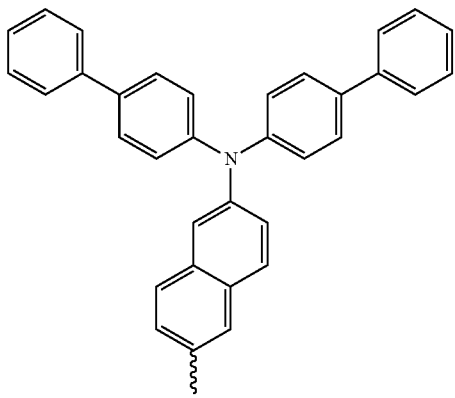 |
| 1-40 | 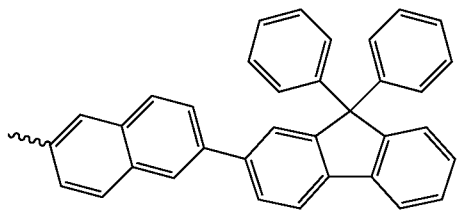 |
| 1-41 | 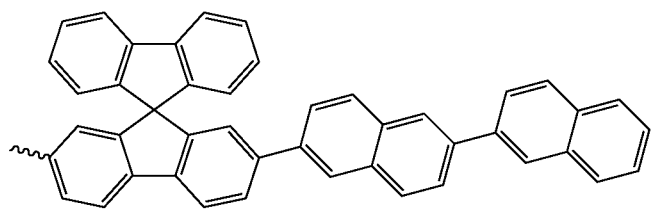 |

TABLE 1-continued
Groups as R2 in the compounds of formula (1) having hydrogen as R1
| No. | R2 |
|---|---|
1-42
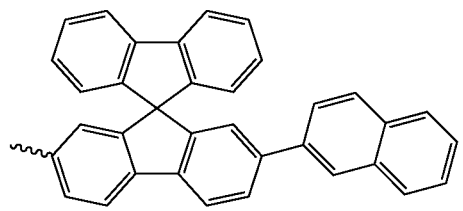
1-43
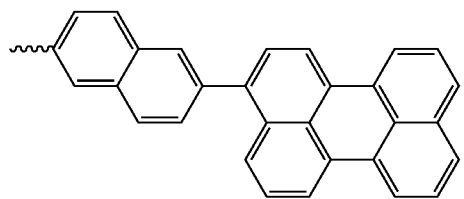
1-44
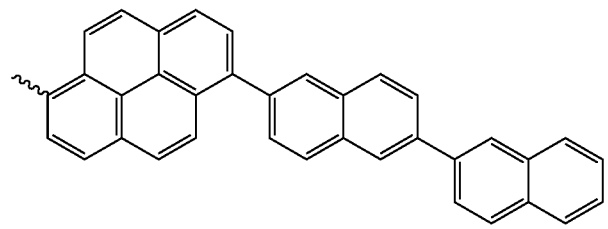
1-45
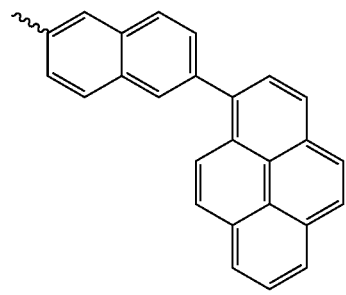
1-46
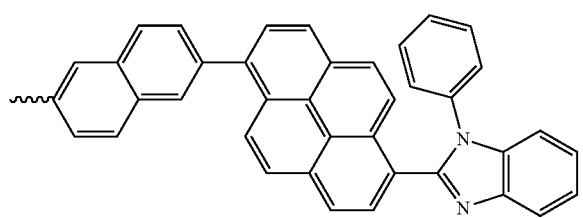

TABLE 1-continued
Groups as R2 in the compounds of formula (1) having hydrogen as R1
| No. | R2 |
|---|---|
| 1-47 | 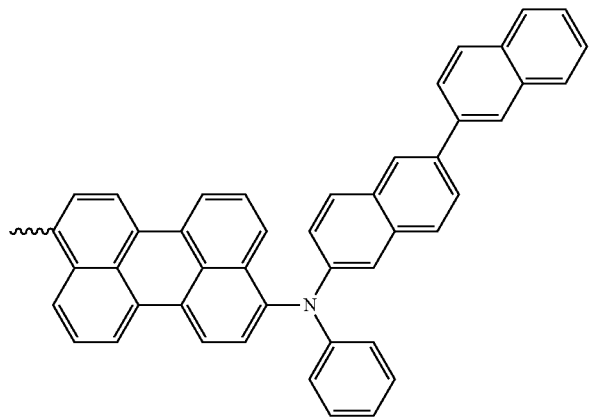 |
| 1-48 | 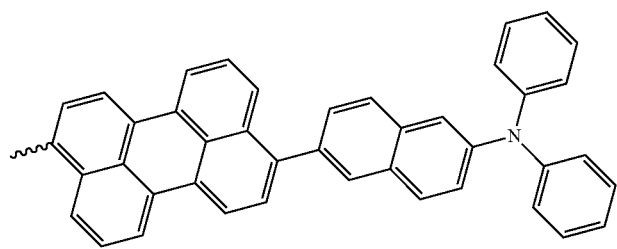 |
| 1-49 | 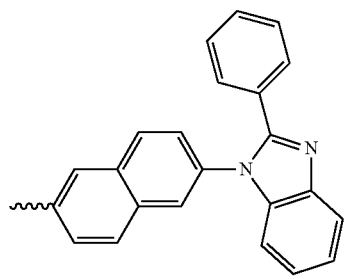 |
| 1-50 | 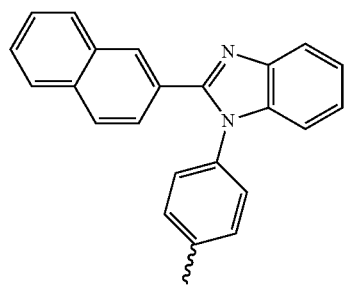 |

TABLE 1-continued
Groups as R2 in the compounds of formula (1) having hydrogen as R1
| No. | R2 |
|---|---|
| 1-51 | 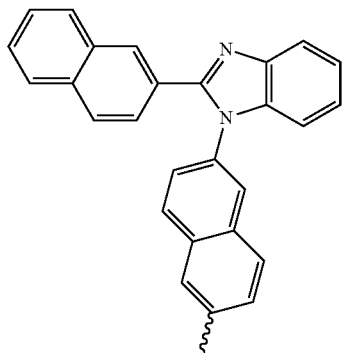 |
| 1-52 | 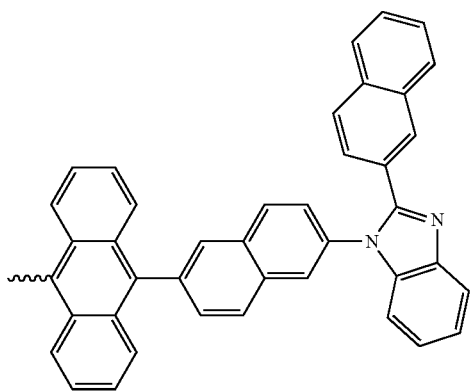 |
| 1-53 | 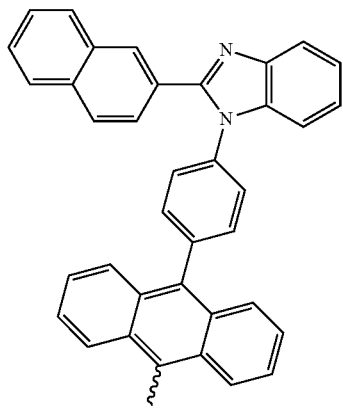 |
| 1-54 | 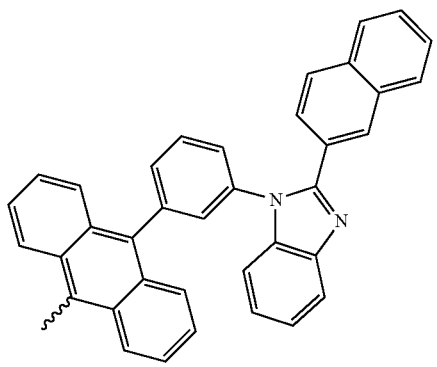 |

TABLE 1-continued
Groups as R2 in the compounds of formula (1) having hydrogen as R1
No.  R2
1-55
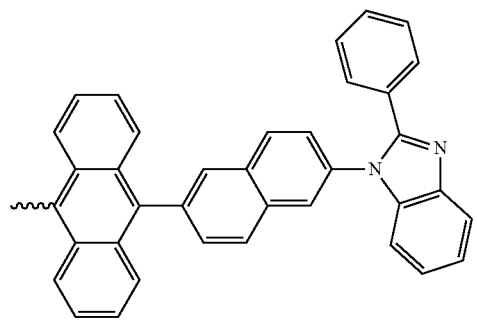
1-56
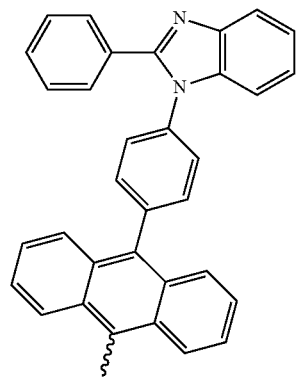
1-57
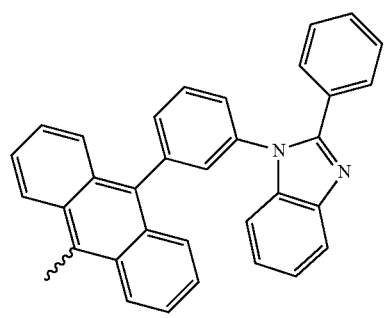
1-58
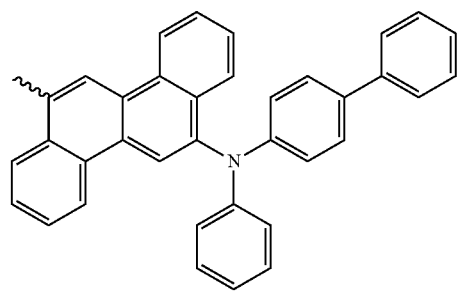

TABLE 1-continued
Groups as R2 in the compounds of formula (1) having hydrogen as R1
| No. | R2 |
|---|---|
| 1-59 | 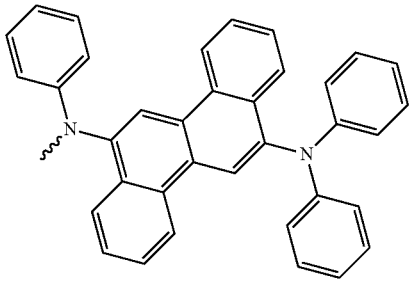 |
| 1-60 | 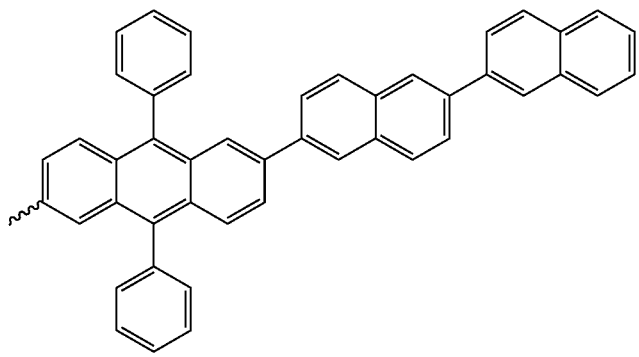 |
| 1-61 | 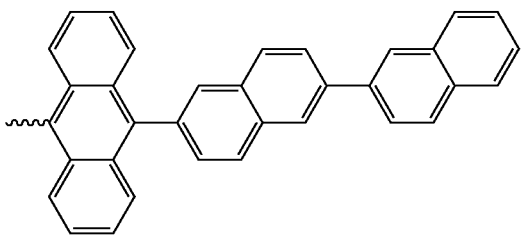 |
| 1-62 | 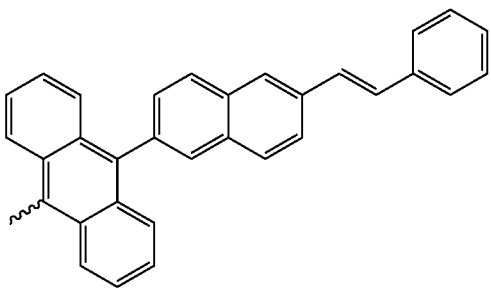 |
| 1-63 | 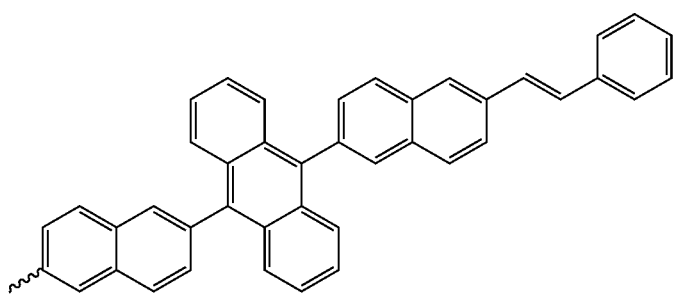 |

TABLE 1-continued
Groups as R2 in the compounds of formula (1) having hydrogen as R1
| No. | R2 |
|---|---|
| 1-64 | 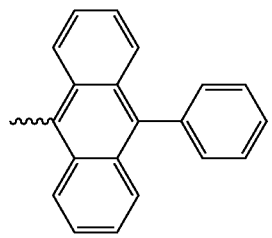 |
| 1-65 | 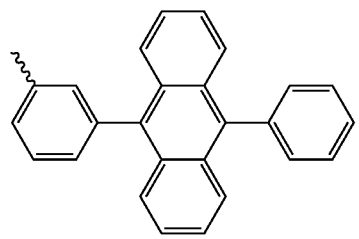 |
| 1-66 | 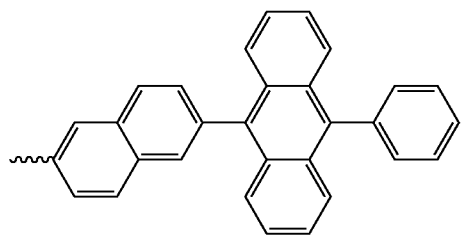 |
| 1-67 | 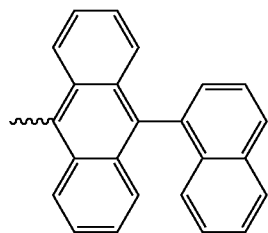 |
| 1-68 | 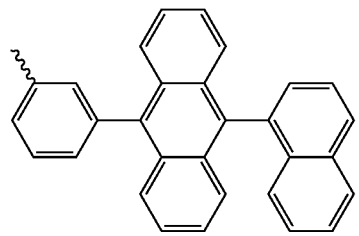 |
| 1-69 | 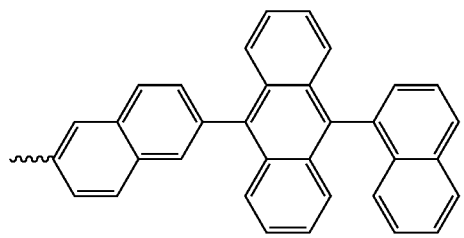 |

TABLE 1-continued
Groups as R2 in the compounds of formula (1) having hydrogen as R1
| No. | R2 |
|---|---|
| 1-70 | 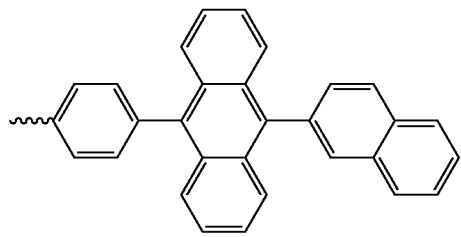 |
| 1-71 | 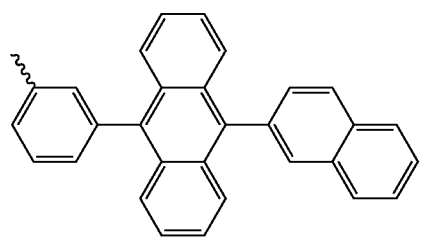 |
| 1-72 | 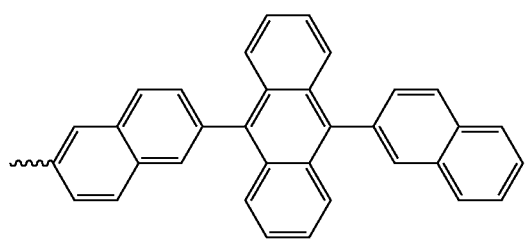 |
| 1-73 | 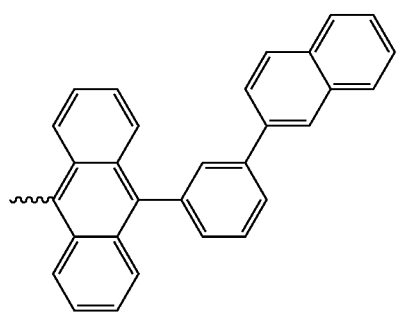 |
| 1-74 | 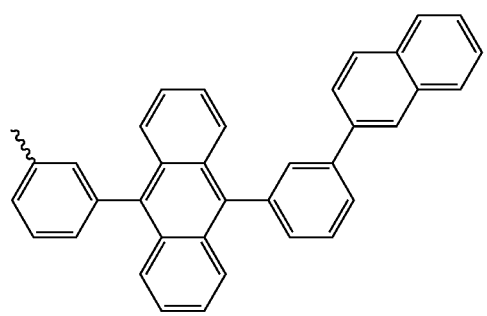 |

TABLE 1-continued
Groups as R2 in the compounds of formula (1) having hydrogen as R1
| No. | R2 |
| --- | --- |
1-75
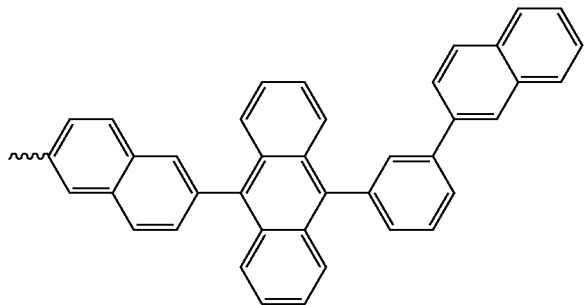
1-76
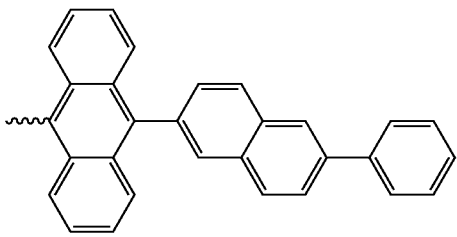
1-77
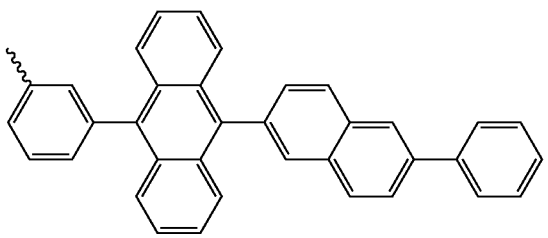
1-78
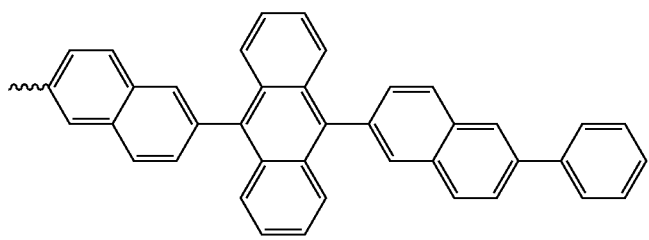
1-79
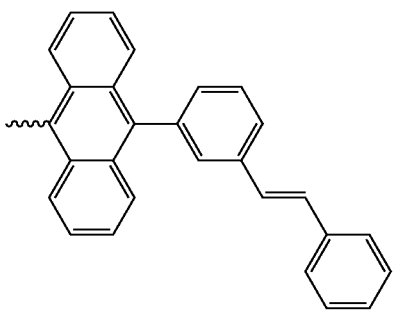

TABLE 1-continued
Groups as R2 in the compounds of formula (1) having hydrogen as R1
| No. | R2 |
|---|---|
| 1-80 | 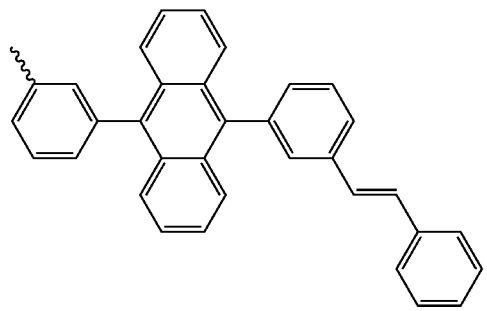 |
| 1-81 | 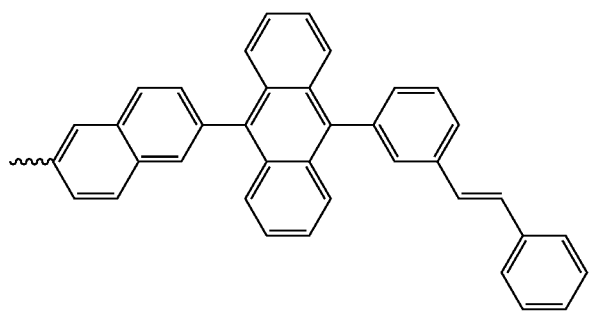 |
| 1-82 | 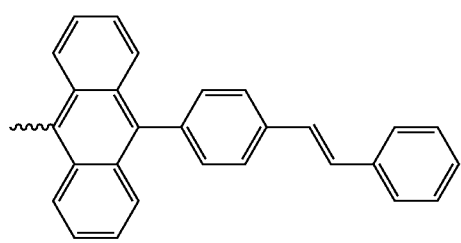 |
| 1-83 | 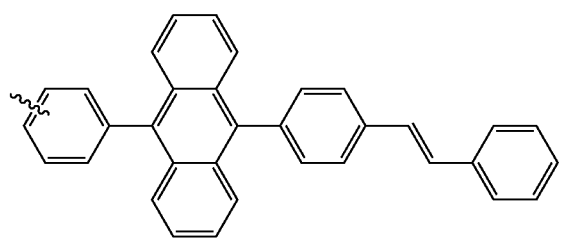 |
| 1-84 | 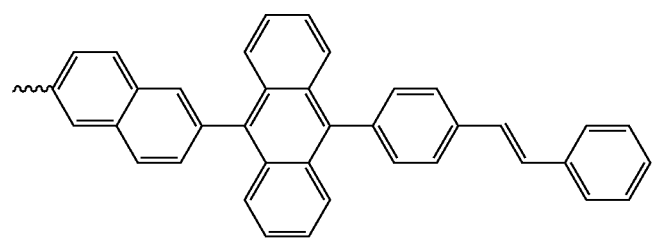 |

TABLE 1-continued
Groups as R2 in the compounds of formula (1) having hydrogen as R1
| No. | R2 |
|---|---|
| 1-85 | 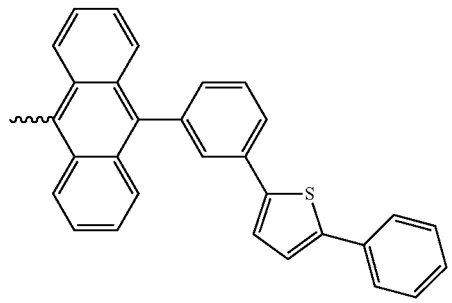 |
| 1-86 | 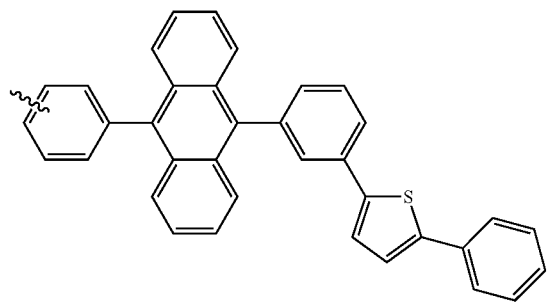 |
| 1-87 | 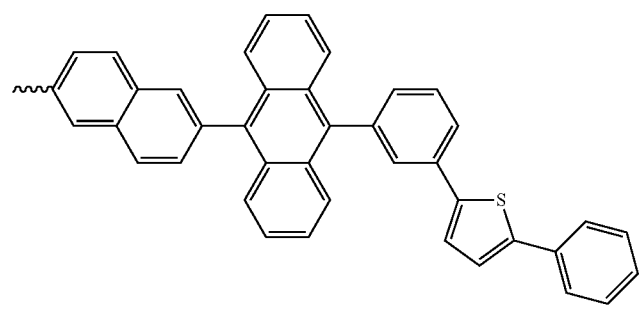 |
| 1-88 | 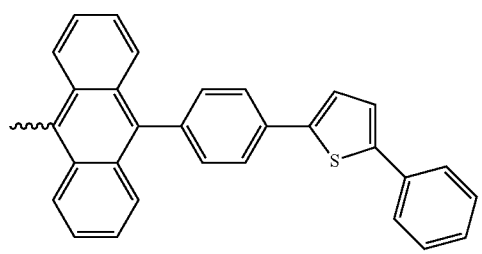 |
| 1-89 | 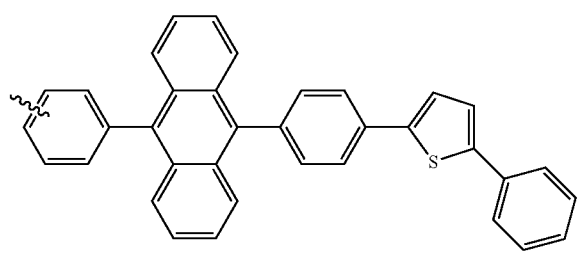 |

TABLE 1-continued
Groups as R2 in the compounds of formula (1) having hydrogen as R1
| No. | R2 |
|---|---|
| 1-90 | 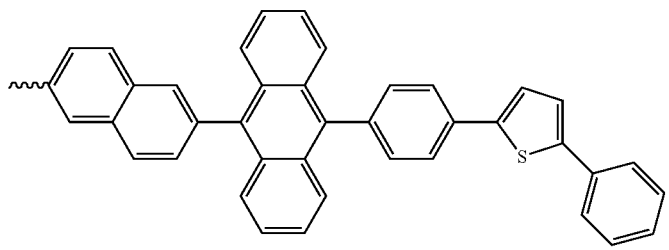 |
| 1-91 | 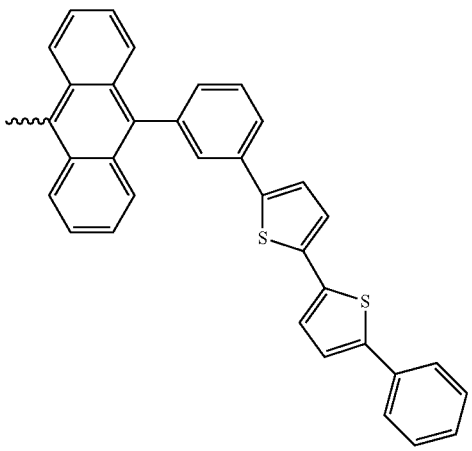 |
| 1-92 | 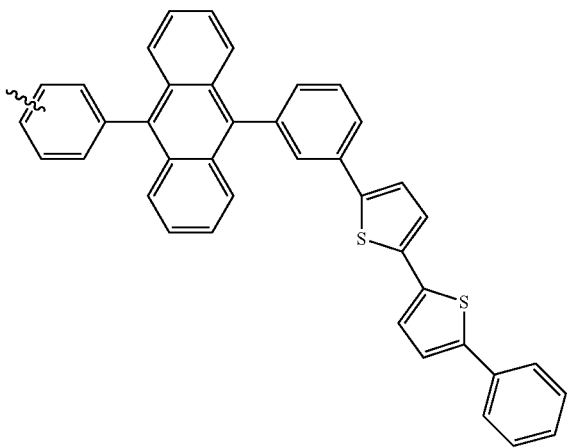 |

TABLE 1-continued
Groups as R2 in the compounds of formula (1) having hydrogen as R1
| No. | R2 |
|---|---|
| 1-93 | 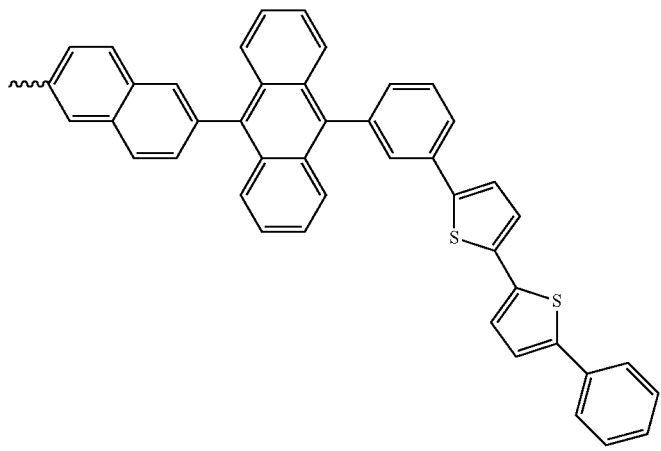 |
| 1-94 | 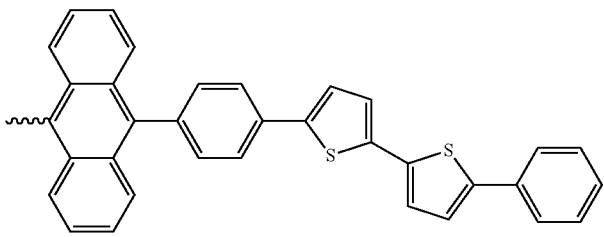 |
| 1-95 | 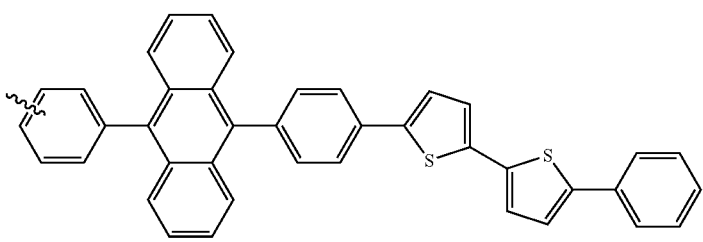 |
| 1-96 | 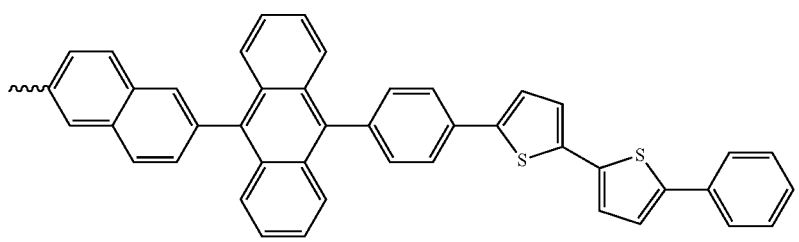 |

TABLE 1-continued
Groups as R2 in the compounds of formula (1) having hydrogen as R1
| No. | R2 |
|-----|----|
| 1-97 | 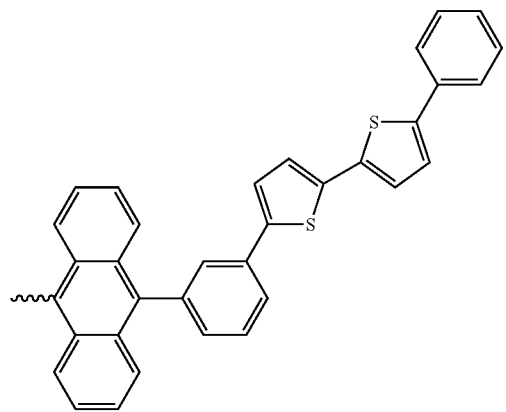 |
| 1-98 | 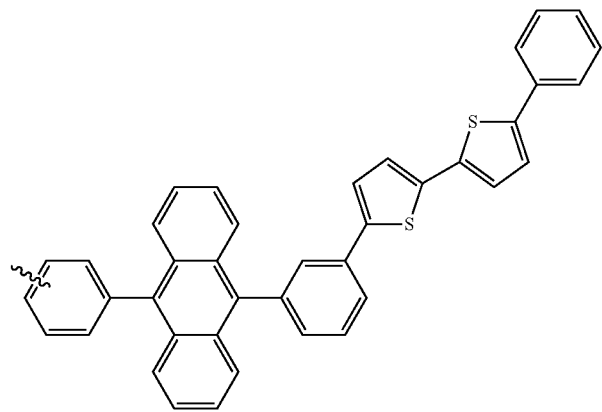 |
| 1-99 | 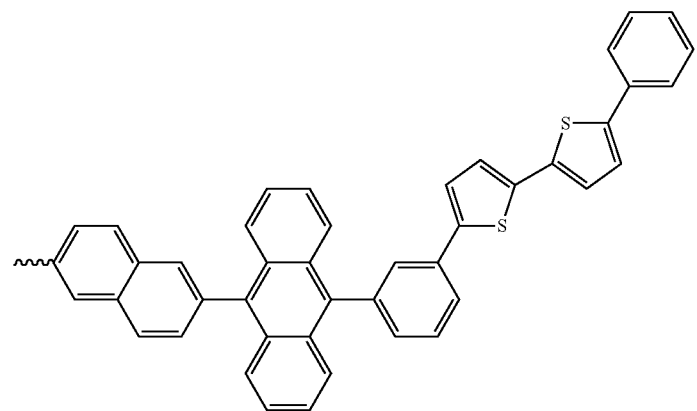 |
| 1-100 | 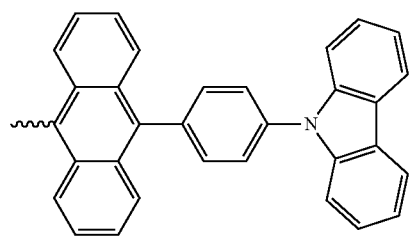 |

TABLE 1-continued
Groups as R2 in the compounds of formula (1) having hydrogen as R1
No.  R2
1-101
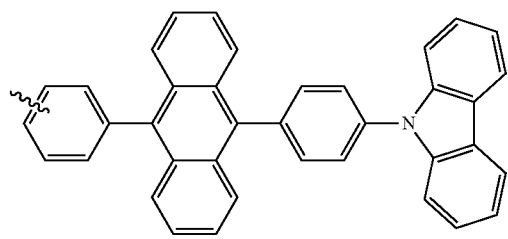
1-102
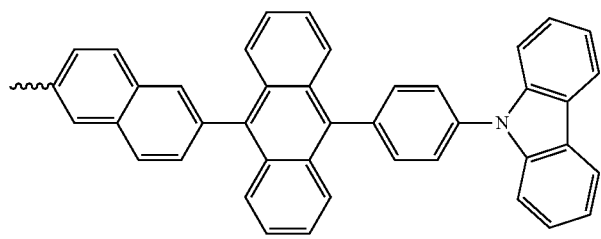
1-103
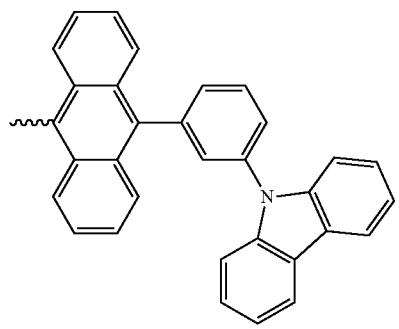
1-104
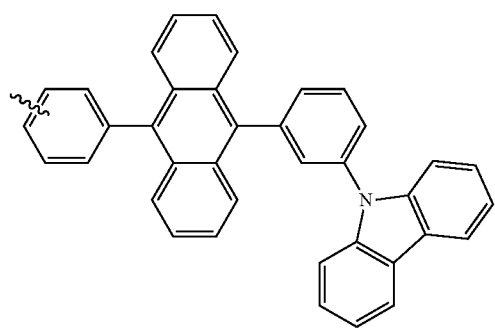
1-105
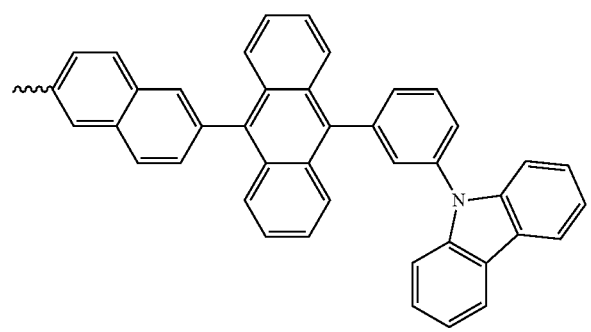

TABLE 1-continued
Groups as R2 in the compounds of formula (1) having hydrogen as R1
No.　R2
1-106
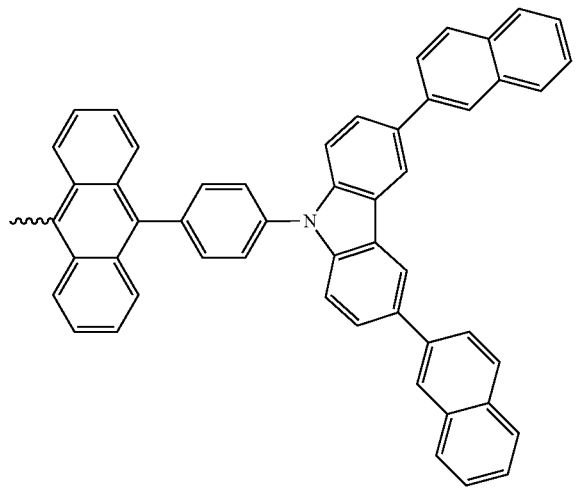
1-107
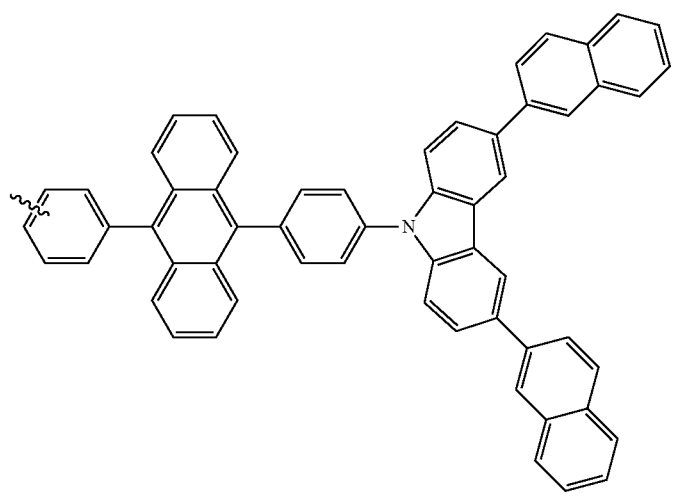
1-108
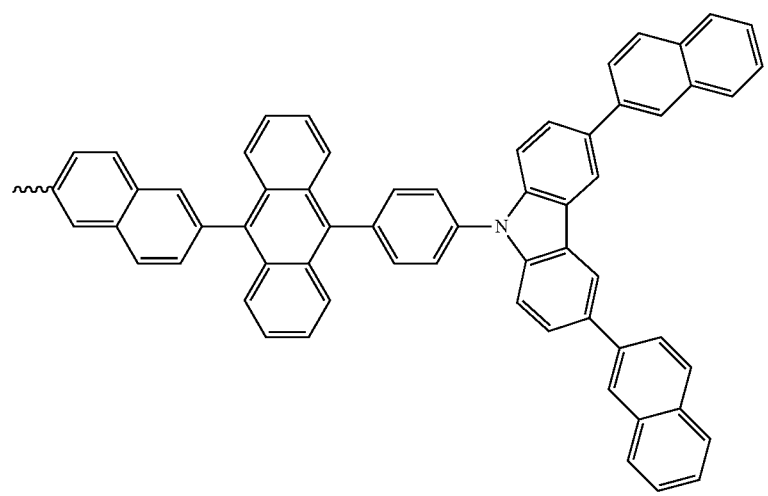

TABLE 1-continued
Groups as R2 in the compounds of formula (1) having hydrogen as R1
| No. | R2 |
|---|---|
| 1-109 | 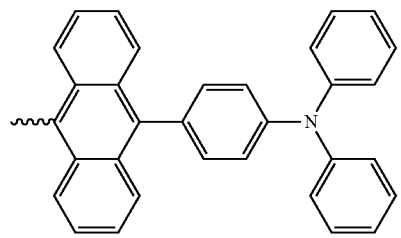 |
| 1-110 | 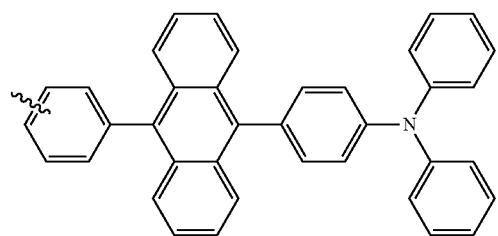 |
| 1-111 | 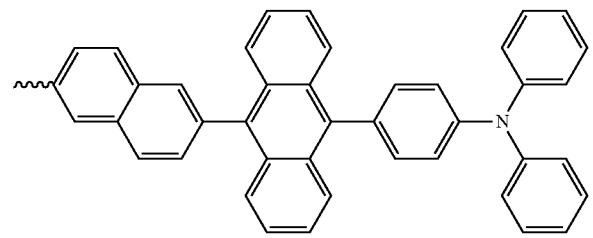 |
| 1-112 | 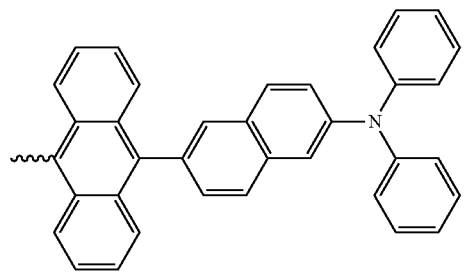 |
| 1-113 | 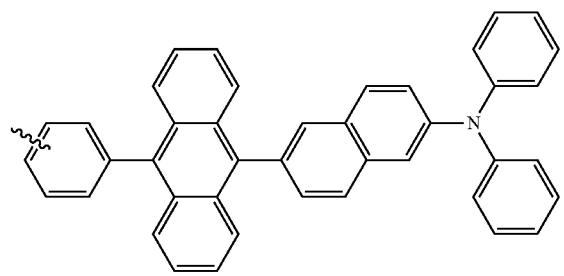 |
| 1-114 | 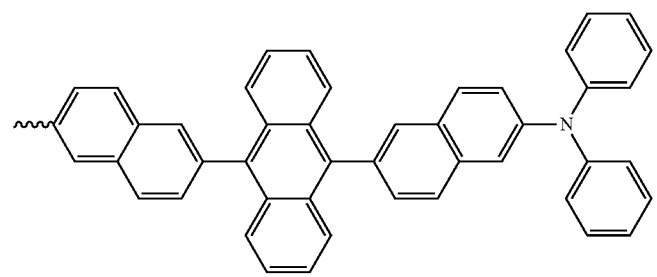 |

TABLE 1-continued
Groups as R2 in the compounds of formula (1) having hydrogen as R1
No. R2
1-115
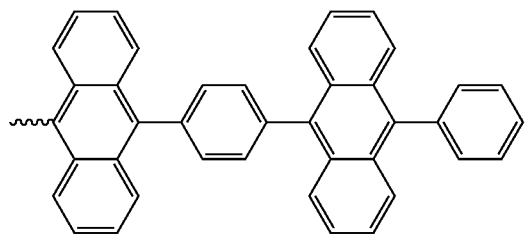
1-116
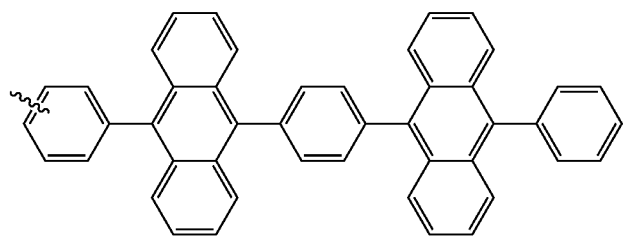
1-117
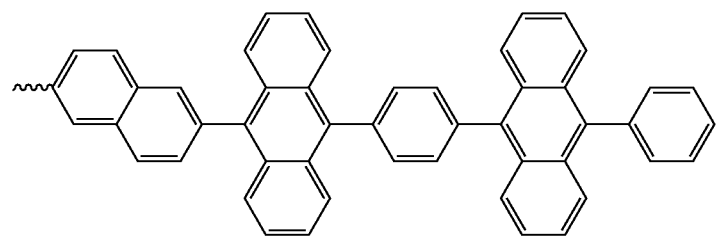
1-118
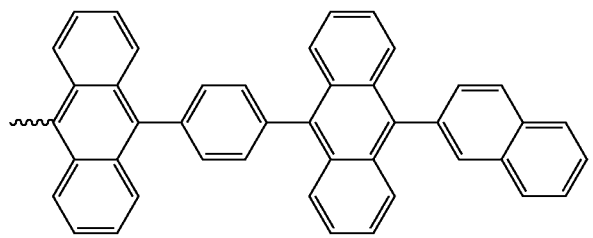
1-119
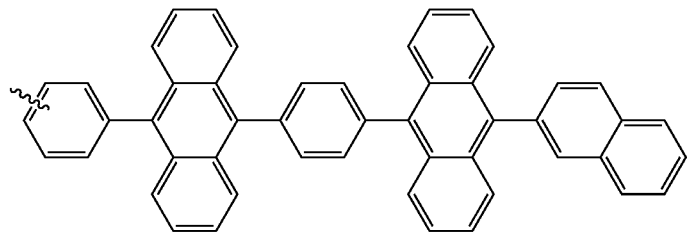
1-120
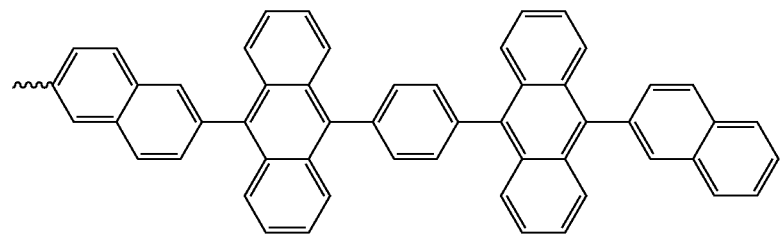

TABLE 1-continued
Groups as R2 in the compounds of formula (1) having hydrogen as R1
No. R2
1-121
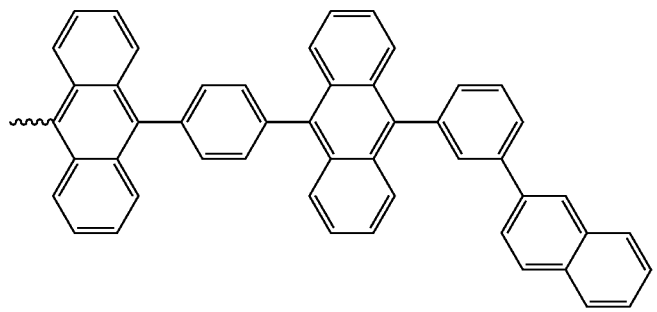
1-122
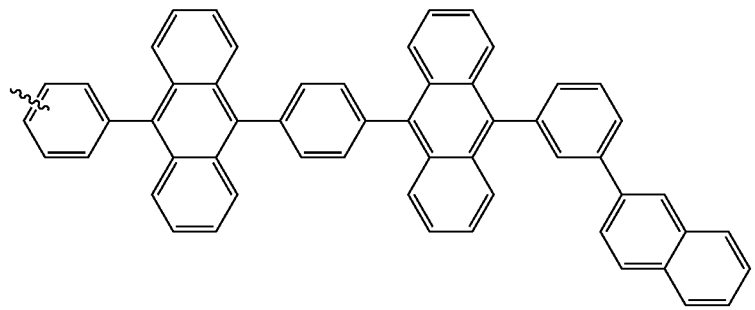
1-123
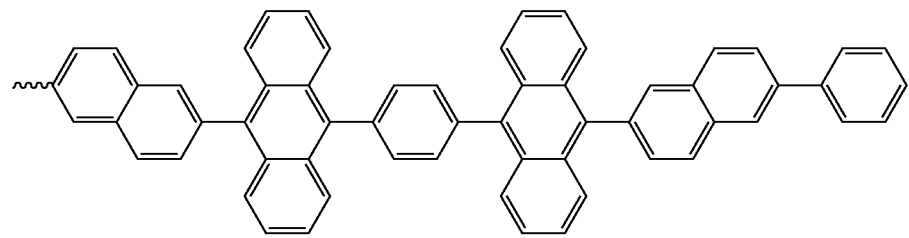
1-124
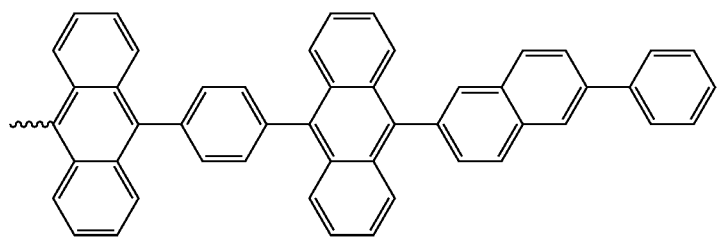
1-125
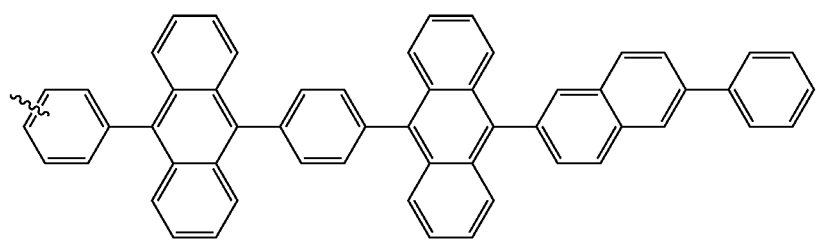

TABLE 1-continued
Groups as R2 in the compounds of formula (1) having hydrogen as R1
| No. | R2 |
|---|---|
| 1-126 | 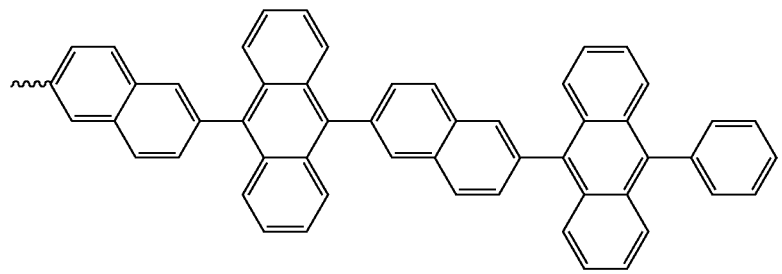 |
| 1-127 | 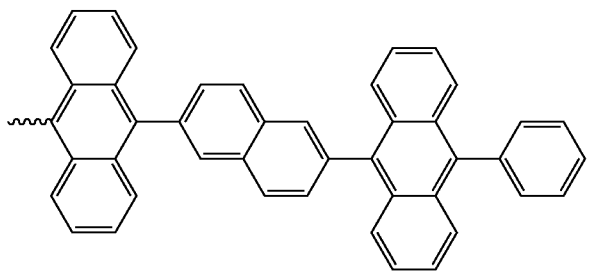 |
| 1-128 | 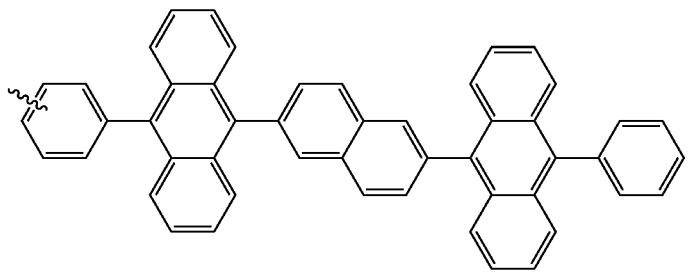 |
| 1-129 | 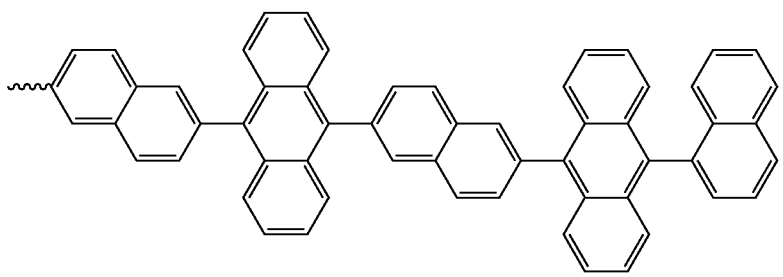 |
| 1-130 | 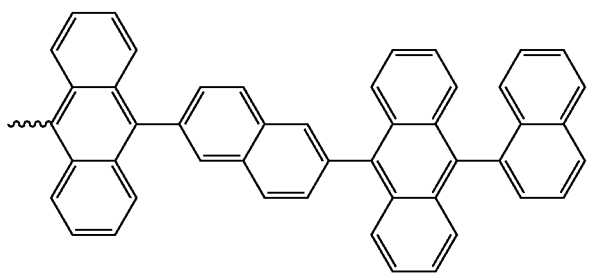 |

TABLE 1-continued
Groups as R2 in the compounds of formula (1) having hydrogen as R1
| No. | R2 |
|---|---|
| 1-131 | 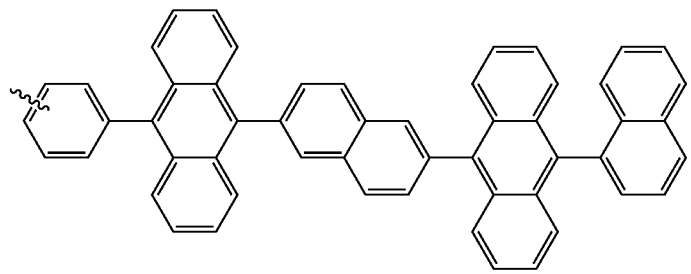 |
| 1-132 | 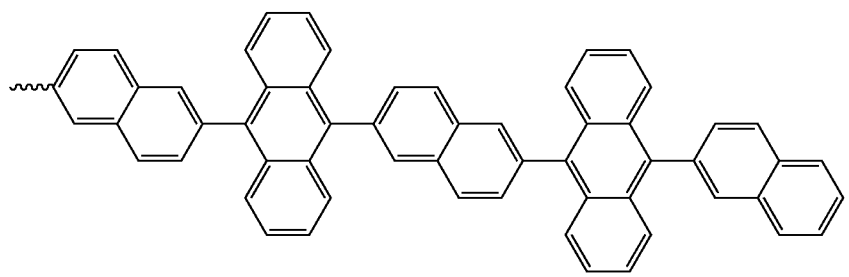 |
| 1-133 | 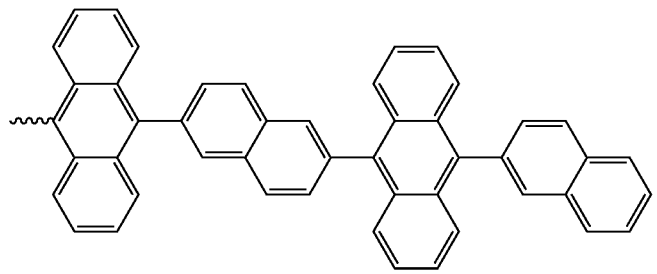 |
| 1-134 | 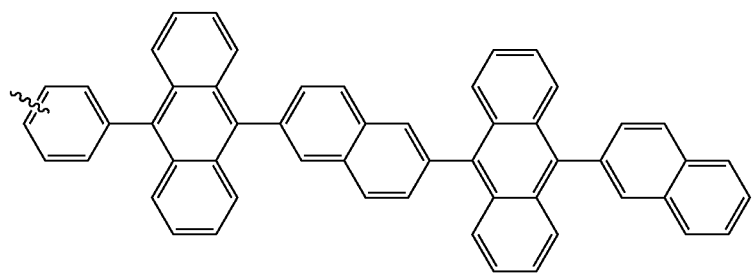 |
| 1-135 | 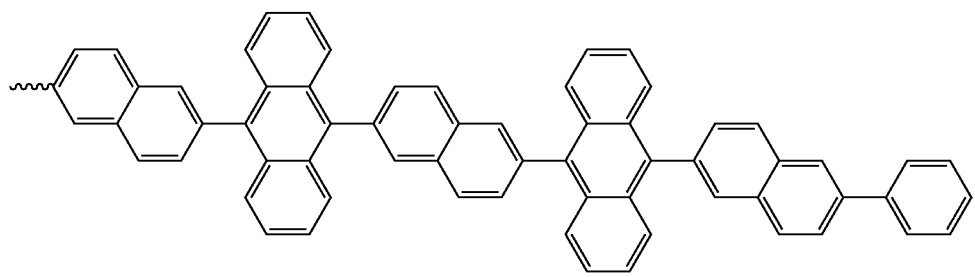 |

TABLE 1-continued
Groups as R2 in the compounds of formula (1) having hydrogen as R1
| No. | R2 |
|---|---|
| 1-136 | 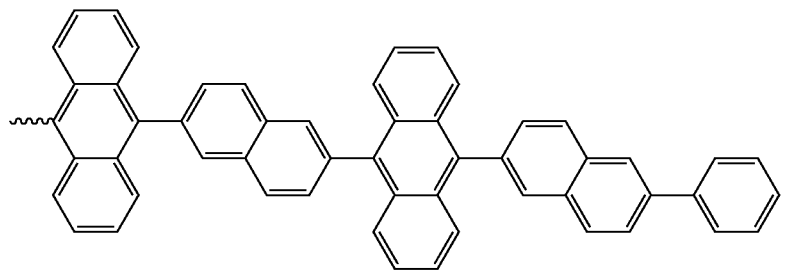 |
| 1-137 | 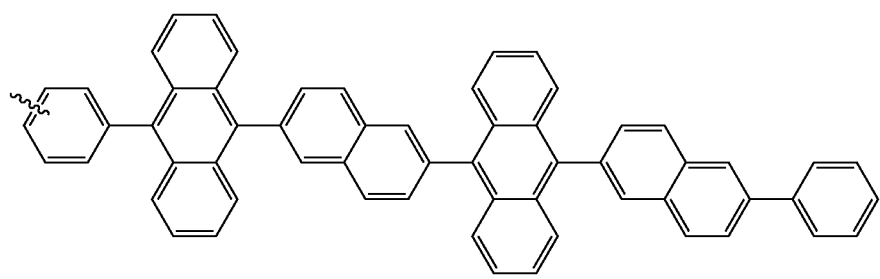 |
| 1-138 | 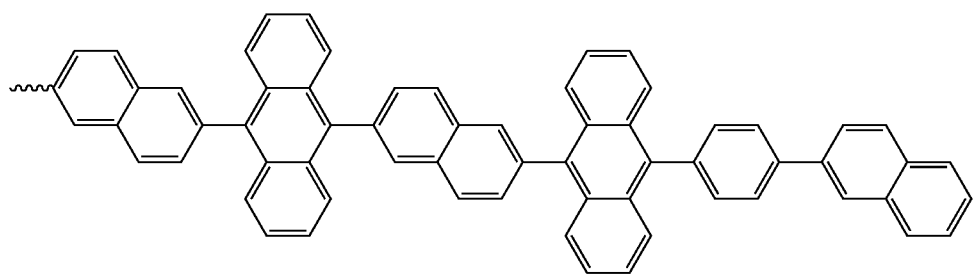 |
| 1-139 | 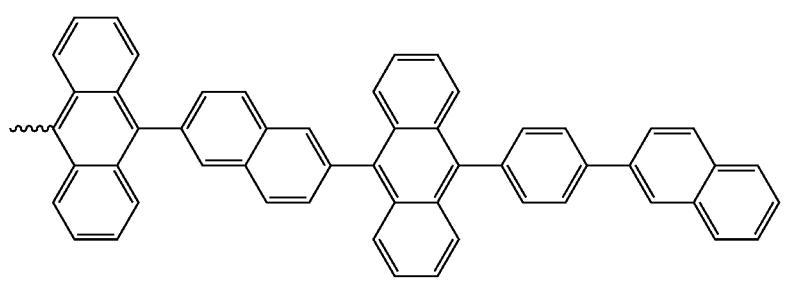 |
| 1-140 | 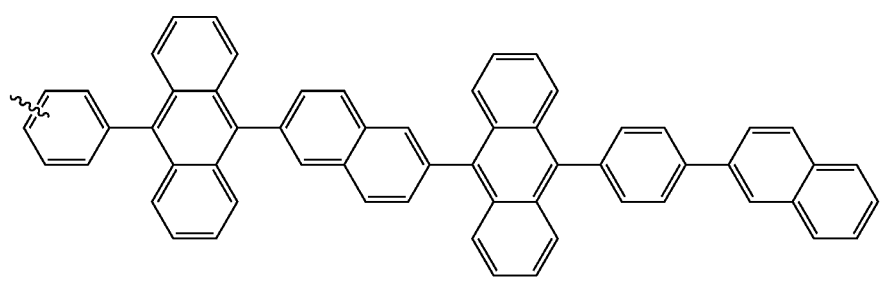 |

TABLE 1-continued
Groups as R2 in the compounds of formula (1) having hydrogen as R1
| No. | R2 |
|---|---|
| 1-141 | 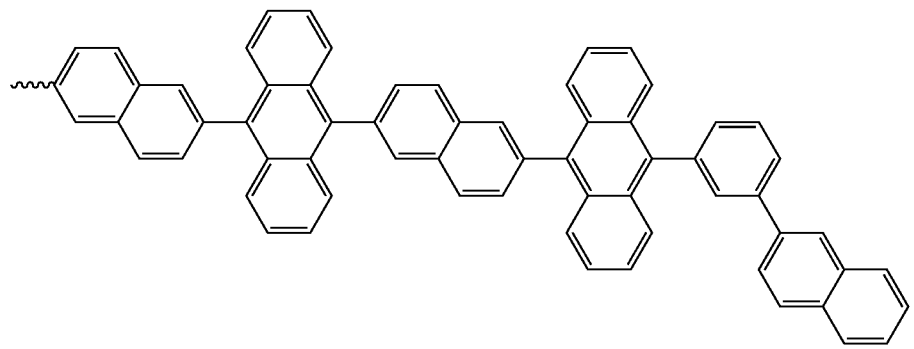 |
| 1-142 | 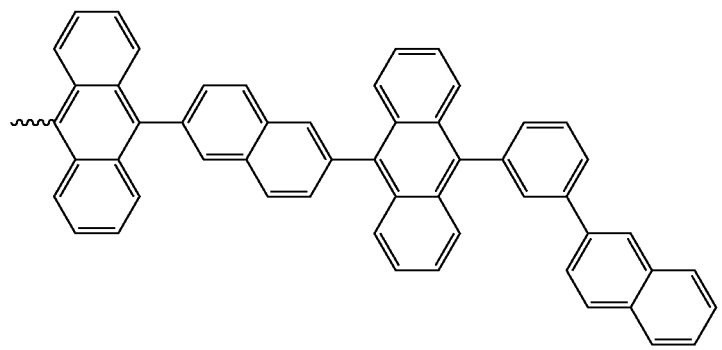 |
| 1-143 | 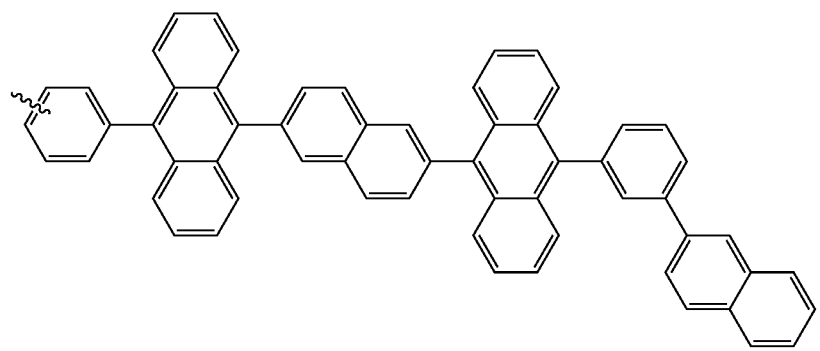 |
| 1-144 | 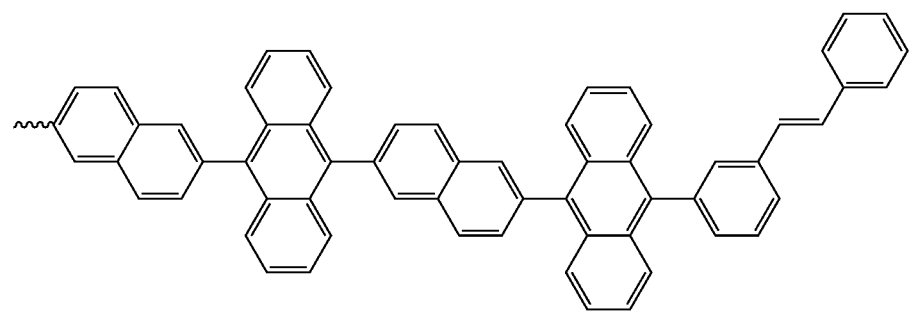 |

TABLE 1-continued
Groups as R2 in the compounds of formula (1) having hydrogen as R1
| No. | R2 |
|---|---|
| 1-145 | 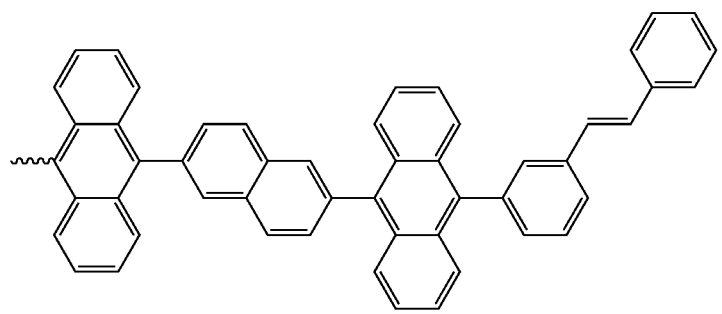 |
| 1-146 | 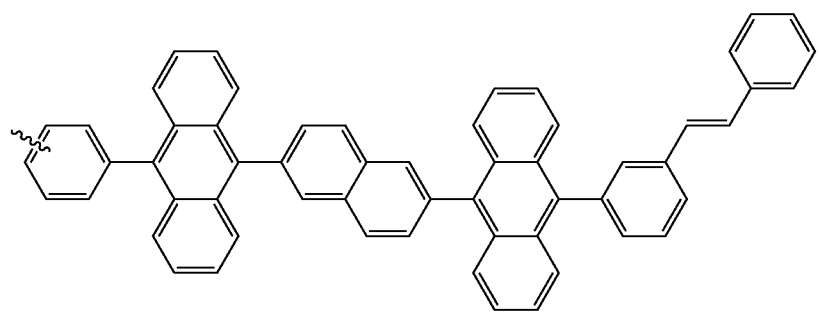 |
| 1-147 | 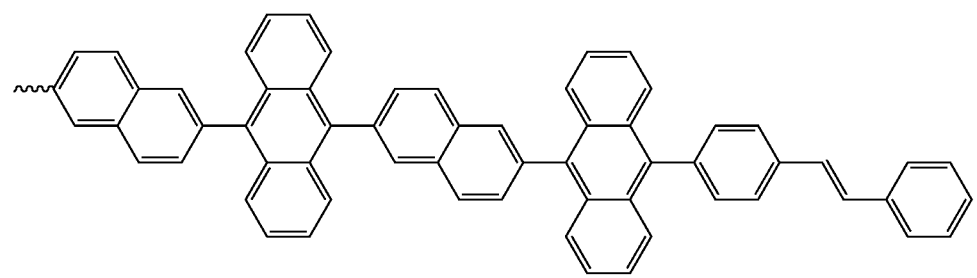 |
| 1-148 | 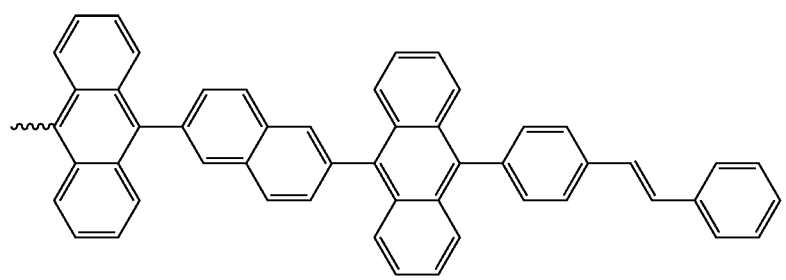 |
| 1-149 | 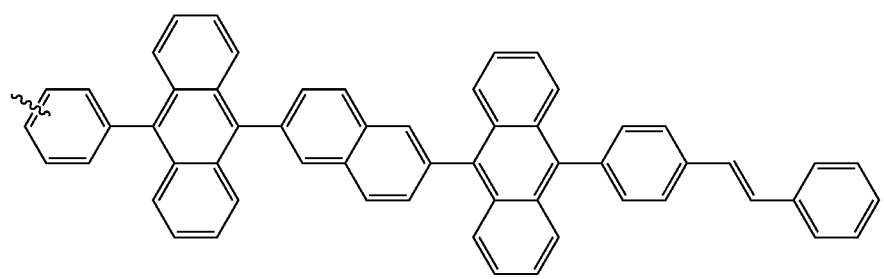 |

TABLE 1-continued
Groups as R2 in the compounds of formula (1) having hydrogen as R1
| No. | R2 |
|---|---|
| 1-150 | 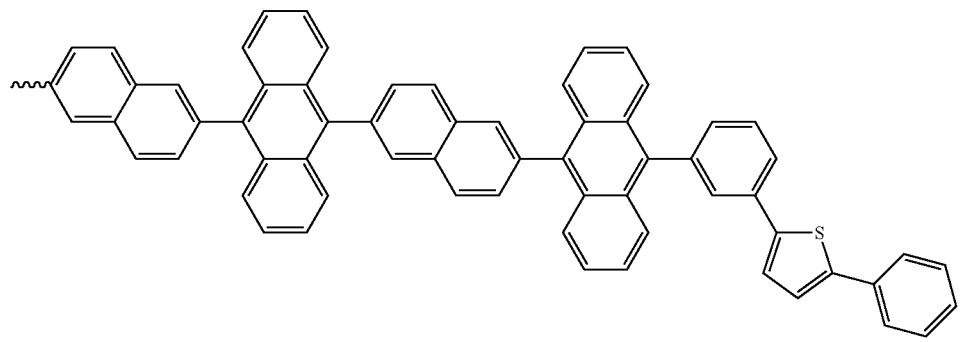 |
| 1-151 | 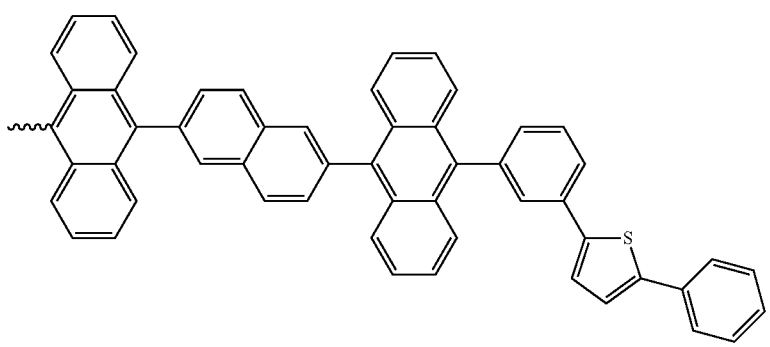 |
| 1-152 | 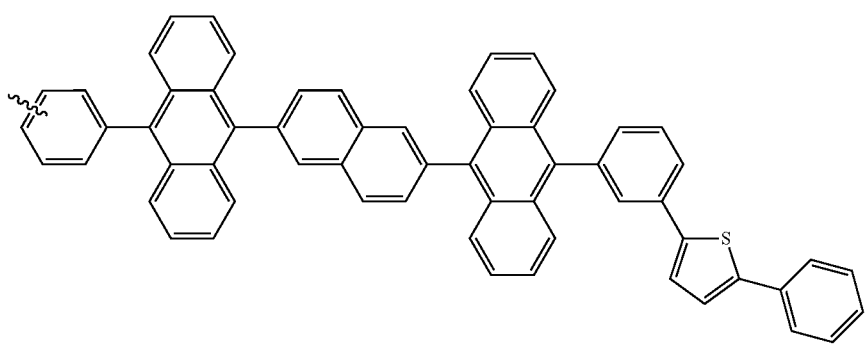 |
| 1-153 | 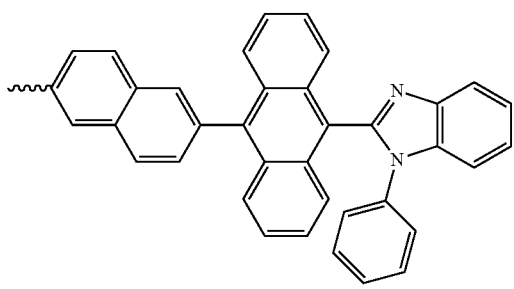 |

TABLE 1-continued
Groups as R2 in the compounds of formula (1) having hydrogen as R1
| No. | R2 |
|---|---|
| 1-154 | 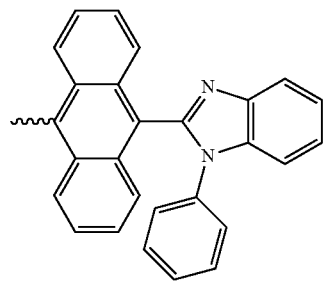 |
| 1-155 | 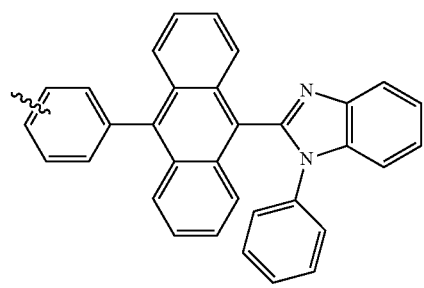 |
| 1-156 | 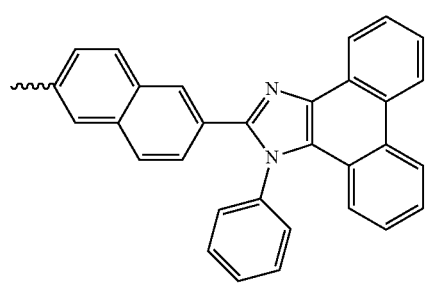 |
| 1-157 | 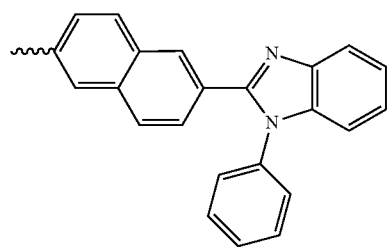 |
| 1-158 | 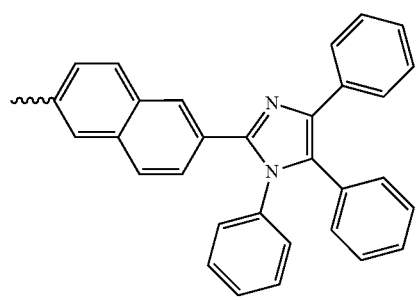 |

TABLE 1-continued
Groups as R2 in the compounds of formula (1) having hydrogen as R1
| No. | R2 |
|---|---|
| 1-159 | 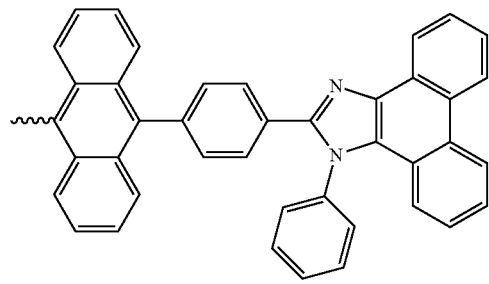 |
| 1-160 | 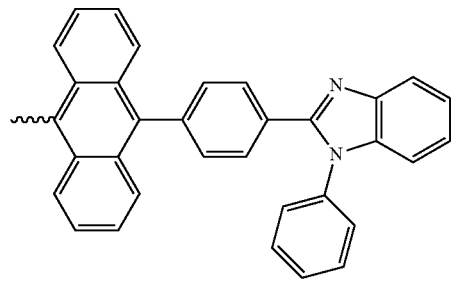 |
| 1-161 | 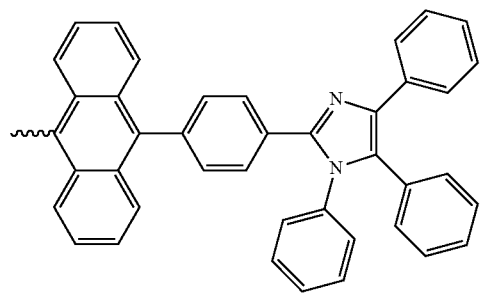 |
| 1-162 | 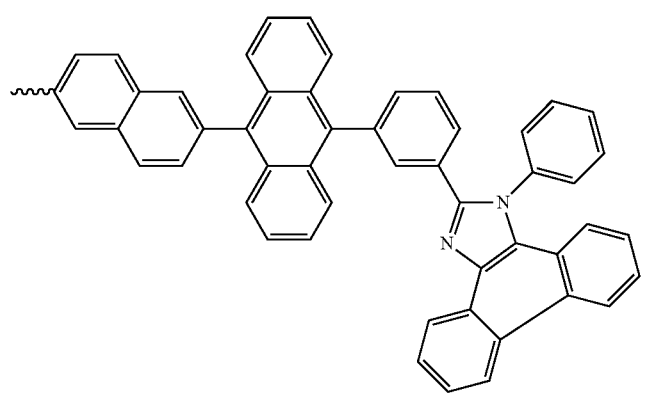 |
| 1-163 | 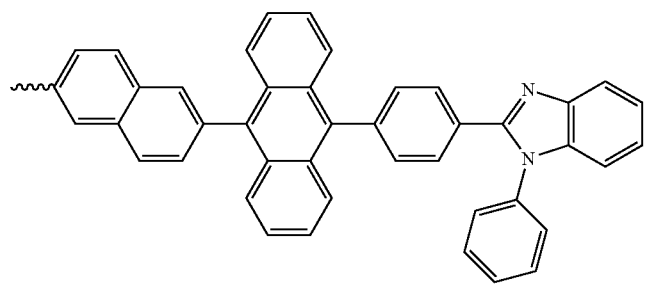 |

TABLE 1-continued
Groups as R2 in the compounds of formula (1) having hydrogen as R1
| No. | R2 |
|---|---|
| 1-164 | 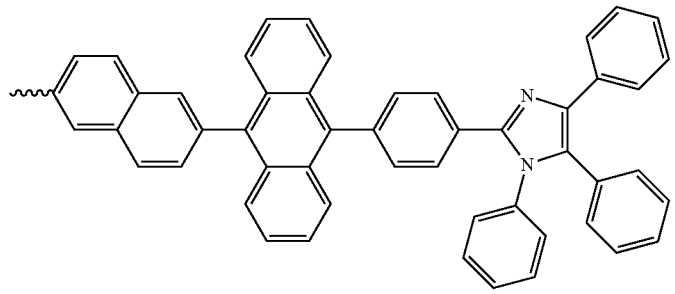 |
| 1-165 | 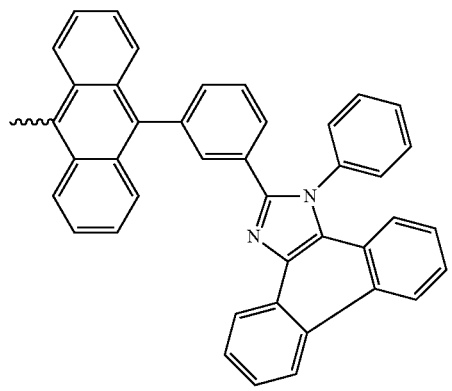 |
| 1-166 | 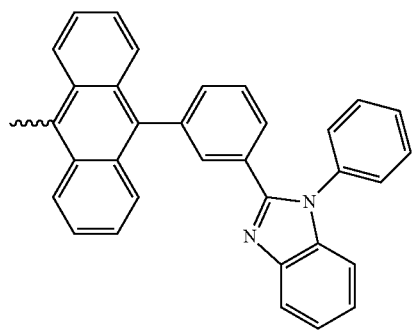 |
| 1-167 | 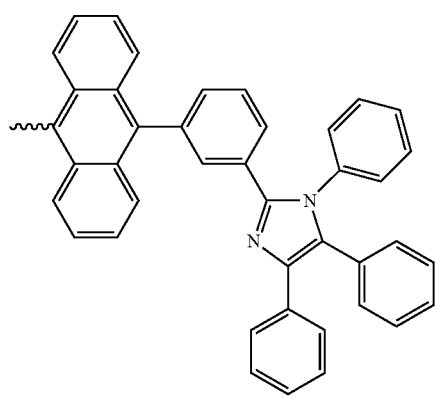 |

TABLE 1-continued
Groups as R2 in the compounds of formula (1) having hydrogen as R1
| No. | R2 |
|---|---|
| 1-168 | 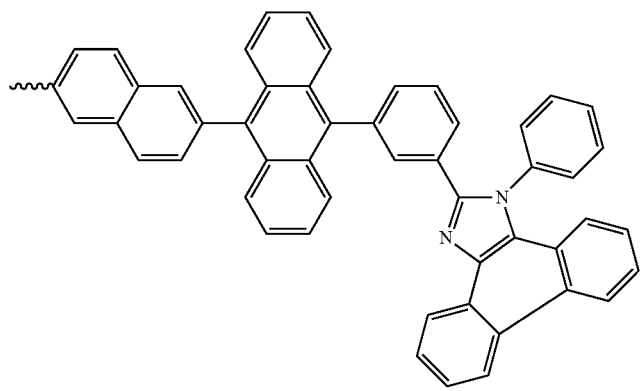 |
| 1-169 | 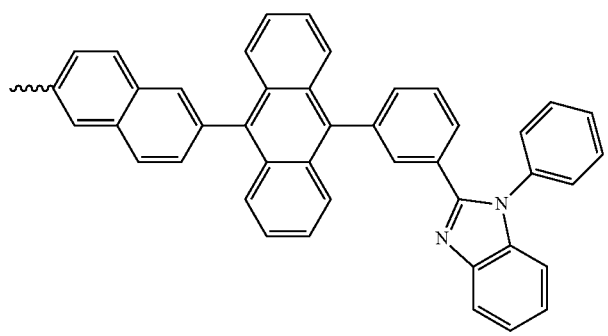 |
| 1-170 | 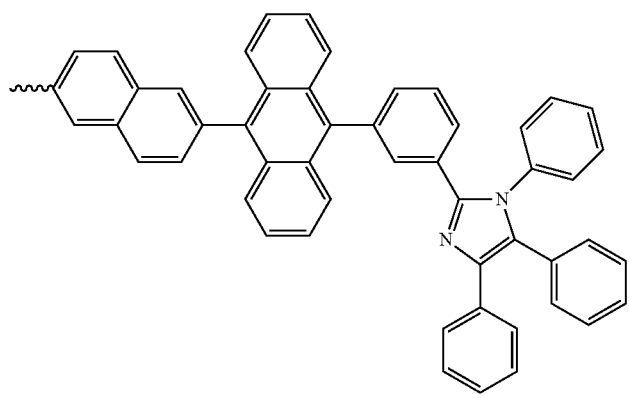 |
| 1-171 | 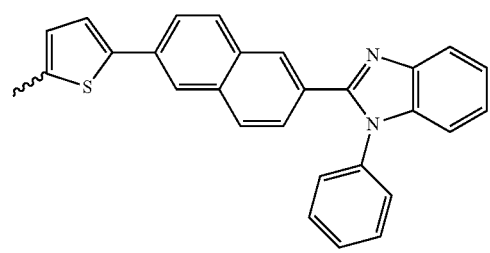 |

TABLE 1-continued
Groups as R2 in the compounds of formula (1) having hydrogen as R1
| No. | R2 |
|---|---|
| 1-172 | 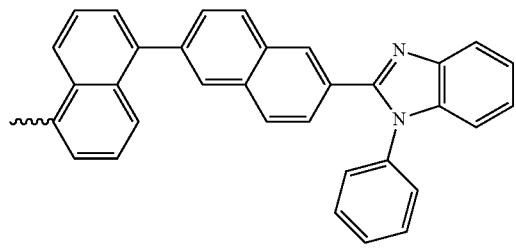 |
| 1-173 | 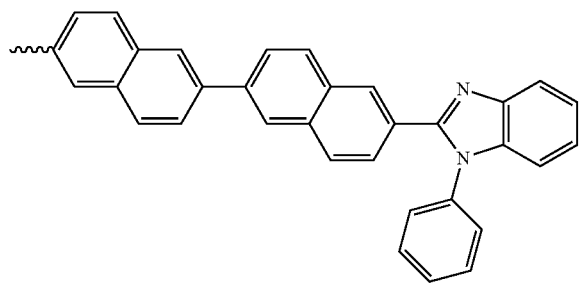 |
| 1-174 | 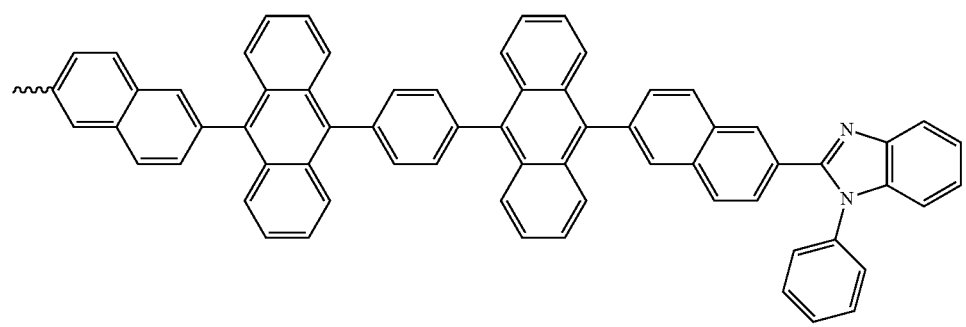 |
| 1-175 | 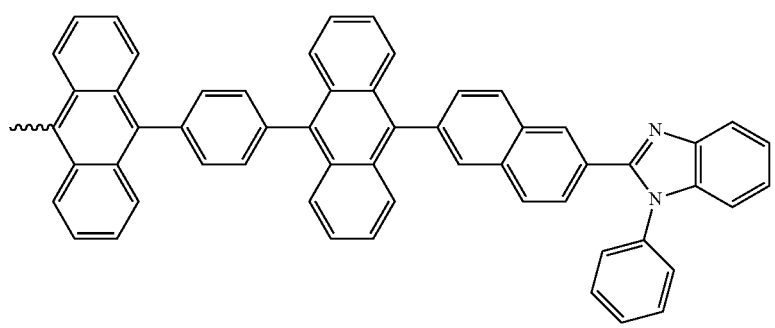 |
| 1-176 | 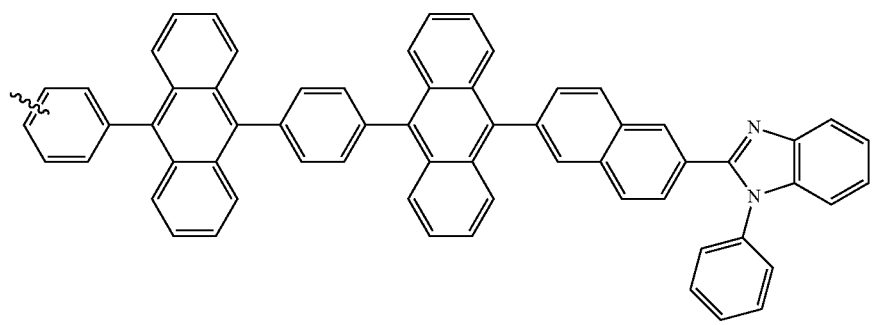 |

TABLE 1-continued
Groups as R2 in the compounds of formula (1) having hydrogen as R1
| No. | R2 |
|---|---|
| 1-177 | 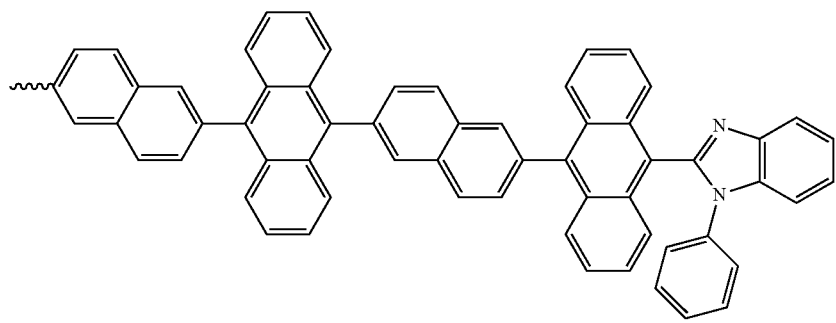 |
| 1-178 | 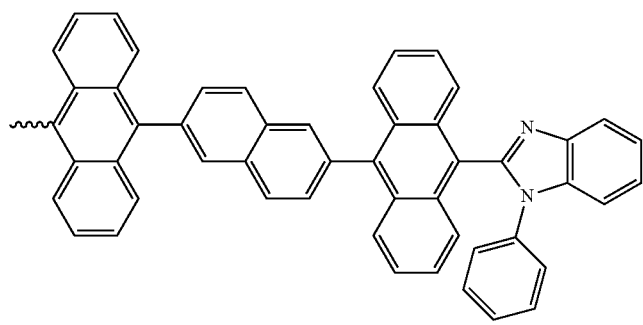 |
| 1-179 | 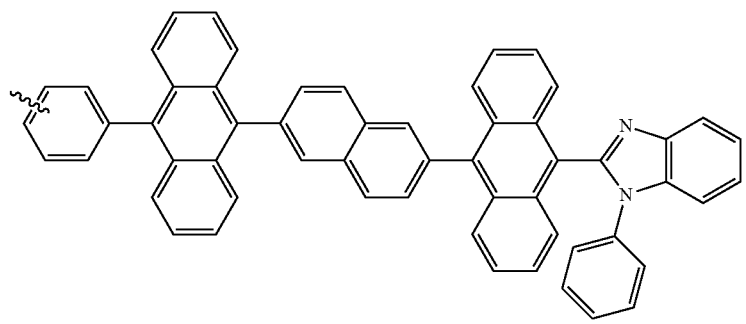 |
| 1-180 | 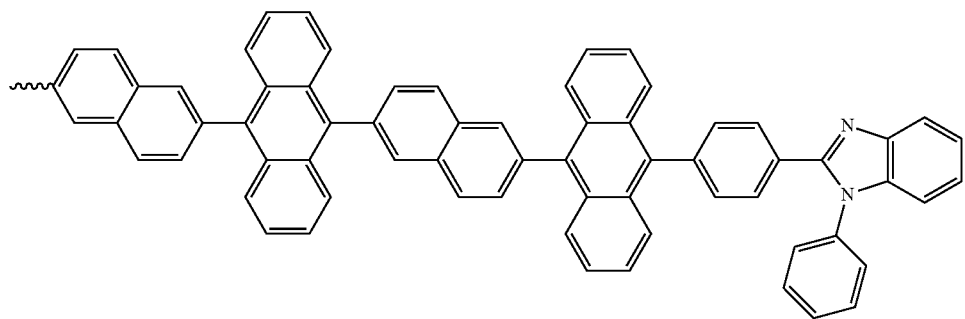 |

TABLE 1-continued
Groups as R2 in the compounds of formula (1) having hydrogen as R1
No.  R2
1-181
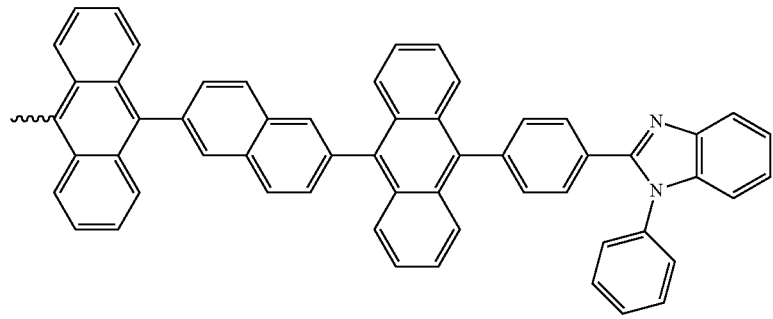
1-182
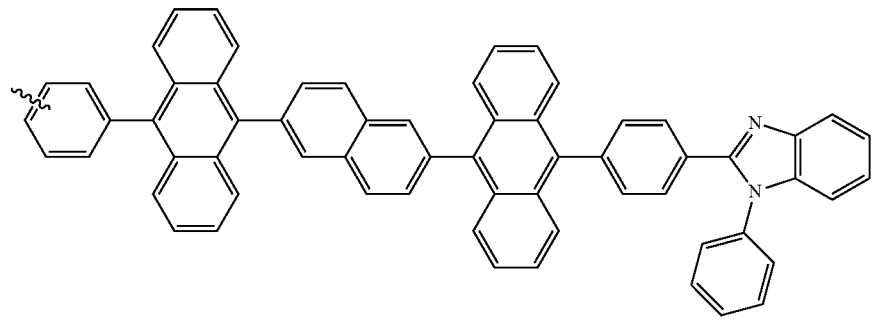
1-183
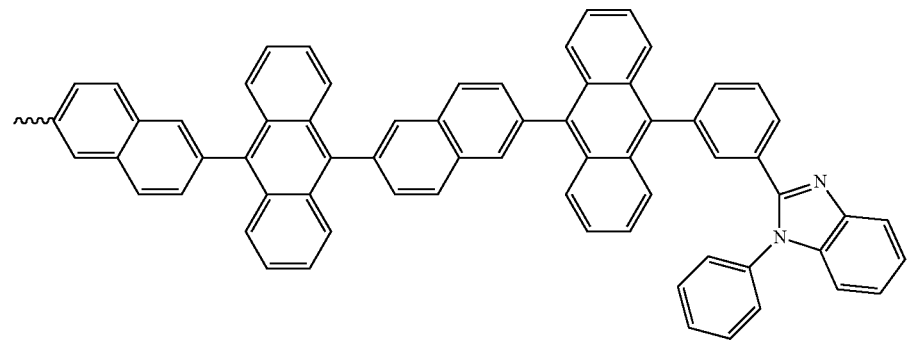
1-184
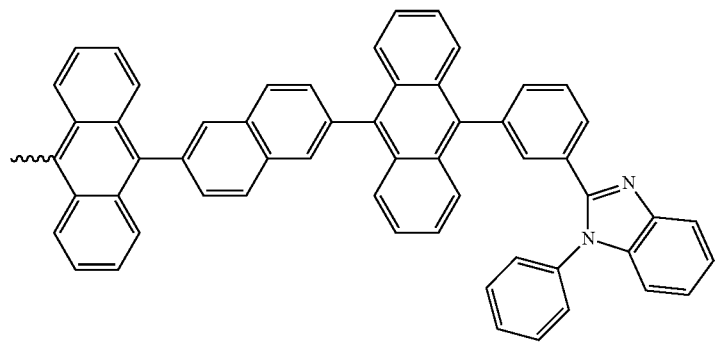

TABLE 1-continued
Groups as R2 in the compounds of formula (1) having hydrogen as R1
No.   R2
1-185
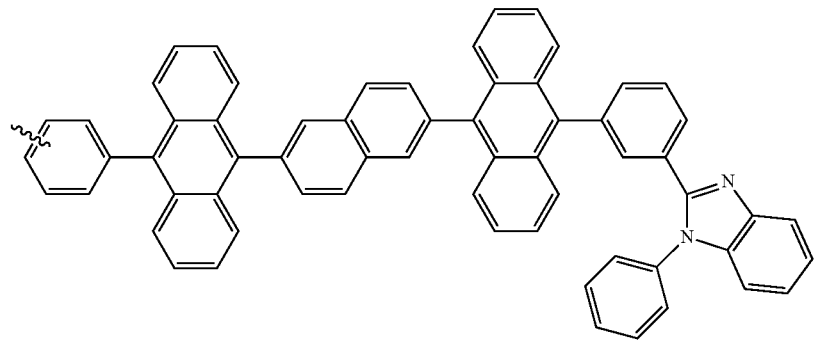
1-186
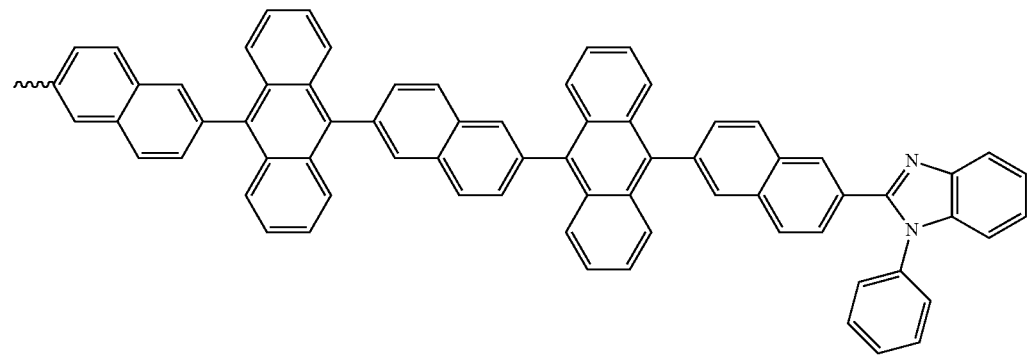
1-187
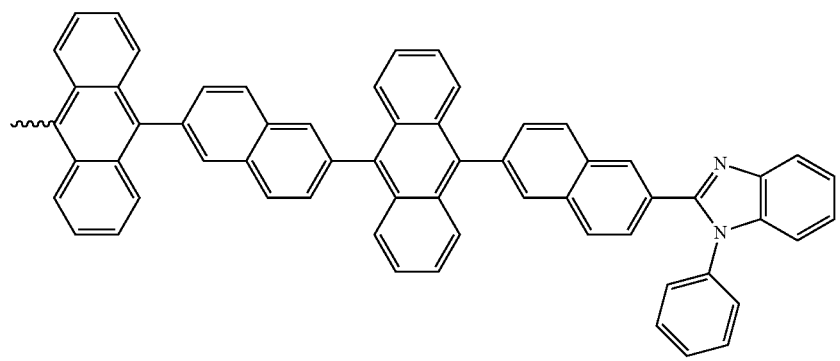
1-188
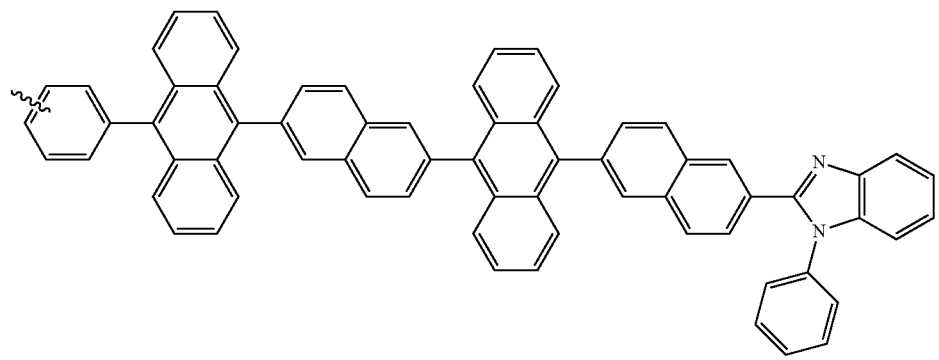

TABLE 1-continued
Groups as R2 in the compounds of formula (1) having hydrogen as R1
| No. | R2 |
|---|---|
| 1-189 | 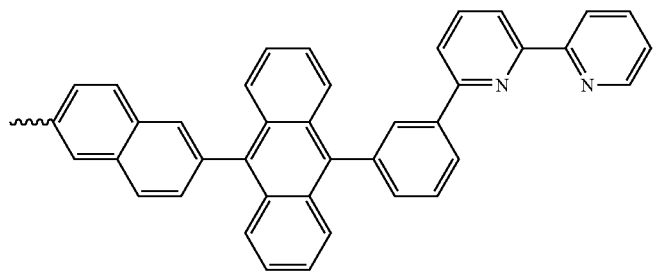 |
| 1-190 | 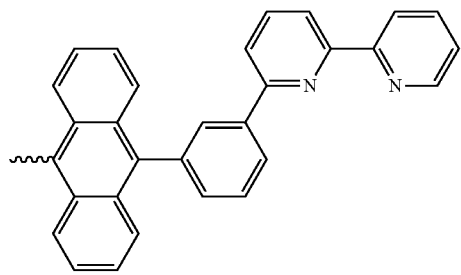 |
| 1-191 | 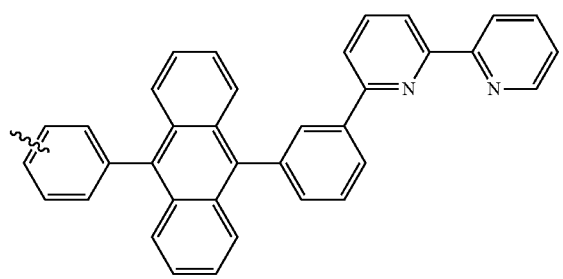 |
| 1-192 | 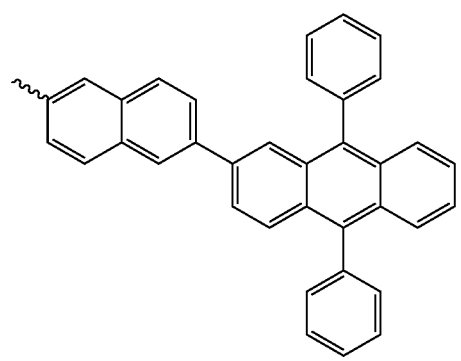 |
| 1-193 | 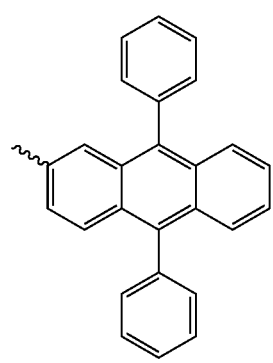 |

TABLE 1-continued
Groups as R2 in the compounds of formula (1) having hydrogen as R1
| No. | R2 |
|---|---|
| 1-194 | 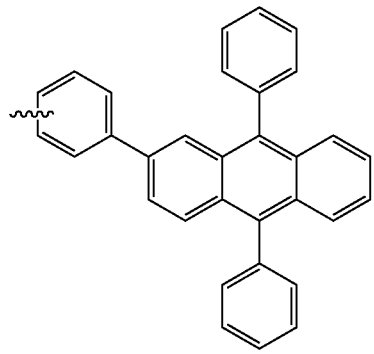 |
| 1-195 | 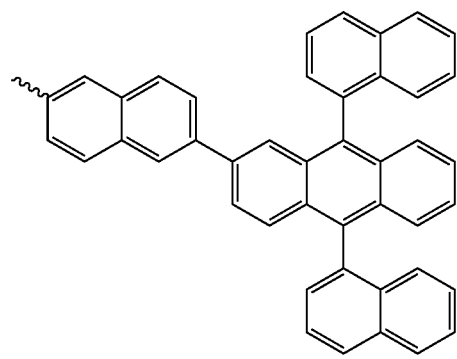 |
| 1-196 | 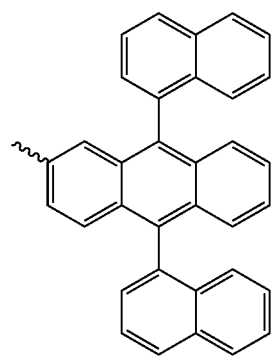 |
| 1-197 | 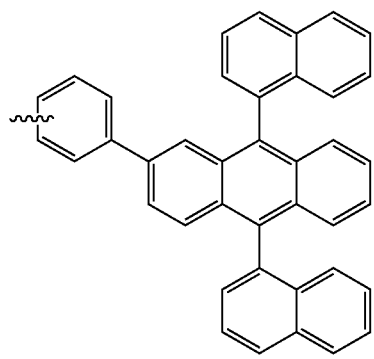 |

TABLE 1-continued
Groups as R2 in the compounds of formula (1) having hydrogen as R1
| No. | R2 |
|---|---|
1-198
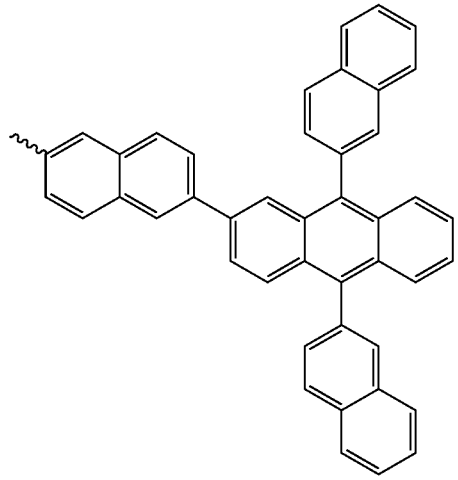
1-199
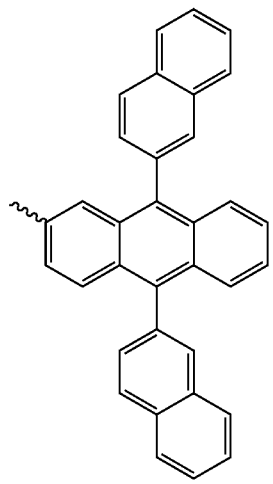
1-200
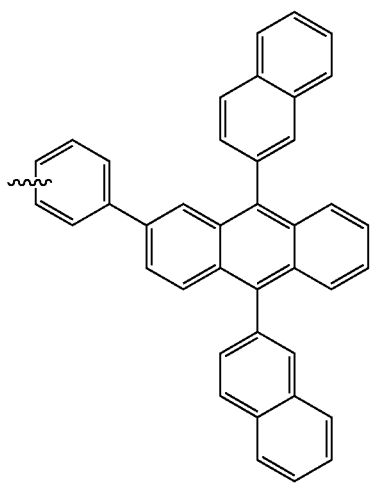

TABLE 1-continued
Groups as R2 in the compounds of formula (1) having hydrogen as R1
| No. | R2 |
|---|---|
1-201
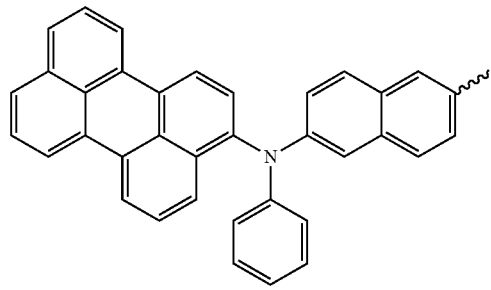
1-202
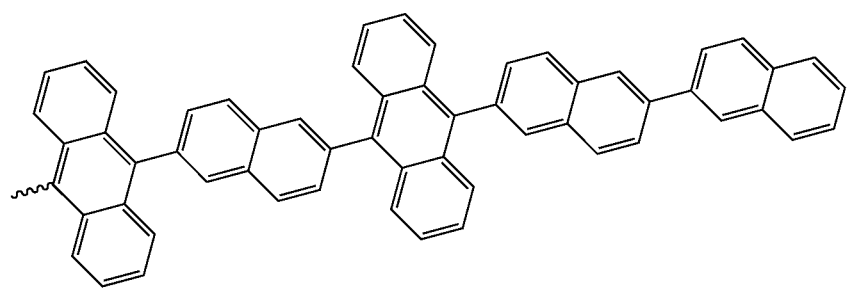
1-203
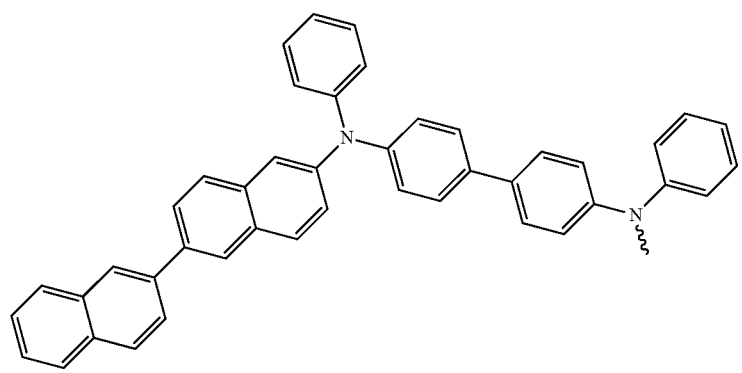
1-204
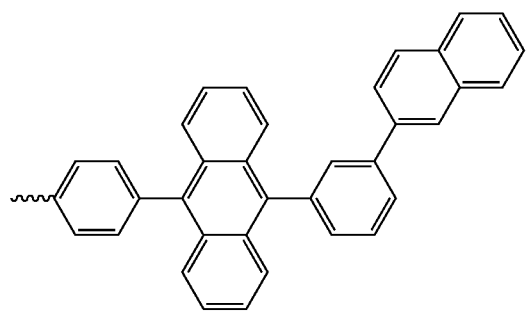
1-205
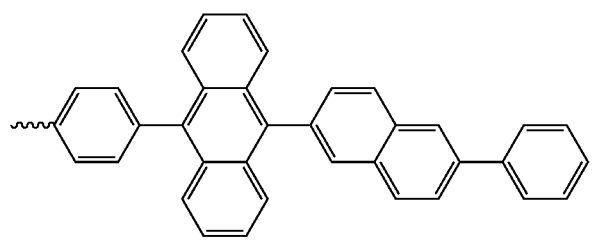

TABLE 1-continued
Groups as R2 in the compounds of formula (1) having hydrogen as R1
| No. | R2 |
|---|---|
| 1-206 | 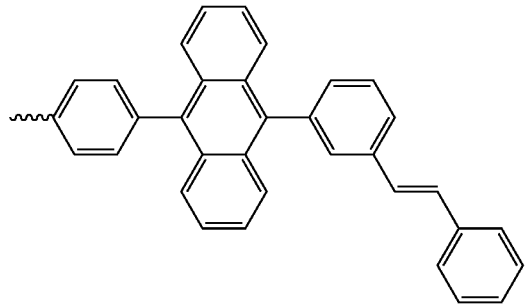 |
| 1-207 | 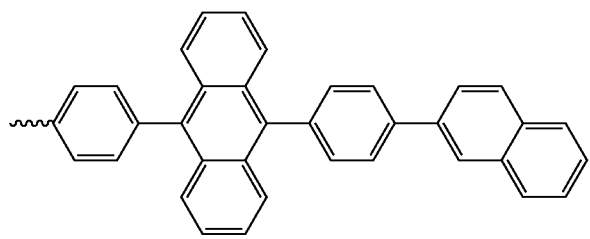 |
| 1-208 | 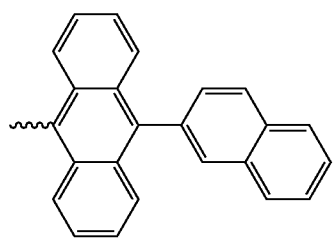 |
| 1-209 | 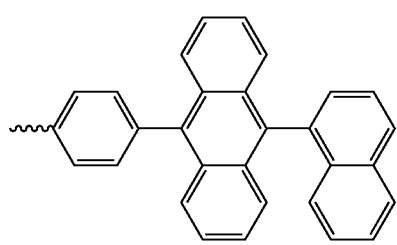 |
| 1-210 | 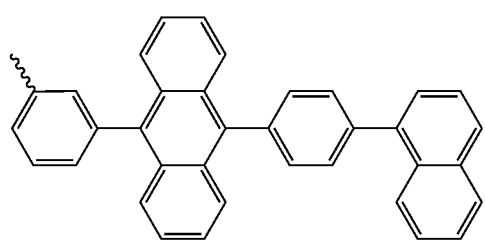 |
| 1-211 | 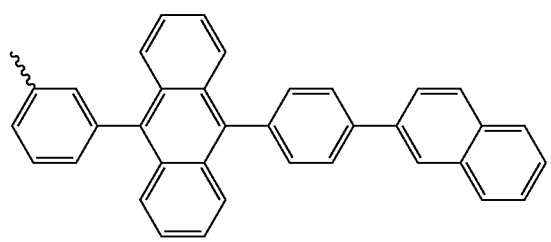 |

TABLE 1-continued
Groups as R2 in the compounds of formula (1) having hydrogen as R1
| No. | R2 |
|---|---|
| 1-212 | 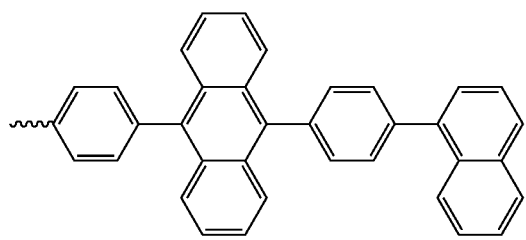 |
| 1-213 | 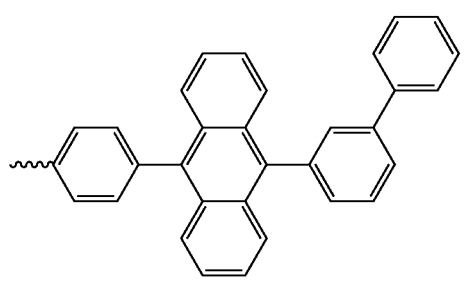 |
| 1-214 | 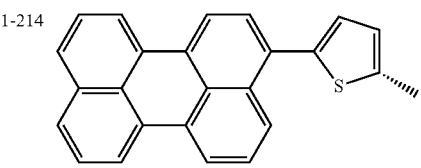 |
| 1-215 | 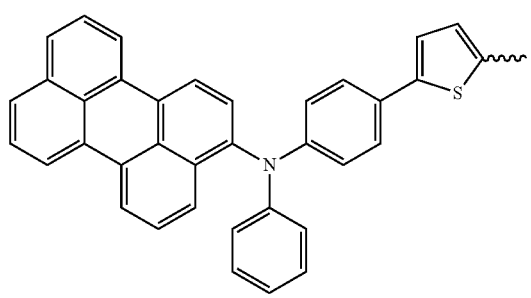 |
| 1-216 | 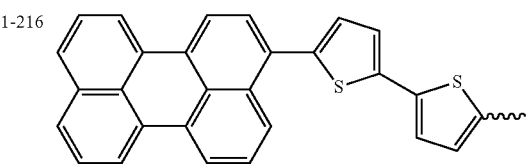 |
TABLE 2
Groups as R1 and R2 in the compounds of formula (1)
| No. | R1 | R2 |
|---|---|---|
| 2-1 | 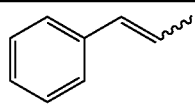 | 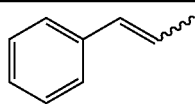 |

TABLE 2-continued

Groups as R1 and R2 in the compounds of formula (1)

| No. | R1 | R2 |
| --- | --- | --- |
| 2-2 | styryl | naphthyl-CH=C(phenyl)₂ |
| 2-3 | naphthyl-CH=CH-phenyl | styryl |
| 2-4 | styryl | naphthyl-naphthyl-(1-phenyl-benzimidazol-2-yl) |
| 2-5 | styryl | naphthyl-(1-phenyl-benzimidazol-2-yl) |
| 2-6 | naphthyl-(1-phenyl-benzimidazol-2-yl) | naphthyl-(1-phenyl-benzimidazol-2-yl) |
| 2-7 | naphthyl-CH=C(phenyl)₂ | naphthyl-(1-phenyl-benzimidazol-2-yl) |

TABLE 2-continued
Groups as R1 and R2 in the compounds of formula (1)
| No. | R1 | R2 |
|---|---|---|
| 2-8 | 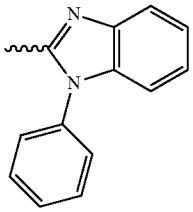 | 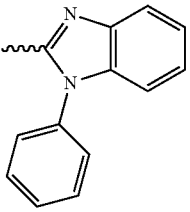 |
| 2-9 | 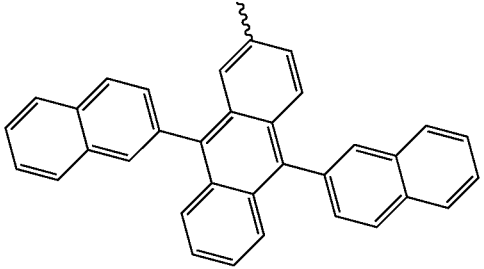 | 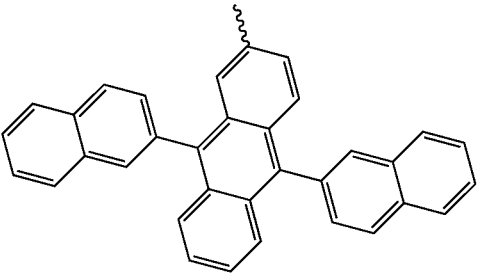 |
| 2-10 | 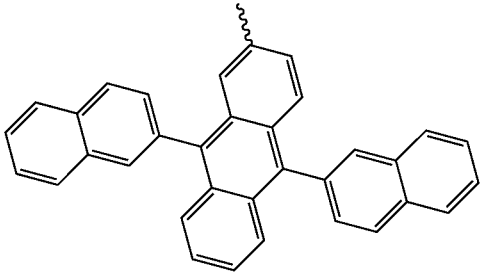 | 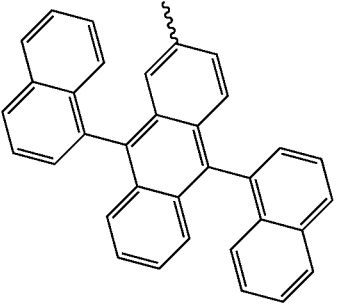 |
| 2-11 | 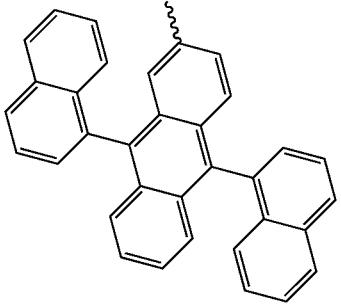 | 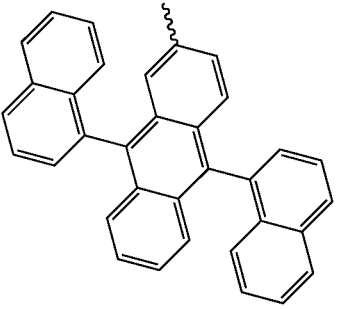 |
| 2-12 | 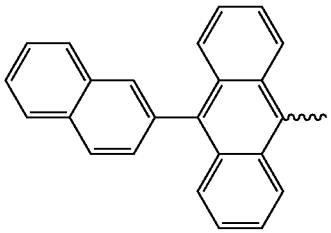 | 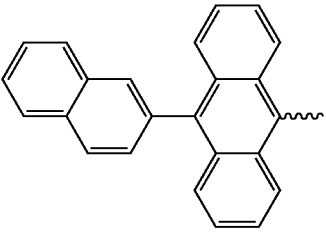 |

TABLE 2-continued

Groups as R1 and R2 in the compounds of formula (1)

| No. | R1 | R2 |
|---|---|---|
| 2-13 | 1-naphthyl-anthracenyl | 1-naphthyl-anthracenyl |
| 2-14 | 2-naphthyl-anthracenyl | N-carbazolyl |
| 2-15 | 1-naphthyl-anthracenyl | 4-(N-phenyl-N-(4-styrylphenyl)amino)phenyl |
| 2-16 | 4-(N-phenyl-N-(4-styrylphenyl)amino)phenyl | 4-(N-phenyl-N-(4-styrylphenyl)amino)phenyl |
| 2-17 | 9,9-diphenylfluorenyl-naphthyl-styryl | 1-phenyl-benzimidazol-2-yl |
| 2-18 | 2-naphthyl-anthracenyl | 1-naphthyl-anthracenyl |

TABLE 2-continued
Groups as R1 and R2 in the compounds of formula (1)
| No. | R1 | R2 |
|---|---|---|
| 2-19 | 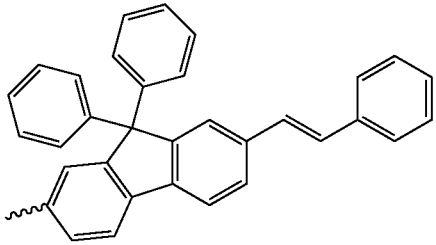 | 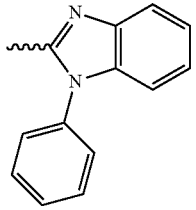 |
| 2-20 | 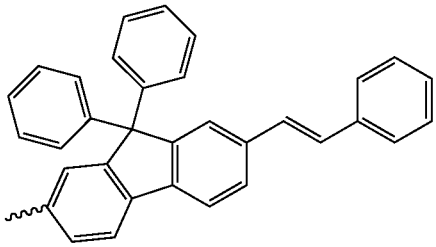 | 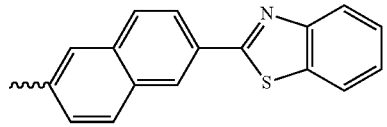 |
| 2-21 | 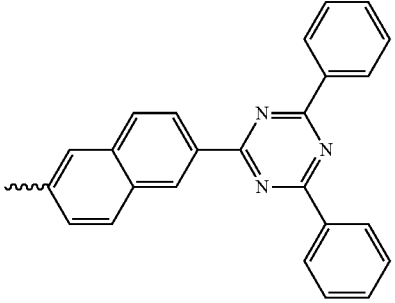 | 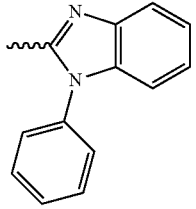 |
| 2-22 | 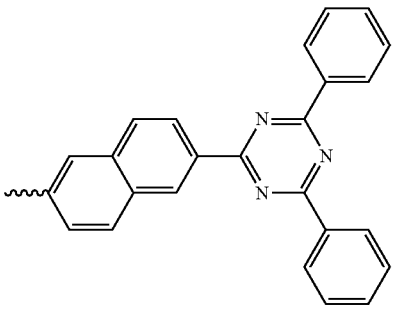 | 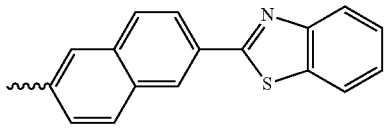 |
| 2-23 | 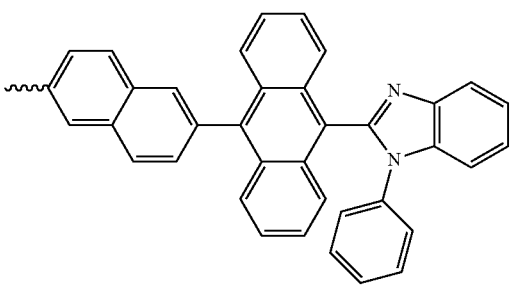 | 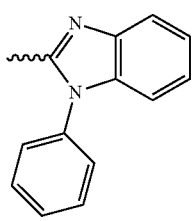 |

TABLE 2-continued

Groups as R1 and R2 in the compounds of formula (1)

| No. | R1 | R2 |
|---|---|---|
| 2-24 | naphthyl-anthracenyl-(1-phenylbenzimidazol-2-yl) group | benzothiazol-2-yl |
| 2-25 | naphthyl-anthracenyl-phenyl-(1-phenylbenzimidazol-2-yl) group | 1-phenylbenzimidazol-2-yl |
| 2-26 | anthracenyl-phenyl-(1-phenylbenzimidazol-2-yl) group | 1-phenylbenzimidazol-2-yl |
| 2-27 | naphthyl-anthracenyl-phenyl-(1-phenylbenzimidazol-2-yl) group | benzothiazol-2-yl |

TABLE 2-continued
Groups as R1 and R2 in the compounds of formula (1)
| No. | R1 | R2 |
|---|---|---|
| 2-28 | 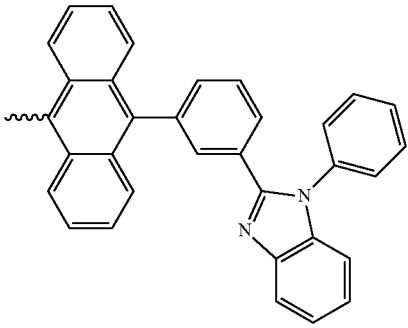 | 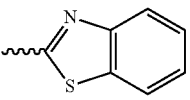 |
| 2-29 | 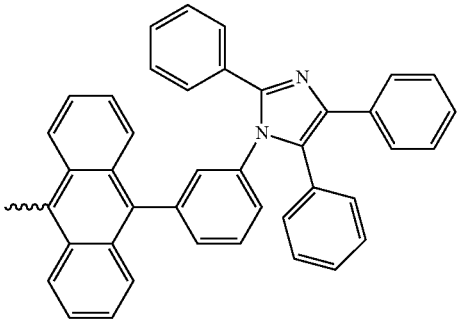 | 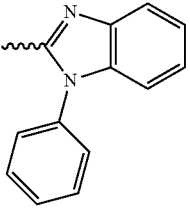 |
| 2-30 | 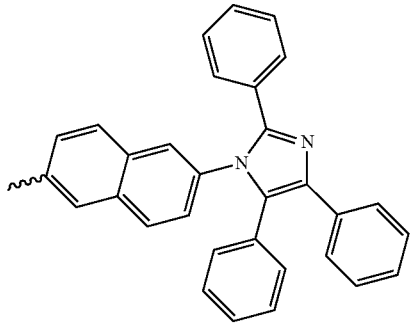 | 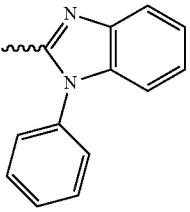 |
| 2-31 | 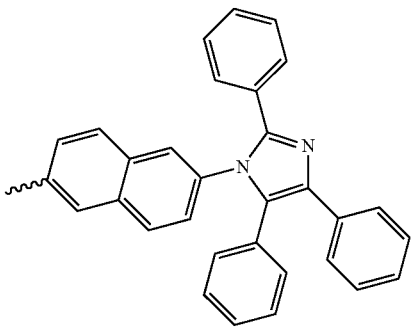 | 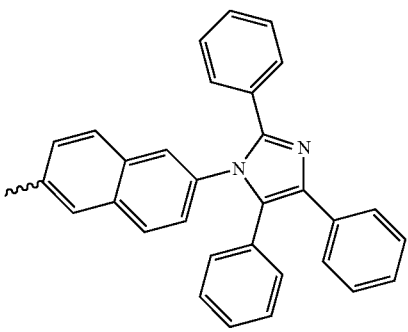 |

TABLE 2-continued
Groups as R1 and R2 in the compounds of formula (1)
| No. | R1 | R2 |
|---|---|---|
| 2-32 | 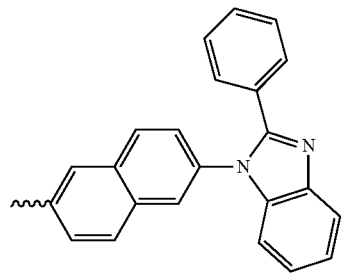 | 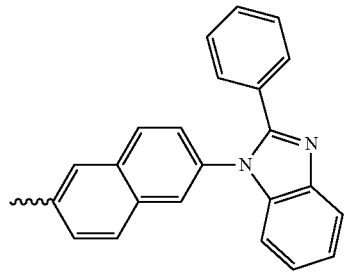 |
| 2-33 | 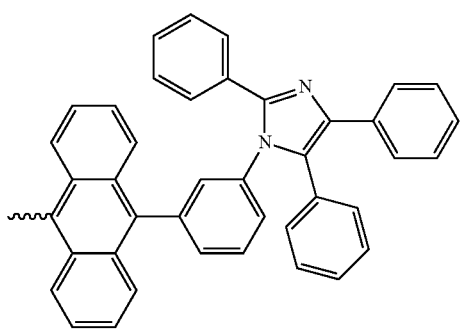 | 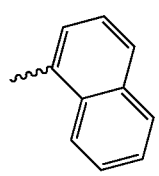 |
| 2-34 | 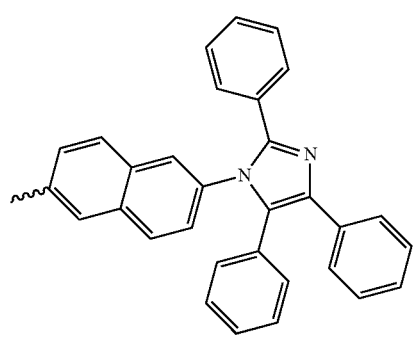 | 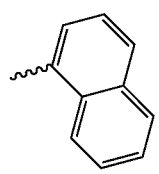 |
| 2-35 | 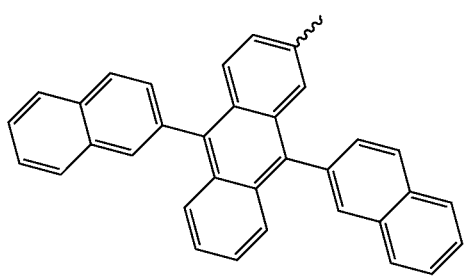 | 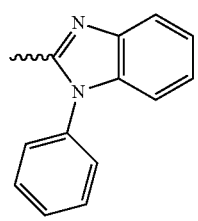 |
| 2-36 | 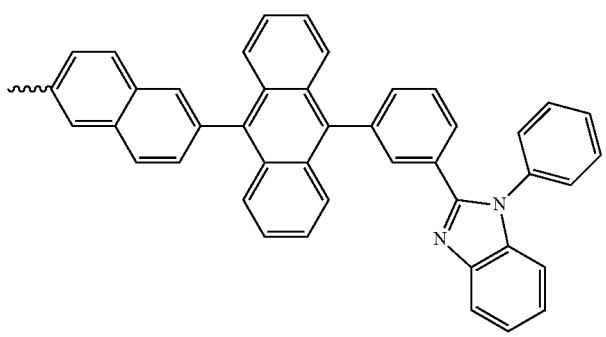 | 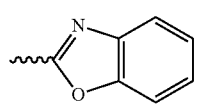 |

TABLE 2-continued
Groups as R1 and R2 in the compounds of formula (1)
| No. | R1 | R2 |
|---|---|---|
| 2-37 | 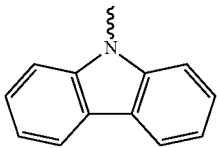 | 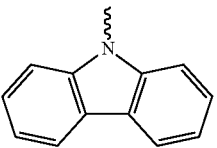 |
| 2-38 | 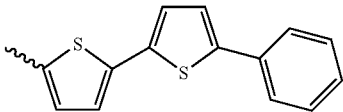 | 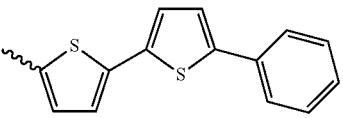 |
| 2-39 | 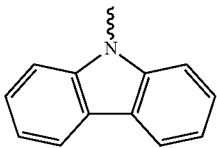 | 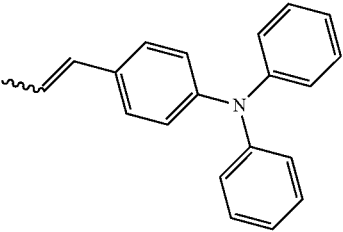 |
| 2-40 | 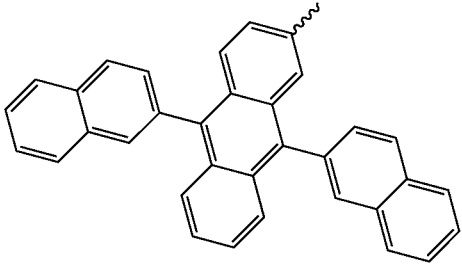 | 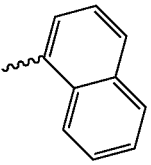 |
| 2-41 | 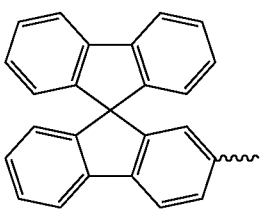 | 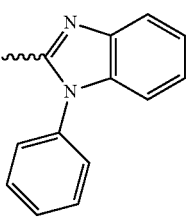 |
| 2-42 | 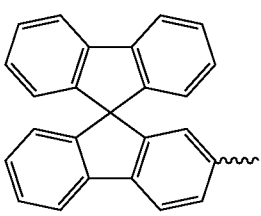 | 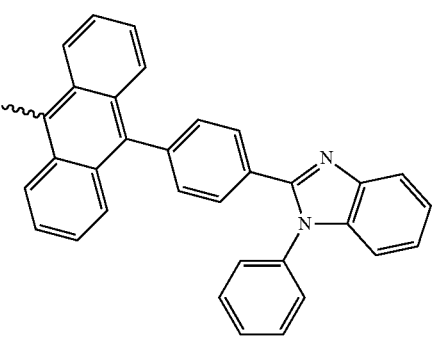 |

TABLE 2-continued
Groups as R1 and R2 in the compounds of formula (1)
| No. | R1 | R2 |
|---|---|---|
| 2-43 | 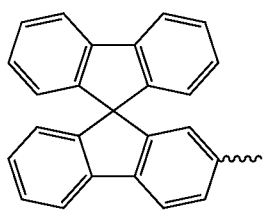 | 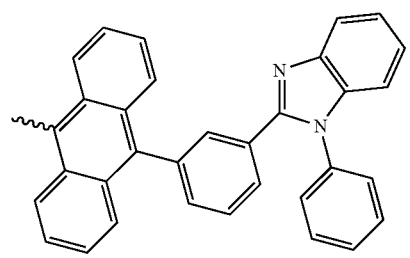 |
| 2-44 | 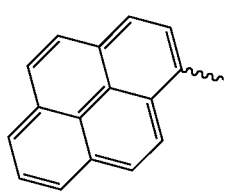 | 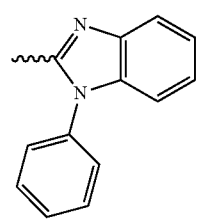 |
| 2-45 | 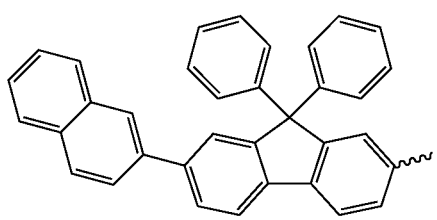 | 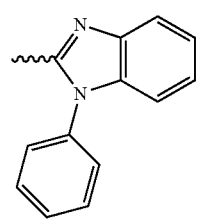 |
| 2-46 | 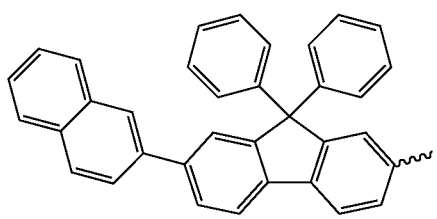 | 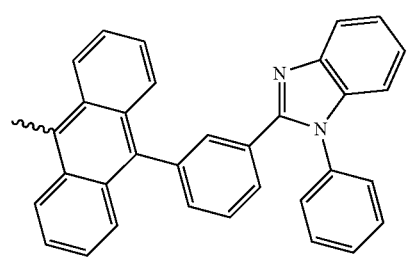 |
| 2-47 | 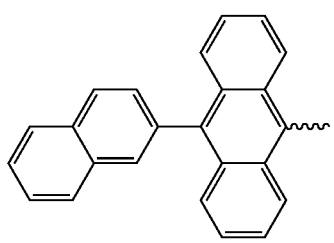 | 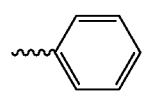 |
| 2-48 | 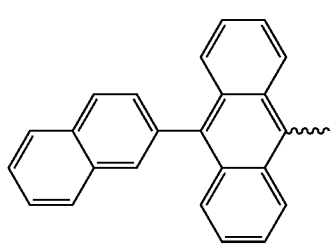 | 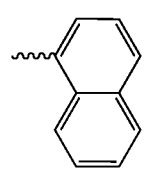 |

TABLE 2-continued

Groups as R1 and R2 in the compounds of formula (1)

| No. | R1 | R2 |
|---|---|---|
| 2-49 | | |
| 2-50 | | |
| 2-51 | | |
| 2-52 | | |
| 2-53 | | |
| 2-54 | | |
| 2-55 | | |

TABLE 2-continued
Groups as R1 and R2 in the compounds of formula (1)
| No. | R1 | R2 |
|---|---|---|
| 2-56 | 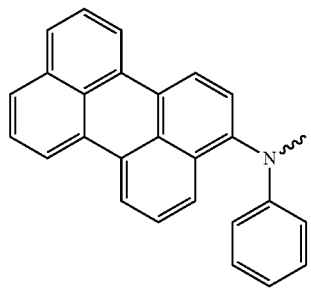 | 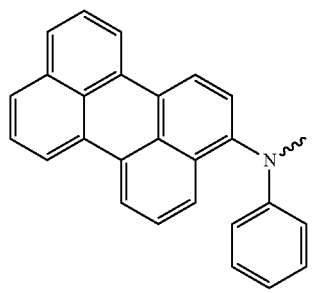 |
| 2-57 | 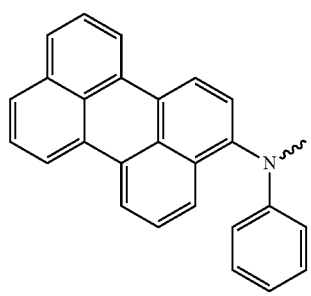 | 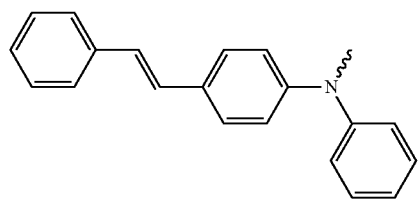 |
| 2-58 | 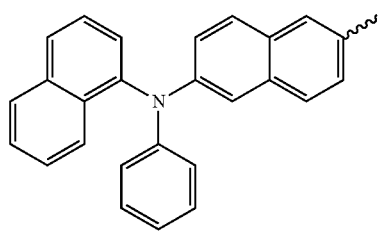 | 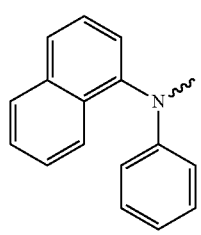 |
| 2-59 | 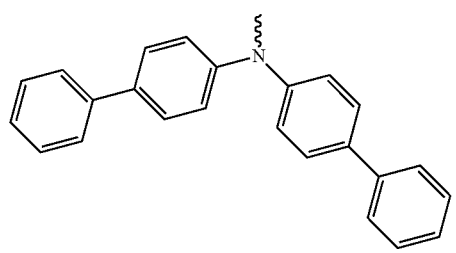 | 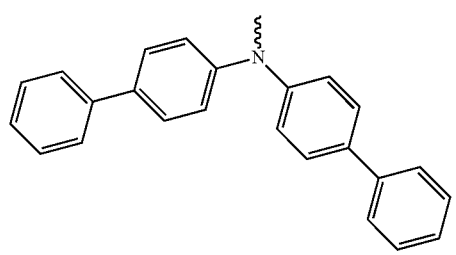 |
| 2-60 | 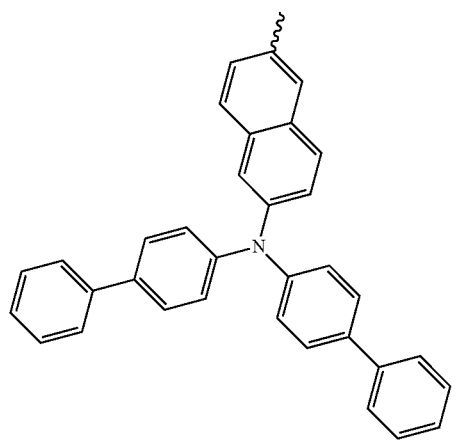 | 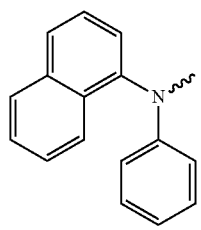 |

TABLE 2-continued
Groups as R1 and R2 in the compounds of formula (1)
| No. | R1 | R2 |
|---|---|---|
| 2-61 | 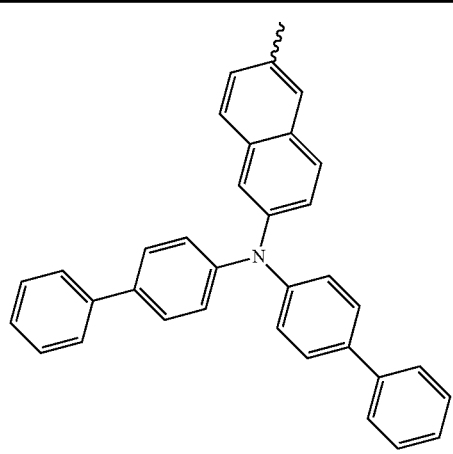 | 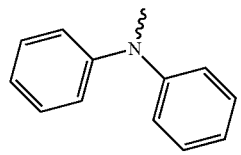 |
| 2-62 | 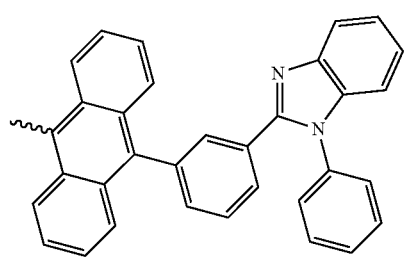 | 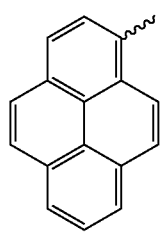 |
| 2-63 | 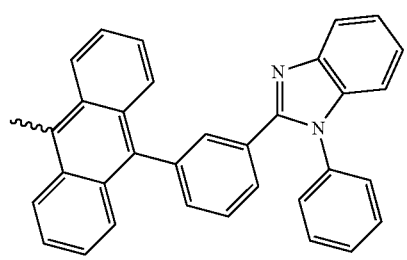 | 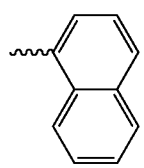 |
| 2-64 | 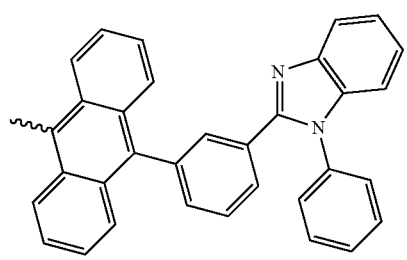 | 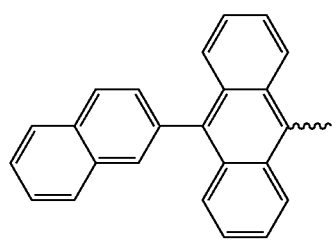 |
| 2-65 | 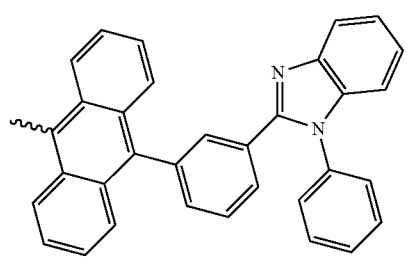 | 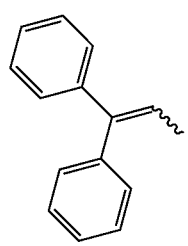 |

TABLE 2-continued
Groups as R1 and R2 in the compounds of formula (1)
| No. | R1 | R2 |
|---|---|---|
| 2-66 | 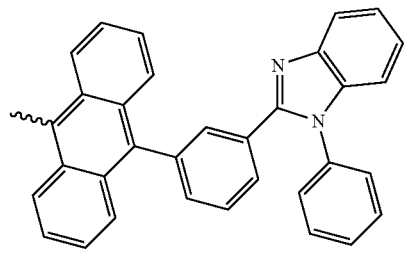 | 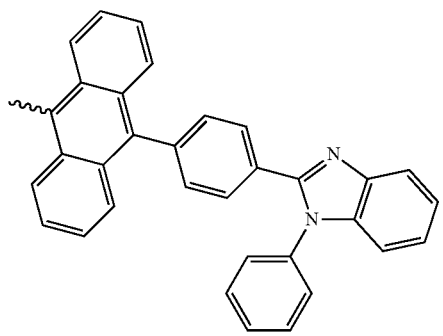 |
| 2-67 | 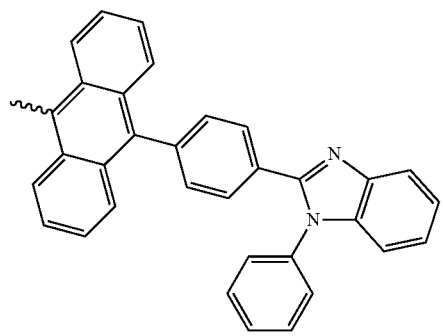 | 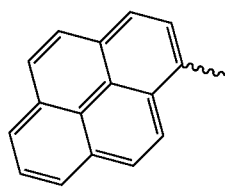 |
| 2-68 | 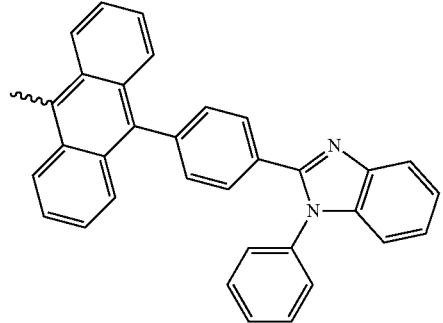 | 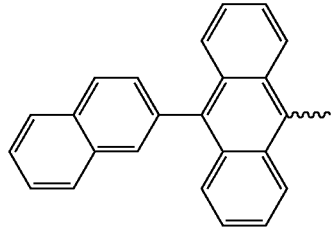 |
| 2-69 | 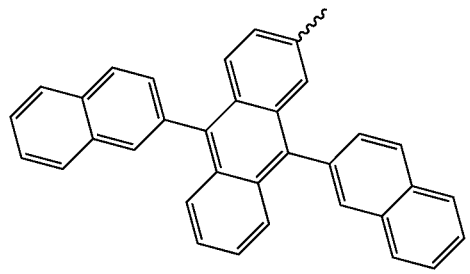 | 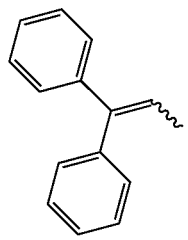 |
| 2-70 | 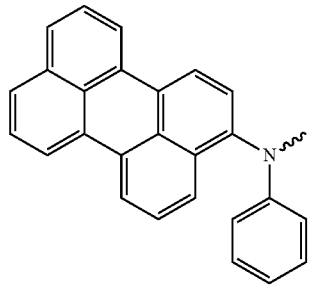 | 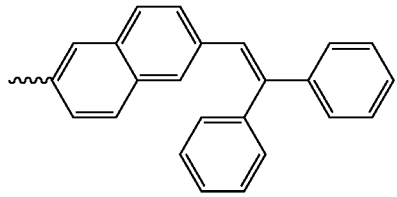 |

TABLE 2-continued
Groups as R1 and R2 in the compounds of formula (1)
| No. | R1 | R2 |
|---|---|---|
| 2-71 | 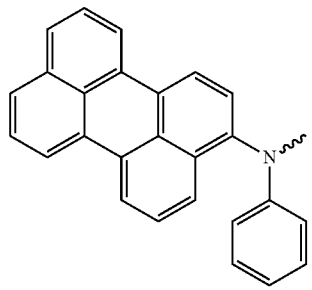 | 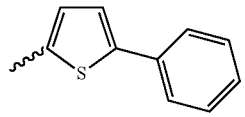 |
| 2-72 | 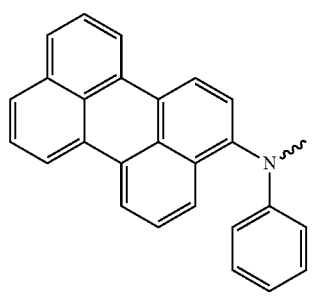 | 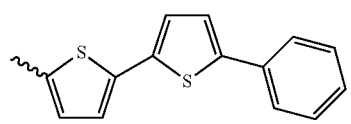 |
| 2-73 | 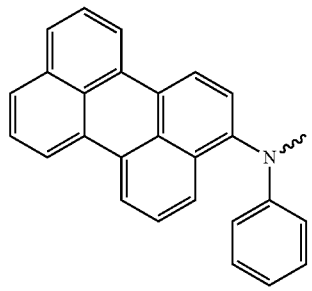 | 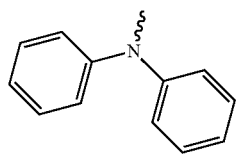 |
| 2-74 | 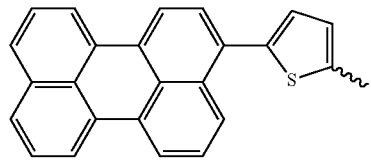 | 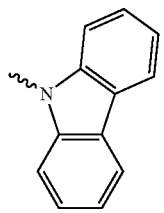 |
Further, the present invention provides a representative method for preparing a binaphthalene derivative represented by the formula 1, and the method is represented by Reaction Scheme 1.
[Reaction Scheme 1]
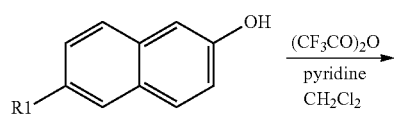

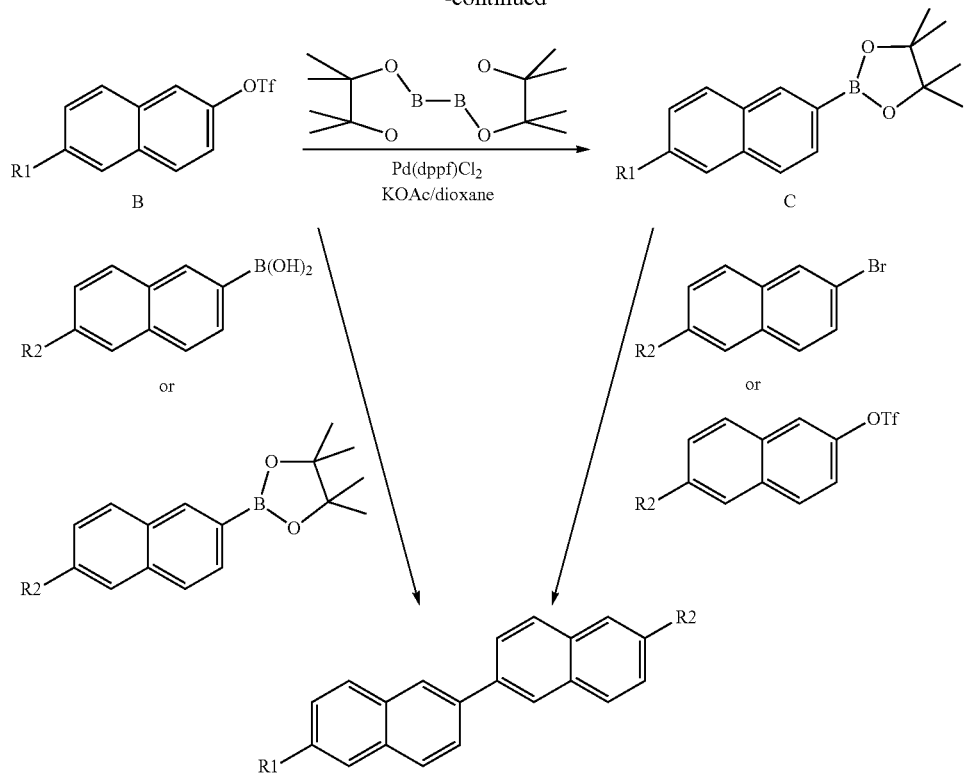

In the Reaction Scheme 1, R1 and R2 have the same meaning as defined in the formula 1.

As shown in the Reaction Scheme 1, the compound (B) can be easily prepared by reacting trifluoroacetic anhydride and the naphtol derivatives (A) as a starting material under the presence of a base such pyridine or triethylamine. The compound (C) can be prepared by reacting the compound (B) and a bispinacolatodiboron reagent.

The compounds of the formula (1) can be prepared by Suzuki coupling reaction between the compound (B) and a naphthalene boron ester compound or a naphthalene boronic acid compound under the presence of a palladium catalyst [II] and a base (for example, an inorganic base such as potassium carbonate).

In addition, the compounds of the formula (1) can be prepared by Suzuki coupling reaction between a naphthyl boron ester compound (C) and a bromonaphthalene derivative or a trifluoroacetoxynaphthalene derivative under the presence of a palladium catalyst [II] and a base (for example, an inorganic base such as potassium carbonate).

The present invention also provides an organic electronic device using the binaphthalene derivative of the formula 1.

The organic electronic device of the present invention can be prepared by a usual method and materials for preparing an organic electronic device, except that the above-described compounds are used to form an organic material layer having at least one layer.

Hereinbelow, the organic light-emitting device will be exemplified.

The compound of the formula 1 can be used as an organic material layer in the organic light-emitting device due to its structural specificity.

In one embodiment of the present invention, the organic light-emitting device can have a structure comprising a first electrode, a second electrode, an organic material layer interposed therebetween, and can be prepared by a usual method and materials for preparing an organic electronic device, except that the above-described compound according to the present inventions are used in at least one layer of the organic material layers in the organic light-emitting device.

The organic material layer in the organic light-emitting device of the present invention may be a monolayer structure comprising a single layer, or a multilayer structure comprising two or more layers including a light-emitting layer. If the organic material layer in the organic light-emitting device of the present invention has a multilayer structure, it can has a structure in which a hole-injecting layer, a hole-transporting layer, a light-emitting layer, electron-transporting layer, and the like are laminated. However, the structure of the organic light-emitting device is not limited thereto, and it can further include a fewer number of organic materials layer. In such the multilayer structure of organic material layer, the compound of the formula 1 can be contained in a hole-injecting layer, a hole-transporting layer, a light-emitting layer, a hole-injecting/hole-transporting and light-emitting layer, and a hole-transporting and light-emitting layer, or an electron-transporting and light-emitting layer, an electron-transporting layer, an electron-injecting and electron-transporting layer, and the like.

For example, the structure of the organic light-emitting device of the present invention can be those as shown FIGS. 1 to 4, but not limited thereto.

FIG. 1 illustrates a structure of an organic light-emitting device in which an anode (102), a light-emitting layer (105) and a cathode (107) are sequentially laminated on a substrate (101). In this structure, the compound of the formula 1 can be contained in the light-emitting layer (105).

FIG. 2 illustrates a structure of an organic light-emitting device in which an anode (102), a hole-injecting/hole-transporting, and light-emitting layer (105), an electron-transporting layer (106) and a cathode (107) are sequentially laminated on a substrate (101). In this structure, the compound of the formula 1 can be contained in the hole-injecting/hole-transporting, and light-emitting layer (105) or the electron-transporting layer (106).

FIG. 3 illustrates a structure of an organic light-emitting device in which a substrate (101), an anode (102), a hole-injecting layer (103), a hole-transporting and light-emitting layer (105), an electron-transporting layer (106) and a cathode (107) are sequentially laminated. In this structure, the compound of the formula 1 can be contained in the hole-injecting layer (103), the hole-transporting and light-emitting layer (105) or the electron-transporting layer (106).

FIG. 4 illustrates a structure of an organic light-emitting device in which a substrate (101), an anode (102), a hole-injecting layer (103), a hole-transporting layer (104), an electron-transporting and light-emitting layer (105) and a cathode (107) are sequentially laminated. In this structure, the compound of the formula 1 can be contained in the hole-injecting layer (103), the hole-transporting layer (104) or the electron-transporting and light-emitting layer (105).

For example, the organic light-emitting device according to the present invention can be prepared by depositing a metal, a metal oxide having conductivity, or metal alloys thereof on a substrate to form an anode; forming an organic material layer comprising a hole-injecting layer, a hole-transporting layer, a light-emitting layer and an electron-transporting layer on the anode; and depositing a material, which can be used as a cathode, thereon, using a PVD (physical vapor deposition) process such as sputtering and e-beam evaporation. Alternatively, an organic light-emitting device can be prepared by depositing a cathode material, an organic material layer, and an anode material on a substrate.

The organic material layer may be of a multilayer structure containing a hole-injecting layer, a hole-transporting layer, a light-emitting layer, an electron-transporting layer, and the like, but not limited thereto, and may be of a monolayer structure. Further, the organic material layer can be produced to have a fewer number of layers, by using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to an organic material layer. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and $SnO_2$:Sb; conductive polymers such as poly(3-methylthiophene), poly[3,4-(ethylene-1,2-dioxy)thiophene](PEDT), polypyrrole and polyaniline, but not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and $LiO_2$/Al, but not limited thereto.

The hole-injecting material is a material facilitating hole injection from an anode at low voltage. The HOMO (highest occupied molecular orbital) level of the hole-injecting material is preferably located between the work function of the anode materials and the HOMO level of its neighboring organic material layer. Specific examples of the hole-injecting material include organic materials of metal porphyrin, oligothiophene and arylamine series, organic materials of hexanitrile hexaazatriphenylene, organic materials of quinacridone series, organic materials of perylene series, and conductive polymers of anthraquinone, polyaniline, and polythiophene series, but are not limited thereto.

The hole-transporting material is a material having high hole mobility, which can transfer holes from the anode or the hole-injecting layer toward the light-emitting layer. Specific examples thereof include organic materials of arylamine series, conductive polymers and block copolymers having both conjugated portions and non-conjugated portions, but are not limited thereto.

The light-emitting material are a material capable of emitting visible light by accepting and recombining holes from the hole-transporting layer and electrons from the electron-transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; and compounds of polyfluorene and rubrene series, but are not limited thereto.

The electron-transporting material is suitably a material having high electron mobility, which can transfer electrons from the cathode to the light-emitting layer. Specific examples thereof include 8-hydroxyquinoline aluminum complex ($Alq_3$); complexes including $Alq_3$; organic radical compounds; and hydroxyflavone-metal complexes, but are not limited thereto.

The organic light-emitting device according to the invention may be of a top emission structure, a bottom emission structure or a top and bottom emission structure according to the materials used.

The compound according to the invention can function in an organic electronic device including an organic solar cell, an organic photoconductor and an organic transistor, according to a principle similar to that applied to the organic light-emitting device.

Advantageous Effects

The binaphthalene derivative according to the present invention can perform functions of hole injection and transportation, electron injection and transportation, or light emission in an organic electronic device including an organic light-emitting device, and the device according to the present invention has excellent characteristics in terms of efficiency, drive voltage and stability, and in particular excellent effects such as a low voltage and a long life time.

BEST MODE

Mode for Invention

Figure 1:
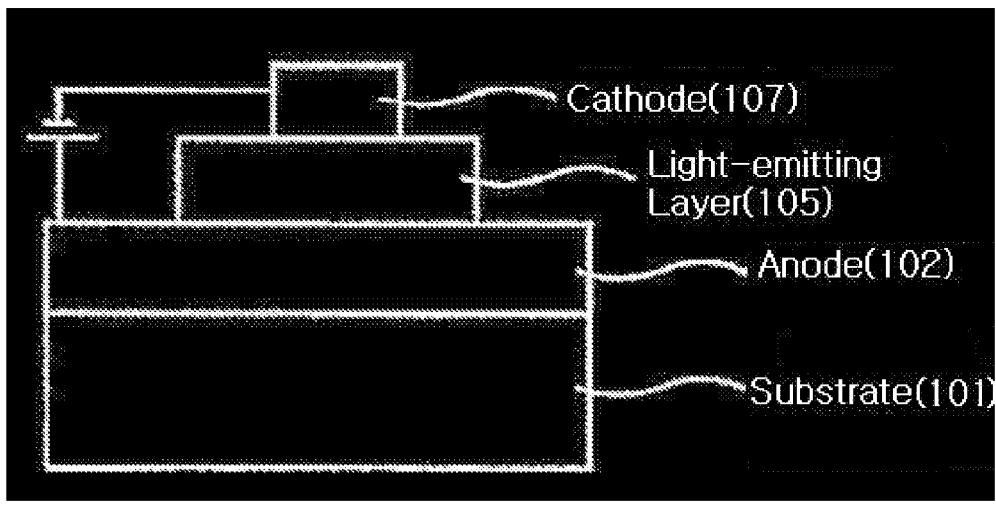
FIGS. 1 to 4 illustrate the structures of the organic light-emitting devices applicable to the present invention.
Figure 2:
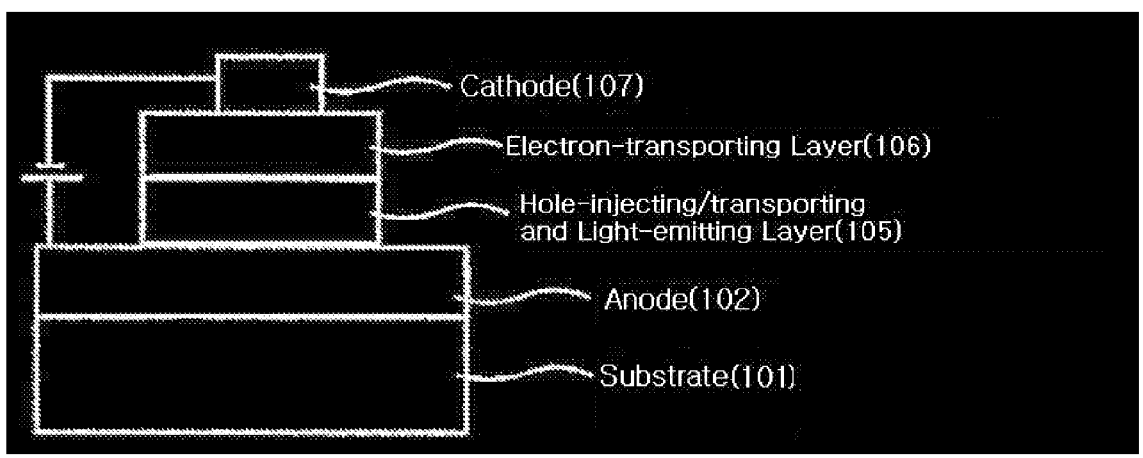
Figure 3:
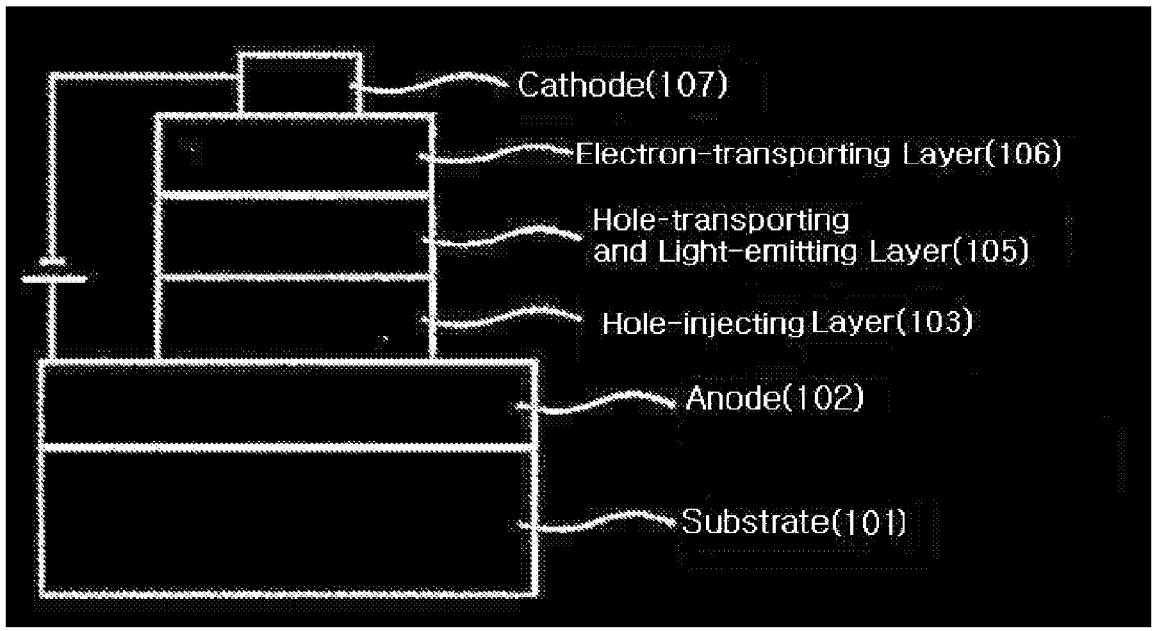
Figure 4:
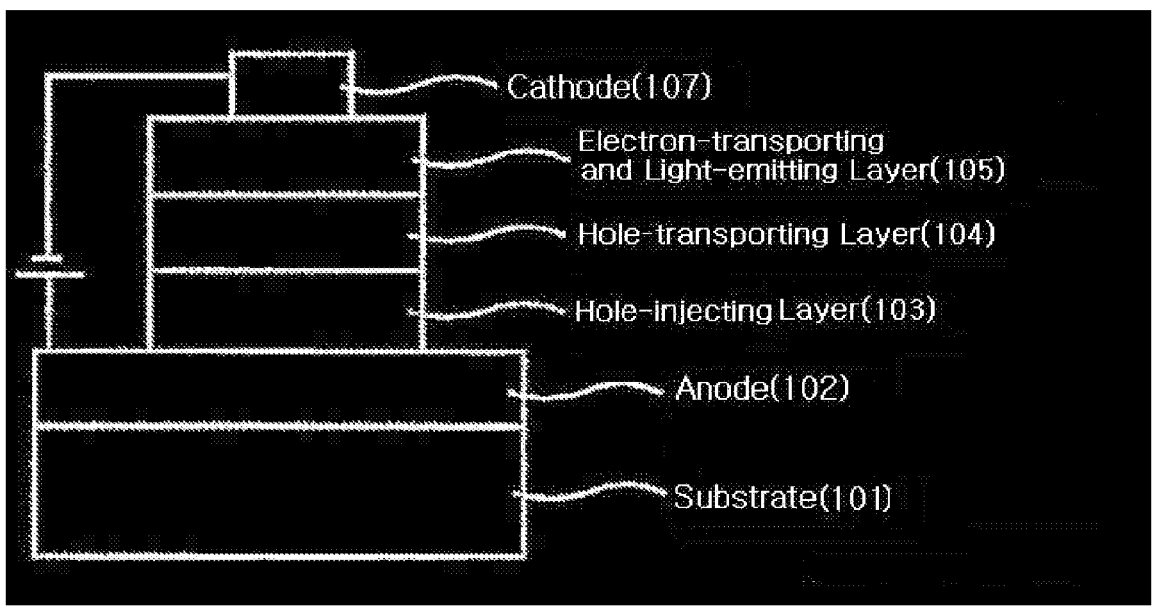

Hereinafter, the present invention will be described in more detail by means of Synthesis Examples and Experimental Examples, but the scope of the invention is not limited thereto.

Preparation Example I-1

Preparation of Compound A-1

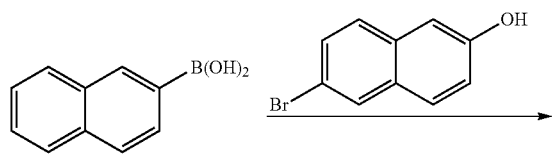

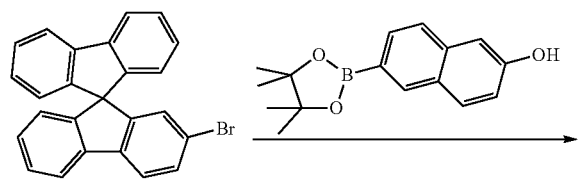

Naphthyl-2-boronic acid (17.2 g, 100 mmol), 6-bromo-2-naphtol (22.3 g, 100 mmol) and sodium carbonate (27.6 g, 200 mmol) were suspended in a mixture of tetrahydrofuran (500 mL) and water (100 mL). To the suspension, tetrakis(triphenylphosphine)palladium [II](4.6 g, 4 mmol) was added. The resulting mixture was stirred under reflux for about 24 hours and then cooled to room temperature. The organic layer was separated and the aqueous layer was extracted from tetrahydrofuran. The combined organic extract was dried over magnesium sulfate, and concentrated in vacuum. The residue was purified with THF/EtOH to prepare a compound A-1 (23.5 g, yield 87%): MS [M+H]$^+$=271.

Preparation Example I-2

Preparation of Compound A-2

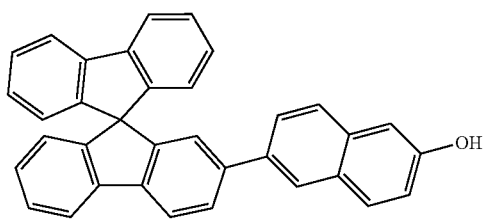

A compound A-2 was prepared in the same manner as in the method for preparing the compound A-1 of Preparation Example I-1, except that in the method for preparing the compound A-1 of Preparation Example I-1, bromo spiro compound (26.5 g, 67 mmol) shown in the above reaction scheme was used instead of 6-bromo-2-naphtol, and 6-hydroxynaphthyl-2-boronate (18.0 g, 67 mmol) was used instead of naphthyl-2-boronic acid. (27.5 g, yield 90%): MS [M+H]$^+$=459

Preparation Example I-3

Preparation of Compound A-3

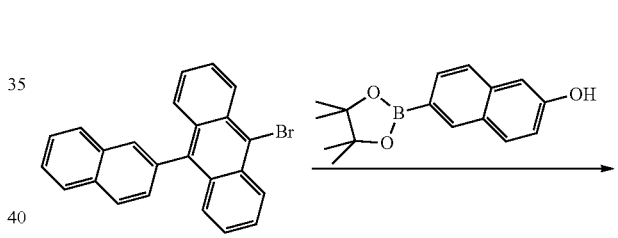

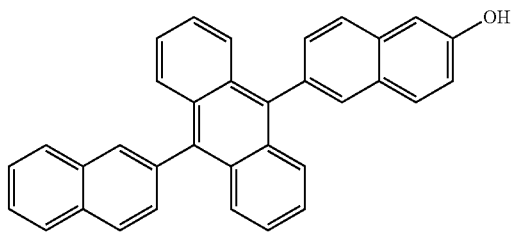

A compound A-3 was prepared in the same manner as in the method for preparing the compound A-1 of Preparation Example I-1, except that in the method for preparing the compound A-1 of Preparation Example I-1, 9-bromo-10-naphthylanthracene compound (19.1 g, 50 mmol) was used instead of 6-bromo-2-naphtol, and 6-hydroxynaphthyl-2-boronate (13.5 g, 50 mmol) was used instead of naphthyl-2-boronic acid. (20.5 g, yield 92%): MS [M+H]$^+$=447

Preparation Example I-4

Preparation of Compound A-4

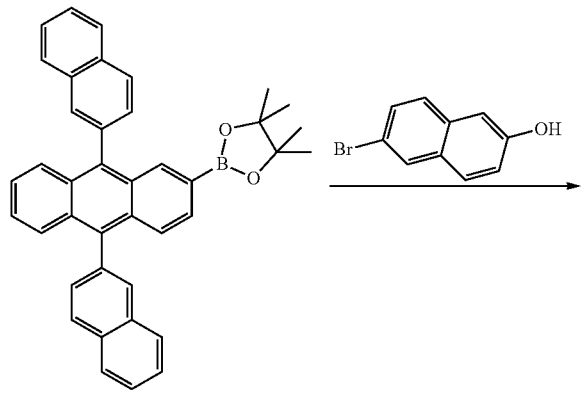

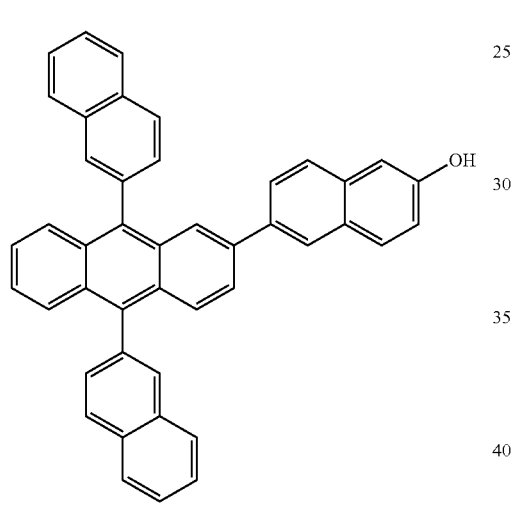

A compound A-4 was prepared in the same manner as in the method for preparing the compound A-1 of Preparation Example I-1, except that in the method for preparing the compound A-1 of Preparation Example I-1, 6-bromo-2-naphtol (4.5 g, 20 mmol) was used, and 9,10-dinaphthylanthrace-nyl-2-boronate compound (11.1 g, 20 mmol) was used instead of naphthyl-2-boronic acid. (10 g, yield 87%): MS $[M+H]^+ = 573$

Preparation Example I-5

Preparation of Compound A-5

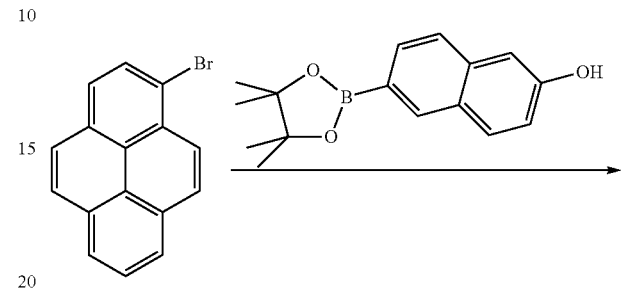

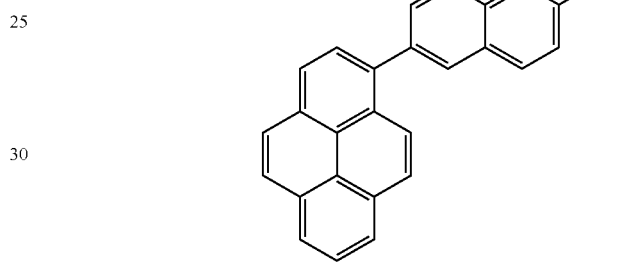

A compound A-5 was prepared in the same manner as in the method for preparing the compound A-1 of Preparation Example I-1, except that in the method for preparing the compound A-1 of Preparation Example I-1, 1-bromopyrene compound (10 g, 35.6 mmol) was used instead of 6-bromo-2-naphtol, and 6-hydroxynaphthyl-2-boronate (9.6 g, 35.6 mmol) was used instead of naphthyl-2-boronic acid (9.3 g, yield 76%): MS $[M+H]^+ = 345$

Preparation Example I-6

Preparation of Compound A-6

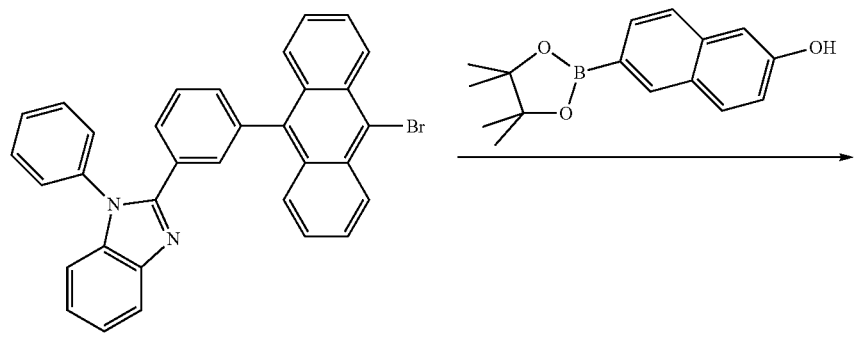

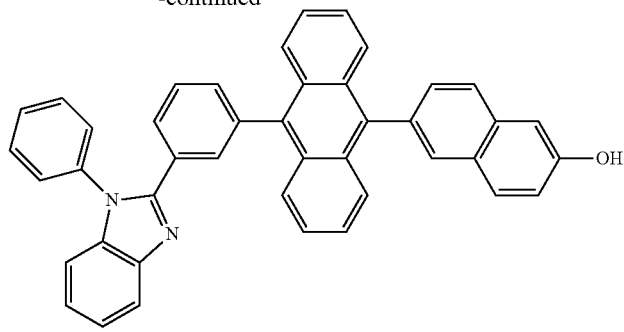

[Compound A-6-1]

A compound A-6 was prepared in the same manner as in the method for preparing the compound A-1 of Preparation Example I-1, except that in the method for preparing the compound A-1 of Preparation Example I-1, the compound A-6-1 shown in the above reaction scheme (10.5 g, 20 mmol) was used instead of 6-bromo-2-naphtol, and 6-hydroxynaphthyl-2-boronate (5.4 g, 20 mmol) was used instead of naphthyl-2-boronic acid. (8.0 g, yield 68%): MS [M+H]$^+$=589

Preparation Example I-7

Preparation of Compound A-7

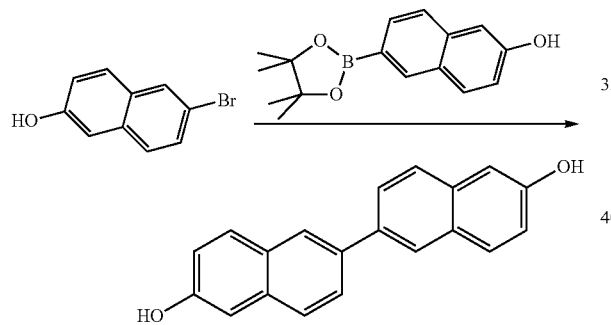

A compound A-7 was prepared in the same manner as in the method for preparing the compound A-1 of Preparation Example I-1, except that in the method for preparing the compound A-1 of Preparation Example I-1, 6-bromo-2-naphtol (11.2 g, 50 mmol) was used, and 6-hydroxynaphthyl-2-boronate (13.5 g, 50 mmol) was used instead of naphthyl-2-boronic acid. (11.2 g, yield 78%): MS [M+H]$^+$=287

Preparation Example II-1

Preparation of Compound B-1

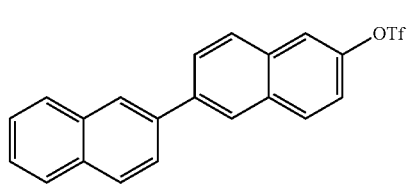 [SMILES: O=S(=O)(Oc1ccc2cc(-c3ccc4ccccc4c3)ccc2c1)C(F)(F)F]

To the compound A-1 prepared in the Preparation Example I-1 (23.5 g, 87 mmol), 100 mL of CH$_2$Cl$_2$ was added, and then triethylamine (13.3 g, 130.5 mmol) and trifluoroacetic acid anhydride (25.8 g, 130.5 mmol) were slowly added dropwise while stirring the mixture. The resulting mixture was stirred at room temperature for 2 hours. Water and CH$_2$Cl$_2$ were added to separate the organic layer, and the organic extract was dried over magnesium sulfate, and concentrated in vacuum. The residue was purified with CH$_2$Cl$_2$/EtOH to prepare a compound B-1. (28.7 g, yield 90%): MS [M+H]$^+$=403

Preparation Example II-2

Preparation of Compound B-2

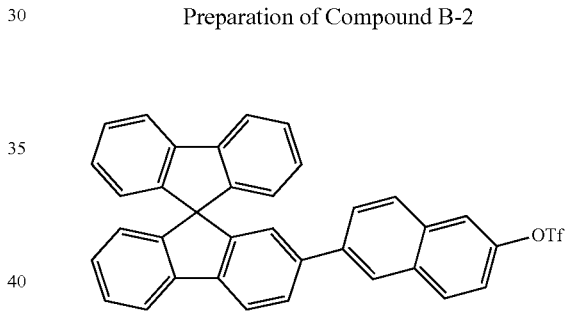

A compound B-2 was prepared in the same manner as in the method for preparing the compound B-1 of Preparation Example II-1, except that in the method for preparing the compound B-1 of Preparation Example II-1, the compound A-2 prepared in the Preparation Example I-2 (27.5 g, 60 mmol) was used instead of the compound A-1 (29.6 g, yield 89%): MS [M+H]$^+$=555

Preparation Example II-3

Preparation of Compound B-3

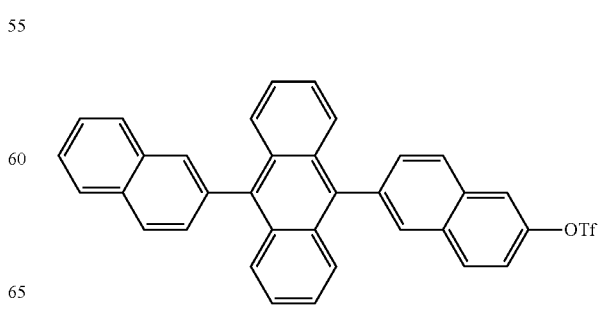

A compound B-3 was prepared in the same manner as in the method for preparing the compound B-1 of Preparation Example II-1, except that in the method for preparing the compound B-1 of Preparation Example II-1, the compound A-3 prepared in the Preparation Example I-3 (20.5 g, 45.9 mmol) was used instead of the compound A-1. (19.7 g, yield 79%): MS [M+H]$^+$=543

Preparation Example II-4

Preparation of Compound B-4

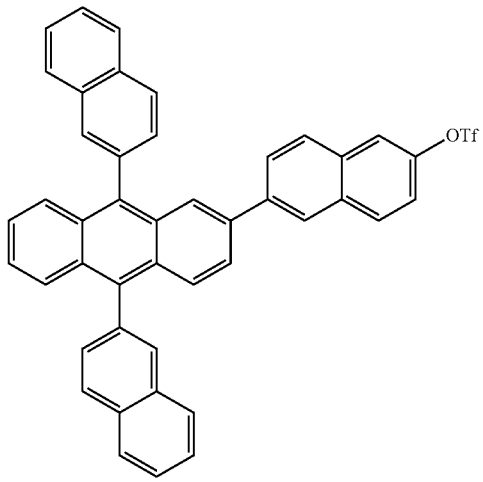 [SMILES: O=S(=O)(Oc1ccc2cc(-c3ccc4c(-c5ccc6ccccc6c5)c5ccccc5c(-c5ccc6ccccc6c5)c4c3)ccc2c1)C(F)(F)F]

A compound B-4 was prepared in the same manner as in the method for preparing the compound B-1 of Preparation Example II-1, except that in the method for preparing the compound B-1 of Preparation Example II-1, the compound A-4 prepared in the Preparation Example I-4 (10 g, 17.5 mmol) was used instead of the compound A-1. (7.83 g, yield 67%): MS [M+H]$^+$=669

Preparation Example II-5

Preparation of Compound B-5

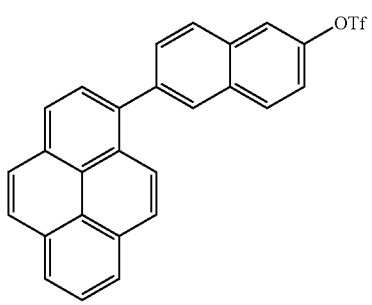 [SMILES: O=S(=O)(Oc1ccc2cc(-c3ccc4ccc5cccc6ccc3c4c56)ccc2c1)C(F)(F)F]

A compound B-5 was prepared in the same manner as in the method for preparing the compound B-1 of Preparation Example II-1, except that in the method for preparing the compound B-1 of Preparation Example II-1, the compound A-5 prepared in the Preparation Example I-5 (12 g, 34.8 mmol) was used instead of the compound A-1. (12.1 g, yield 79%): MS [M+H]$^+$ 441

Preparation Example II-6

Preparation of Compound B-6

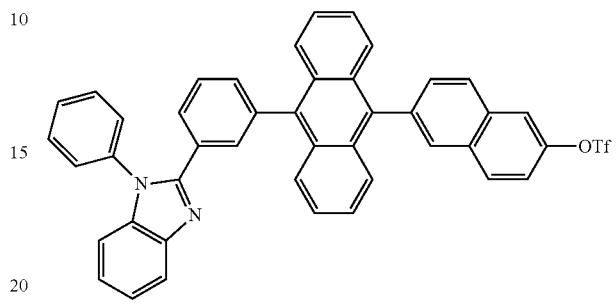

A compound B-6 was prepared in the same manner as in the method for preparing the compound B-1 of Preparation Example II-1, except that in the method for preparing the compound B-1 of Preparation Example II-1, the compound A-6 prepared in the Preparation Example I-6 (12 g, 20.4 mmol) was used instead of the compound A-1. (7.5 g, yield 54%): MS [M+H]$^+$=685

Preparation Example II-7

Preparation of Compound B-7

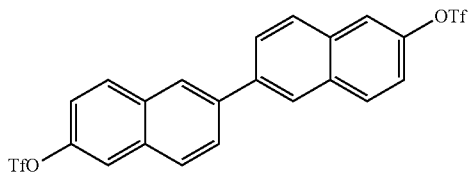 [SMILES: O=S(=O)(Oc1ccc2cc(-c3ccc4cc(OS(=O)(=O)C(F)(F)F)ccc4c3)ccc2c1)C(F)(F)F]

A compound B-7 was prepared in the same manner as in the method for preparing the compound B-1 of Preparation Example II-1, except that in the method for preparing the compound B-1 of Preparation Example II-1, the compound A-7 prepared in the Preparation Example I-7 (10 g, 35 mmol), triethylamine (8.6 g, 84 mmol) and trifluoroacetic acid anhydride (4.5 g, 84 mmol) were used instead of the compound A-1. (2.2 g, yield 45%): MS [M+H]$^+$=479

Preparation Example II-8

Preparation of Compound B-8

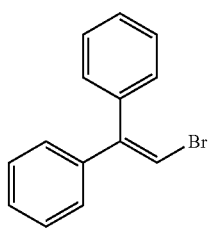 [SMILES: BrC=C(c1ccccc1)c1ccccc1]

A solution of diphenylethylene (7.8 g, 43.3 mmol) in 100 mL of CCl₄ was maintained at −15° C., and bromine (Br₂, 2.45 mL, 47.6 mmol) was slowly added thereto. 10 g of well-dried silica gel was added to the reactant, and then the resultant was stirred at 80° C. for 1 hour. The temperature of the reactant was lowered to ambient temperature, and the resultant was purified by column chromatography to prepare a compound B-8 having a bromine group introduced (10.7 g, yield 95%).

MS [M+H]⁺=259

Preparation Example II-9

Preparation of Compound B-9

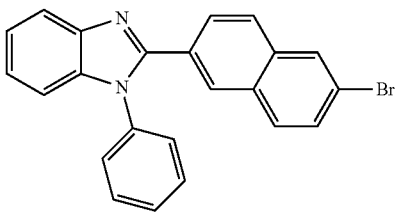 [SMILES: Brc1ccc2cc(-c3nc4ccccc4n3-c3ccccc3)ccc2c1]

To 6-bromo-2-naphthoic acid (5.0 g, 20 mmol), 20 mL of thionyl chloride (SOCl₂), and dimethylformaldehyde (DMF, 1 mL) were added, and the mixture was stirred under heating for 4 hours. An excessive amount of thionyl chloride (SOCl₂) was distilled off in vacuum, and then to the reaction mixture, 20 mL of N-methylpyrrolidine (NMP), and N-phenyl-1,2-diaminobenzene (3.7 g, 20 mmol) were added, and the mixture was stirred at 160° C. for 12 hours. The mixture was cooled to ambient temperature, and then an excessive amount of water was added thereto to form a solid. The solid was filtered, washed with water and then ethanol, and dried to prepare a compound B-9 (6.2 g, yield 78%).

MS [M+H]⁺=399

Preparation Example II-10

Preparation of Compound B-10

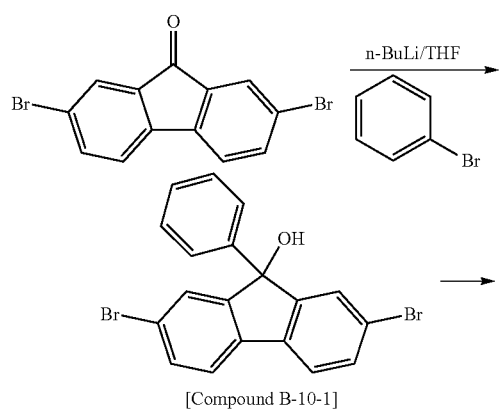

[Compound B-10-1]

-continued

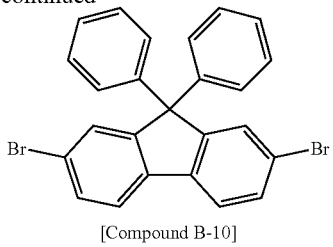

[Compound B-10]

Bromobenzene (4.24 g, 27 mmol) was diluted by 100 mL of tetrahydrofuran anhydride and maintained at −78° C. To the resulting mixture, n-BuLi (2.5M in Hex, 13.0 mL, 32.4 mmol) was added dropwise and then stirred for 40 minutes. 2,7-dibromofluorene (7.6 g, 22.5 mmol) was added. The reaction solution was stirred at −78 for 4 hours. The temperature of the reaction solution was raised to ambient temperature, and the aqueous solution of 2N HCl was added to the reaction solution and then stirred for 6 hours. The layer was separated using ethylether and dried over magnesium anhydride. The separated organic solvent layer was subjected to reduced pressure in vacuum and purified by column chromatography (SiO₂, EtOAc/Hexane=1/10) to prepare a compound B-10-1 (6.6 g, yield 70%).

MS: [M−H2O]⁺=398

The compound B-10-1 (6.6 g, 15.9 mmol) and benzene (100 mL) were mixed, CF₃SO₃H (1.6 mL, 18.4 mmol) was added thereto, and the mixture was refluxed at 80° C. for 6 hours. Using an ice-bath, the reaction solution was cooled to 0° C. and a saturated aqueous solution of NaHCO₃ was added thereto. The layer was separated using water and ethylacetate, and the organic layer was separated and dried over magnesium anhydride. Then, the organic layer was subjected to reduced pressure in vacuum, and recrystallized with THF/Hexane to prepare a compound B-10 (7.0 g, yield 93%).

MS: [M]⁺=476

Preparation Example II-11

Preparation of Compound B-11

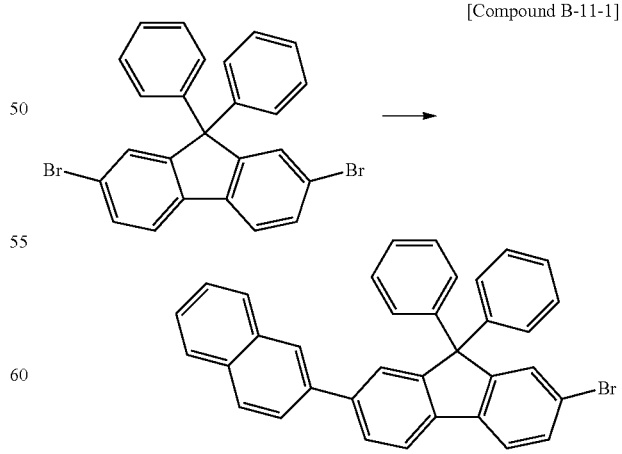

A compound B-11-1 was prepared in the same manner as in the method for preparing the compound A-1 of Preparation Example I-1, except that in the method for preparing the compound A-1 of Preparation Example I-1, the compound B-10 prepared in Preparation Example II-10 (9.5 g, 20 mmol) was used instead of 6-bromo-2-naphtol, and naphthyl-2-boronic acid (3.4 g, 20 mmol) was used. (4.5 g, yield 43%): MS [M]$^+$=523

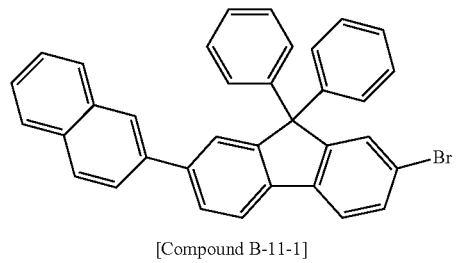

[Compound B-11-1]

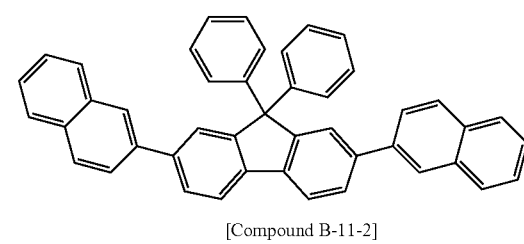

[Compound B-11-2]

A compound B-11-2 was prepared in the same manner as in the method for preparing the compound A-1 of Preparation Example I-1, except that the compound B-11-1 (4.5 g, 8.6 mmol) was used instead of 6-bromo-2-naphtol, and 6-hydroxynaphthyl-2-boronate (2.3 g, 8.6 mmol) was used instead of naphthyl-2-boronic acid. (4.84 g, yield 96%): MS [M+H]$^+$=587

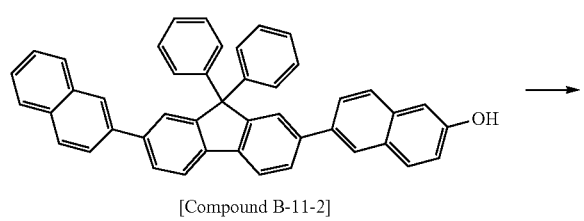

[Compound B-11-2]

[Compound B-11]

A compound B-11 was prepared in the same manner as in the method for preparing the compound B-1 of Preparation Example II-1, except that in the method for preparing the compound B-1 of Preparation Example II-1, the compound B-11-2 (4.8 g, 8.2 mmol) was used instead of the compound A-1. (4.3 g, yield 76%): MS [M+H]$^+$=683

Preparation Example II-12

Preparation of Compound B-12

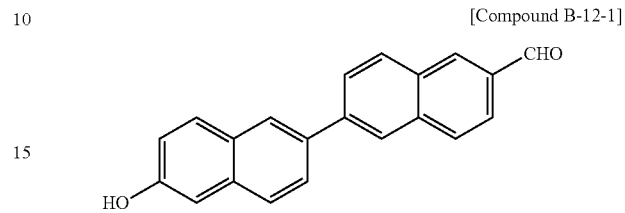

[Compound B-12-1]

A compound B-12-1 was prepared in the same manner as in the method for preparing the compound A-1 of Preparation Example I-1, except that 6-bromo-2-naphthaldehyde (5.1 g, 21.5 mmol) was used instead of 6-bromo-2-naphtol, and 6-hydroxynaphthyl-2-boronate (5.8 g, 21.5 mmol) was used instead of naphthyl-2-boronic acid. (5.3 g, yield 82%): MS [M+H]$^+$=299

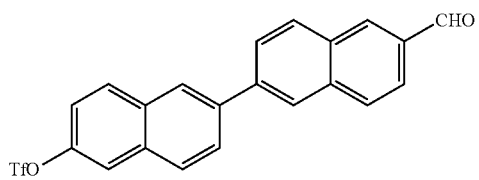

[Compound B-12]

A compound B-12 was prepared in the same manner as in the method for preparing the compound B-1 of Preparation Example II-1, except that in the method for preparing the compound B-1 of Preparation Example II-1, the compound B-12-1 (5.3 g, 17.8 mmol) was used instead of the compound A-1. (3.9 g, yield 56%): MS [M+H]$^+$=395

Preparation Example II-13

Preparation of Compound B-13

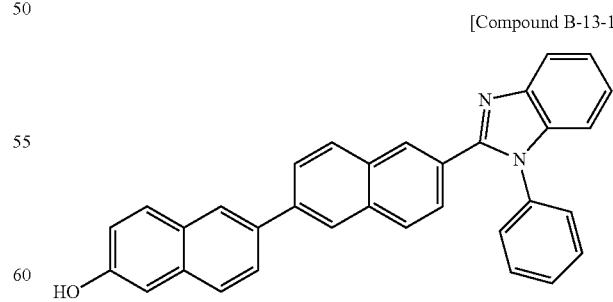

[Compound B-13-1]

To the compound B-12-1 of Preparation Example II-12 (6.0 g, 20 mmol), N-phenyl-1,2-diamino benzene (3.7 g, 20 mmol), 30 mL of toluene and 10 mL of acetic acid were added and stirred at 150° C. for 12 hours. The mixture was cooled to ambient temperature and an excessive amount of water was added thereto to form a solid. The solid was filtered, washed with water and then ethanol, and dried to prepare a compound B-13-1. (7.2 g, yield 78%): MS [M+H]$^+$=463

[Compound B-13]

A compound B-13 was prepared in the same manner as in the method for preparing the compound B-1 of Preparation Example II-1, except that in the method for preparing the compound B-1 of Preparation Example II-1, the compound B-13-1 (6.2 g, 13.4 mmol) was used instead of the compound A-1. (5.8 g, yield 77%): MS [M+H]$^+$=559

Preparation Example II-14

Preparation of Compound B-14

[Compound B-14-1]

5,5'-Dibromo-2,2'-dithiophene (5.00 g, 15.4 mmol), phenylboric acid (2.07 g, 17.0 mmol) and sodium carbonate (4.90 g, 46.3 mmol) were suspended in a mixture of toluene (30 mL) and water (15 mL). To the suspension, tetrakis(triphenylphosphine)palladium (0.50 g, 0.46 mmol) was added. The resulting mixture was stirred under reflux for about 24 hours. The refluxed mixture was cooled to room temperature and extracted using chloroform. The organic extract was dried over magnesium sulfate, and concentrated in vacuum. The residue was purified by column chromatography (n-hexane) to prepare a phenylthiophene compound B-14-1 (2.80 g, yield 75%).
MS [M+H]$^+$=243

[Compound B-14]

To a solution of the compound B-14-1 prepared as the above (2.80 g, 11.6 mmol) in a mixture of chloroform (40 mL) and acetic acid (40 mL), N-bromosuccinimide (5.60 g, 2.1 mmol) was added at 0° C. The mixture was heated to 60° C., and stirred at the same temperature for about 1 hour. Thereafter, the mixture was cooled to room temperature, and stirred for about 24 hours. Then, the mixture was added to an aqueous potassium hydroxide solution, and the mixture was extracted using chloroform. The organic layer was dried over magnesium sulfate and concentrated in vacuum. The resultant was recrystallized from ethanol and purified to obtain a compound B-14 (1.83 g, yield 49%).
MS [M+H]$^+$=321

Preparation Example III-1

Preparation of Compound C-1

[Compound C-1]

The compound B-1 prepared in the Preparation Example II-1 (28.7 g, 78 mmol), bis(pinacolato)diboron (23.4 g, 92 mmol) and potassium acetic acid (23 g, 234 mmol) were suspended in dioxane (400 mL). To the suspension, palladium (diphenylphosphinoferrocene)chloride (1.7 g, 2.34 mmol) was added. The mixture was stirred at 120° C. for about 6 hours and cooled to room temperature. The mixture was diluted by water (50 mL) and extracted using dichloromethane (3×50 mL). The organic extract was dried over magnesium sulfate and concentrated in vacuum. The resultant was washed with ethanol and dried in vacuum to prepare a compound C-1 (27.3 g, yield 92%): MS [M+H]$^+$=381

Preparation Example III-2

Preparation of Compound C-2

[Compound C-2]

A compound C-2 was prepared in the same manner as in the method for preparing the compound C-1 of Preparation Example III-1, except that in the method for preparing the compound C-1 of Preparation Example III-1, the compound B-2 prepared in the Preparation Example II-2 (12 g, 21.6 mmol) was used instead of the compound B-1. (11.3 g, yield 92%): MS [M+H]⁺=569

Preparation Example III-3

Preparation of Compound C-3

[Compound C-3]

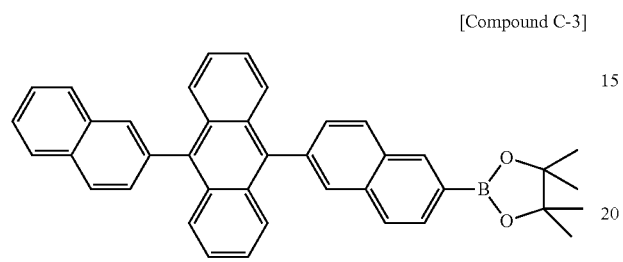

A compound C-3 was prepared in the same manner as in the method for preparing the compound C-1 of Preparation Example III-1, except that in the method for preparing the compound C-1 of Preparation Example III-1, the compound B-3 prepared in the Preparation Example II-3 (10 g, 18.4 mmol) was used instead of the compound B-1. (6.86 g, yield 67%): MS [M+H]⁺=557

Preparation Example III-4

Preparation of Compound C-4

[Compound C-4]

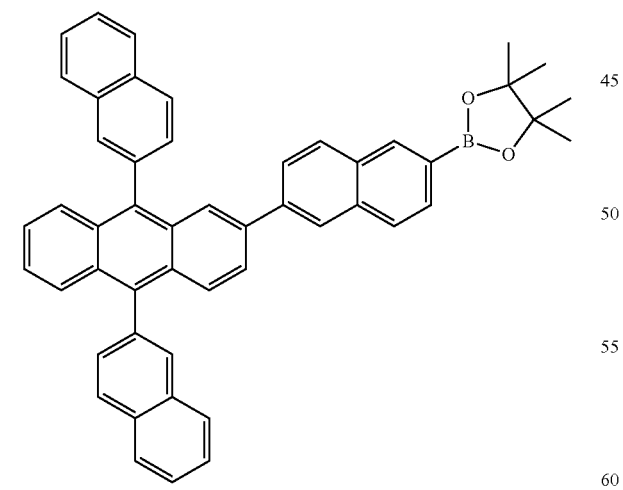

A compound C-4 was prepared in the same manner as in the method for preparing the compound C-1 of Preparation Example III-1, except that in the method for preparing the compound C-1 of Preparation Example III-1, the compound B-4 prepared in the Preparation Example II-4 (5 g, 7.5 mmol) was used instead of the compound B-1. (4.5 g, yield 87%): MS [M+H]⁺=683

Preparation Example I-5

Preparation of Compound C-5

[Comound C-5]

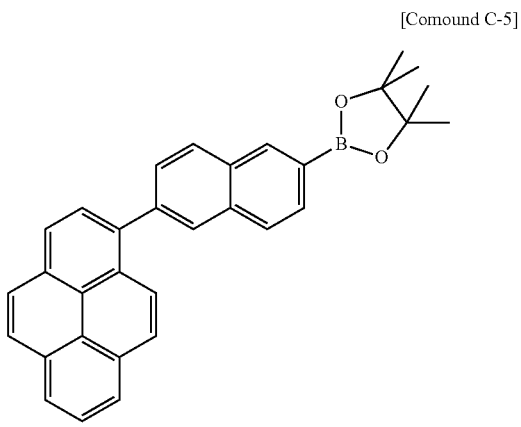 [SMILES: CC1(C)OB(c2ccc3cc(-c4ccc5ccc6cccc7ccc4c5c67)ccc3c2)OC1(C)C]

A compound C-5 was prepared in the same manner as in the method for preparing the compound C-1 of Preparation Example III-1, except that in the method for preparing the compound C-1 of Preparation Example III-1, the compound B-5 prepared in the Preparation Example II-5 (20 g, 45.4 mmol) was used instead of the compound B-1. (11.6 g, yield 56%): MS [M+H]⁺=455

Preparation Example III-6

Preparation of Compound C-6

[Compound C-6]

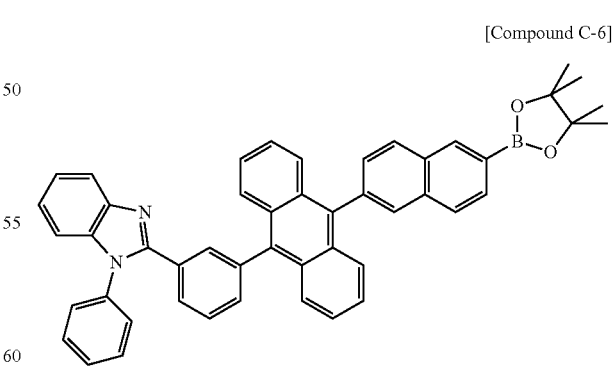

A compound C-6 was prepared in the same manner as in the method for preparing the compound C-1 of Preparation Example III-1, except that in the method for preparing the compound C-1 of Preparation Example III-1, the compound B-6 prepared in the Preparation Example II-6 (20.5 g, 30 mmol) was used instead of the compound B-1. (15.1 g, yield 72%): MS [M+H]⁺=699

Preparation Example III-7

Preparation of Compound C-7

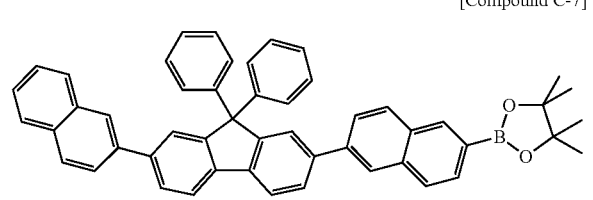

[Compound C-7]

A compound C-7 was prepared in the same manner as in the method for preparing the compound C-1 of Preparation Example III-1, except that in the method for preparing the compound C-1 of Preparation Example III-1, the compound B-11 prepared in the Preparation Example II-11 (31 g, 45.4 mmol) was used instead of the compound B-1. (28.8 g, yield 91%): MS [M]⁺=697

Preparation Example III-8

Preparation of Compound C-8

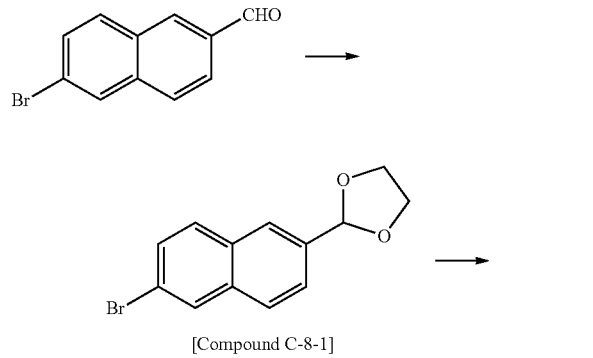

[Compound C-8-1]

[Compound C-8]

6-bromo-2-naphthaldehyde (4.7 g, 20 mmol) was mixed with 100 mL of toluene, 20 mL of ethylene glycol and p-toluene sulfonic acid (0.2 g, 1.2 mmol) and the mixture was stirred under heating for 48 hours. The reaction mixture was cooled to ambient temperature and the toluene solvent was distilled off in vacuum under reduced pressure. Ethanol and a small amount of water were added thereto, and thus formed solid was filtered and dried to prepare a compound C-8-1 (5.14 g, yield 92%).
MS [M]⁺=279

The compound C-8-1 prepared as the above, 2-(6-bromonaphthalene)-1,3-dioxolane (5 g, 17.9 mmol), was dissolved in anhydrous THF (60 mL), and n-BuLi (26.9 mmol, 2.5M in hexane solution, 10.7 mL) was added dropwise thereto at −78□ under nitrogen atmosphere. The mixture was stirred for about 1 hour and trimethylborate (6.2 mL, 53.7 mmol) was added dropwise at −78°. After about 30 minutes, the ice bath was removed and the mixture was stirred at room temperature for about 3 hours. 1N HCl (80 ml) was added to the mixture and the mixture was extracted using ethylacetate. The organic layer was dried over magnesium sulfate and concentrated in vacuum. A crude product was slurrified in petroleum ether, suction filtered, and dried to prepare 2-(6-formylnaphthalene)boronic acid compound C-8 (2.07 g, yield 57.8%).

Preparation Example III-9

Preparation of Compound C-9

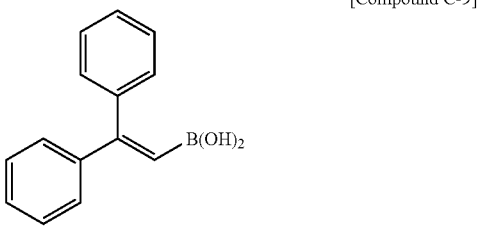

[Compound C-9]

A compound C-9 was prepared in the same manner as in the method for preparing the compound C-8 of Preparation Example III-8, except that in the method for preparing the compound C-8 of Preparation Example III-8, the compound B-8 prepared in the Preparation Example II-8 (10.7 g, 41.3 mmol) was used instead of the compound C-8-1. (4.44 g, yield 48%)

Preparation Example III-10

Preparation of Compound C-10

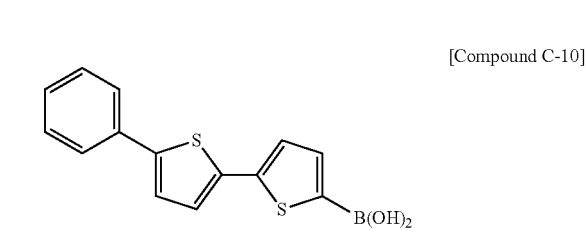 [SMILES: OB(O)c1ccc(-c2ccc(-c3ccccc3)s2)s1]

[Compound C-10]

A compound C-10 was prepared in the same manner as in the method for preparing the compound C-8 of Preparation Example III-8, except that in the method for preparing the compound C-8 of Preparation Example III-8, the compound B-14 prepared in the Preparation Example II-14 (18.3 g, 56.8 mmol) was used instead of the compound C-8-1 (7.1 g, yield 48.8%).

Preparation Example III-11

Preparation of Compound C-11

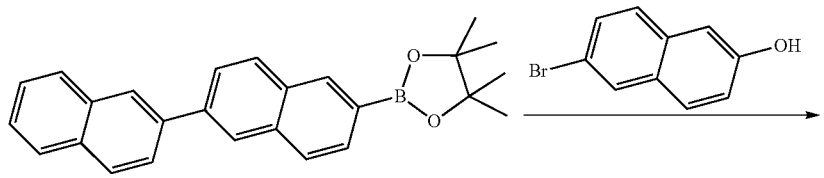

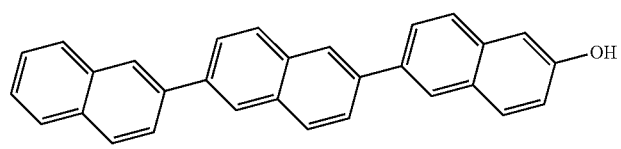

[Compound C-11-1]

A compound C-11-1 was prepared in the same manner as in the method for preparing the compound A-1 of Preparation Example I-1, except that in the method for preparing the compound A-1 of Preparation Example I-1, 6-bromo-2-naphtol (4.4 g, 20 mmol) was used, and the compound C-1 of the Preparation Example III-1 (7.6 g, 20 mmol) was used instead of naphthyl-2-boronic acid. (6.1 g, yield 77%): MS [M+H]$^+$=397

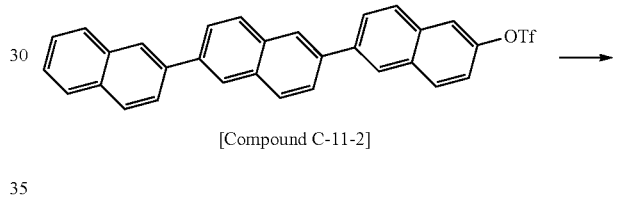

[Compound C-11-2]

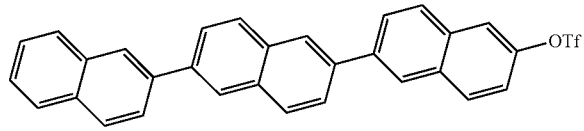

[Compound C-11-2]

A compound C-11-2 was prepared in the same manner as in the method for preparing the compound B-1 of Preparation Example II-1, except that in the method for preparing the compound B-1 of Preparation Example II-1, the compound C-11-1 (6.1 g, 15.4 mmol) was used instead of the compound A-1. (6.9 g, yield 91%): MS [M+H]$^+$=699

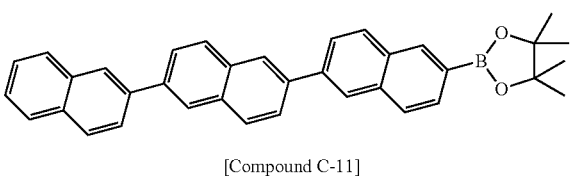

[Compound C-11]

A compound C-11 was prepared in the same manner as in the method for preparing the compound C-1 of Preparation Example III-1, except that in the method for preparing the compound C-1 of Preparation Example III-1, the compound C-11-2 (6.0 g, 12.2 mmol) was used instead of the compound B-1. (3.5 g, yield 56%): MS [M+H]$^+$=507

Example I-1

Preparation of Compound 1-17

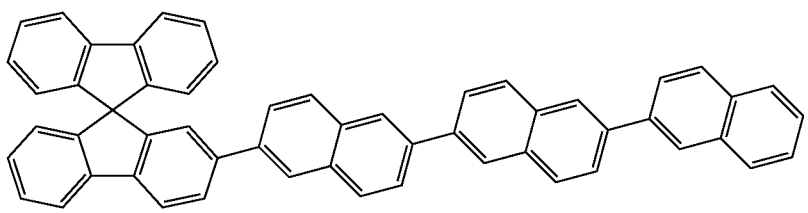 [SMILES: c1ccc2c(c1)-c1ccccc1C21c2ccccc2-c2ccc(-c3ccc4cc(-c5ccc6cc(-c7ccc8ccccc8c7)ccc6c5)ccc4c3)cc21]

A compound 1-17 was prepared in the same manner as in the method for preparing the compound A-1 of Preparation Example I-1, except that in the method for preparing the compound A-1 of Preparation Example I-1, the compound C-1 of the Preparation Example III-1 (1.9 g, 5 mmol) was used instead of naphthyl-2-boronic acid, and the compound B-2 of the Preparation Example II-2 (2.8 g, 5 mmol) was used instead of 6-bromo-2-naphtol. (3.0 g yield 86%): MS [M+H]$^+$=695

Example 1-2

Preparation of Compound 2-41

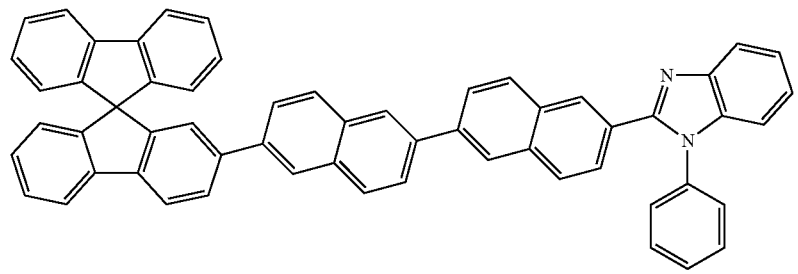 [SMILES: c1ccc(-n2c(-c3ccc4cc(-c5ccc6cc(-c7ccc8c(c7)C7(c9ccccc9-c9ccccc97)c7ccccc7-8)ccc6c5)ccc4c3)nc3ccccc32)cc1]

A compound 2-41 was prepared in the same manner as in the method for preparing the compound A-1 of Preparation Example I-1, except that in the method for preparing the compound A-1 of Preparation Example I-1, the compound C-2 of the Preparation Example III-2 (2.8 g, 5 mmol) was used instead of naphthyl-2-boronic acid, and the compound B-9 (2.0 g, 5 mmol) was used instead of 6-bromo-2-naphtol. (2.9 g, yield 77%): MS [M+H]$^+$=761

Figure 5:
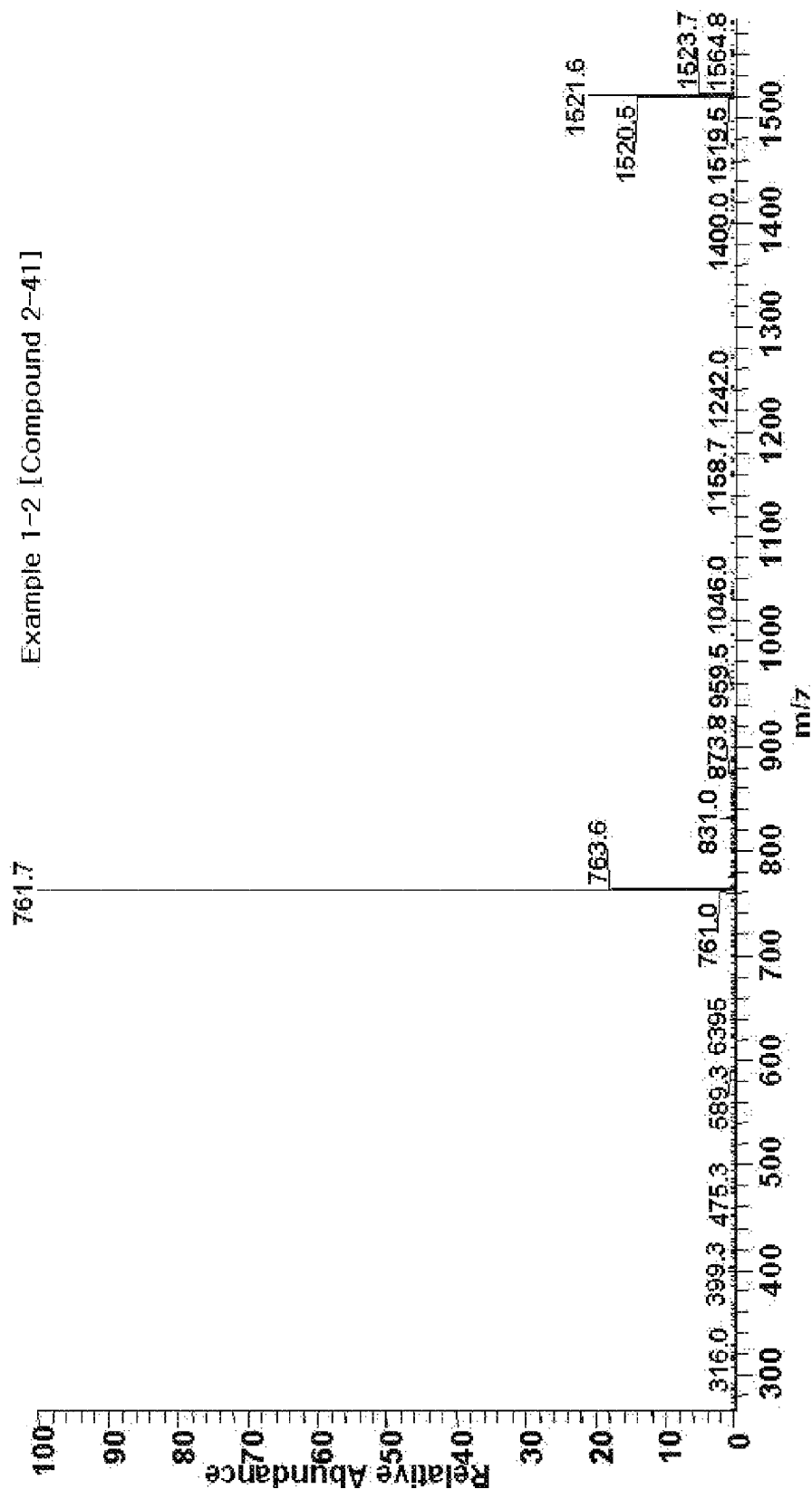
FIGS. 5 to 14 show data to confirm the synthesis of compounds prepared in Examples 1-2, 1-4, 1-5, 1-6, 1-7, 1-8, 1-9, 1-10, 2-1 and 2-4.

FIG. 5 shows the synthesis data of the compound 2-41.

Example 1-3

Preparation of Compound 2-43

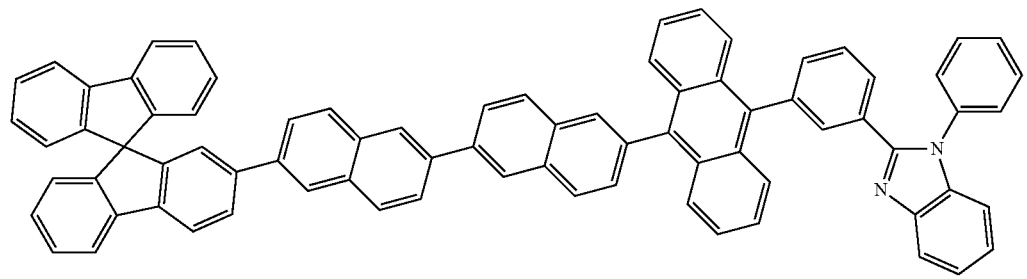 [SMILES: c1ccc(-n2c(-c3cccc(-c4c5ccccc5c(-c5ccc6cc(-c7ccc8cc(-c9ccc%10c(c9)C9(c%11ccccc%11-c%11ccccc%119)c9ccccc9-%10)ccc8c7)ccc6c5)c5ccccc45)c3)nc3ccccc32)cc1]

A compound 2-43 was prepared in the same manner as in the method for preparing the compound A-1 of Preparation Example I-1, except that in the method for preparing the compound A-1 of Preparation Example I-1, the compound C-2 of the Preparation Example III-2 (2.8 g, 5 mmol) was used instead of naphthyl-2-boronic acid, and the compound B-6 of the Preparation Example II-6 (3.4 g, 5 mmol) was used instead of 6-bromo-2-naphtol. (3.4 g, yield 67%): MS [M+H]$^+$=1013

Example 1-4

Preparation of Compound 1-157

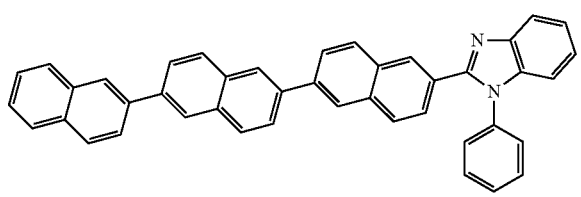 [SMILES: c1ccc(-n2c(-c3ccc4cc(-c5ccc6cc(-c7ccc8ccccc8c7)ccc6c5)ccc4c3)nc3ccccc32)cc1]

A compound 1-157 was prepared in the same manner as in the method for preparing the compound A-1 of Preparation Example I-1, except that in the method for preparing the compound A-1 of Preparation Example I-1, the compound C-1 of the Preparation Example III-1 (3.8 g, 10 mmol) was used instead of naphthyl-2-boronic acid, and the compound B-9 of the Preparation Example II-9 (4.0 g, 10 mmol) was used instead of 6-bromo-2-naphtol. (4.0 g, yield 70%): MS [M+H]$^+$=573

Figure 6:
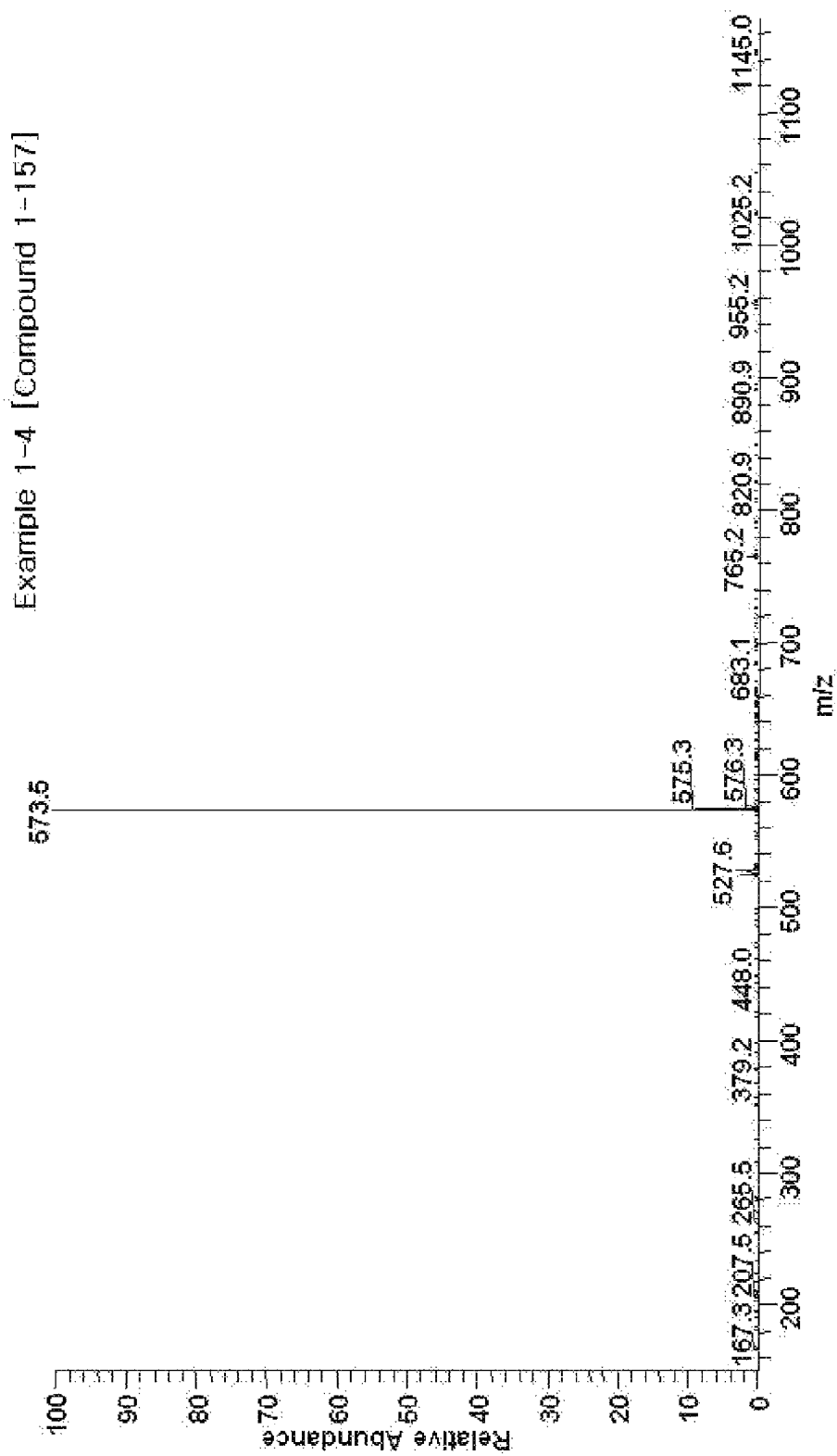

FIG. 6 shows the synthesis data of the compound 1-157.

Example 1-5

Preparation of Compound 1-173

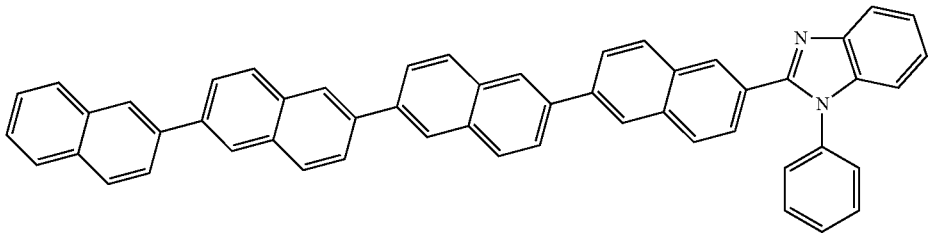 [SMILES: c1ccc(-n2c(-c3ccc4cc(-c5ccc6cc(-c7ccc8cc(-c9ccc%10ccccc%10c9)ccc8c7)ccc6c5)ccc4c3)nc3ccccc32)cc1]

A compound 1-173 was prepared in the same manner as in the method for preparing the compound A-1 of Preparation Example I-1, except that in the method for preparing the compound A-1 of Preparation Example I-1, the compound C-11 of the Preparation Example III-11 (5.1 g, 10 mmol) was used instead of naphthyl-2-boronic acid, and the compound B-9 of the Preparation Example II-9 (4.0 g, 10 mmol) was used instead of 6-bromo-2-naphtol. (3.4 g, yield 49%): MS [M+H]$^+$=699

Figure 7:
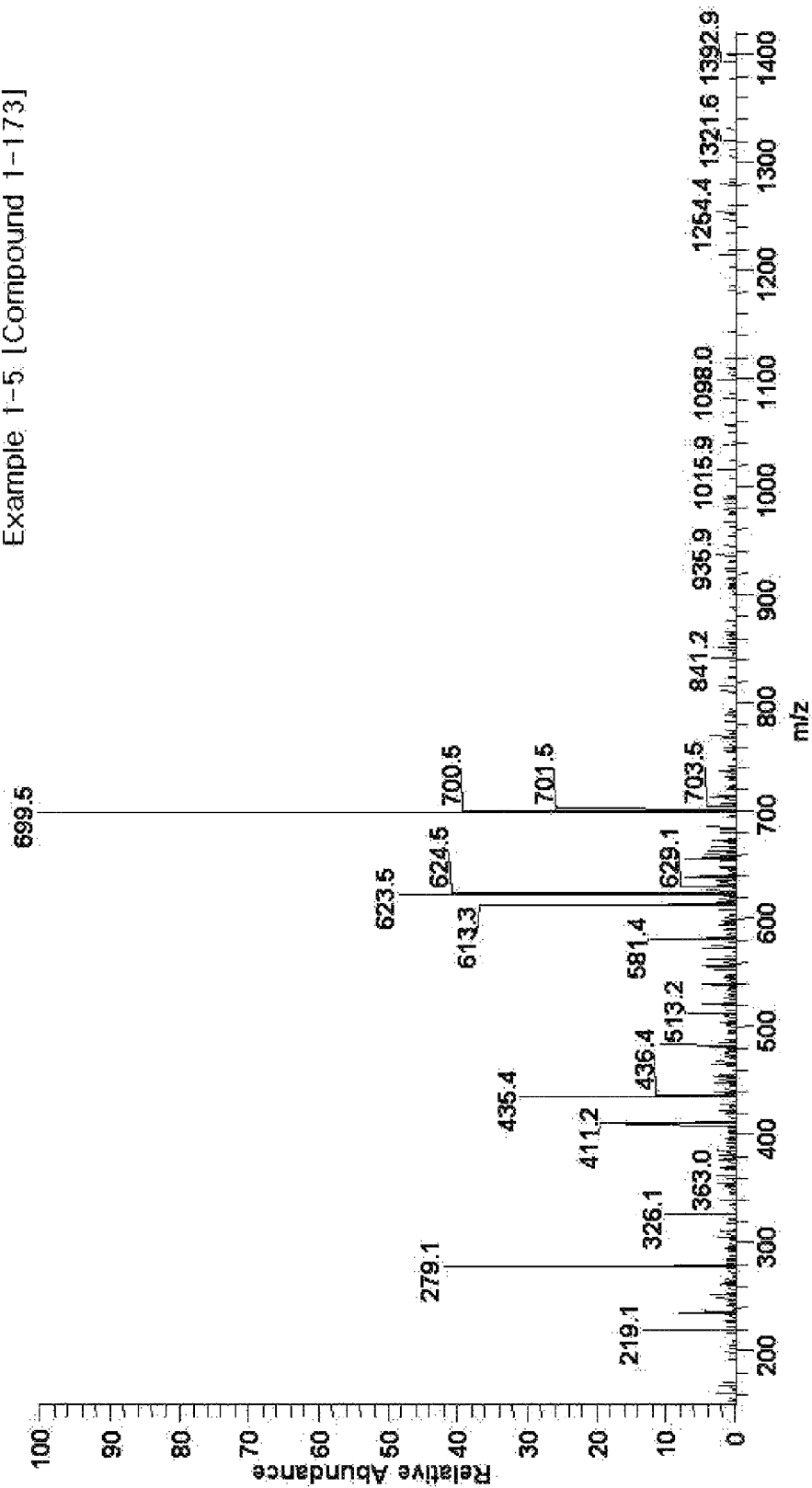

FIG. 7 shows the synthesis data of the compound 1-173.

Example 1-6

Preparation of Compound 1-166

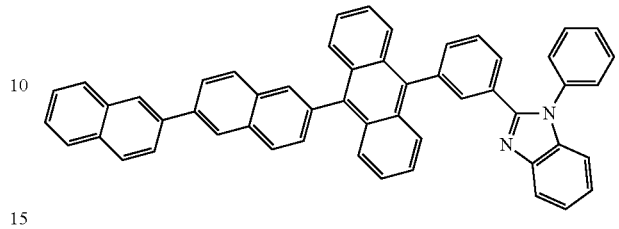

A compound 1-166 was prepared in the same manner as in the method for preparing the compound A-1 of Preparation Example I-1, except that in the method for preparing the compound A-1 of Preparation Example I-1, naphthyl-2-boronic acid (1.7 g, 10 mmol) was used, and the compound B-6 of the Preparation Example II-6 (6.5 g, 9.5 mmol) was used instead of 6-bromo-2-naphtol. (6.0 g, yield 90%): MS [M+H]$^+$=699

Figure 8:
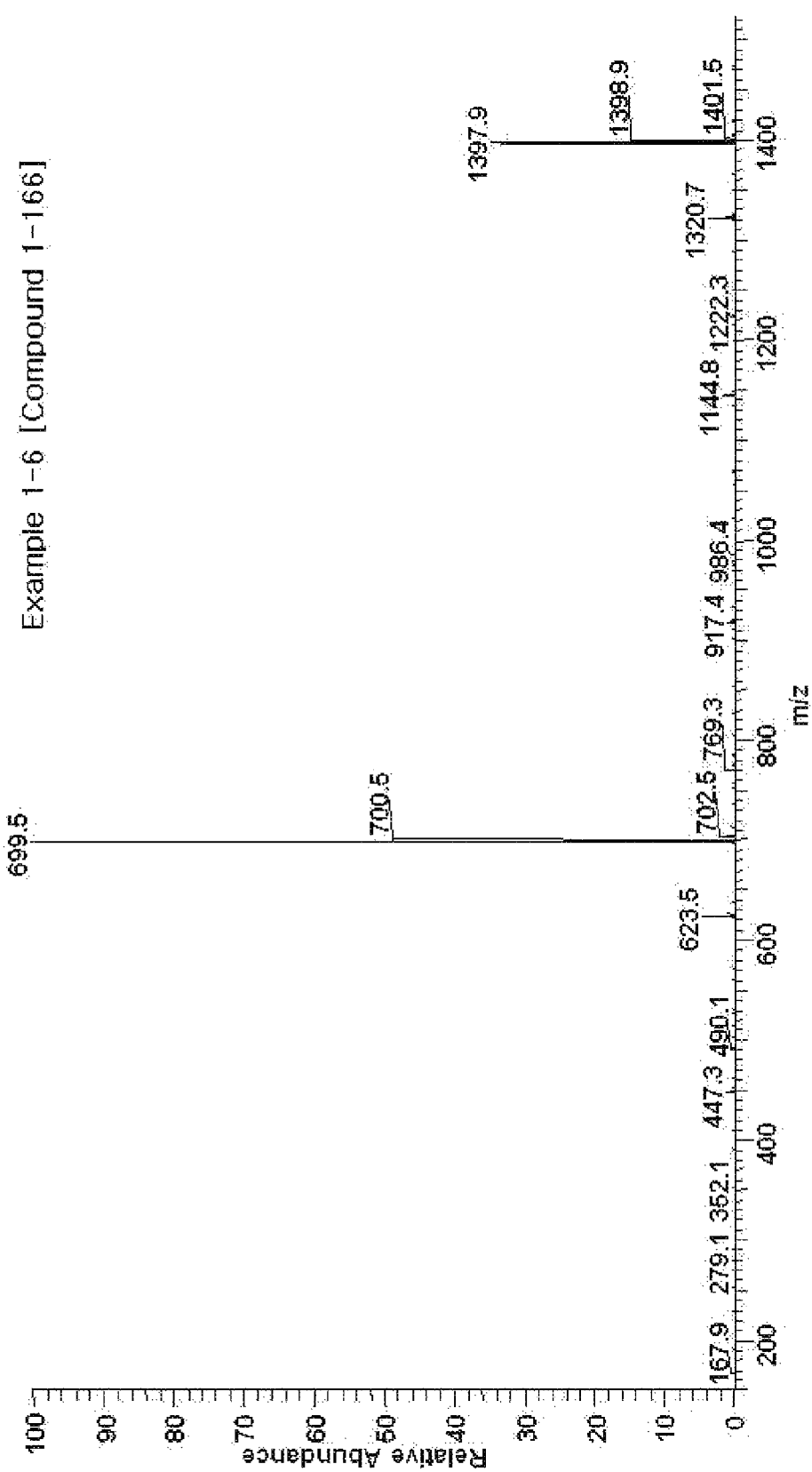

FIG. 8 shows the synthesis data of the compound 1-166.

Example 1-7

Preparation of Compound 2-44

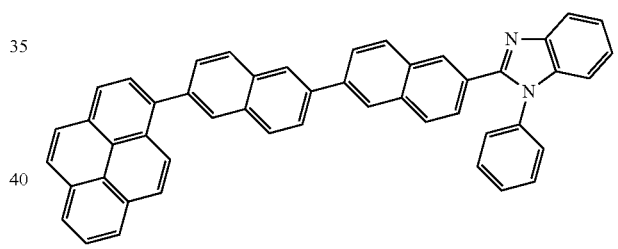

A compound 2-44 was prepared in the same manner as in the method for preparing the compound A-1 of Preparation Example I-1, except that in the method for preparing the compound A-1 of Preparation Example I-1, the compound C-5 of the Preparation Example III-5 (4.5 g, 10 mmol) was used instead of naphthyl-2-boronic acid, and the compound B-9 of the Preparation Example II-9 (4.0 g, 10 mmol) was used instead of 6-bromo-2-naphtol. (3.6 g, yield 56%): MS [M+H]$^+$=647

Figure 9:
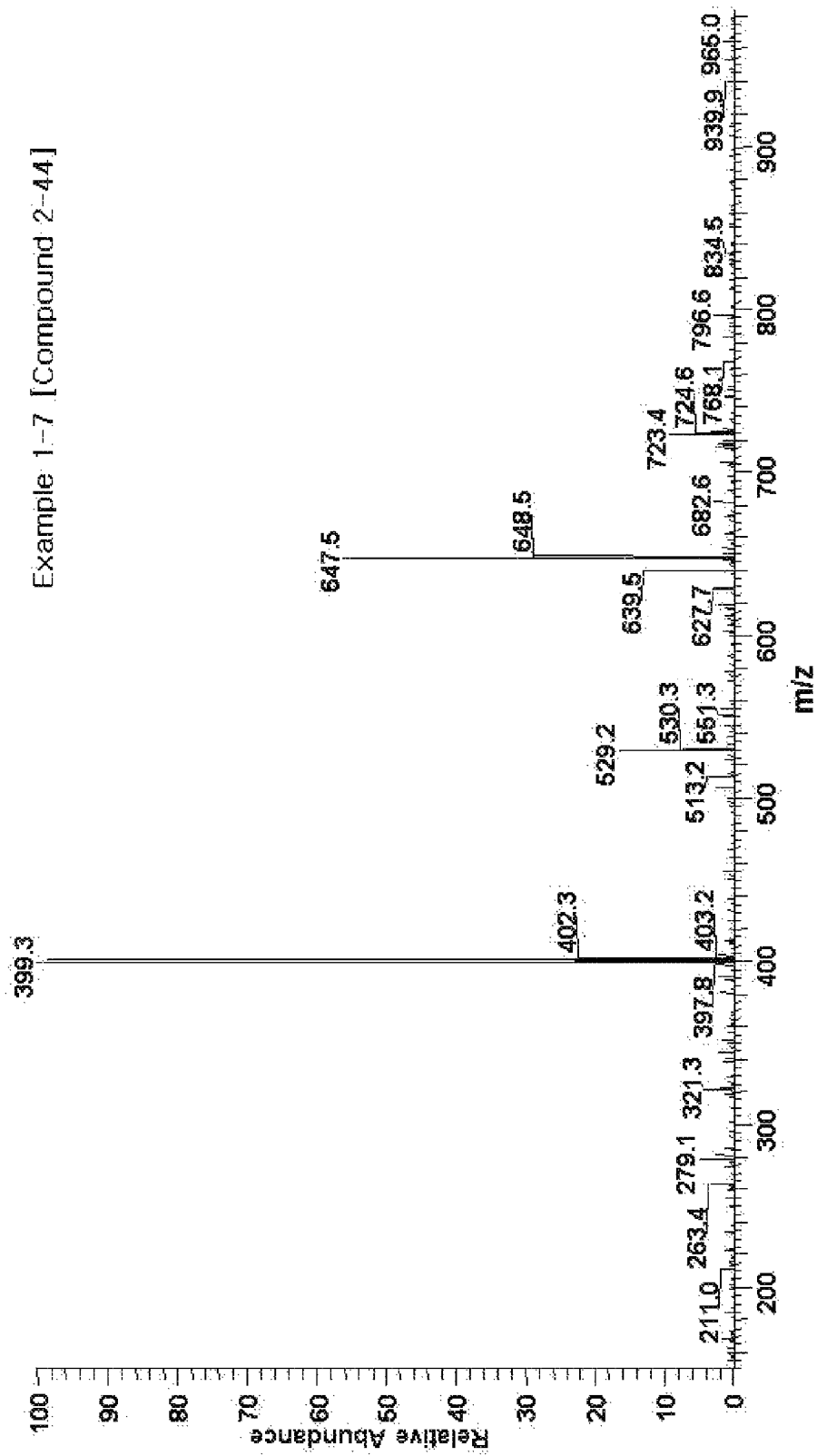

FIG. 9 shows the synthesis data of the compound 2-44.

Example 1-8

Preparation of Compound 1-70

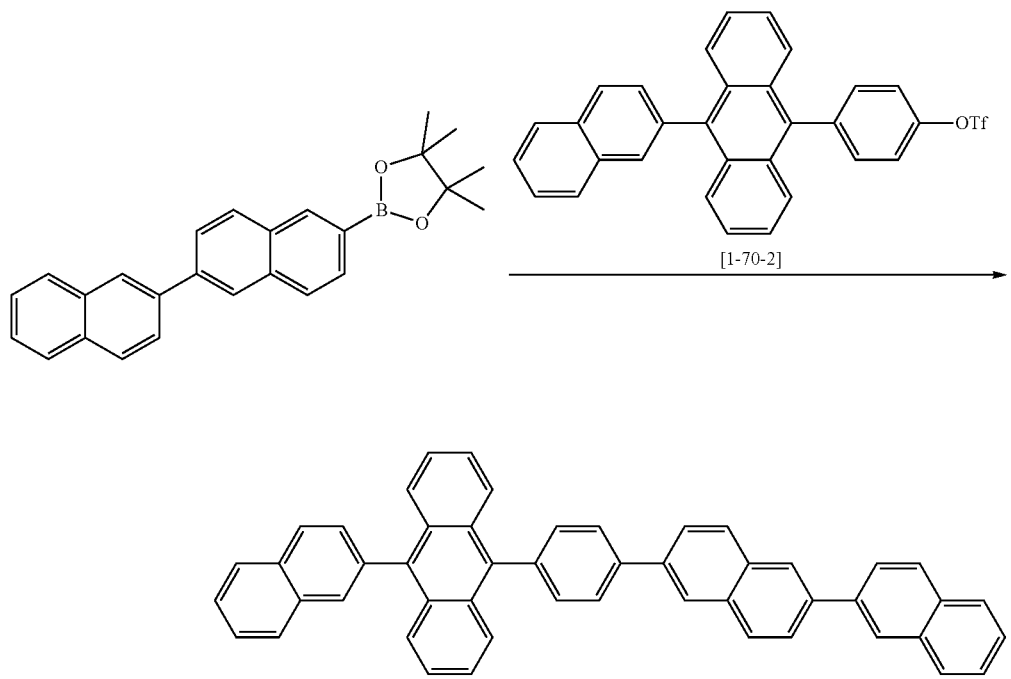

A compound 1-70 was prepared in the same manner as in the method for preparing the compound A-1 of Preparation Example I-1, except that in the method for preparing the compound A-1 of Preparation Example I-1, the compound C-1 of the Preparation Example III-1 (3.8 g, 10 mmol) was used instead of naphthyl-2-boronic acid, and the compound 1-70-2 shown in the above reaction scheme (4.9 g, 10 mmol) was used instead of 6-bromo-2-naphtol. (4.6 g, yield 72%): MS $[M+H]^+$=633

Figure 10:
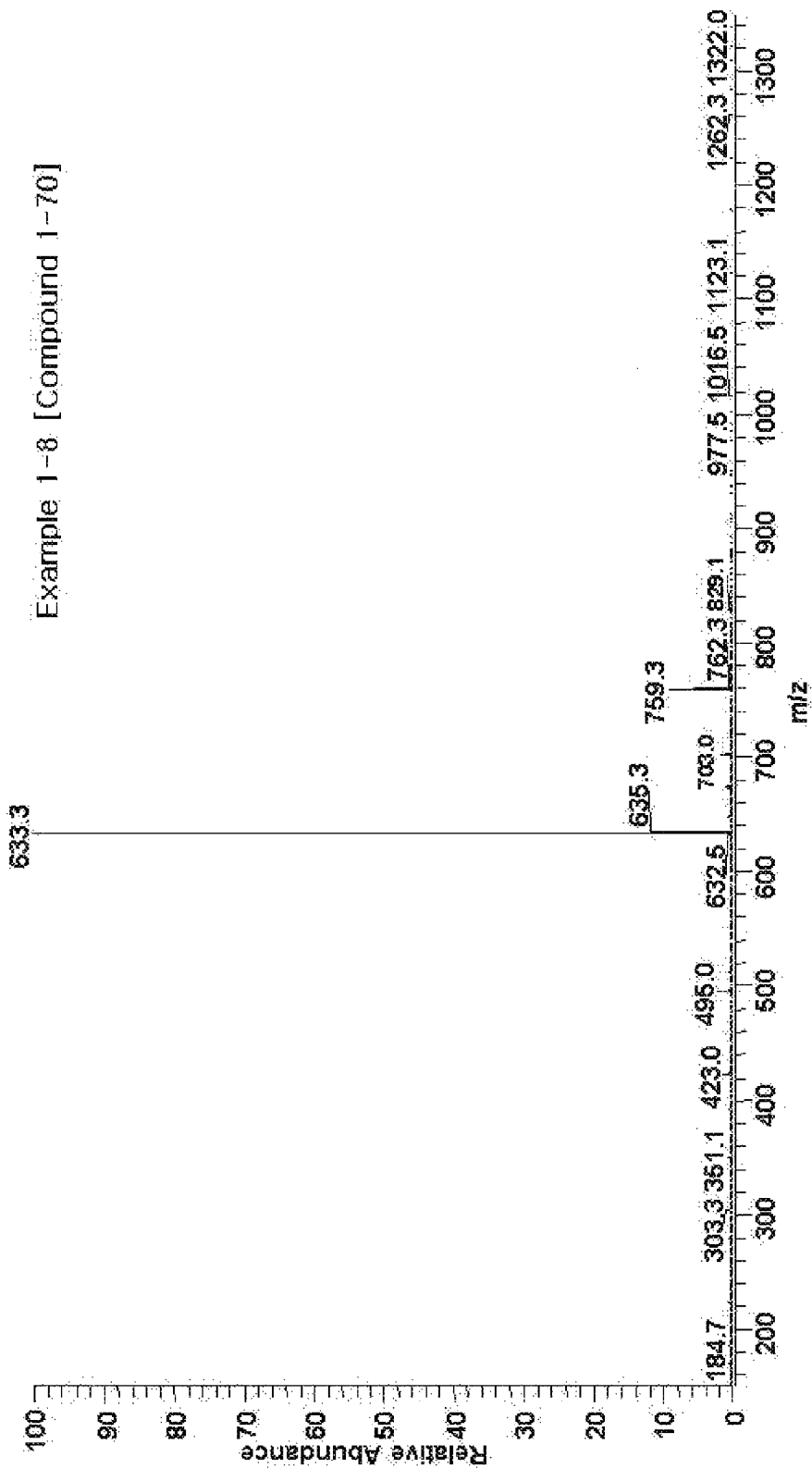

FIG. 10 shows the synthesis data of the compound 1-70.

Example 1-9

Preparation of Compound 1-71

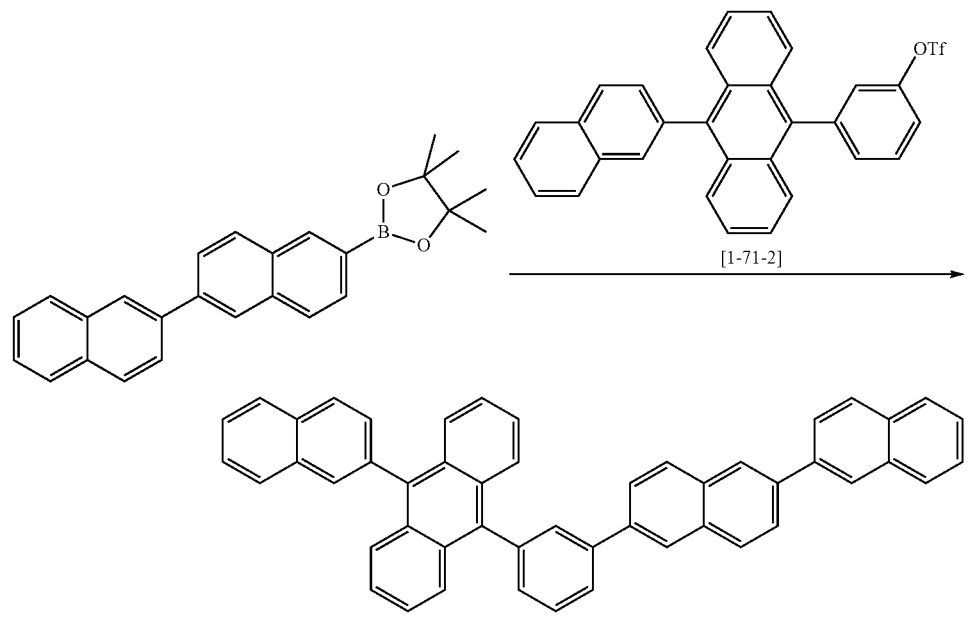

A compound 1-71 was prepared in the same manner as in the method for preparing the compound A-1 of Preparation Example I-1, except that in the method for preparing the compound A-1 of Preparation Example I-1, the compound C-1 of the Preparation Example III-1 (3.8 g, 10 mmol) was used instead of naphthyl-2-boronic acid, and the compound 1-71-2 shown in the above reaction scheme (4.9 g, 10 mmol) was used instead of 6-bromo-2-naphtol. (4.2 g, yield 66%): MS [M+H]$^+$=633

Figure 11:
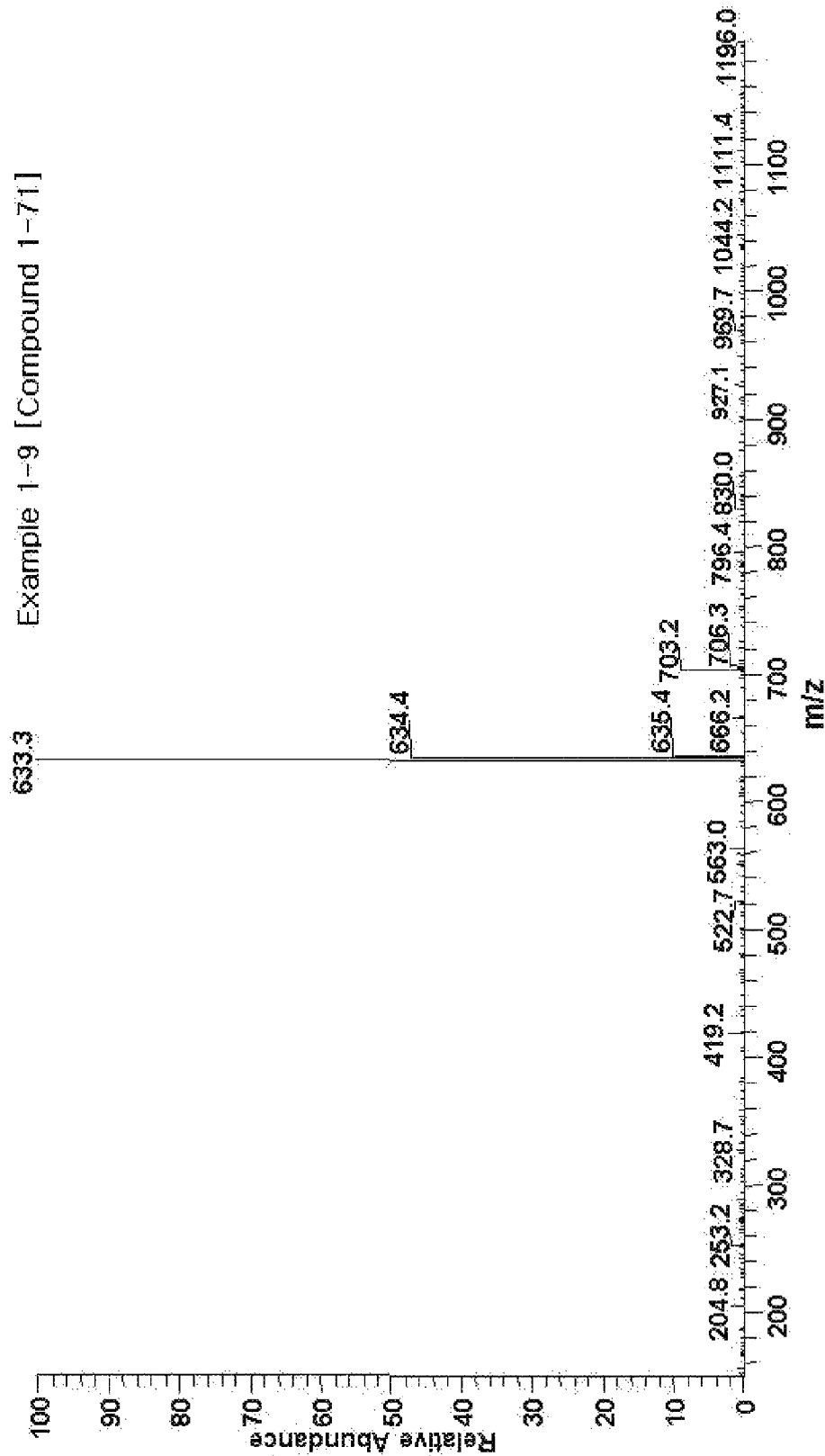

FIG. 11 shows the synthesis data of the compound 1-71.

Example 1-10

Preparation of Compound 1-72

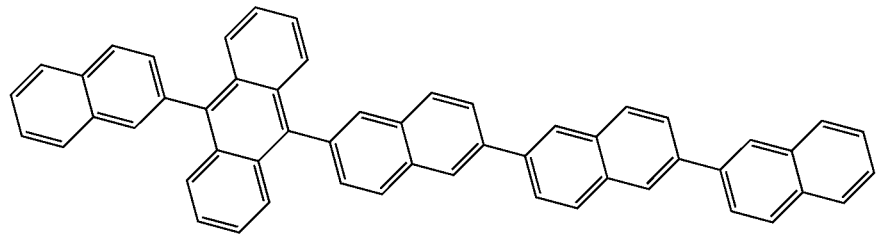 [SMILES: c1ccc2cc(-c3ccc4cc(-c5ccc6cc(-c7c8ccccc8c(-c8ccc9ccccc9c8)c8ccccc78)ccc6c5)ccc4c3)ccc2c1]

A compound 1-72 was prepared in the same manner as in the method for preparing the compound A-1 of Preparation Example I-1, except that in the method for preparing the compound A-1 of Preparation Example I-1, the compound C-1 of the Preparation Example III-1 (3.8 g, 10 mmol) was used instead of naphthyl-2-boronic acid, and the compound B-3 of the Preparation Example II-3 (5.4 g, 10 mmol) was used instead of 6-bromo-2-naphtol. (5.0 g, yield 73%): MS [M+H]$^+$=683

Figure 12:
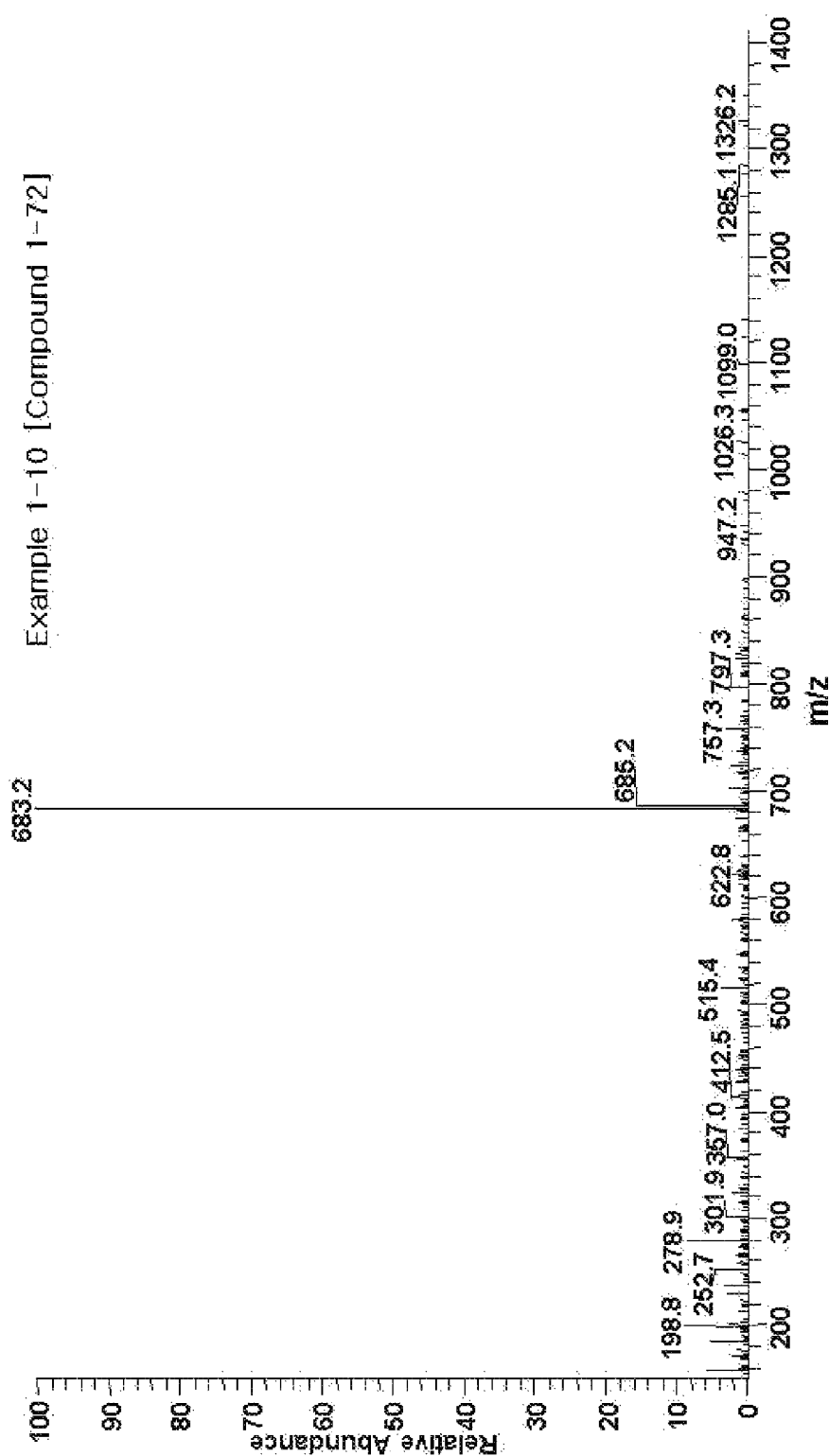

FIG. 12 shows the synthesis data of the compound 1-72.

Example 1-11

Preparation of Compound 1-201

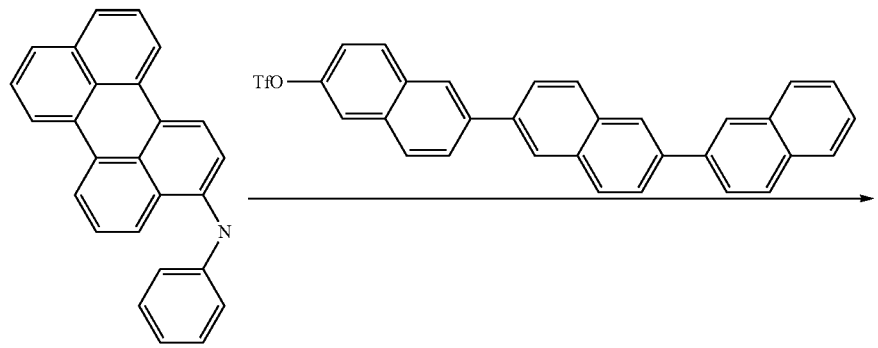

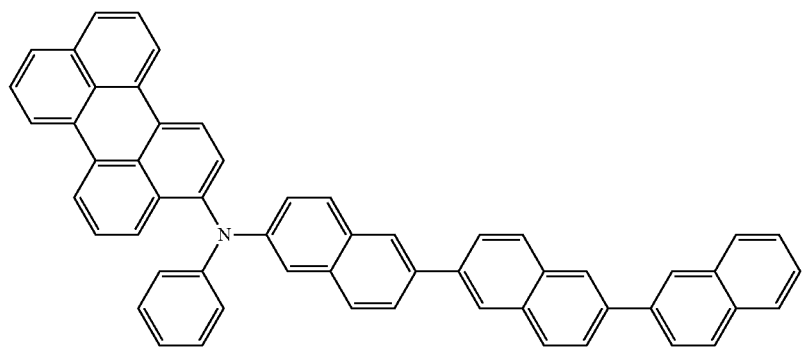

To the compound C-11-2 prepared in the Preparation Example III-11 (2.5 g, 5.1 mmol), 80 mL of xylene was added, N-phenyl-3-perylenamine (1.7 g, 5.0 mmol), Na(O$^t$Bu) (0.97 g, 10 mmol), Pd(OAc)$_2$[0.01 g, 0.048 mmol] and P(t-Bu)$_3$ (0.01 g, 0.072 mmol) were added, and the mixture was stirred under heating at 140° C. for 3 hours. The reaction temperature was lowered to ambient temperature and ethanol was added to the mixture to form a precipitate. The resulting solid was filtered, and dried. The solid was dissolved in an excessive amount of THF, and passed through a silica gel layer for purification. THF was removed in vacuum under reduced pressure, and purified with ethylacetate and ethanol to prepare a compound 1-201 (2.3 g, yield 64%). MS [M+H]$^+$=722

Example 2-1

Preparation of Compound 1-18

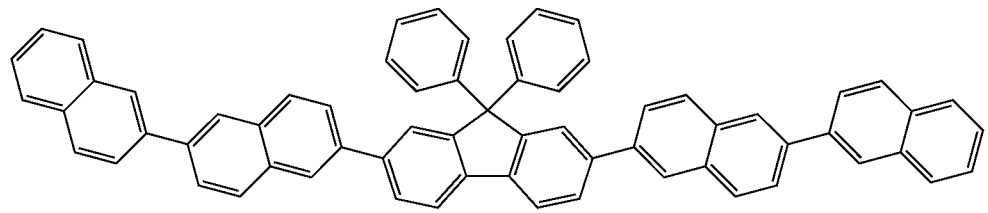 [SMILES: c1ccc(C2(c3ccccc3)c3cc(-c4ccc5cc(-c6ccc7ccccc7c6)ccc5c4)ccc3-c3ccc(-c4ccc5cc(-c6ccc7ccccc7c6)ccc5c4)cc32)cc1]

A compound 1-18 was prepared in the same manner as in the method for preparing the compound A-1 of Preparation Example I-1, except that in the method for preparing the compound A-1 of Preparation Example I-1, the compound C-1 of the Preparation Example III-1 (3.8 g, 10 mmol) was used instead of naphthyl-2-boronic acid, and the compound B-10 of the Preparation Example II-10 (2.1 g, 4.4 mmol) was used instead of 6-bromo-2-naphtol. (3.5 g, yield 97%): MS [M+H]$^+$=823

Figure 13:
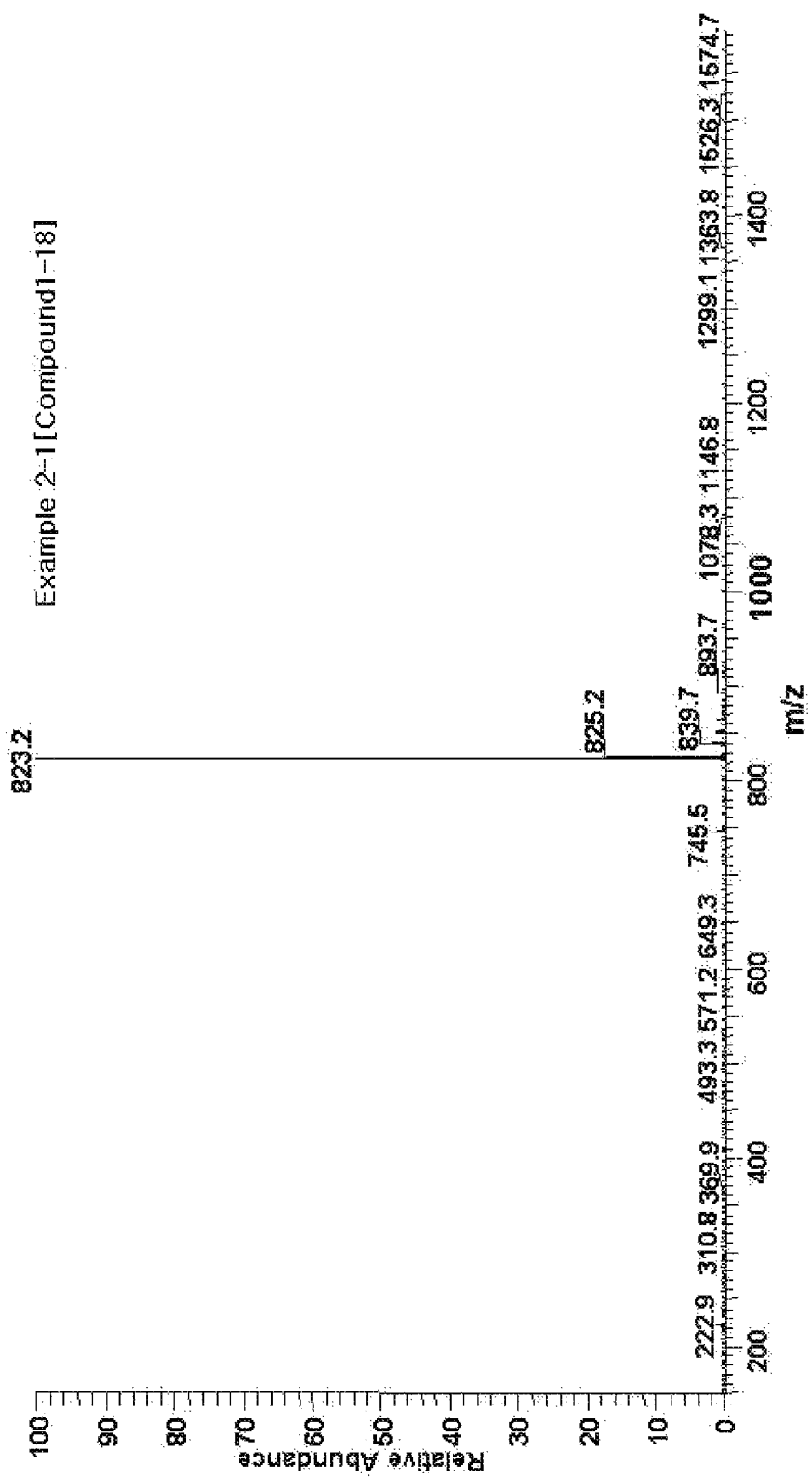

FIG. 13 shows the synthesis data of the compound 1-18.

Example 2-2

Preparation of Compound 2-45

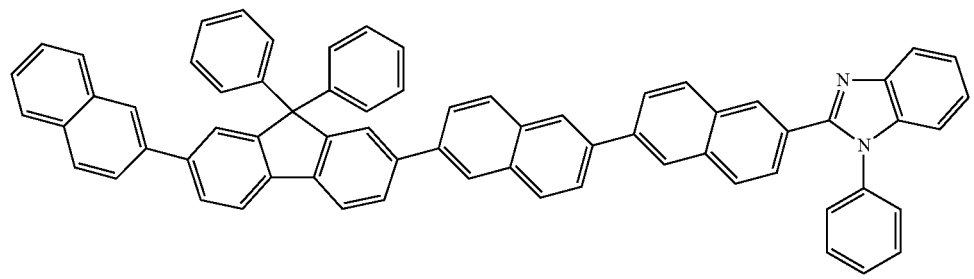 [SMILES: c1ccc(-n2c(-c3ccc4cc(-c5ccc6cc(-c7ccc8c(c7)C(c7ccccc7)(c7ccccc7)c7cc(-c9ccc%10ccccc%10c9)ccc7-8)ccc6c5)ccc4c3)nc3ccccc32)cc1]

A compound 2-45 was prepared in the same manner as in the method for preparing the compound A-1 of Preparation Example I-1, except that in the method for preparing the compound A-1 of Preparation Example I-1, the compound C-7 of the Preparation Example III-7 (3.5 g, 5 mmol) was used instead of naphthyl-2-boronic acid, and the compound B-9 of the Preparation Example II-9 (1.9 g, 5 mmol) was used instead of 6-bromo-2-naphtol. (2.5 g, yield 56%): MS [M+H]$^+$=889

Example 2-3

Preparation of Compound 2-47

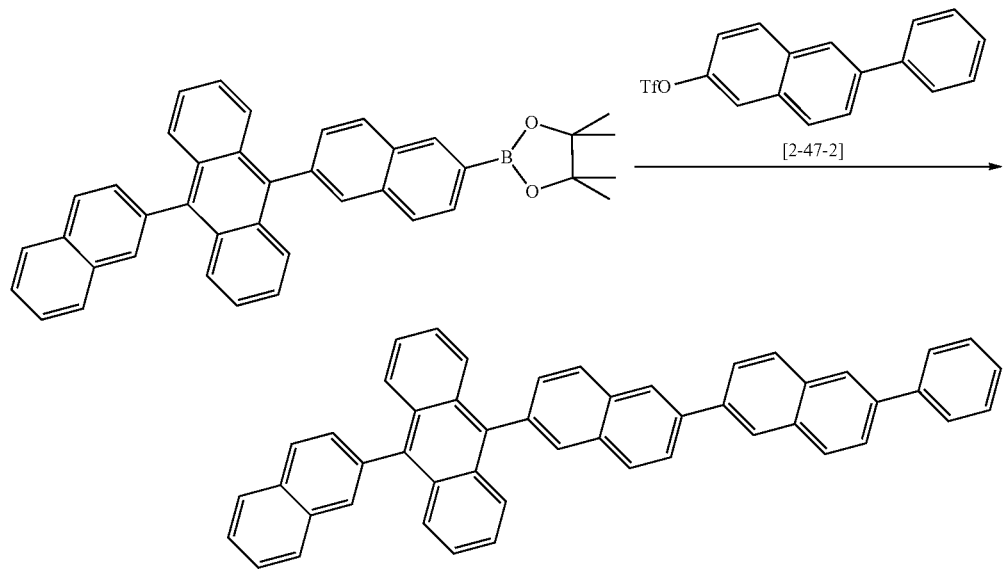

A compound 2-47 was prepared in the same manner as in the method for preparing the compound A-1 of Preparation Example I-1, except that in the method for preparing the compound A-1 of Preparation Example I-1, the compound C-3 of the Preparation Example III-3 (5.6 g, 10 mmol) was used instead of naphthyl-2-boronic acid, and the compound 2-47-2 shown in the above reaction scheme (3.2 g, 10 mmol) was used instead of 6-bromo-2-naphtol. (3.5 g, yield 56%): MS $[M+H]^+$=633

Example 2-4

Preparation of Compound 2-8

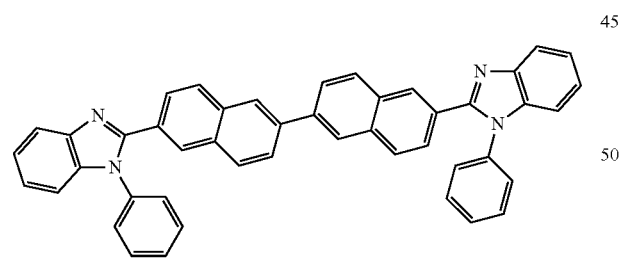

The compound C-1 of the Preparation Example III-1 (5 g, 12.6 mmol), $Pd(OAc)_2$ [0.14 g, 0.63 mmol], n-$Bu_4NBr$ (2.03 g, 6.3 mmol), $K_2CO_3$ (1.74 g, 12.6 mmol), dimethylformaldehyde (DMF, 40 mL) and distilled water ($H_2O$, 10 mL) were mixed, and the mixture was stirred under heating for 12 hours. The mixture was cooled to ambient temperature, and then purified by column chromatography (THF/n-Hex=1/4) to prepare a compound 2-8 (0.6 g, yield 7.4%).

Figure 14:
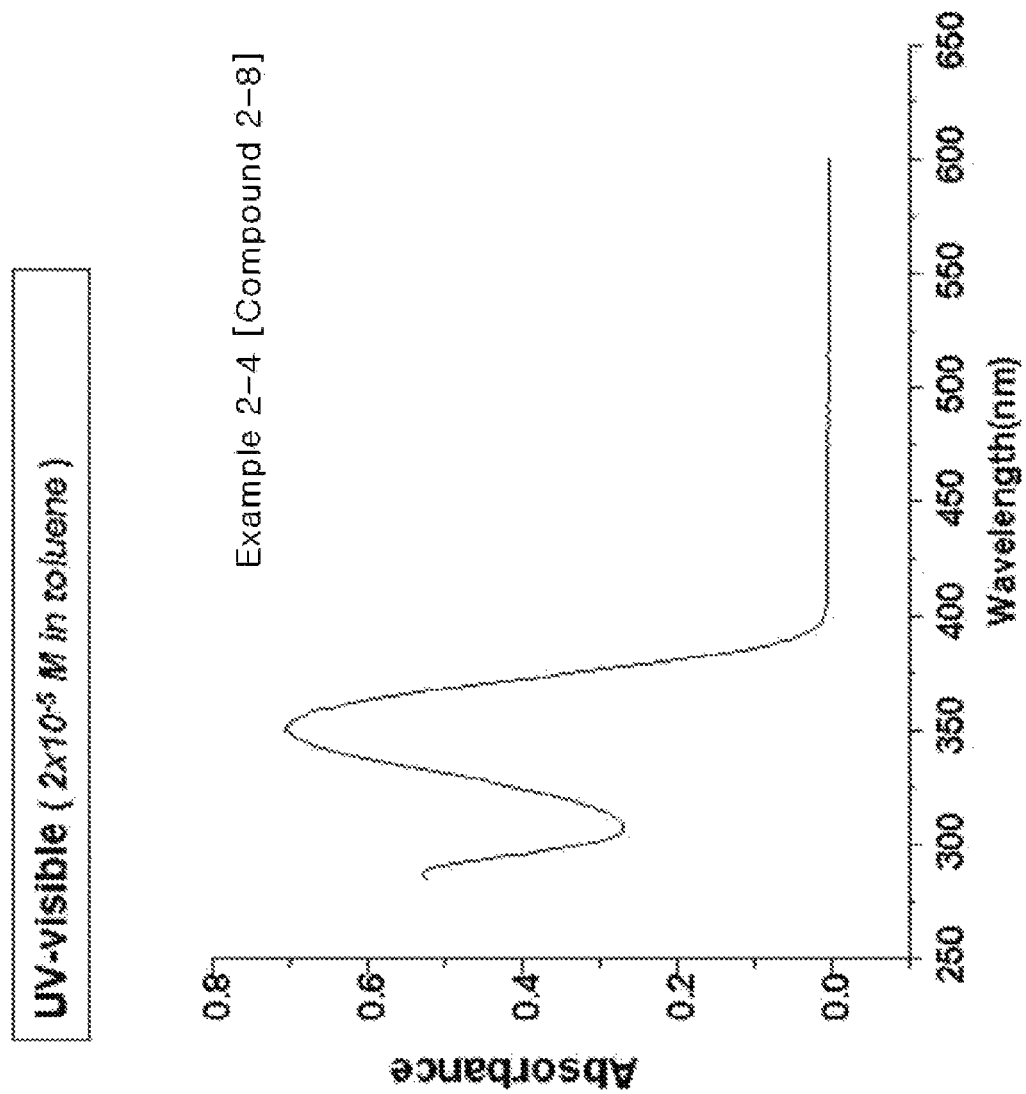

MS $[M+H]^+$=639
Tm; 306.5° C.
Tg; 130.9° C.
FIG. 14 shows the synthesis data of the compound 2-8.

Example 2-5

Preparation of Compound 2-50

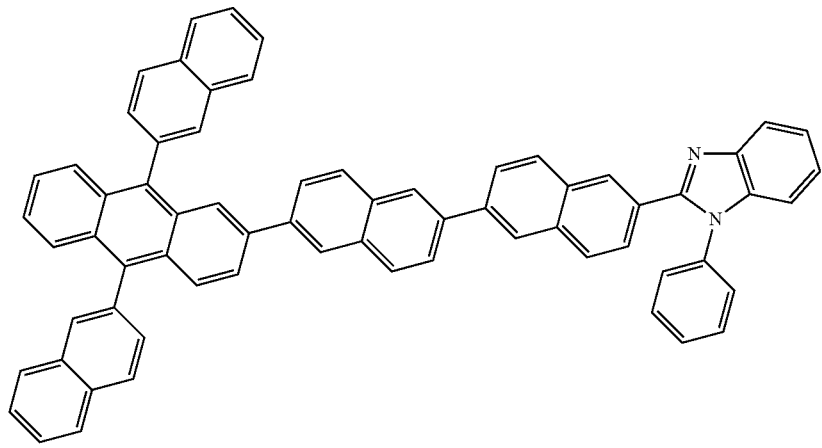 [SMILES: c1ccc(-n2c(-c3ccc4cc(-c5ccc6cc(-c7ccc8c(-c9ccc%10ccccc%10c9)c9ccccc9c(-c9ccc%10ccccc%10c9)c8c7)ccc6c5)ccc4c3)nc3ccccc32)cc1]

A compound 2-50 was prepared in the same manner as in the method for preparing the compound A-1 of Preparation Example I-1, except that in the method for preparing the compound A-1 of Preparation Example I-1, the compound C-4 of the Preparation Example III-4 (3.4 g, 5 mmol) was used instead of naphthyl-2-boronic acid, and the compound B-9 of the Preparation Example II-9 (1.9 g, 5 mmol) was used instead of 6-bromo-2-naphtol.

(2.5 g, yield 56%): MS [M+H]$^{+}$=875

Example 2-6

Preparation of Compound 2-51

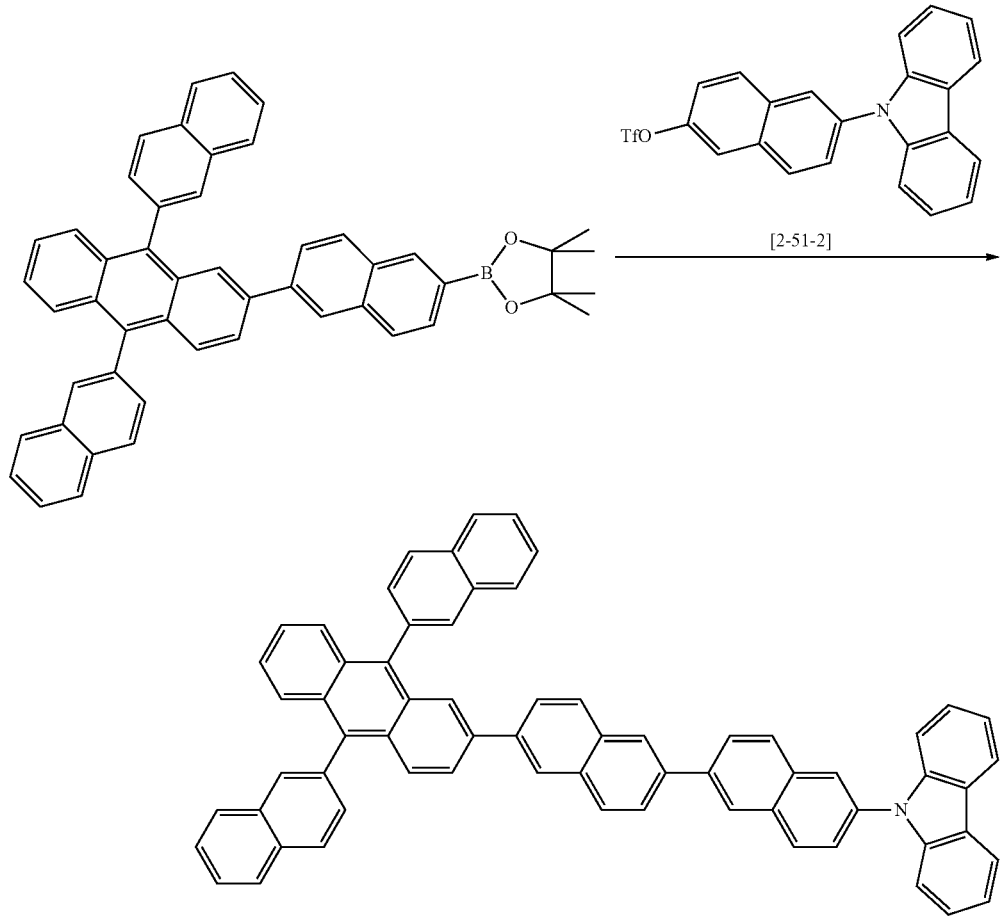

A compound 2-51 was prepared in the same manner as in the method for preparing the compound A-1 of Preparation Example I-1, except that in the method for preparing the compound A-1 of Preparation Example I-1, the compound C-4 of the Preparation Example III-4 (3.4 g, 5 mmol) was used instead of naphthyl-2-boronic acid, and the compound 2-51-2 shown in the above reaction scheme (2.0 g, 5 mmol) was used instead of 6-bromo-2-naphtol.

(2.8 g, yield 67%): MS [M+H]$^+$=848

Example 2-7

Preparation of Compound 2-9

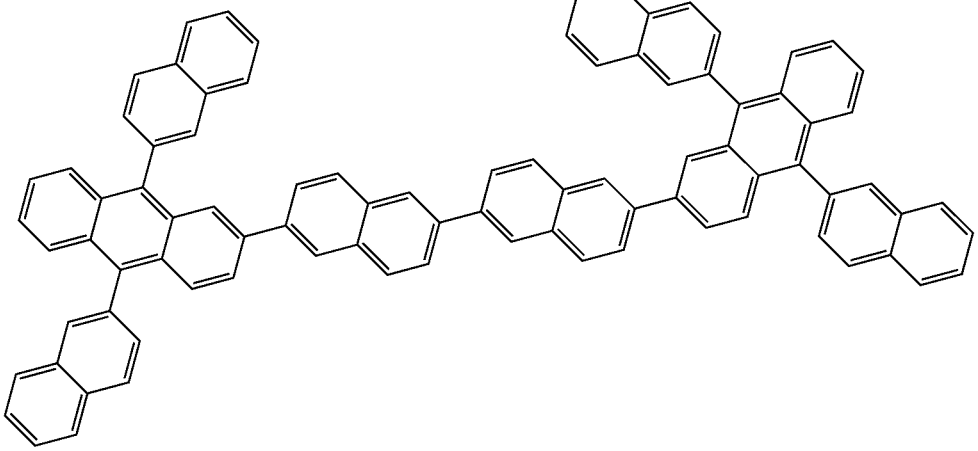

The compound B-7 prepared in the Preparation Example II-7 (1.2 g, 2.5 mmol), 9,10-dinaphthylanthracenyl-2-boronate compound (4.1 g, 7.4 mmol), and sodium carbonate (1.34 g, 9.72 mmol) were suspended in a mixture of tetrahydrofuran (60 mL) and water (10 mL). To the suspension, tetrakis(triphenylphosphine)palladium (0.06 g, 0.05 mmol) was added. The mixture was stirred under reflux for about 24 hours, and then cooled to room temperature. The organic layer was separated, and the aqueous layer was extracted using tetrahydrofuran. The combined organic extract was dried over magnesium sulfate, and concentrated in vacuum. The residue was purified with THF/EtOH to prepare a compound 2-9 (1.81 g, yield 65%): MS [M+H]$^+$=1111

Example 2-8

Preparation of Compound 2-12

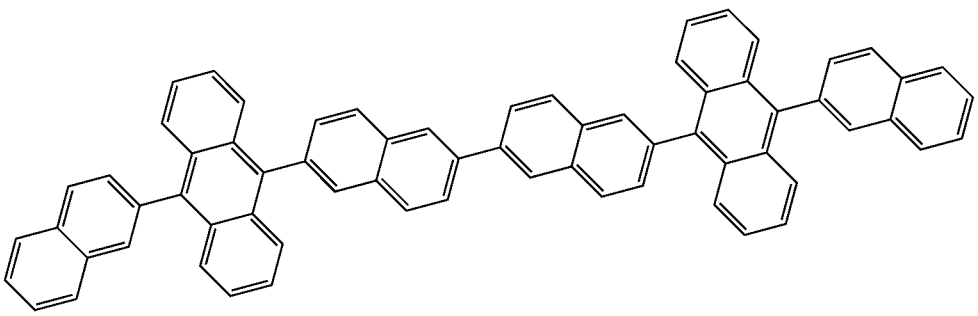 [SMILES: c1ccc2cc(-c3c4ccccc4c(-c4ccc5cc(-c6ccc7cc(-c8c9ccccc9c(-c9ccc%10ccccc%10c9)c9ccccc89)ccc7c6)ccc5c4)c4ccccc34)ccc2c1]

A compound 2-12 was prepared in the same manner as in the method for preparing the compound A-1 of Preparation Example I-1, except that in the method for preparing the compound A-1 of Preparation Example I-1, the compound C-3 of the Preparation Example III-3 (5.6 g, 10 mmol) was used instead of naphthyl-2-boronic acid, and the compound B-3 of the Preparation Example II-3 (5.4 g, 10 mmol) was used instead of 6-bromo-2-naphtol. (4.6 g, yield 54%): MS [M+H]$^+$=859

Example 2-9

Preparation of Compound 2-38

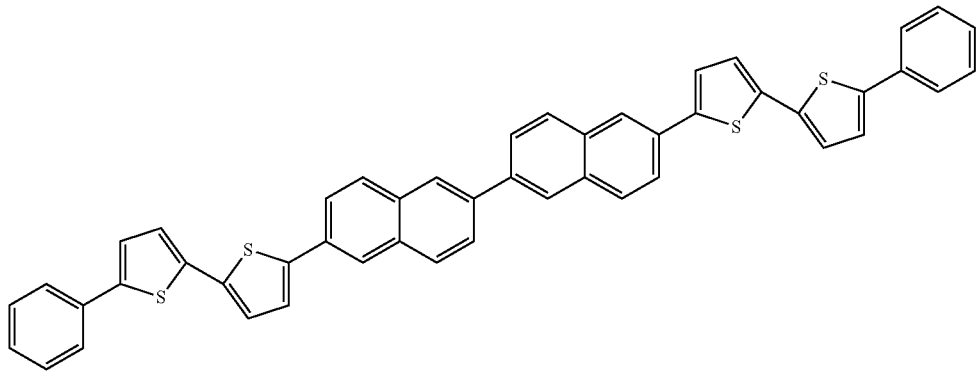 [SMILES: c1ccc(-c2ccc(-c3ccc(-c4ccc5cc(-c6ccc7cc(-c8ccc(-c9ccc(-c%10ccccc%10)s9)s8)ccc7c6)ccc5c4)s3)s2)cc1]

The compound B-7 prepared in the Preparation Example II-7 (1.1 g, 2.30 mmol), the compound C-10 prepared in the Preparation Example III-10 (1.86 g, 7.29 mmol), and sodium carbonate (1.34 g, 9.72 mmol) were suspended in a mixture of tetrahydrofuran (60 mL) and water (10 mL). To the suspension, tetrakis(triphenylphosphine)palladium (0.06 g, 0.05 mmol) was added. The mixture was stirred under reflux for about 24 hours, and then cooled to room temperature. The organic layer was separated, and the aqueous layer was extracted using tetrahydrofuran. The combined organic extract was dried over magnesium sulfate, and concentrated in vacuum. The residue was purified with THF/EtOH to prepare a compound 2-38. (0.78 g, yield 44%)

MS $[M+H]^+$=735

Example 2-10

Preparation of Compound 2-49

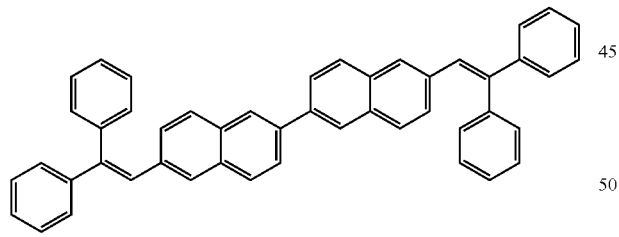

The compound B-7 prepared in the Preparation Example II-7 (1.16 g, 2.43 mmol), the compound C-9 prepared in the Preparation Example III-9 (1.3 g, 5.83 mmol), and sodium carbonate (1.34 g, 9.72 mmol) were suspended in a mixture of tetrahydrofuran (60 mL) and water (10 mL). To the suspension, tetrakis(triphenylphosphine)palladium (0.06 g, 0.05 mmol) was added. The mixture was stirred under reflux for about 24 hours, and then cooled to room temperature. The organic layer was separated, and the aqueous layer was extracted using tetrahydrofuran. The combined organic extract was dried over magnesium sulfate, and concentrated in vacuum. The residue was purified with THF/EtOH to prepare a compound 2-49. (0.9 g, yield 61%):

MS $[M+H]^+$=611

Example 2-11

Preparation of Compound 2-53

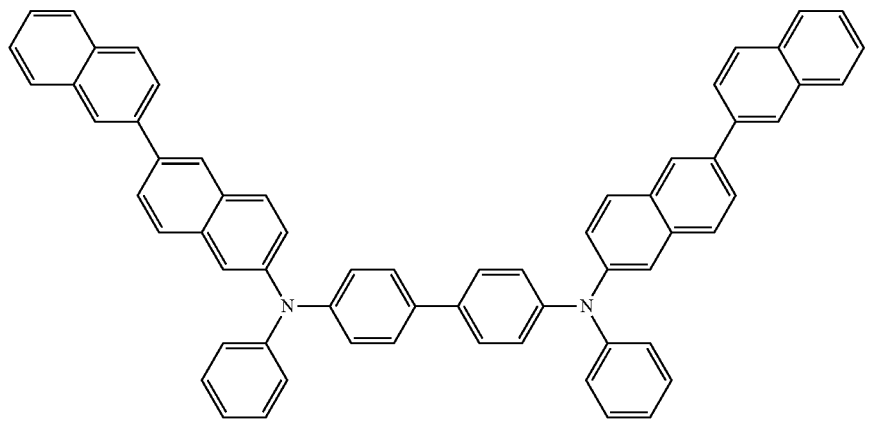 [SMILES: c1ccc(N(c2ccc(-c3ccc(N(c4ccccc4)c4ccc5cc(-c6ccc7ccccc7c6)ccc5c4)cc3)cc2)c2ccc3cc(-c4ccc5ccccc5c4)ccc3c2)cc1]

To the compound B-1 prepared in the Preparation Example II-1 (3.7 g, 10 mmol), 100 mL of xylene was added, N-phenylbenzidine (1.4 g, 4.2 mmol), Na(O$^t$Bu) (0.97 g, 10 mmol), Pd(OAc)$_2$ (0.02 g, 0.096 mmol] and P(t-Bu)$_3$ (0.02 g, 0.144 mmol) were added, and the mixture was stirred under heating at 140° C. for 3 hours. The reaction temperature was lowered to ambient temperature and ethanol was added to the mixture to form a precipitate. The resulting solid was filtered, and dried. The solid was dissolved in an excessive amount of THF, and passed through a silica gel layer for purification. THF was removed in vacuum under reduced pressure, and purified with ethylacetate and ethanol to prepare a compound 2-53 (5.2 g, yield 62%).

MS [M+H]$^+$=841

As described in the Preparation Examples, a variety of intermediates can be synthesized. In addition, as described in the Examples, a variety of derivatives as shown in Table 1 and 2 can be prepared under a Pd catalyst by a variety of combination of the intermediates synthesized as above.

Experimental Example 1

A glass substrate on which a thin film of ITO (indium tin oxide) was coated to a thickness of 1500 Å was immersed in distilled water having a detergent dissolved therein to wash the substrate with ultrasonic waves. At this time, the detergent was a product commercially available from Fisher Co. and the distilled water was distilled water which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried, and then transported to a plasma washing machine. Using an oxygen plasma, the substrate was washed for 5 minutes and then transported to a vacuum depositing machine.

On the ITO transparent electrode thus prepared, hexanitrile hexaazatriphenylene was coated to thicknesses of 500 Å by thermal vacuum deposition to form a hole-injecting layer. NPB (400 Å) as a hole-transporting material was vacuum deposited, and then an Alq3 compound was vacuum deposited to thicknesses of 300 Å for a light-emitting layer.

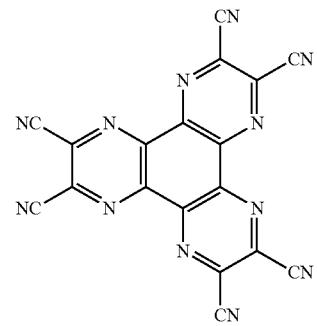

[Hexanitrile hexaazatriphenylene]

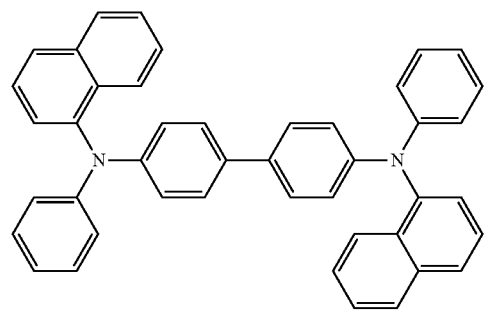

[NBP]

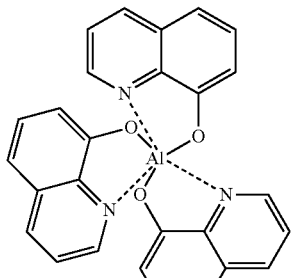

[Alq$_3$]

The compound 2-41 as prepared in Example I-2 was vacuum deposited on the light-emitting layer to thickness of 200 Å to form an electron-injecting and -transporting layer. Lithium fluoride (LiF) and aluminum were sequentially deposited on the electron-injecting and -transporting layer to thicknesses of 12 Å and 2000 Å respectively, to form a cathode.

In the above process, the deposition rate of the organic material was maintained at 1 Å/sec, the deposition rate of lithium fluoride was maintained at 0.2 Å/sec and the deposition rate of aluminum was maintained at 3 to 7 Å/sec.

When a forward electric field of 7.2 V was applied to the organic light-emitting device as prepared above, green light emission was observed with x=0.33 and y=0.55 based on the 1931 CIE color coordinate at a current density of 50 mA/cm$^2$. When a forward electric field of 7.9 V was applied, green light emission of 3.1 cd/A was observed at a current density of 100 mA/cm$^2$.

Experimental Example 2

On the ITO electrode as prepared as in Experimental Example 1, hexanitrile hexaazatriphenylene (500 Å, 4,4'-bis [N-(1-naphthyl)-N-phenylamino]biphenyl (NPB) (400 Å), Alq$_3$ (300 Å), the compound 1-157 prepared in Example 1-4 (300 Å), lithium fluoride(LiF) (12 Å) were sequentially coated by thermal vacuum deposition, to form a hole-injecting layer, a hole-transporting layer, a light-emitting layer, an electron-transporting layer and an electron-injecting layer in this order. Aluminum was deposited thereon to a thickness of 2000 Å to form a cathode, and then to prepare an organic light-emitting device.

When a forward electric field of 6.12 V was applied to the organic light-emitting device as prepared above, green light emission was observed with x=0.32 and y=0.58 based on the 1931 CIE color coordinate at a current density of 50 mA/cm$^2$. When a forward electric field of 7.4 V was applied, green light emission of 2.9 cd/A was observed at a current density of 100 mA/cm$^2$.

Experimental Example 3

On the ITO electrode as prepared as in Experimental Example 1, hexanitrile hexaazatriphenylene (500 Å), 4,4'-bis [N-(1-naphthyl)-N-phenylamino]biphenyl (NPB) (400 Å), Alq$_3$ (300 Å), the compound 1-166 prepared in Example 1-6 (300 Å), lithium fluoride(LiF) (12 Å) were sequentially coated by thermal vacuum deposition, to form a hole-injecting layer, a hole-transporting layer, a light-emitting layer, an electron-transporting layer and an electron-injecting layer in this order. Aluminum was deposited thereon to a thickness of 2000 Å to form a cathode, and then to prepare an organic light-emitting device.

When a forward electric field of 7.3 V was applied to the organic light-emitting device as prepared above, green light emission was observed with x=0.33 and y=0.56 based on the 1931 CIE color coordinate at a current density of 50 mA/cm$^2$. When a forward electric field of 8.9 V was applied, green light emission of 3.3 cd/A was observed at a current density of 100 mA/cm$^2$.

Experimental Example 4

On the ITO electrode as prepared as in Experimental Example 1, hexanitrile hexaazatriphenylene (500 Å), 4,4'-bis [N-(1-naphthyl)-N-phenylamino]biphenyl (NPB) (400 Å), Alq$_3$ (300 Å), the compound 2-8 prepared in Example 2-4 (300 Å), lithium fluoride(LiF) (12 Å) were sequentially coated by thermal vacuum deposition, to form a hole-injecting layer, a hole-transporting layer, a light-emitting layer, an electron-transporting layer and an electron-injecting layer in this order. Aluminum was deposited thereon to a thickness of 2000 Å to form a cathode, and then to prepare an organic light-emitting device.

When a forward electric field of 8.9 V was applied to the organic light-emitting device as prepared above, green light emission was observed with x=0.33 and y=0.54 based on the 1931 CIE color coordinate at a current density of 50 mA/cm$^2$. When a forward electric field of 10.7 V was applied, green light emission of 3.7 cd/A was observed at a current density of 100 mA/cm$^2$.

Experimental Example 5

On the ITO electrode as prepared as in Experimental Example 1, hexanitrile hexaazatriphenylene (500 Å), 4,4'-bis [N-(1-naphthyl)-N-phenylamino]biphenyl (NPB) (400 Å), Alq$_3$ (300 Å), the compound 2-44 prepared in Example 1-7 (300 Å), lithium fluoride(LiF) (12 Å) were sequentially coated by thermal vacuum deposition, to form a hole-injecting layer, a hole-transporting layer, a light-emitting layer, an electron-transporting layer and an electron-injecting layer in this order. Aluminum was deposited thereon to a thickness of 2000 Å to form a cathode, and then to prepare an organic light-emitting device.

When a forward electric field of 7.1 V was applied to the organic light-emitting device as prepared above, green light emission was observed with x=0.31 and y=0.54 based on the 1931 CIE color coordinate at a current density of 50 mA/cm$^2$. When a forward electric field of 8.6 V was applied, green light emission of 3.5 cd/A was observed at a current density of 100 mA/cm$^2$.

Experimental Example 6

On the ITO electrode as prepared as in Experimental Example 1, hexanitrile hexaazatriphenylene (500 Å), 4,4'-bis [N-(1-naphthyl)-N-phenylamino]biphenyl (NPB) (400 Å), the compound 1-71 prepared in Example 1-9 (300 Å), Alq$_3$ (300 Å), lithium fluoride(LiF) (12 Å) were sequentially coated by thermal vacuum deposition, to form a hole-injecting layer, a hole-transporting layer, a light-emitting layer, an electron-transporting layer and an electron-injecting layer in this order. Aluminum was deposited thereon to a thickness of 2000 Å to form a cathode, and then to prepare an organic light-emitting device.

When a forward electric field of 7.9 V was applied to the organic light-emitting device as prepared above, blue light emission was observed with x=0.137 and y=0.281 based on the 1931 CIE color coordinate at a current density of 50 mA/cm$^2$. When a forward electric field of 9.6 V was applied, blue light emission of 2.6 cd/A was observed at a current density of 100 mA/cm$^2$.

Experimental Example 7

On the ITO electrode as prepared as in Experimental Example 1, hexanitrile hexaazatriphenylene (500 Å), 4,4'-bis [N-(1-naphthyl)-N-phenylamino]biphenyl (NPB) (400 Å), the compound 1-72 prepared in Example 1-10 (300 Å), Alq$_3$ (300 Å), lithium fluoride(LiF) (12 Å) were sequentially coated by thermal vacuum deposition, to form a hole-injecting layer, a hole-transporting layer, a light-emitting layer, an electron-transporting layer and an electron-injecting layer in this order. Aluminum was deposited thereon to a thickness of 2000 Å to form a cathode, and then to prepare an organic light-emitting device.

When a forward electric field of 6.7 V was applied to the organic light-emitting device as prepared above, blue light emission was observed with x=0.136 and y=0.154 based on the 1931 CIE color coordinate at a current density of 50 mA/cm$^2$. When a forward electric field of 7.9 V was applied, blue light emission of 2.9 cd/A was observed at a current density of 100 mA/cm$^2$.

The invention claimed is:

1. An organic electronic device comprising a first electrode, a second electrode, and an organic material layer having at least one layer interposed between the first electrode and the second electrode, wherein at least one layer of the organic material layers comprises a binaphthalene derivative represented by the following formula (1):

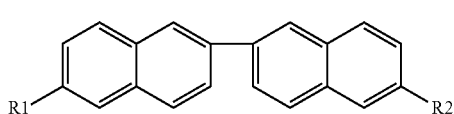

(1)

wherein R1 is selected from the group consisting of hydrogen; a fluorene group which is substituted with an aryl group; a naphthyl group; a pyrene group; and a heteroaromatic group which is substituted with an aryl group, and wherein R2 is selected from the group consisting of a heteroaromatic group which is substituted with an aryl group; and a naphthyl group which is substituted with a heteroaromatic group.

2. The organic electronic device according to claim 1, wherein the organic material layer comprises a hole-injecting layer and a hole-transporting layer, and the hole-injecting layer and the hole-transporting layer comprise the binaphthalene derivative.

3. The organic electronic device according to claim 1, wherein the organic material layer comprises a light-emitting layer, and the light-emitting layer comprises the binaphthalene derivative.

4. The organic electronic device according to claim 1, wherein the organic material layer comprises an electron-transporting layer, and the electron-transporting layer comprises the binaphthalene derivative.

5. The organic electronic device according to claim 1, wherein the organic electronic device is selected from the group consisting of an organic light-emitting device, an organic solar cell, an organic photoconductor (OPC) and an organic transistor.

6. An organic electronic device comprising a first electrode, a second electrode, and an organic material layer having at least one layer interposed between the first electrode and the second electrode, wherein at least one layer of the organic material layers comprises a binaphthalene derivative represented by the following formula (I):

(1)

wherein R1 or R2 in the formula (1) is selected from the following formulas:

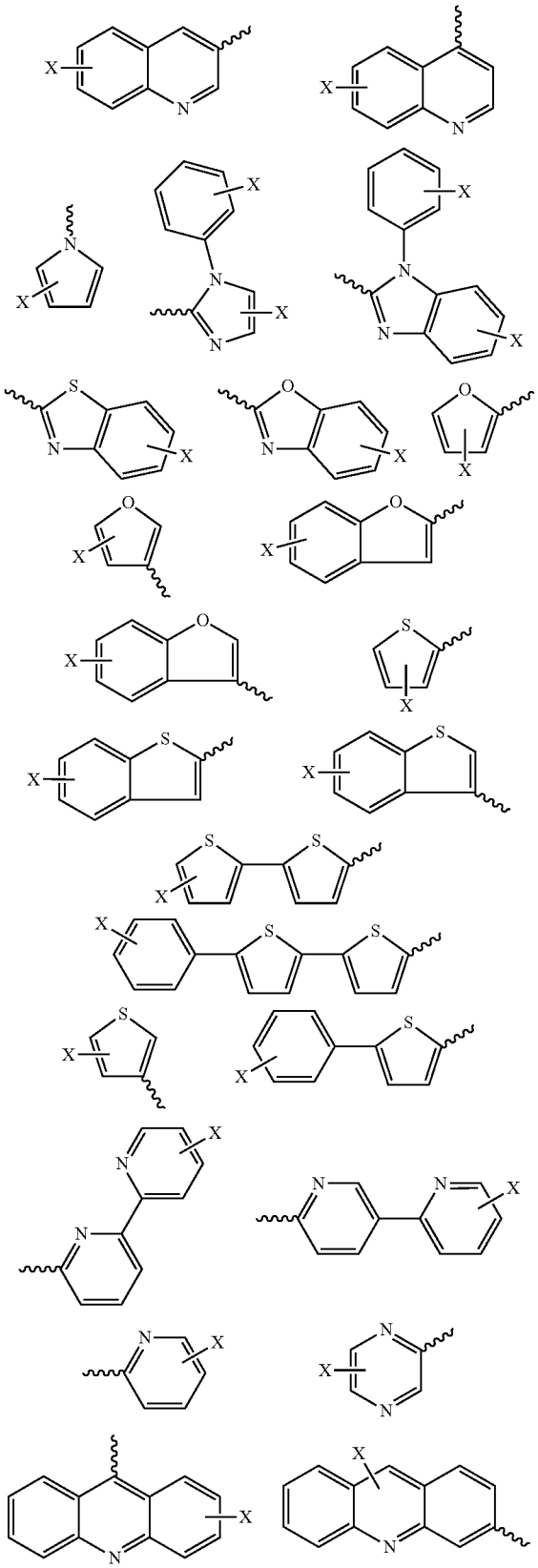

175
-continued
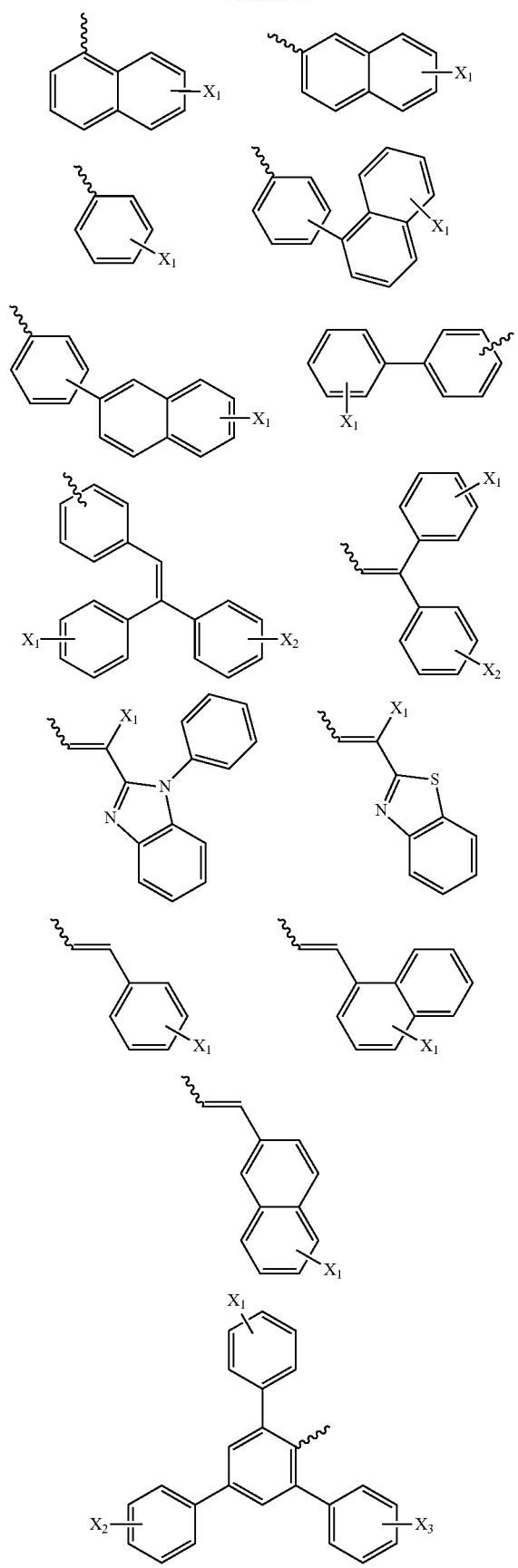
176
-continued
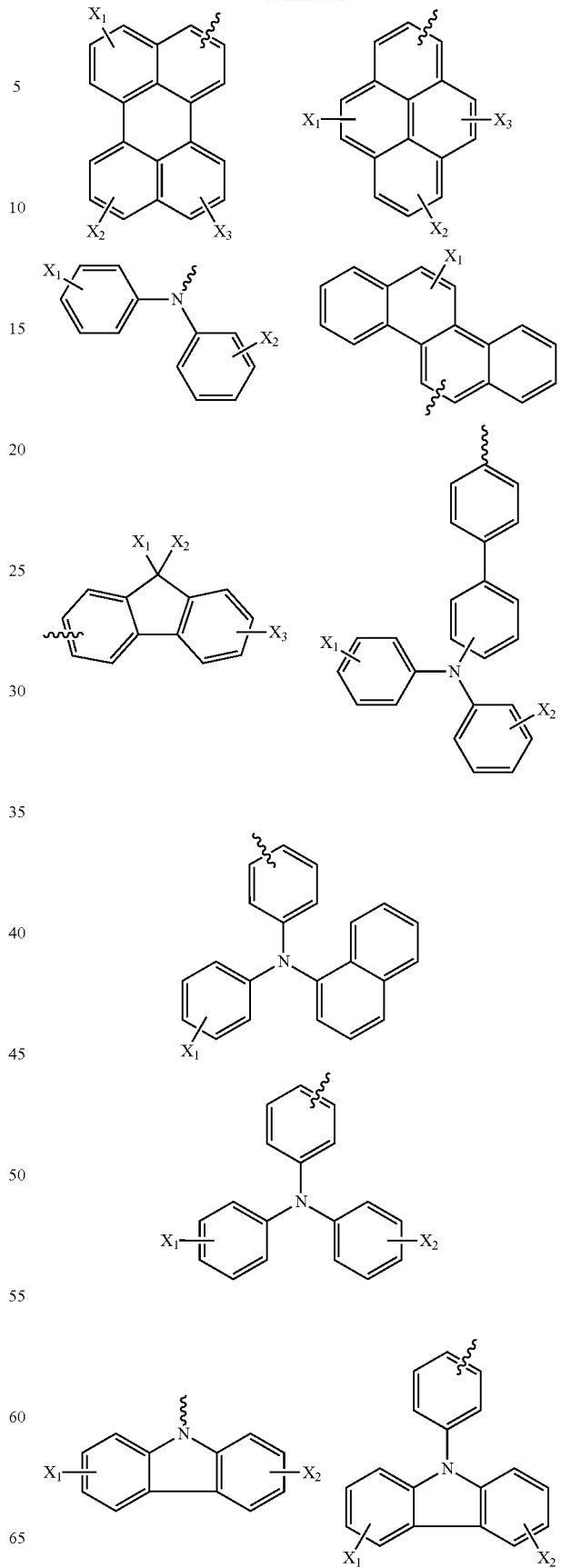

-continued

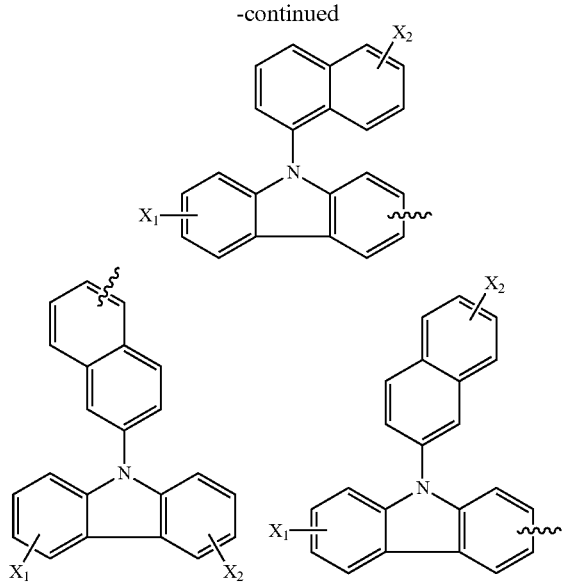

in the above structural formulas, X, X2 and X3 may be each respectivelt the same or different from each other, and are each selected from the group consisting of hydrogen; an alkenyl group; an alkenyl group which is substituted with an aryl group; an aryl group; an aryl group which is substituted with an alkenyl group, an aryl group or a heteroaromatic group; a heteroaromatic group; and a heteroaromatic group which is substituted with an aryl group or a heteroaromatic group X1 is selected from the group consisting of an alkenyl group; an alkenyl group which is substituted with an aryl group; an aryl group which is substituted with an alkenyl group, or a heteroaromatic group; a heteroaromatic group; and a heteroaromatic group which is substituted with an aryl group or a heteroaromatic group.

7. An organic electronic device comprising a first electrode, a second electrode, and an organic material layer having at least one layer interposed between the first electrode and the second electrode, wherein at least one layer of the organic material layers comprises a binaphthalene derivative represented by the following formula (I):

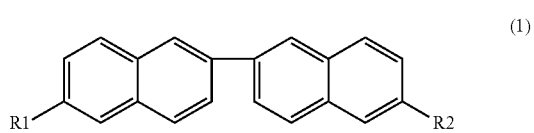

(1)

wherein, in the formula (1), R1 is hydrogen and R2 is selected from the groups shown in the following table:

| No. | R2 |
|---|---|
| 1-1 | ![structure] |
| 1-2 | ![structure] |
| 1-3 | ![structure] |
| 1-4 | ![structure] |

-continued
| No. | R2 |
|---|---|
| 1-5 | 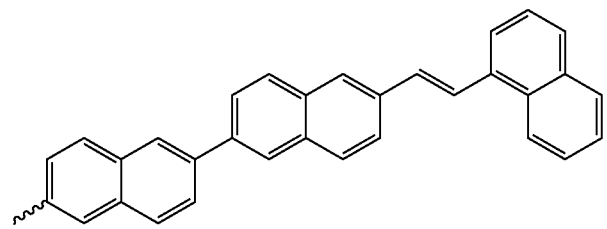 |
| 1-6 | 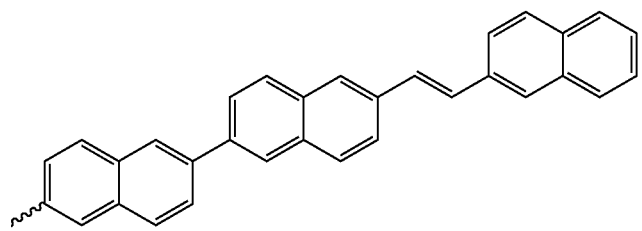 |
| 1-7 | 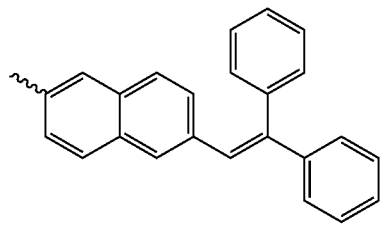 |
| 1-8 | 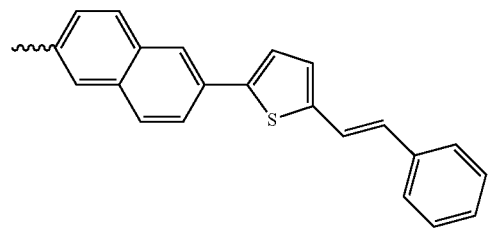 |
| 1-9 | 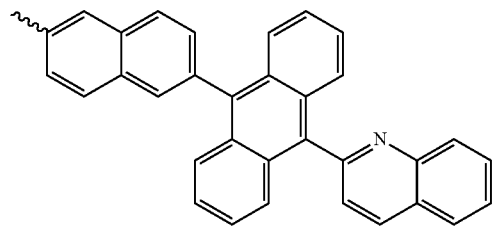 |
| 1-10 | 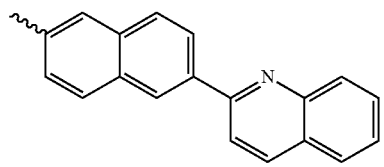 |
| 1-11 |  |

| No. | R2 |
|---|---|
| 1-12 | 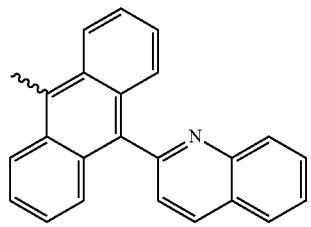 |
| 1-13 | 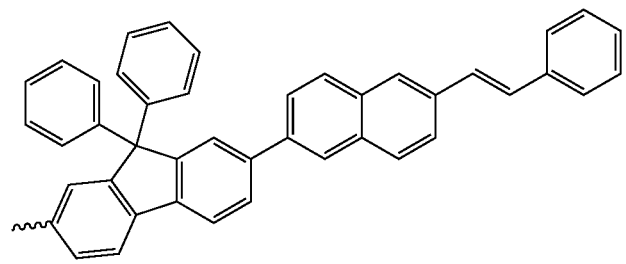 |
| 1-14 | 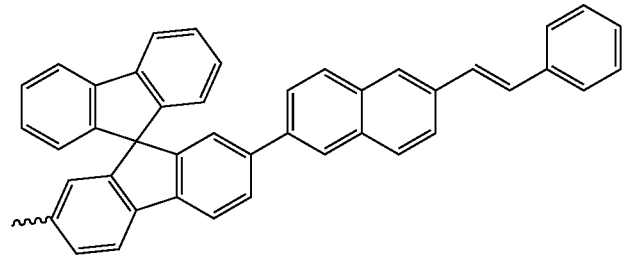 |
| 1-15 | 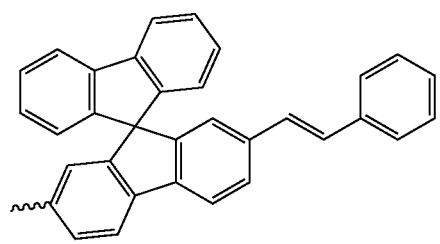 |
| 1-16 | 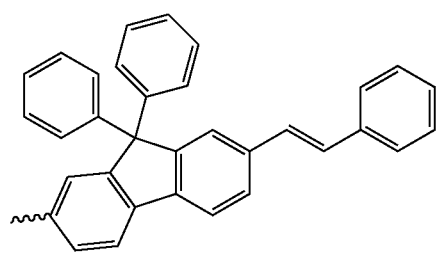 |
| 1-17 | 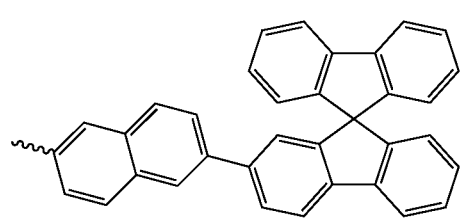 |

-continued
| No. | R2 |
|---|---|
| 1-18 | 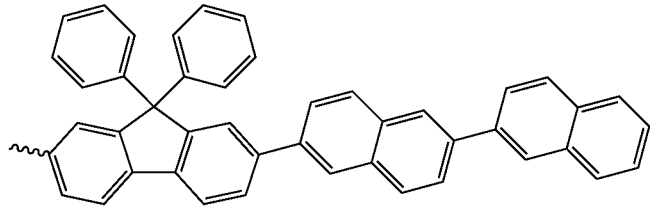 |
| 1-19 | 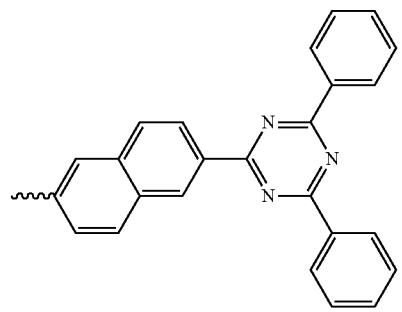 |
| 1-20 | 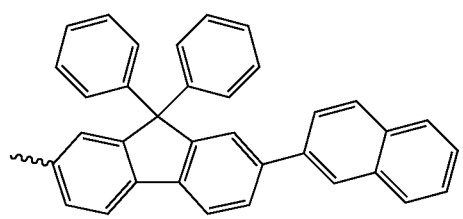 |
| 1-21 | 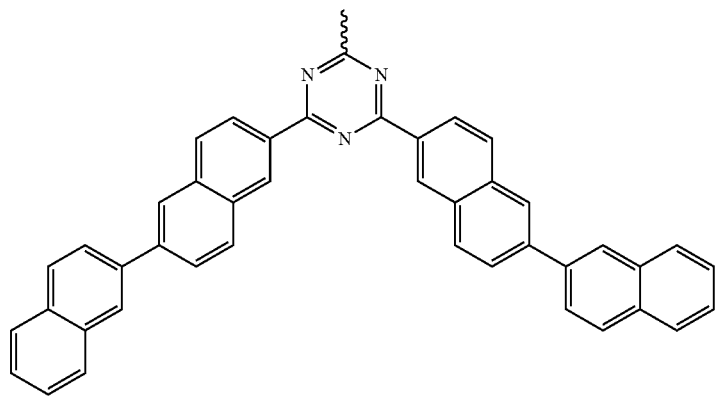 |
| 1-22 | 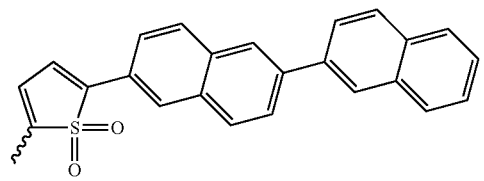 |
| 1-23 | 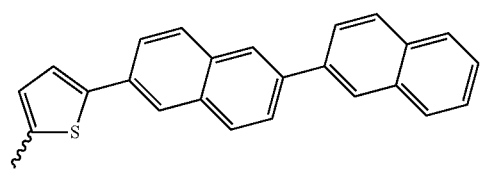 |

| No. | R2 |
|---|---|
| 1-24 | 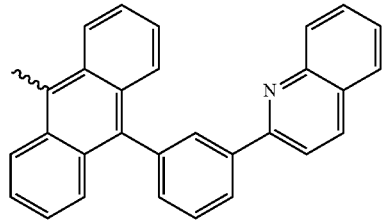 |
| 1-25 | 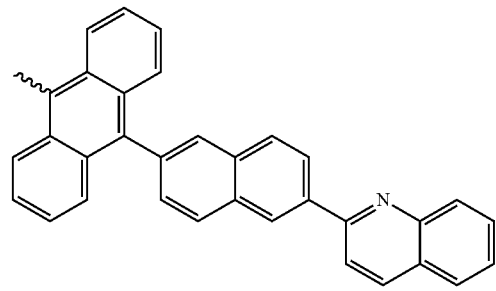 |
| 1-26 | 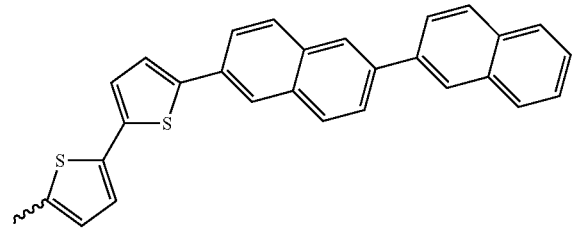 |
| 1-27 | 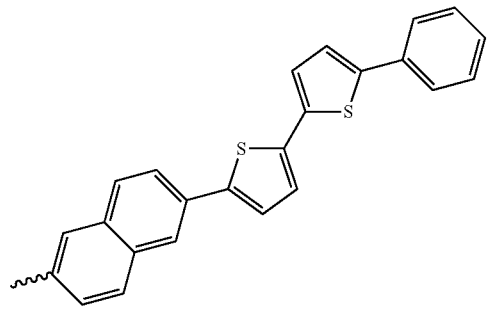 |
| 1-28 | 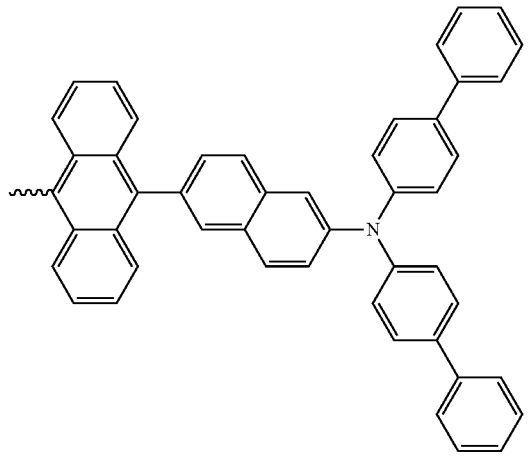 |

-continued
| No. | R2 |
|---|---|
| 1-29 | 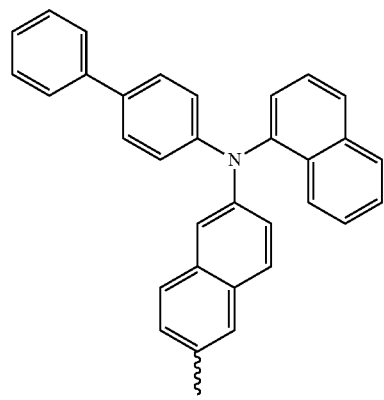 |
| 1-30 | 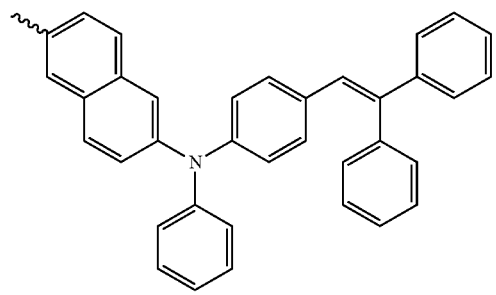 |
| 1-31 | 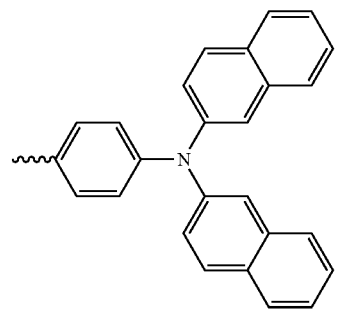 |
| 1-32 | 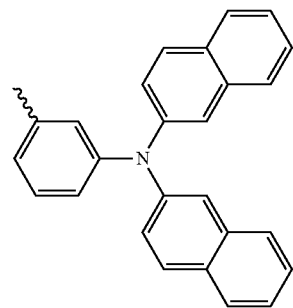 |
| 1-33 | 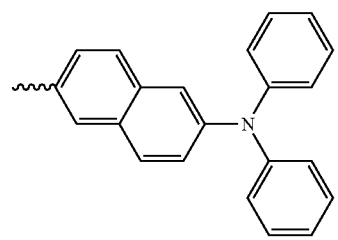 |

-continued
| No. | R2 |
|---|---|
| 1-34 | 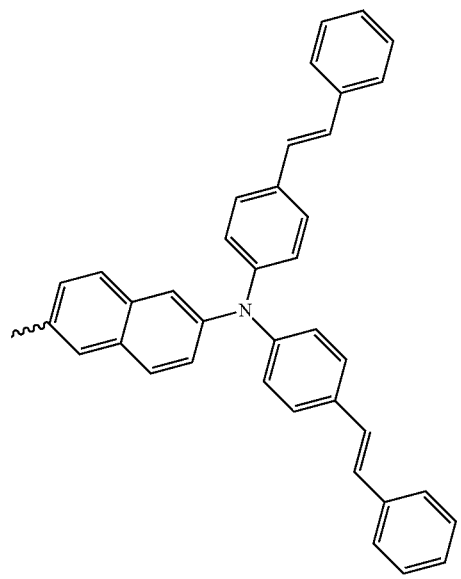 |
| 1-35 | 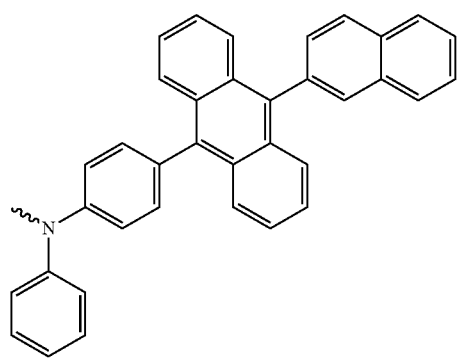 |
| 1-36 | 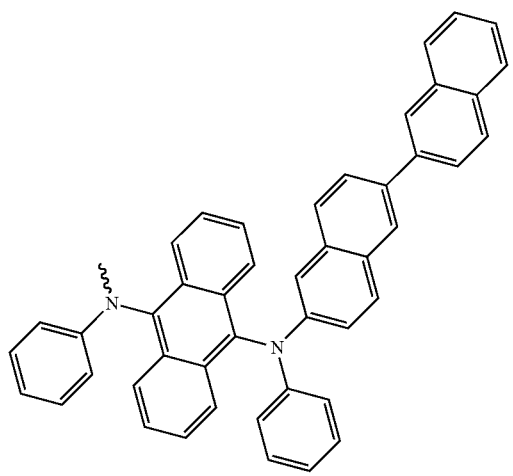 |
| 1-37 | 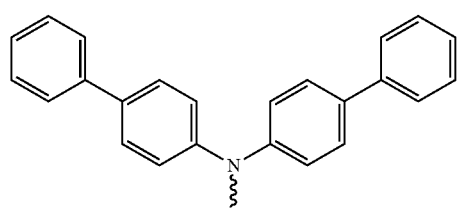 |

-continued
| No. | R2 |
|---|---|
| 1-38 | 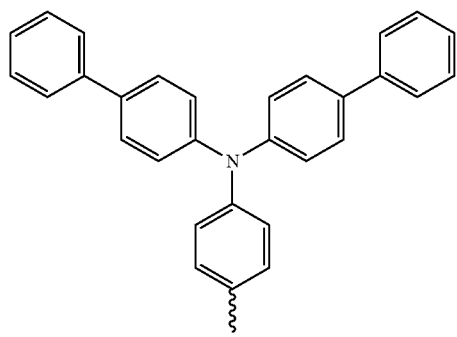 |
| 1-39 | 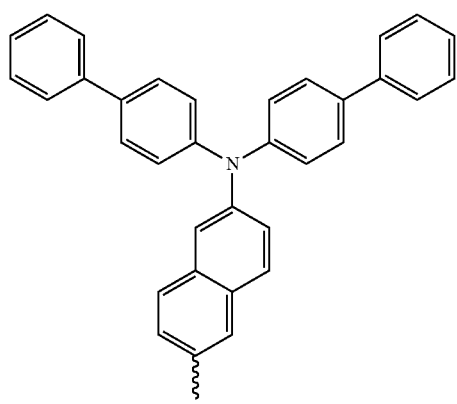 |
| 1-40 | 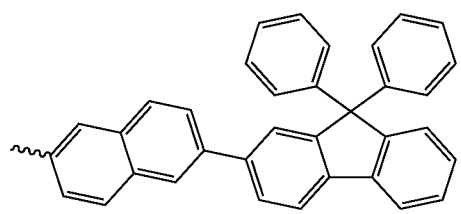 |
| 1-41 | 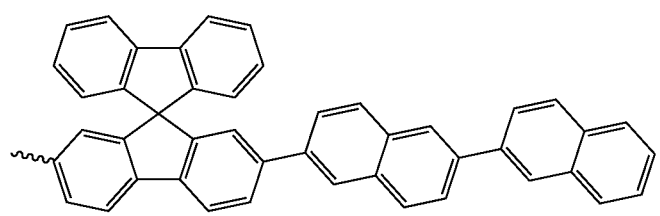 |
| 1-42 | 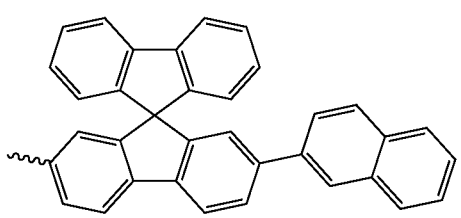 |
| 1-43 | 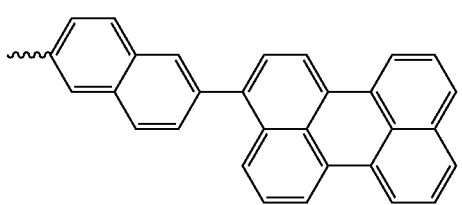 |

| No. | R2 |
|---|---|
| 1-44 | 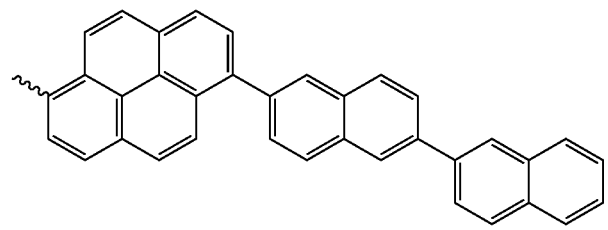 |
| 1-45 | 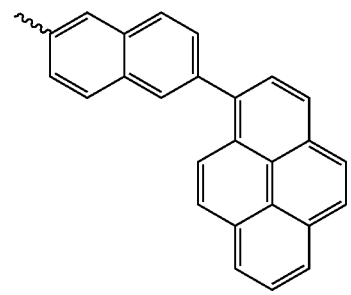 |
| 1-46 | 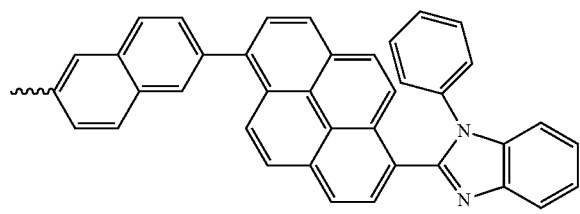 |
| 1-47 | 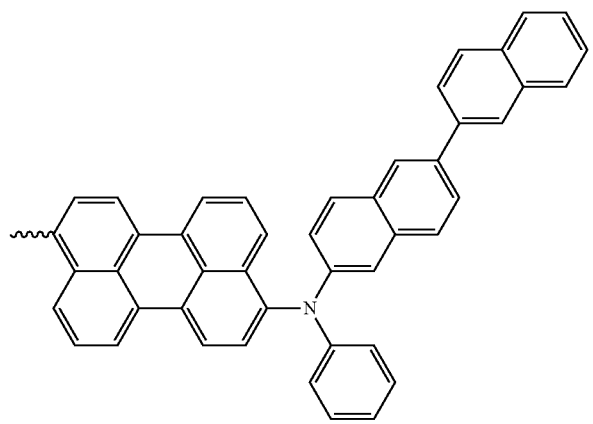 |
| 1-48 | 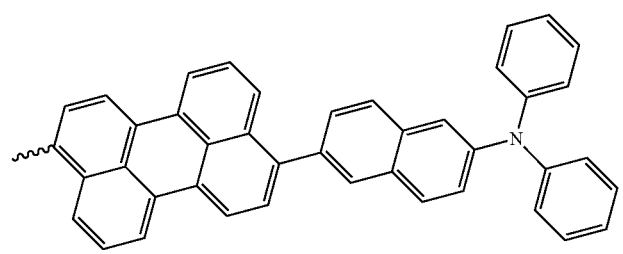 |

-continued
| No. | R2 |
|---|---|
| 1-49 | 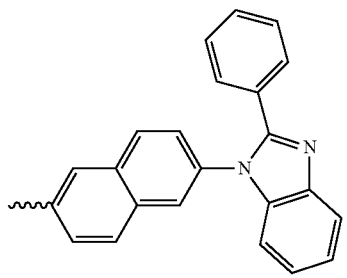 |
| 1-50 | 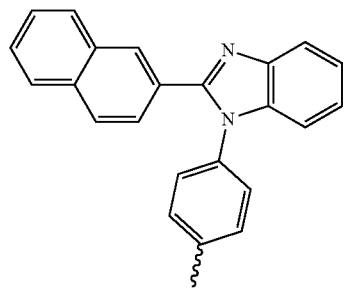 |
| 1-51 | 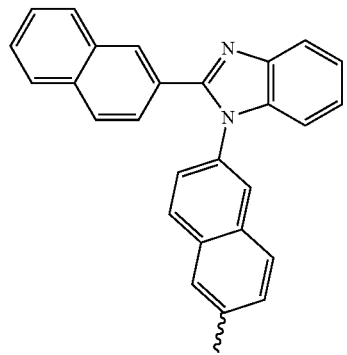 |
| 1-52 | 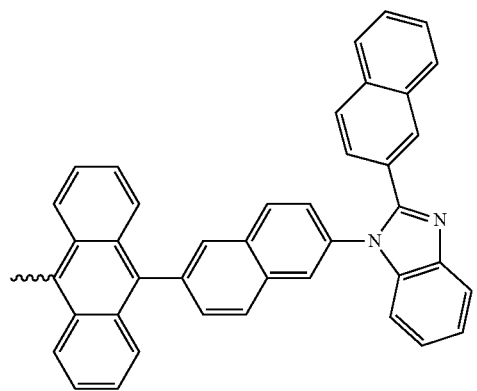 |

-continued
| No. | R2 |
|---|---|
| 1-53 | 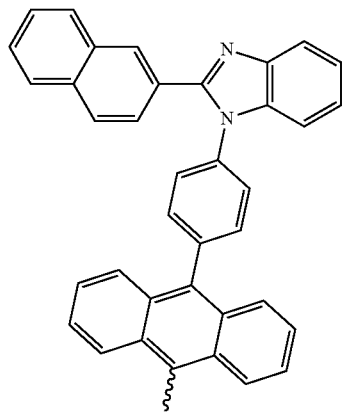 |
| 1-54 | 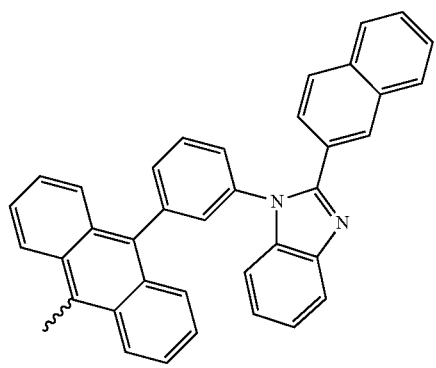 |
| 1-55 | 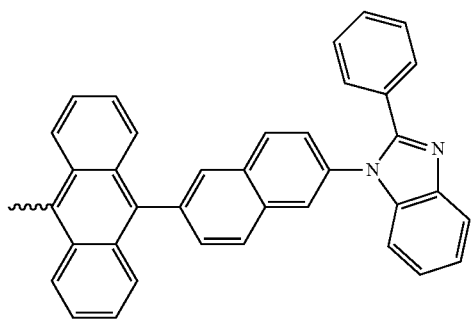 |
| 1-56 | 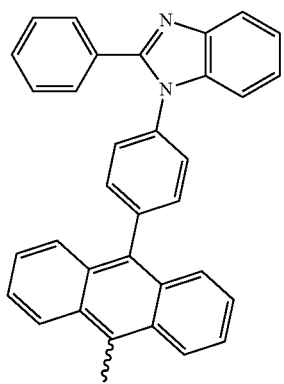 |

-continued
| No. | R2 |
|---|---|
| 1-57 | 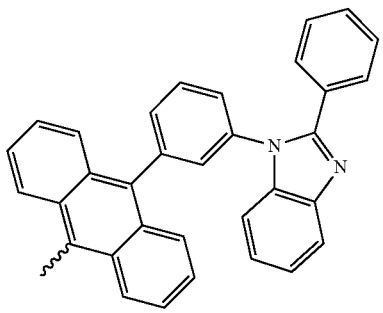 |
| 1-58 | 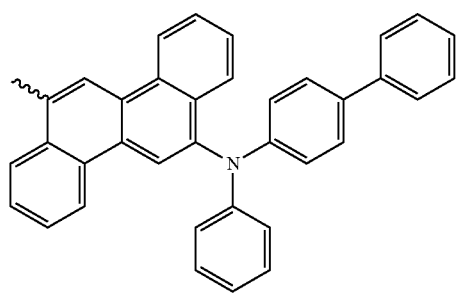 |
| 1-59 | 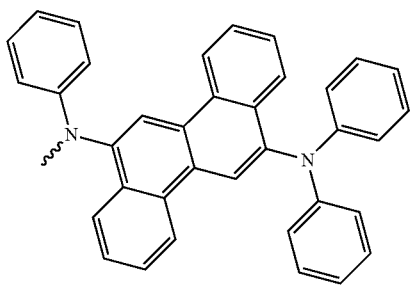 |
| 1-62 | 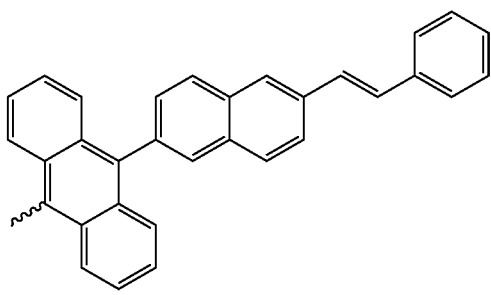 |
| 1-63 | 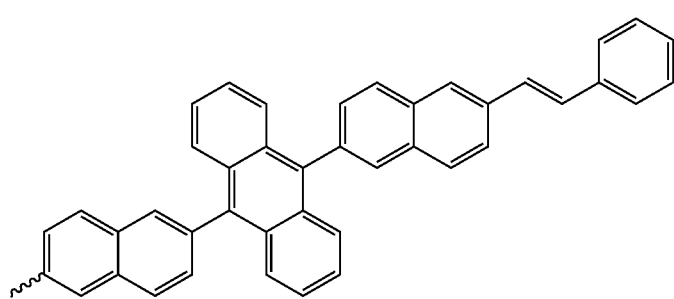 |

-continued
| No. | R2 |
|---|---|
| 1-79 | 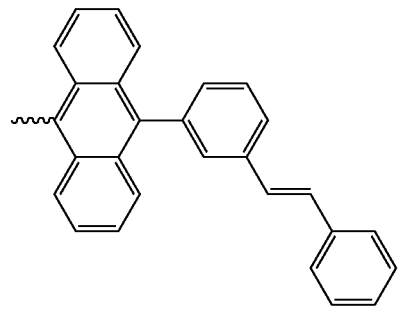 |
| 1-80 | 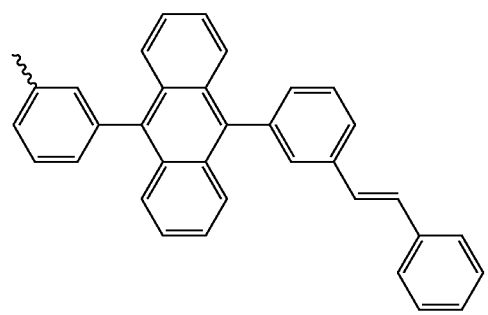 |
| 1-81 | 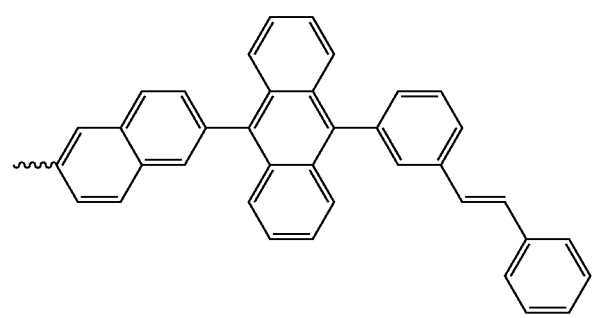 |
| 1-82 | 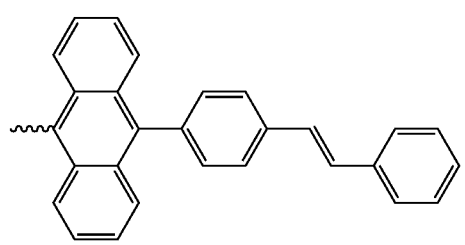 |
| 1-83 | 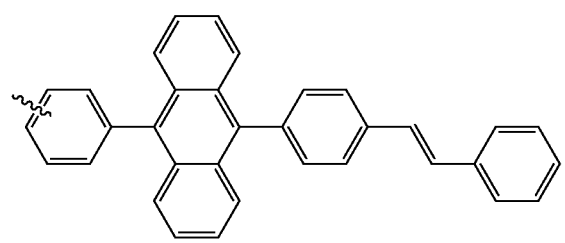 |

| No. | R2 |
|---|---|
| 1-84 | 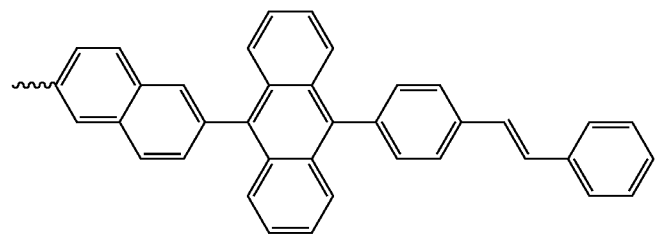 |
| 1-85 | 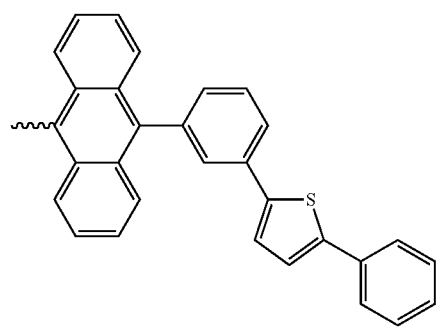 |
| 1-86 | 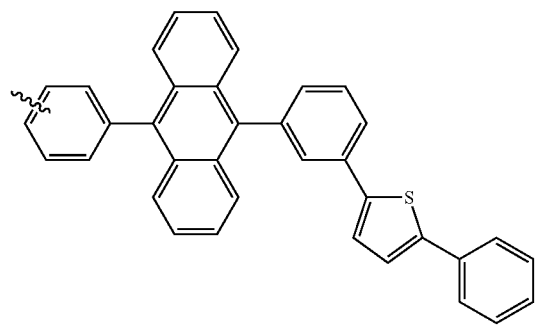 |
| 1-87 | 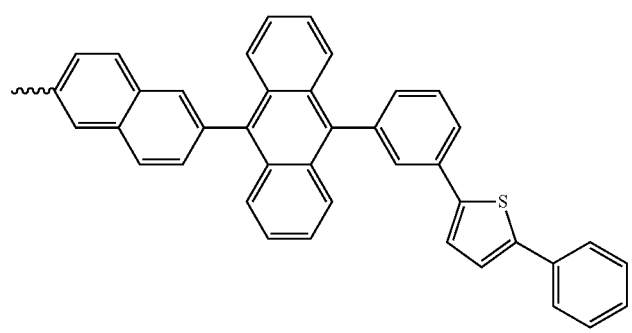 |
| 1-88 | 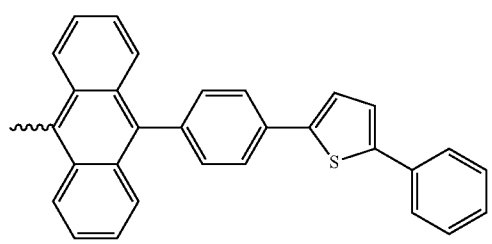 |

| No. | R2 |
|---|---|
| 1-89 | 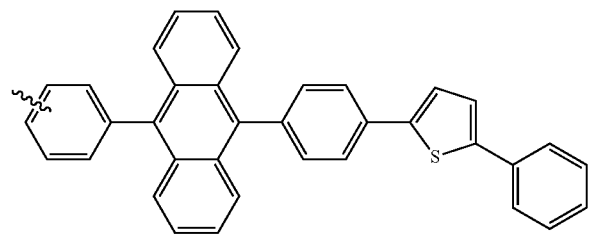 |
| 1-90 | 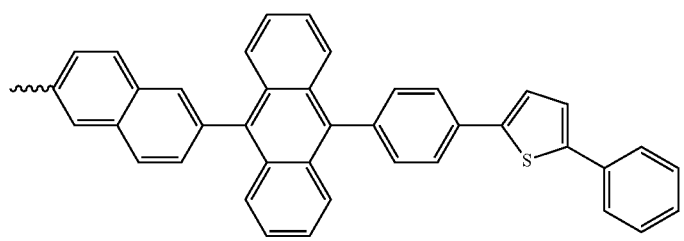 |
| 1-91 | 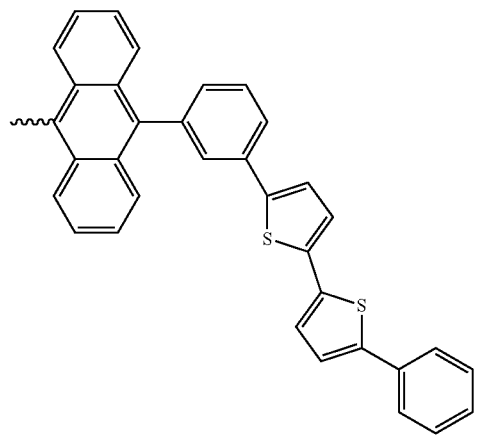 |
| 1-92 | 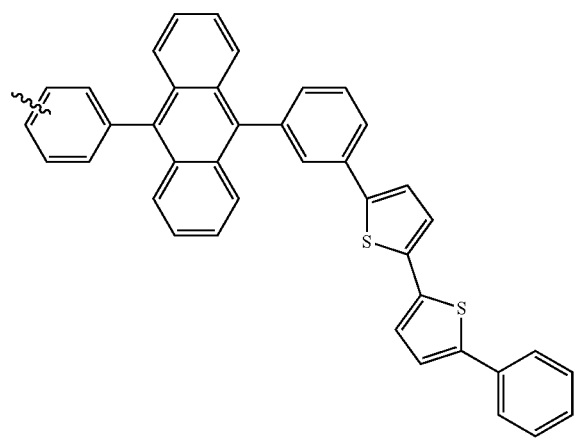 |

| No. | R2 |
|---|---|
| 1-93 | 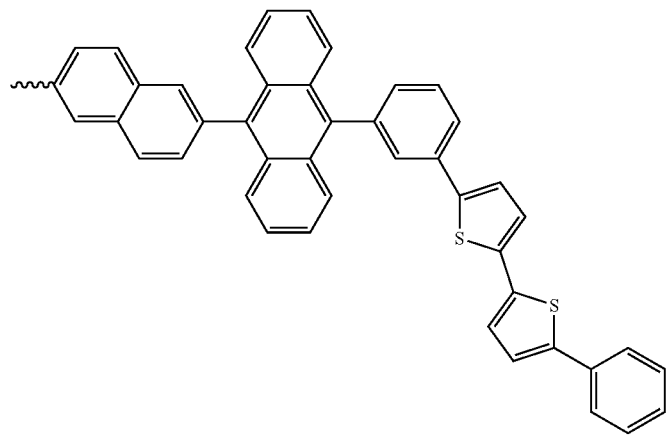 |
| 1-94 | 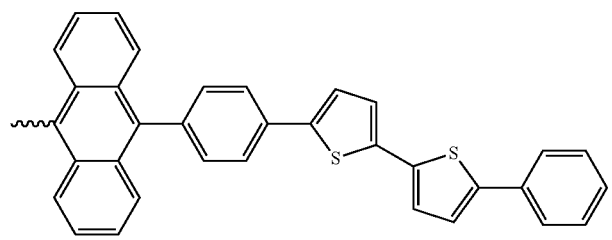 |
| 1-95 | 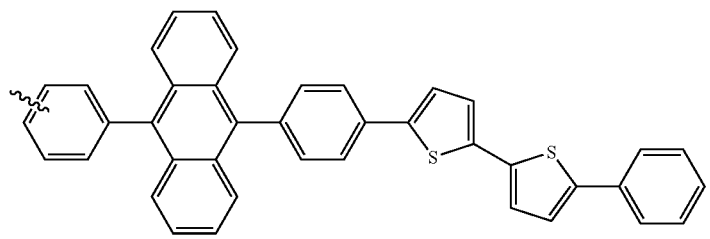 |
| 1-96 | 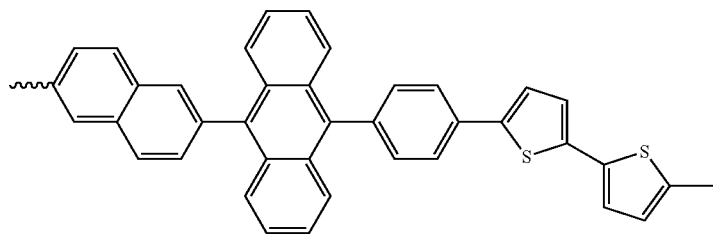 |
| 1-97 | 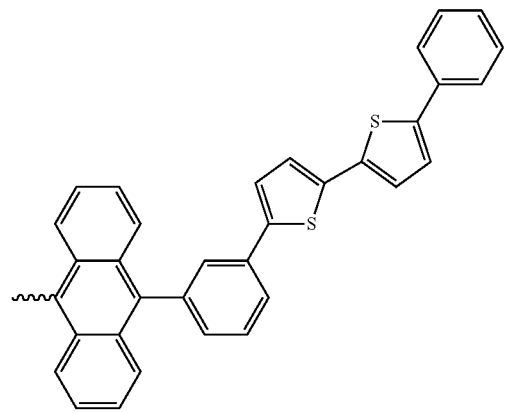 |

-continued
| No. | R2 |
|---|---|
| 1-98 | 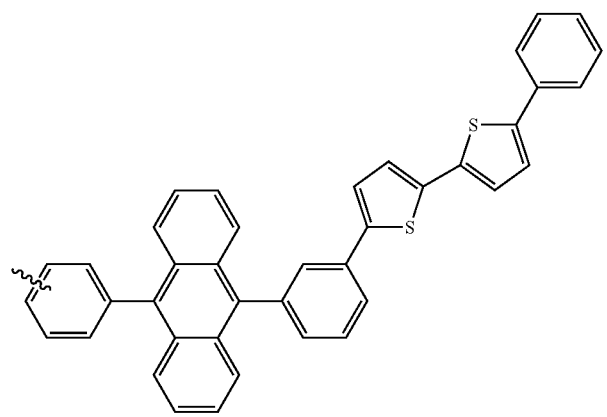 |
| 1-99 | 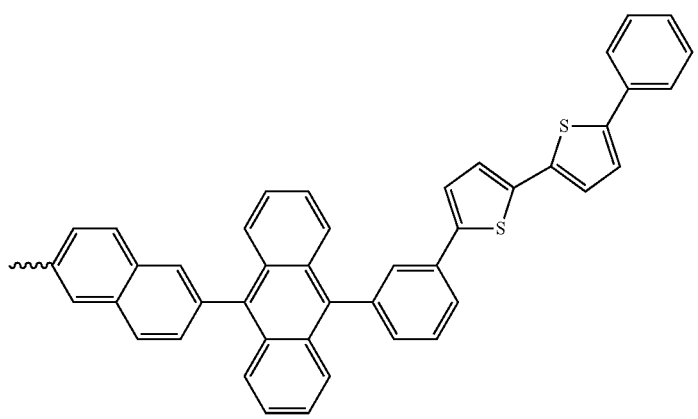 |
| 1-100 | 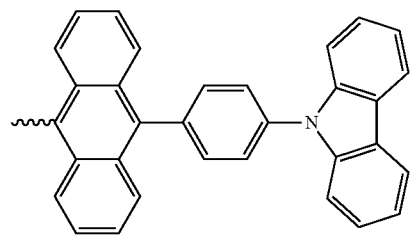 |
| 1-101 | 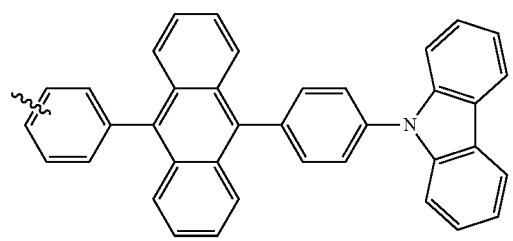 |
| 1-102 | 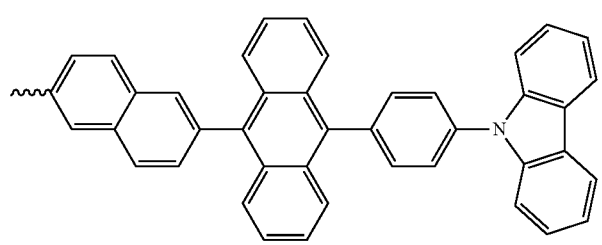 |

-continued
| No. | R2 |
|---|---|
| 1-103 | 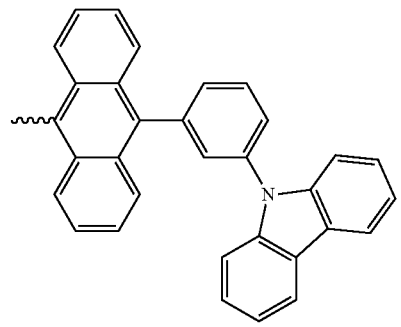 |
| 1-104 | 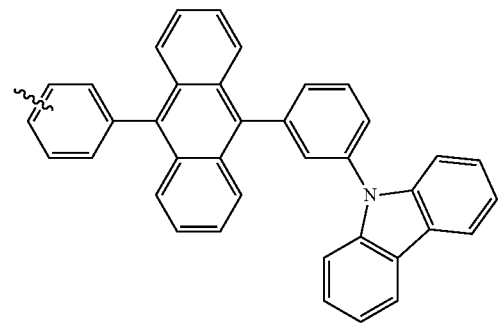 |
| 1-105 | 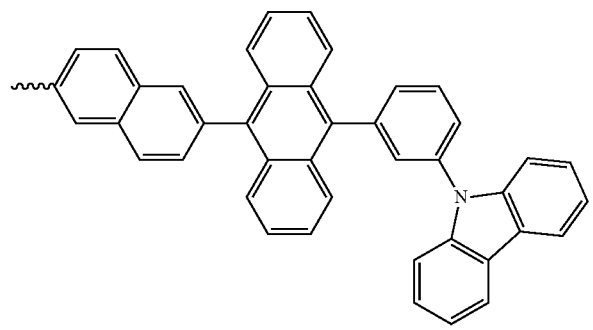 |
| 1-106 | 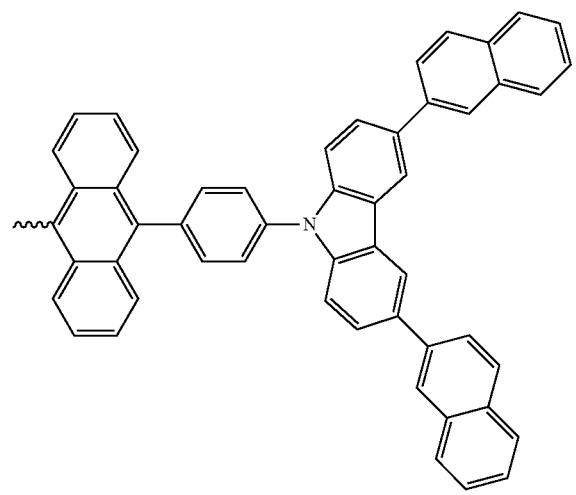 |

-continued
| No. | R2 |
|---|---|
| 1-107 | 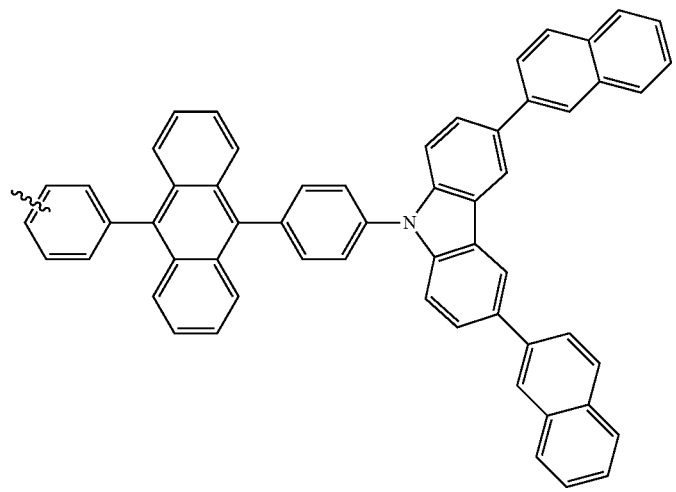 |
| 1-108 | 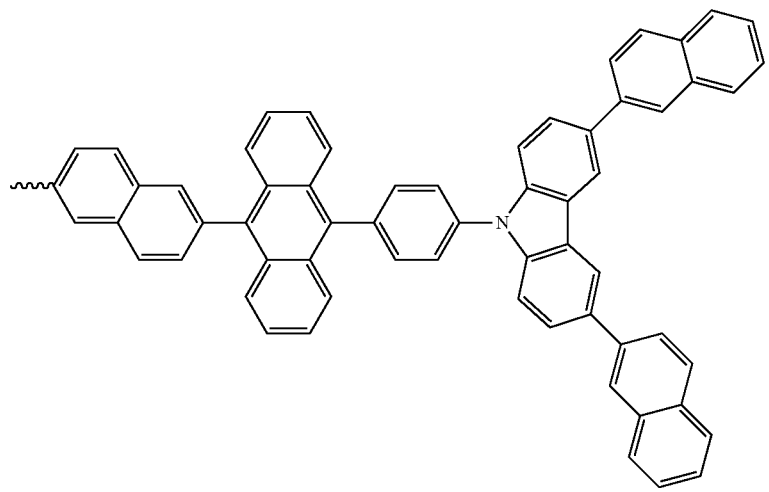 |
| 1-109 | 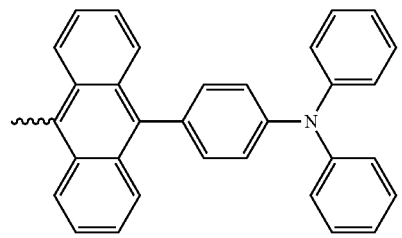 |
| 1-110 | 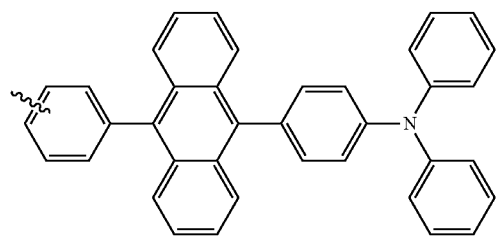 |

-continued
| No. | R2 |
|---|---|
| 1-111 | 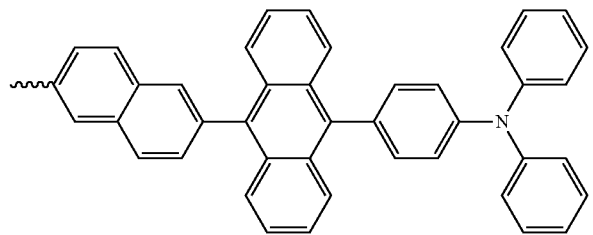 |
| 1-112 | 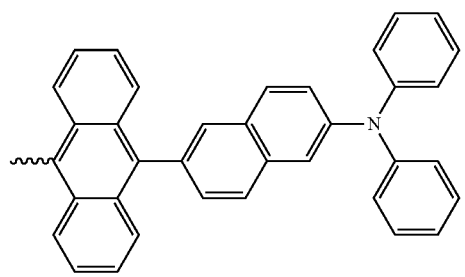 |
| 1-113 | 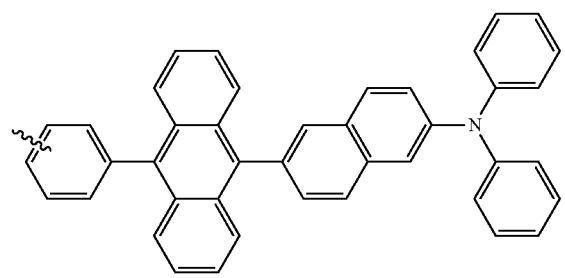 |
| 1-114 | 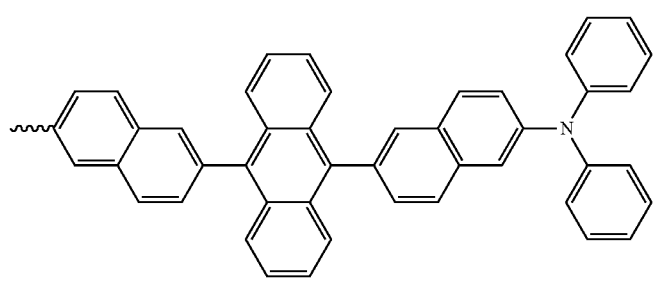 |
| 1-144 | 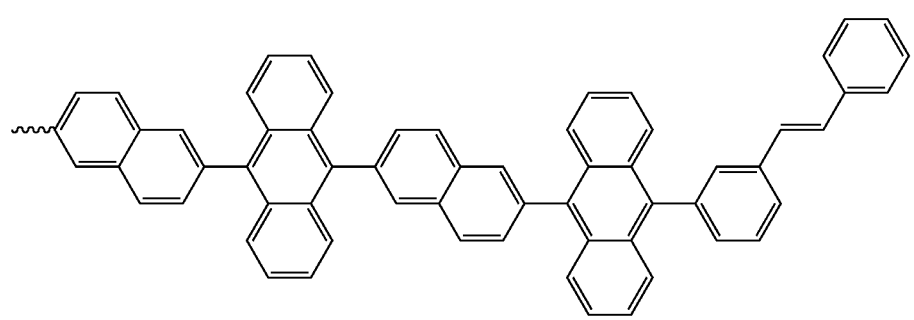 |

-continued
| No. | R2 |
|---|---|
| 1-145 | 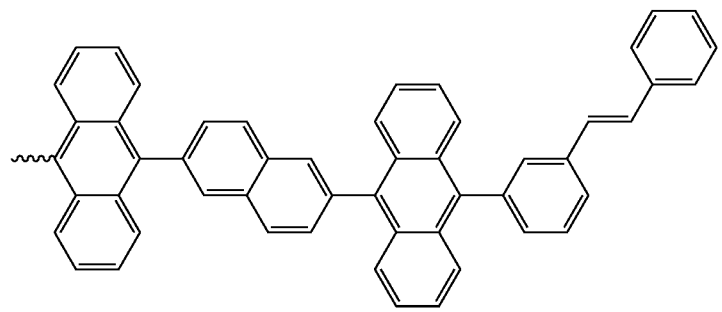 |
| 1-146 | 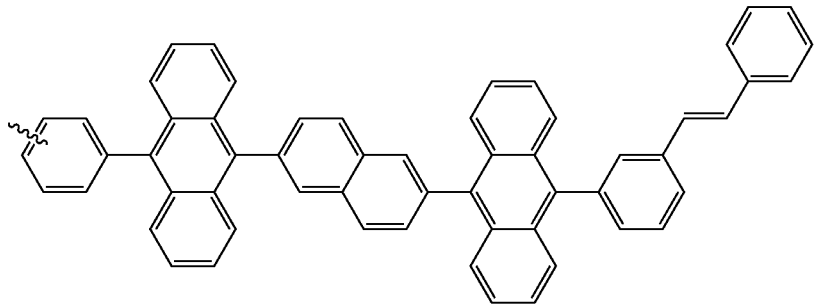 |
| 1-147 | 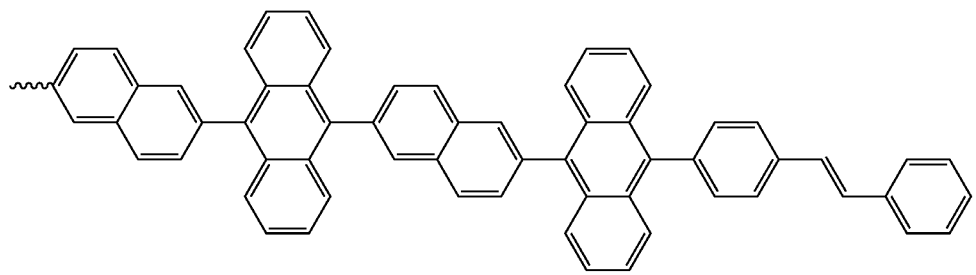 |
| 1-148 | 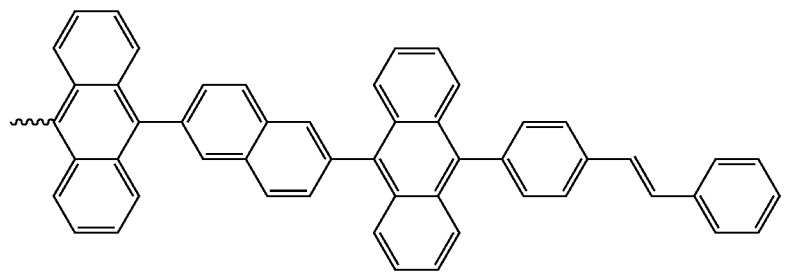 |
| 1-149 | 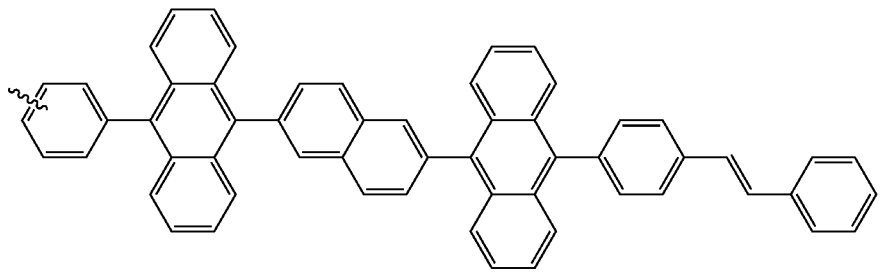 |

-continued
| No. | R2 |
|---|---|
| 1-150 | 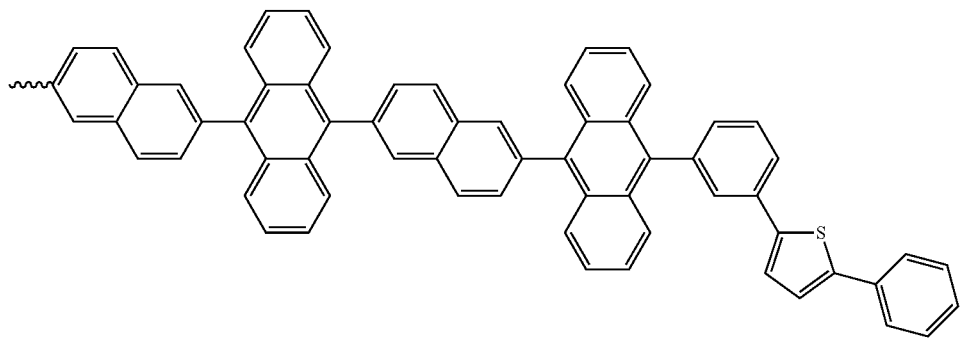 |
| 1-151 | 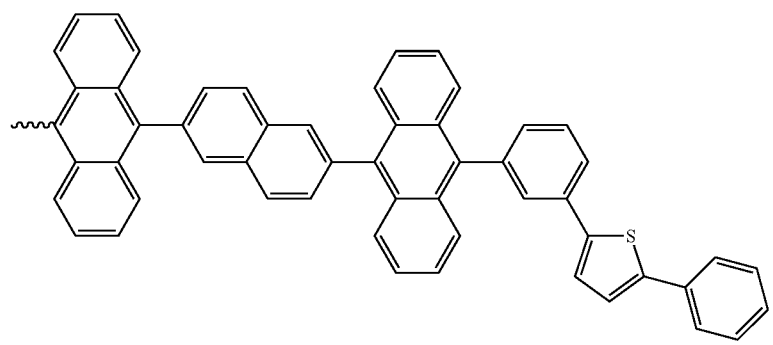 |
| 1-152 | 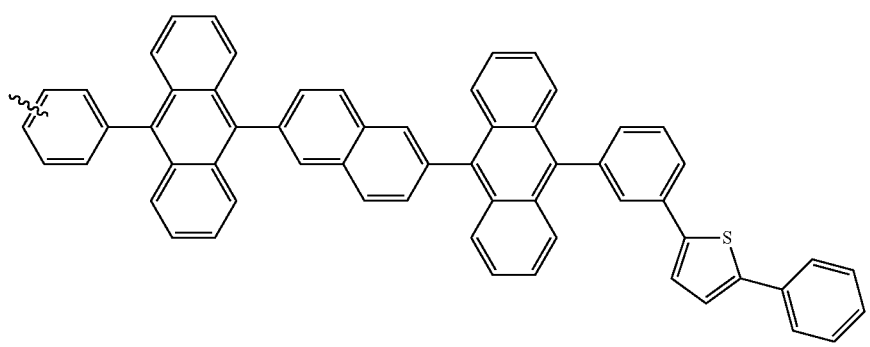 |
| 1-153 | 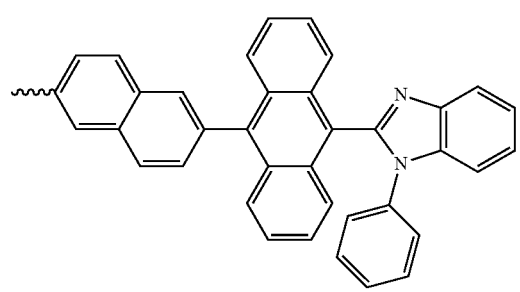 |
| 1-154 | 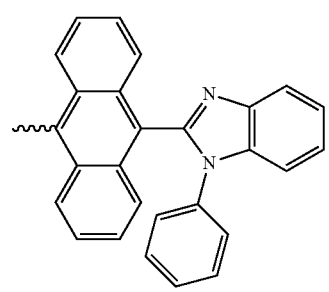 |

| No. | R2 |
|---|---|
| 1-155 | 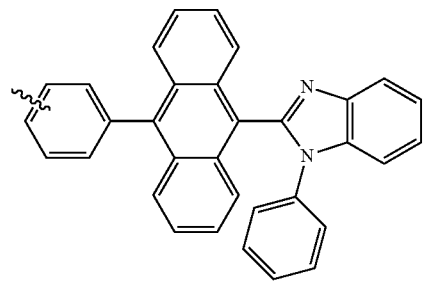 |
| 1-156 | 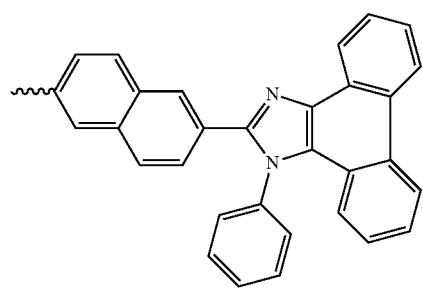 |
| 1-157 | 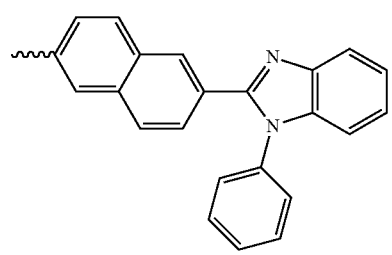 |
| 1-158 | 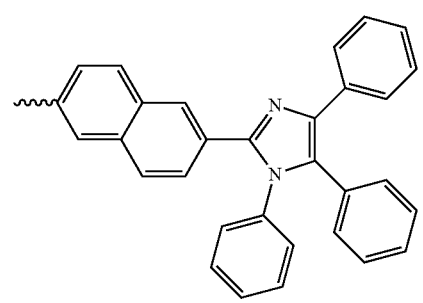 |
| 1-159 | 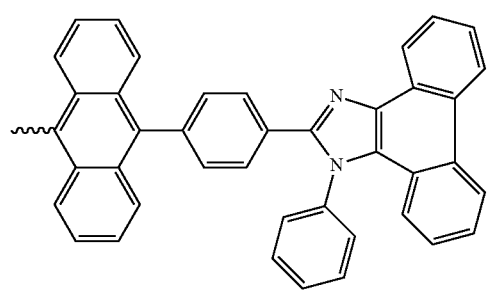 |

-continued
| No. | R2 |
|---|---|
| 1-160 | 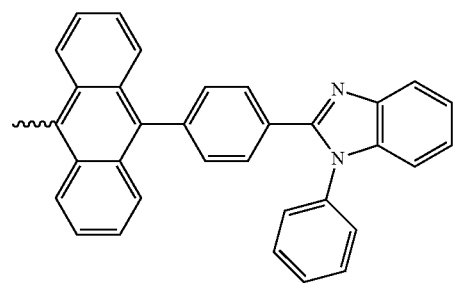 |
| 1-161 | 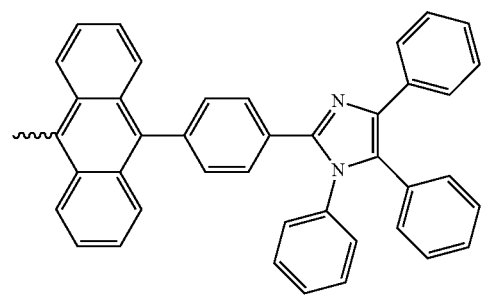 |
| 1-162 | 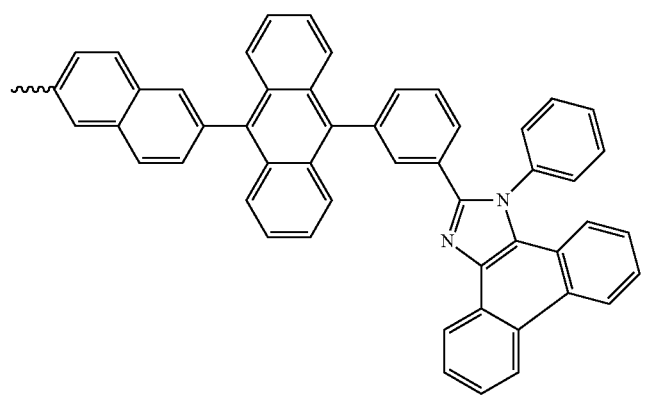 |
| 1-163 | 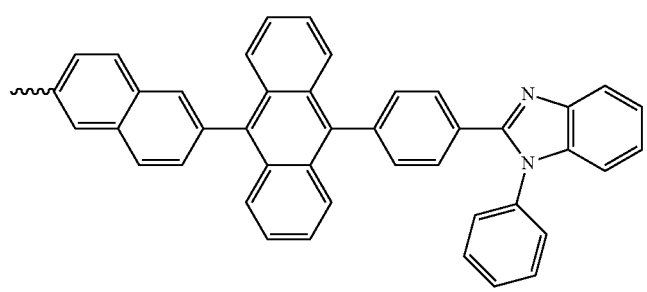 |
| 1-164 | 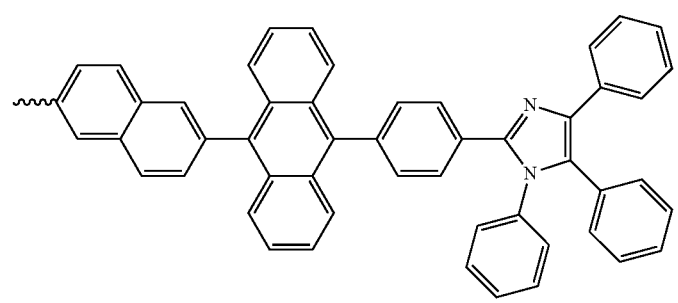 |

-continued
| No. | R2 |
|---|---|
| 1-165 | 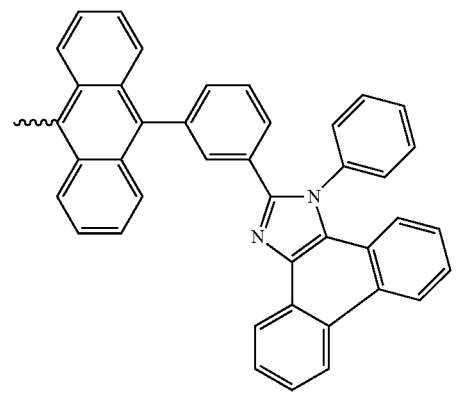 |
| 1-166 | 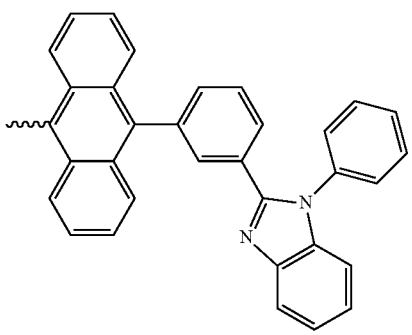 |
| 1-167 | 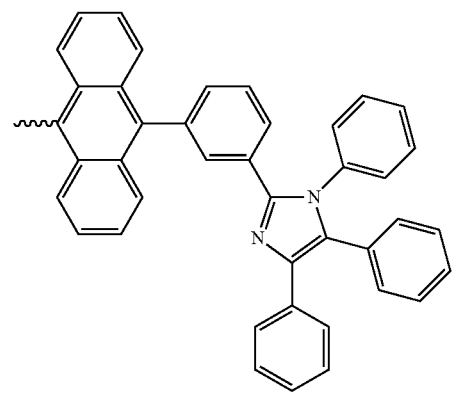 |
| 1-168 | 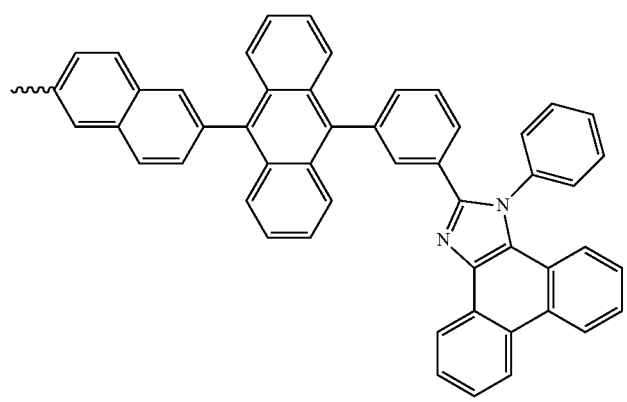 |

| No. | R2 |
|---|---|
| 1-169 | 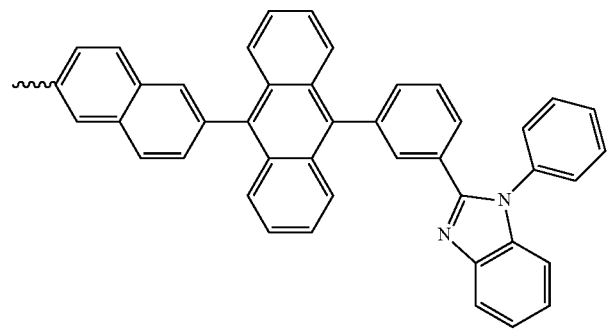 |
| 1-170 | 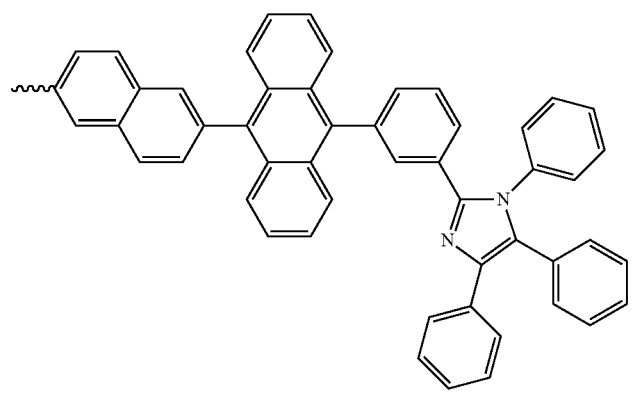 |
| 1-171 | 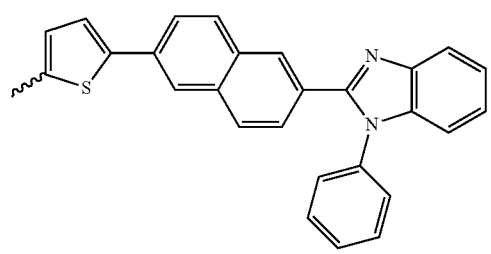 |
| 1-172 | 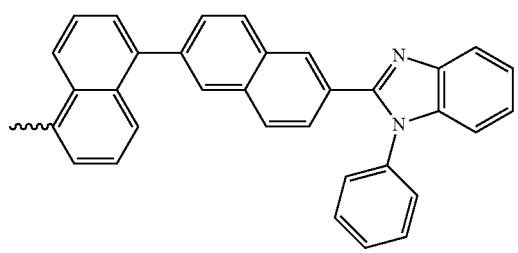 |
| 1-173 | 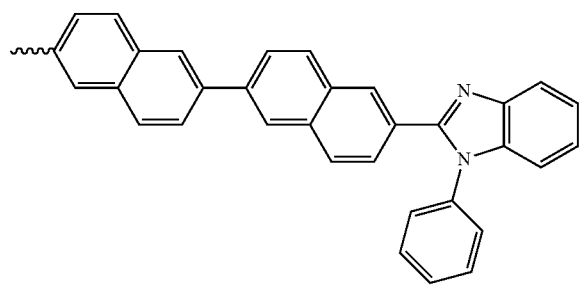 |

| No. | R2 |
|---|---|
| 1-174 | 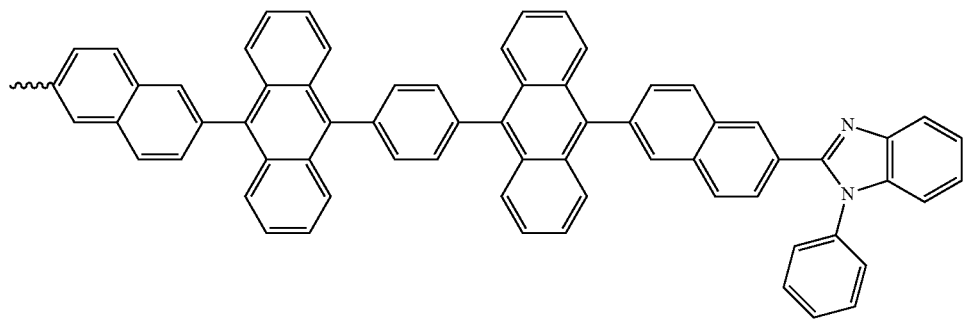 |
| 1-175 | 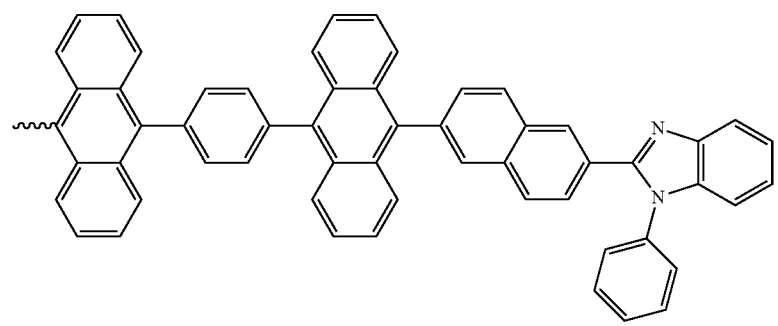 |
| 1-176 | 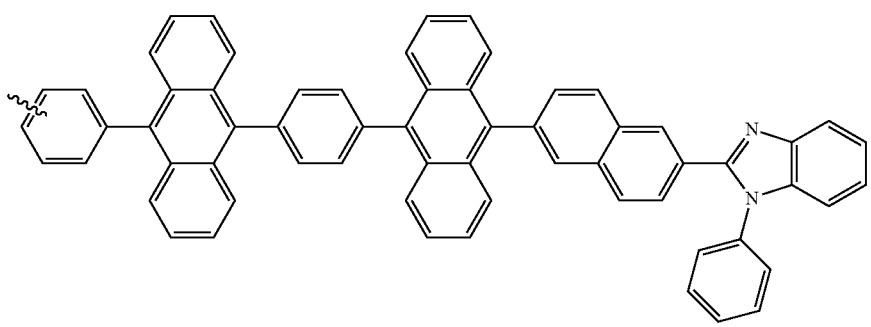 |
| 1-177 | 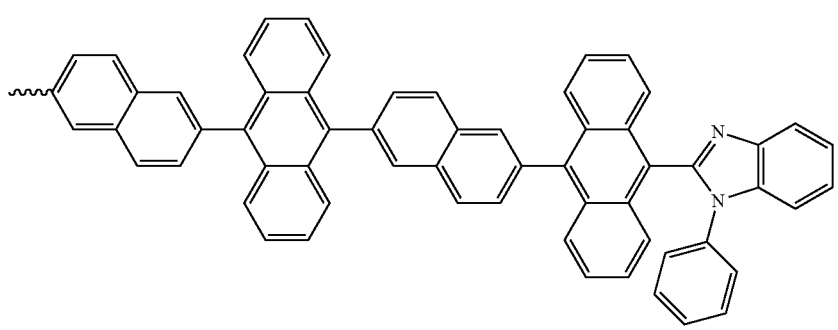 |
| 1-178 | 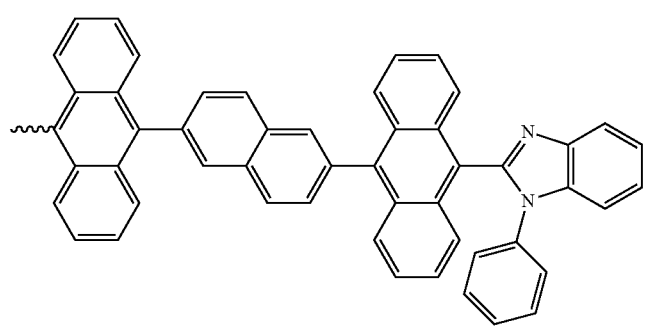 |

| No. | R2 |
|---|---|
| 1-179 | 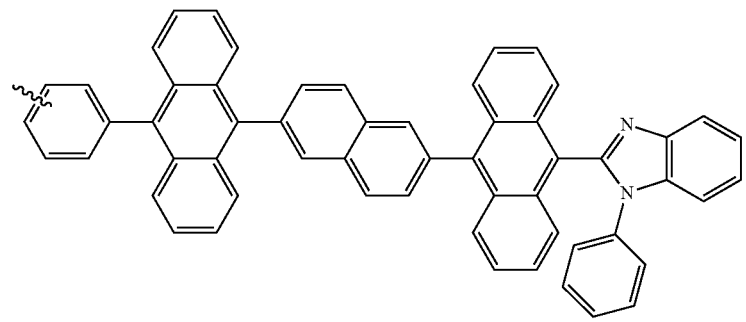 |
| 1-180 | 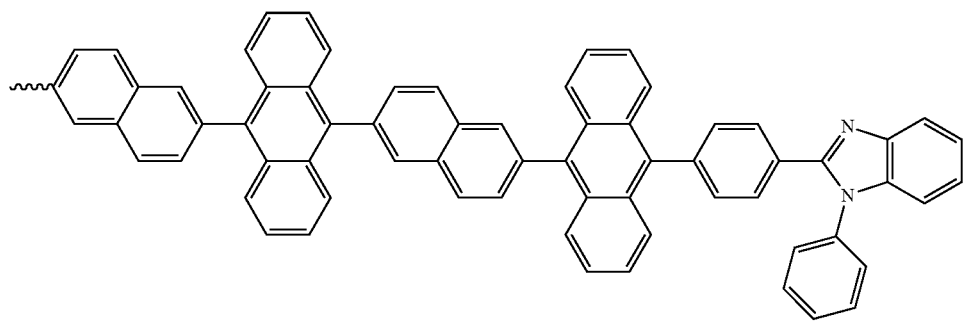 |
| 1-181 | 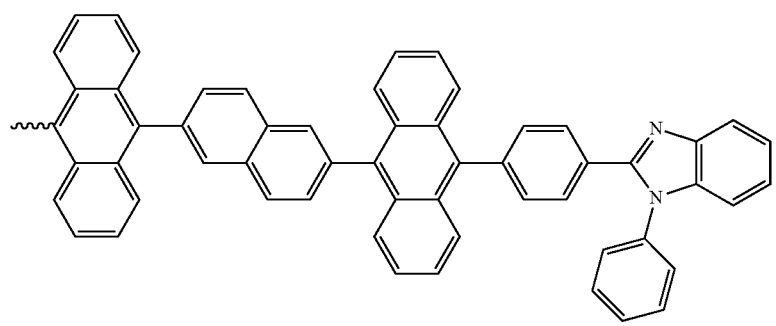 |
| 1-182 | 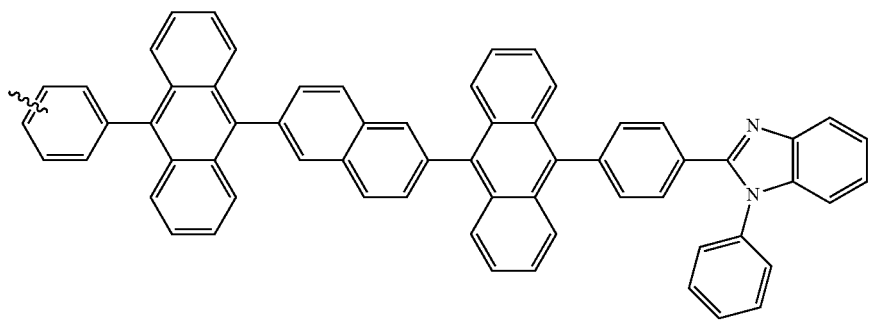 |

| No. | R2 |
|---|---|
| 1-183 | 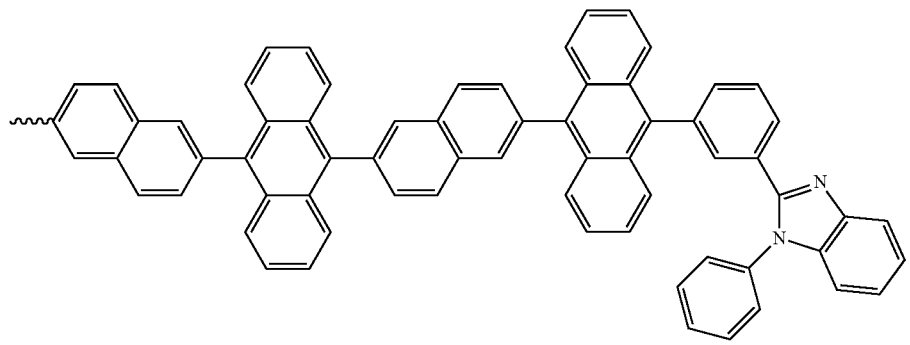 |
| 1-184 | 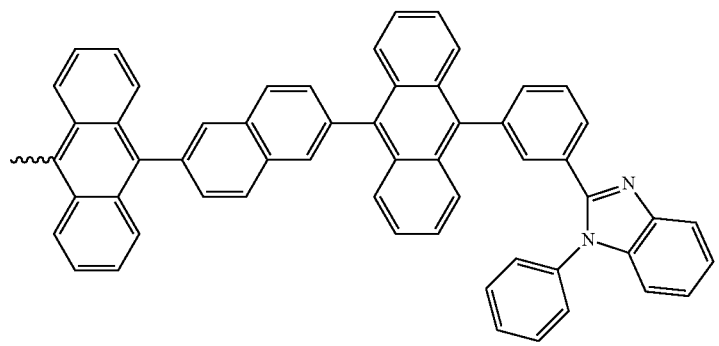 |
| 1-185 | 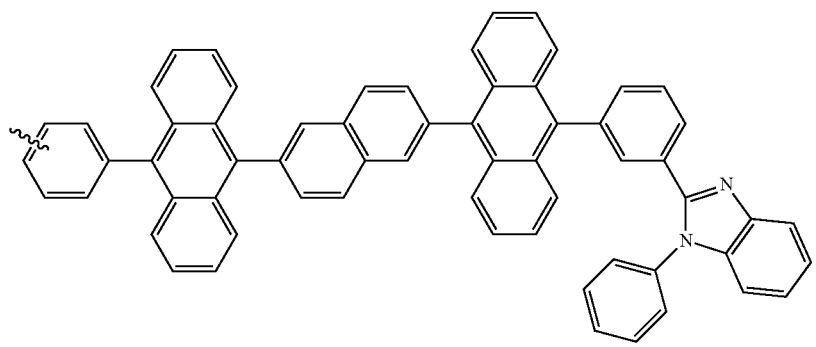 |
| 1-186 | 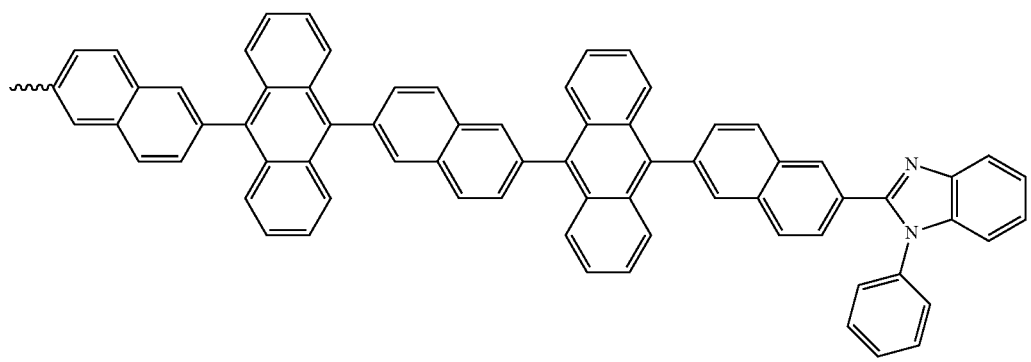 |

| No. | R2 |
|---|---|
| 1-187 | 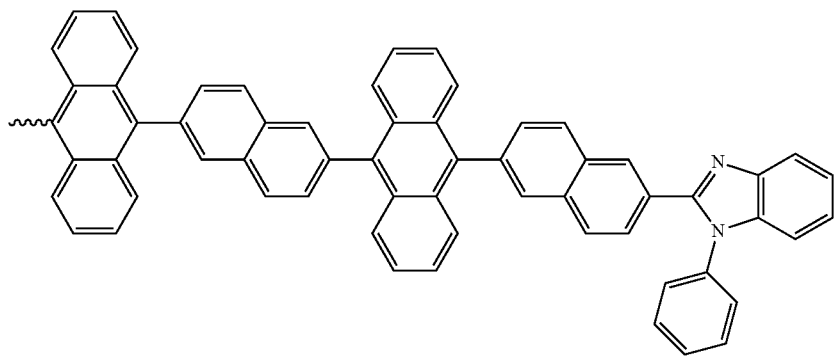 |
| 1-188 | 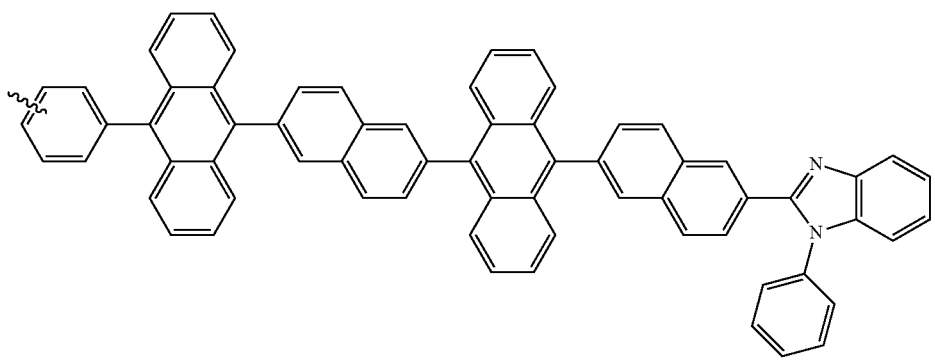 |
| 1-189 | 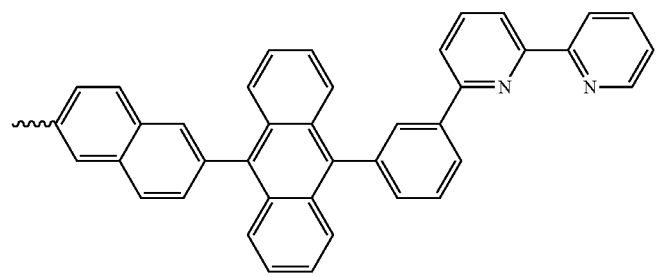 |
| 1-190 | 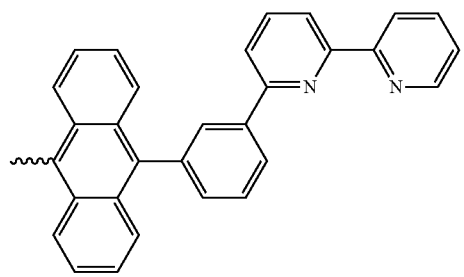 |
| 1-191 | 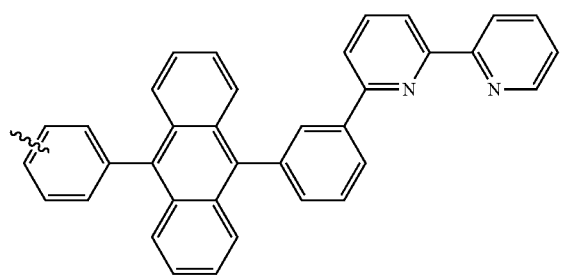 |

-continued
| No. | R2 |
|---|---|
| 1-201 | 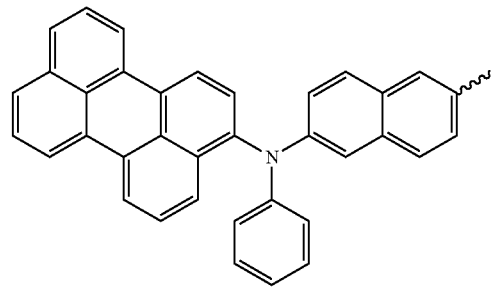 |
| 1-203 | 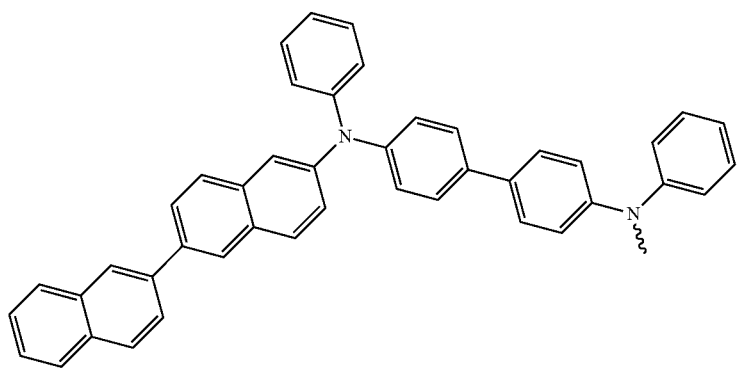 |
| 1-206 | 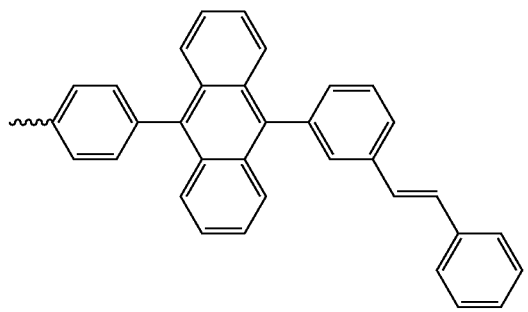 |
| 1-214 | 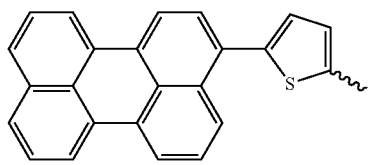 |
| 1-215 | 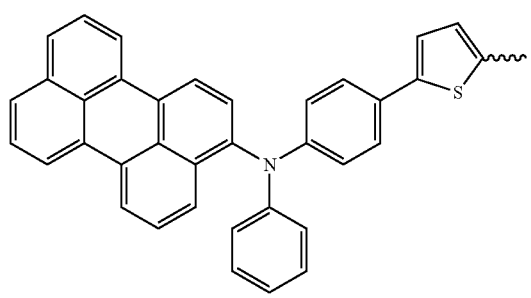 |

| No. | R2 |
|---|---|
| 1-216 | 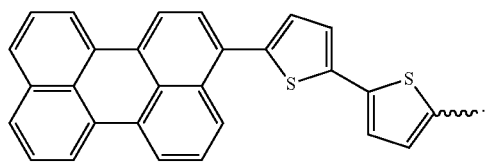 |

8. An organic electronic device comprising a first electrode, a second electrode, and an organic material layer having at least one layer interposed between the first electrode and the second electrode, wherein at least one layer of the organic material layers comprises a binaphthalene derivative represented by the following formula (I):

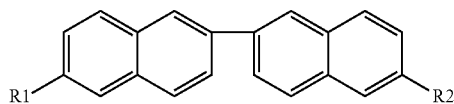

(1)

wherein, in the formula (1), R1 and R2 are selected from the groups shown in the following table:

| No. | R1 | R2 |
|---|---|---|
| 2-1 | 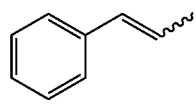 | 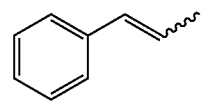 |
| 2-2 | 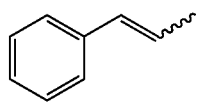 | 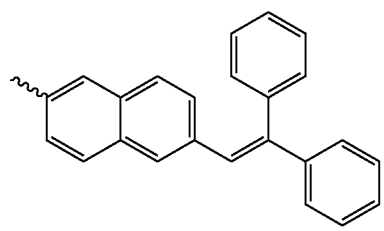 |
| 2-3 | 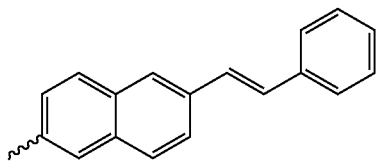 | 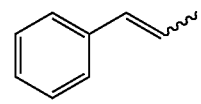 |
| 2-4 | 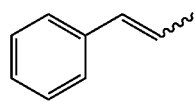 | 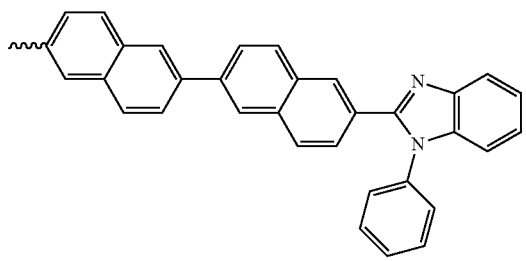 |

| No. | R1 | R2 |
|---|---|---|
| 2-5 | 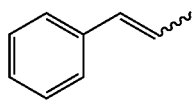 | 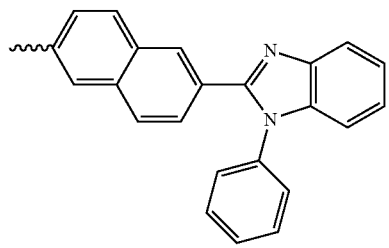 |
| 2-6 | 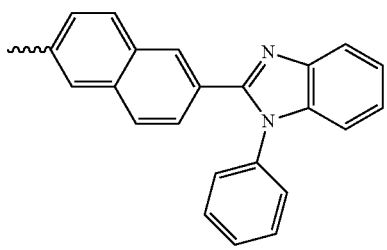 | 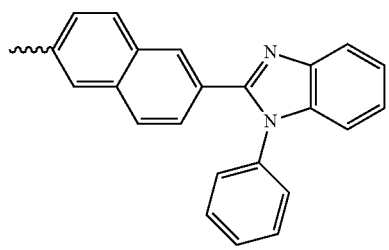 |
| 2-7 | 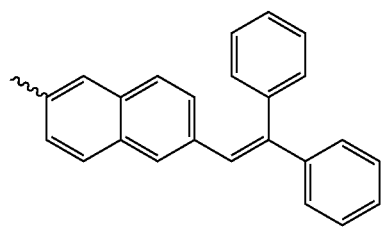 | 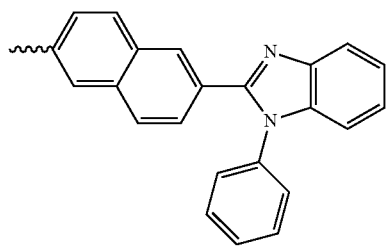 |
| 2-8 | 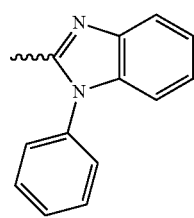 | 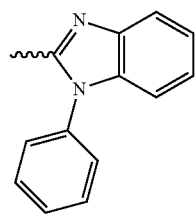 |
| 2-17 | 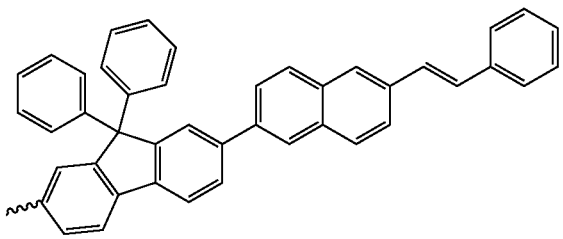 | 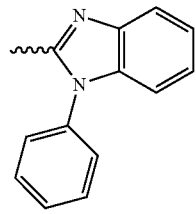 |
| 2-19 | 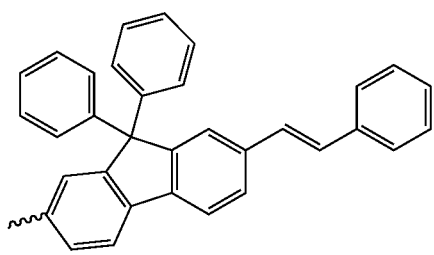 | 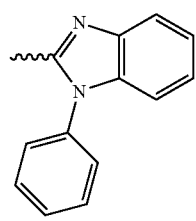 |

| No. | R1 | R2 |
|---|---|---|
| 2-20 | 9,9-diphenyl-2-styrylfluoren-7-yl | 6-(benzothiazol-2-yl)naphthalen-2-yl |
| 2-21 | 6-(4,6-diphenyl-1,3,5-triazin-2-yl)naphthalen-2-yl | 1-phenyl-1H-benzimidazol-2-yl |
| 2-22 | 6-(4,6-diphenyl-1,3,5-triazin-2-yl)naphthalen-2-yl | 6-(benzothiazol-2-yl)naphthalen-2-yl |
| 2-30 | 6-(2,4,5-triphenyl-1H-imidazol-1-yl)naphthalen-2-yl | 1-phenyl-1H-benzimidazol-2-yl |
| 2-31 | 6-(2,4,5-triphenyl-1H-imidazol-1-yl)naphthalen-2-yl | 6-(2,4,5-triphenyl-1H-imidazol-1-yl)naphthalen-2-yl |

-continued
| No. | R1 | R2 |
|---|---|---|
| 2-32 | 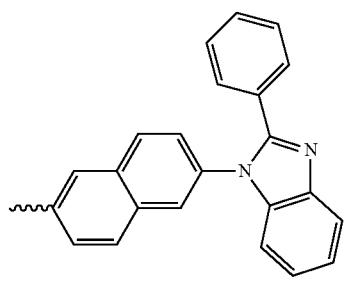 | 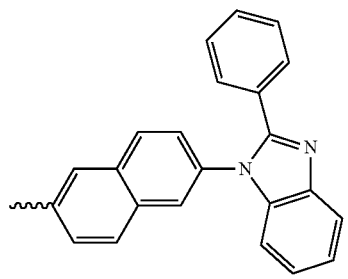 |
| 2-34 | 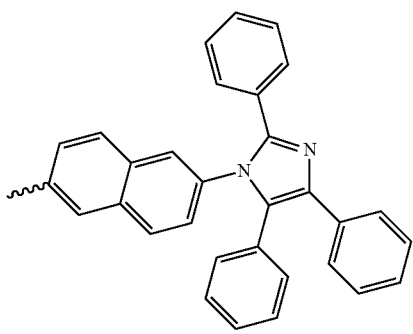 | 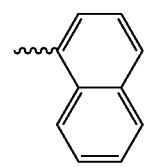 |
| 2-37 | 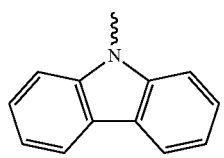 | 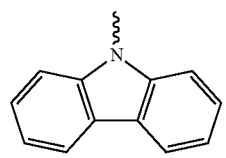 |
| 2-38 | 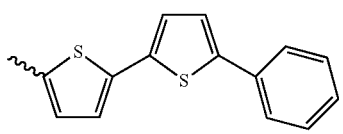 | 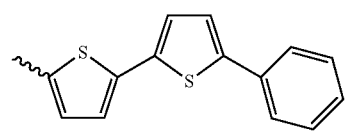 |
| 2-39 | 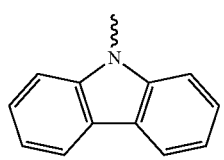 | 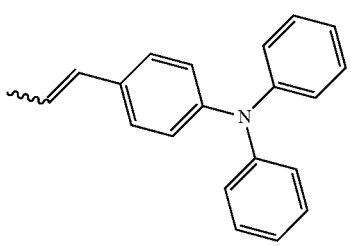 |
| 2-41 | 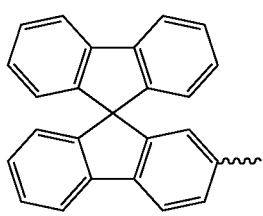 | 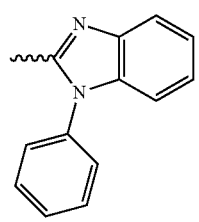 |
| 2-44 | 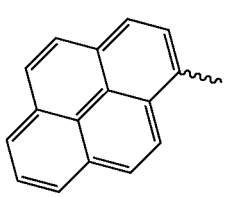 | 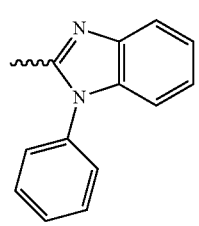 |

-continued
| No. | R1 | R2 |
|---|---|---|
| 2-45 | 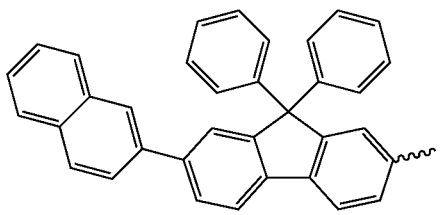 | 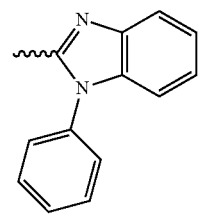 |
| 2-49 | 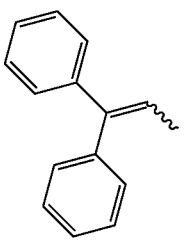 | 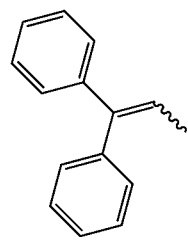 |
| 2-55 | 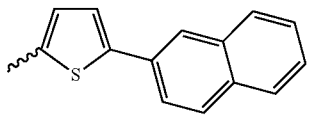 | 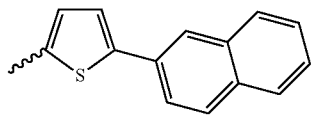 |
| 2-69 | 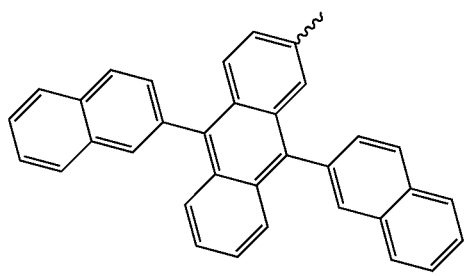 | 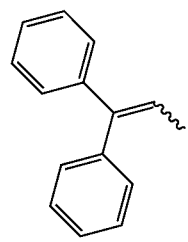 |
| 2-70 | 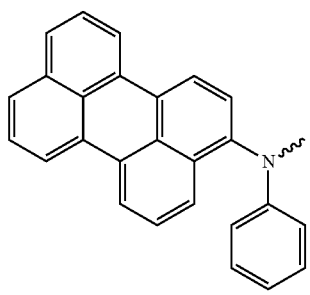 | 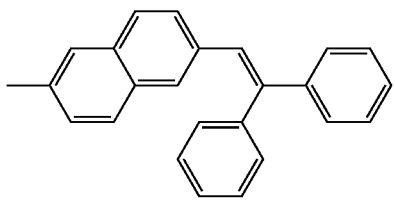 |
| 2-71 | 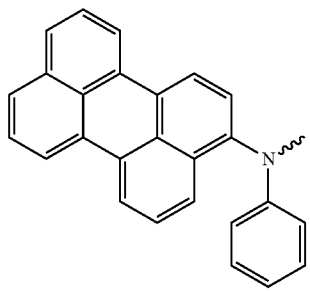 | 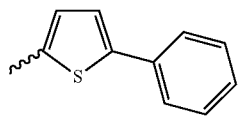 |

-continued
| No. | R1 | R2 |
|---|---|---|
| 2-72 | 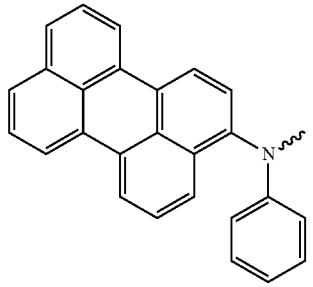 | 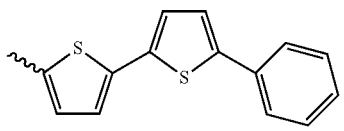 |
| 2-74 | 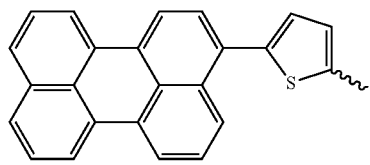 | 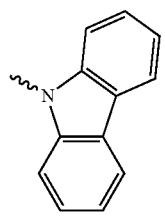 |
* * * * *